(12) United States Patent
Vegas et al.

(10) Patent No.: US 10,898,443 B2
(45) Date of Patent: Jan. 26, 2021

(54) MODIFIED ALGINATES FOR ANTI-FIBROTIC MATERIALS AND APPLICATIONS

(71) Applicants: Massachusetts Institute of Technology, Cambridge, MA (US); The Children's Medical Center Corporation, Boston, MA (US)

(72) Inventors: Arturo J. Vegas, Belmont, MA (US); Joshua C. Doloff, Quincy, MA (US); Omid Veiseh, Bellaire, TX (US); Minglin Ma, Ithaca, NY (US); Robert S. Langer, Newton, MA (US); Daniel G. Anderson, Framingham, MA (US)

(73) Assignees: MASSACHUSETTS INSTITUTE OF TECHNOLOGY, Cambridge, MA (US); THE CHILDREN'S MEDICAL CENTER CORPORATION, Boston, MA (US)

( * ) Notice: Subject to any disclaimer, the term of this patent is extended or adjusted under 35 U.S.C. 154(b) by 105 days.

(21) Appl. No.: 16/108,465

(22) Filed: Aug. 22, 2018

(65) Prior Publication Data

US 2018/0360765 A1 Dec. 20, 2018

Related U.S. Application Data

(62) Division of application No. 14/817,084, filed on Aug. 3, 2015.

(60) Provisional application No. 62/032,148, filed on Aug. 1, 2014, provisional application No. 62/180,415, filed on Jun. 16, 2015.

(51) Int. Cl.
*A61K 35/39* (2015.01)
*A61K 9/00* (2006.01)
*A61K 9/50* (2006.01)
*A61L 29/08* (2006.01)
*A61L 31/10* (2006.01)
*C08B 37/00* (2006.01)
*C12N 5/00* (2006.01)
*C12N 5/071* (2010.01)
*A61L 33/08* (2006.01)

(52) U.S. Cl.
CPC .......... *A61K 9/5036* (2013.01); *A61K 9/0024* (2013.01); *A61K 35/39* (2013.01); *A61L 29/085* (2013.01); *A61L 31/10* (2013.01); *A61L 33/08* (2013.01); *C08B 37/0084* (2013.01); *C12N 5/0012* (2013.01); *C12N 5/0677* (2013.01)

(58) Field of Classification Search
CPC .... A61K 9/5036; A61K 9/0024; A61K 35/39; A61K 31/20; A61L 29/085; A61L 33/08; C08B 37/0084; C12N 5/0012; C12N 5/0677
See application file for complete search history.

(56) References Cited

U.S. PATENT DOCUMENTS

| | | |
|---|---|---|
| 2,881,161 A | 4/1959 | Kohler |
| 4,352,883 A | 10/1982 | Lim |
| 2,860,130 A | 11/1985 | McNeely |
| 4,816,567 A | 3/1989 | Cabilly |
| 4,868,121 A | 9/1989 | Scharp |
| 5,273,904 A | 12/1993 | Langley |
| 5,322,790 A | 6/1994 | Scharp |
| 5,336,668 A | 8/1994 | dellaValle |
| 5,443,505 A | 8/1995 | Wong |
| 5,447,863 A | 9/1995 | Langley |
| 5,624,821 A | 4/1997 | Winter |
| 5,821,121 A | 10/1998 | Brothers |
| 5,876,452 A | 3/1999 | Athanasiou |
| 6,060,053 A | 5/2000 | Atala |
| 6,129,761 A | 10/2000 | Hubbell |
| 6,159,531 A | 12/2000 | Dang |
| 6,194,551 B1 | 2/2001 | Idusogie |
| 7,682,699 B2 * | 3/2010 | Michal |
| 7,807,150 B2 | 10/2010 | Griffith |
| 2004/0253532 A1 | 12/2004 | Wu |
| 2006/0286141 A1 * | 12/2006 | Campbell |
| 2008/0044900 A1 | 2/2008 | Mooney |
| 2008/0177021 A1 | 7/2008 | Berlin |
| 2008/0242738 A1 | 10/2008 | Marks |
| 2008/0268189 A1 | 10/2008 | Sun |
| 2009/0148591 A1 | 6/2009 | Wang |
| 2012/0009159 A1 | 1/2012 | Humayun |
| 2012/0121657 A1 | 5/2012 | Zhou |
| 2012/0308650 A1 * | 12/2012 | Vegas |
| 2013/0149351 A1 | 6/2013 | Lee |
| 2015/0368713 A1 | 12/2015 | Bharti |

FOREIGN PATENT DOCUMENTS

| | | |
|---|---|---|
| CN | 101565469 | 10/2009 |
| DE | 102005049833 | 4/2007 |
| EP | 1614696 | 1/2006 |
| FR | 2699545 | 6/1994 |
| WO | 9107951 | 6/1991 |
| WO | 9900070 | 1/1999 |
| WO | 9958572 | 11/1999 |
| WO | 2003010354 | 2/2003 |
| WO | 2005058382 | 6/2005 |
| WO | 2005063147 | 7/2005 |
| WO | 2009032158 | 3/2009 |

(Continued)

OTHER PUBLICATIONS

Vegas et al. (Nature Biotechnology 34, No. 3, pp. 345-352, Mar. 2016 and Supplemental) (Year: 2016).*

(Continued)

*Primary Examiner* — Alma Pipic
(74) *Attorney, Agent, or Firm* — Pabst Patent Group LLP

(57) ABSTRACT

Covalently modified alginate polymers, possessing enhanced biocompatibility and tailored physiochemical properties, as well as methods of making and use thereof, are disclosed herein. The covalently modified alginates are useful as a matrix for coating of any material where reduced fibrosis is desired, such as encapsulated cells for transplantation and medical devices implanted or used in the body.

19 Claims, 11 Drawing Sheets

(56) References Cited

FOREIGN PATENT DOCUMENTS

| WO | 2010090767 | 8/2010 |
|---|---|---|
| WO | 2012167223 | 12/2012 |
| WO | 2013121983 | 8/2013 |
| WO | 2014044697 | 3/2014 |
| WO | 2016019391 | 3/2017 |

OTHER PUBLICATIONS

Chen, "Differentiation of rat marrow mesenchymal stem cells into pancreatic islet beta-cells", World Journal of Gastroenterology, 10(20): 3016-3020 (2004).
Costa, et al., "Covalent immobilization of antimicrobial peptides (AMPs) onto biomaterial surfaces", Acta Biomaterialia, 7(5): 1431-1440 (2010).
Pedraza, "Engineering an optimal bioartificial pancreas for islet transplantation using bioactive scaffolds", Dissertation (Ph.D.) University of Miami, (2011).
Pedraza, et al., "Macroporous three-dimensional PDMS scaffolds for extrahepatic islet transplantation", Cell Transplantation, 22:1123-1135 (2013).
Tang, et al., "Reprogramming liver-stem WB fcells into functional insulin-prodcuing cells by persistent expression of Pdx1-and Pdx1-VP16 mediated by lentiviral vectors", Lab Invest 86(1)83-93 (2006).
Thevenot, et al., "Surface chemistry influences implant biocompatibility", Curr. Top. Med. Chem.., 8(4):270-80 (2011).
Yang, et al., "Amphiphilic cholesteryl grafted sodium alginate derivative: Synthesis and self-assembly in aqueous solution", Carbohydrate Polymers, 68(2):218-25 (2007).
Aebischer, et al, "Transplantation of polymer encapsulated neurotransmitter secreting cells: effect of the encapsulation technique", J Biomech Eng., 113(2):178-83 (1991).
Angal, et al., "A single amino acid substitution abolishes the heterogeneity of chimeric mouse/human (IgG4) antibody", Mol. Immunol. 30:105-08 (1993).
Bell and Peppas, "Biomedical membranes from hydrogels and interpolymer complexes", Adv. Polym. Sci., 122:125-175 (1995).
Elliot, et al., "Live encapsulated porcine islets from a type 1 diabetic patient 9.5 yr after xenotransplantation",. Xenotransplantation., 14(2):157-61 (2007).
Extended European Search Report issued for EP 18 16 2427 dated Jun. 19, 2018.
Gruber, et al., "Efficient tumor cell lysis mediated by a bispecific single chain antibody expressed in *Escherichia coli*", J. Immunol., 152:5368 (1994).
Hollinger, et al., ""Diabodies": small bivalent and bispecific antibody fragments", PNAS, 90:6444-8 (1993).
International Search Report for corresponding PCT application PCT/US2016/059967 dated Feb. 20, 2017.
Lesney, "Going Cellular", Modern Drug Discovery 4(3), 45-46, 49, 50 (2001).
Morrison, et al., "Chimeric human antibody molecules: mouse antigen-binding domains with human constant region domains.", PNAS, 81:6851-5 (1984).
Vallee, et al., "Synthesis and rheological properties of hydrogels based on amphiphilic alginate-amide derivatives", Carbohydrate Res., 344:223-8 (2009).
Vogelm, et al., "Sustained function of alginate-encapsulated human islet cell implants in the peritoneal cavity of mice leading to a pilot study in a type 1 diabetic patient", Diabetologia 56:1605-14 (2013).
Lee, et al., "Development and characterization of an alignate-impregnated polyester vascular graft", Journal of Biomedical Materials Research, 36(2):200-208 (1997).
Vegas, et al., "Combinatorial hydrogel library enables identification of materials that mitigate the foreign body response in primates", Nat Biotechnol., 34(3):345-52 (2016).
Devos, et al., "Improved biocompatibility but limited graft survival after purification of alginate for microencapsulation of pancreatic islets", Diabetologia 40(3):262-70 (1997).
Kovach, et al., "The Effects of PEG-based surface modification of PDMS microchannels on longterm hemocompatibility", J. of Biomedical Research Pt. A, 102A:4195-4205 (2014).
Ratner, "A pore way to heal and regenerate: 21st century thinking on biocompatibility", Regenerative Biomaterials, 107-110 (2016).
Anderson, et al., "Foreign body reaction to biomaterials", Semin. Immunol. 20:86-100 (2008).
Basta, et al., "Long-term metabolic and immunological follow-up of nonimmunosuppressed patients with type 1 diabetes treated with microencapsulated islet allografts: four cases", Diabetes Care, 34:2406-9 (2011).
Calafiore, et al., "Microencapsulated pancreatic islet allografts into nonimmunosuppressed patients with type 1 diabetes: first two cases", Diabetes Care, 29:137-8, (2006).
Dang, et al., "Spatiotemporal effects of a controlled-release anti-inflammatory drug on the cellular dynamics of host response", Biomaterials, 32:4464-70 (2011).
De Groot, et al., "Causes of limited survival of microencapsulated pancreatic islet grafts" , J Surg Res., 121:141-50 (2004).
De Vos, et al., "Alginate-based microcapsules for immunoisolation of pancreatic islets" , Biomaterials, 27:5603-17 (2006).
Dolgin, "Encapsulate this", Nat. Med. 20:9-11 (2014).
Elliot, et al., "Intraperitoneal alginate-encapsulated neonatal porcine islets in a placebo-controlled study with 16 diabetic cynomolgus primates", Transplant Proc., 37:3505-8 (2005).
Ferreira, et al., "Biocompatibility of chemoenzymatically derived dextran-acrylate hydrogels"., J. Biomed. Mater. Res., 68A :584-96 (2004).
Ferreira, et al., "Enzymatic synthesis of dextran-containing hydrogels". Biomaterials, 23: 3957-67 (2002).
Field, et al., "Improved islet isolation from rat pancreas using 35% bovine serum albumin in combination with Dextran gradient separation", Transplantation 61:1554-6 (1996).
Gardner, et al., "Biomaterials-Based Modulation of the Immune System", BioMed Res Intl., Article ID 732182, 7 pages (2013).
Garrett, et al., "New observations on peptide bond formation using CDMT", Tetrahedron Lett., 43(23):4161-4 (2002).
Gibly, et al., "Advancing islet transplantation: from engraftment to the immune response", Diabetologia, 54:2494-2505 (2011).
Grainger, "All charged up about implanted biomaterials", Nat. Biotechnol., 31:507-9 (2013).
Harding and Reynolds, "Combating medical device fouling", Trends Biotechnol. 32:140-6 (2014).
Hetrick, et al., "Reduced foreign body response at nitric oxide-releasing subcutaneous implants", Biomaterials 28:4571-80 (2007).
Hirshberg, "Lessons learned from the international trial of the edmonton protocol for islet transplantation", Curr Diab Rep., 7:301-3 (2007).
Jacobs-Tulleneers-Thevissen, et al., "Sustained function of alginate-encapsulated human islet cell implants in the peritoneal cavity of mice leading to a pilot study in a type 1 diabetic patient", Diabetologia, 56:1605-14 (2013).
Kang, et al., "Combined confocal Raman and quantitative phase microscopy system for biomedical diagnosis", Biomed. Opt. Exp., 2(9):2484-92 (2011).
Kang, et al., "Measuring uptake dynamics of multiple identifiable carbon nanotube species via high-speed confocal Raman imaging of live cells", Nano Letters, 12(12):6170-4 (2012).
King, et al., "The effect of host factors and capsule composition on the cellular overgrowth on implanted alginate capsules", J Biomed Mat Res., 57:374-83 (2001).
Kolb and Sharpless, "The growing impact of click chemistry on drug discovery", Drug Discov Today, 8(24):1128-37 (2003).
Kolb, et al., "Click Chemistry: Diverse Chemical Function from a Few Good Reactions", Angew. Chem. Int. Ed., 40:2004-21 (2001).
Kolb, et al., "Differences in the fibrogenic response after transfer of active transforming growth factor-beta1 gene to lungs of "fibrosis-prone" and "fibrosis-resistant" mouse strains", J. Respir. Cell. Mol. Biol., 27:141-50 (2002).
Langer, "Perspectives and Challenges in Tissue Engineering and Regenerative Medicine", Adv. Mater. 21:3235-3236 (2009).
Lee and Mooney, "Alginate: Properties and biomedical applications", Prog Polym Sci., 37:106-126 (2012).

(56) References Cited

OTHER PUBLICATIONS

Lee and Mooney, "Hydrogels for tissue engineering", Chem. Rev. 101:1869-79 (2001).
Lim and Sun, "Microencapsulated islets as bioartificial endocrine pancreas", Science, 210:908-10 (1980).
Linetsky, et al., "Improved human islet isolation using a new enzyme blend, liberase", Diabetes 46:1120-3 (1997).
Massia and Stark, "Immobilized RGD peptides on surface-grafted dextran promote biospecific cell attachment", Biomed. Mater. Res., 56 :390-9 (2001).
Mehvar, "Dextrans for targeted and sustained delivery of therapeutic and imaging agents", J. Control. Rel., 69:1-25 (2000).
Moses and Moorhouse, "The growing applications of click chemistry", Chem Soc. Rev., 36:1249-62 (2007).
O\Sullivan, et al , "Islets transplanted in immunoisolation devices: a review of the progress and the challenges that remain", Endocrine Reviews, 32:827-44 (2011).
Omer, et al., "Survival and maturation of microencapsulated porcine neonatal pancreatic cell clusters transplanted into immunocompetent diabetic mice", Diabetes, 52:69-75 (2003).
Onuk, et al., "A Review of the Biocompatibility of Implantable Devices: Current Challenges to Overcome Foreign Body Response", J Diabetes Sci. Tech., 2 (6):1003-15 (2006).
Osterberg, et al., "Protein-rejecting ability of surface-bound dextran in end-on and side-on configurations: comparison to PEG", J. Biomed. Mat. Res., 29:741-7 (1995).
Peppas, et al., "Hydrogels in pharmaceutical formulations", Eur. J. Pharm. Biopharm. 50:27-46 (2000).
Pickup, "Insulin-pump therapy for type 1 diabetes mellitus", N. Engl. J. Med. 366:1616-24 (2012).
Qi, et al., "Five-year follow-up of patients with type 1 diabetes transplanted with allogeneic islets: the UIC experience", Acta Diabetol., 51:833-43 (2014).
Ratner, "Reducing capsular thickness and enhancing angiogenesis aroundimplant drug release systems", J. Control Release., 78:211-8 (2002).
Robertson, "Islet transplantation as a treatment for diabetes—a work in progress", N. Engl. J. Med., 350:694-705 (2004).
Rodriguez, et al., "Quantitative in vivo cytokine analysis at synthetic biomaterial implant sites", J. Biomed. Mater. Res A, 89:152-159 (2009).
Scharp, et al., "Encapsulated islets for diabetes therapy: history, current progress, and critical issues requiring solution", Adv Drug Deliv Rev., 67-68:35-73 (2014).
Schneider, et al., "Long-term graft function of adult rat and human islets encapsulated in novel alginate-based microcapsules after transplantation in immunocompetent diabetic mice", Diabetes 54:687-93 (2005).
Shapiro, et al., "Islet transplantation in seven patients with type 1 diabetes mellitus using a glucocorticoid-free immunosuppressive regimen", N. Engl. J. Med. 343:230-8 (2000).
Shapiro, et al., "International trial of the Edmonton protocol for islet transplantation", N. Engl. J. Med., 355:1318-30 (2006).
Shapiro ,et al., "Islet transplantation in type 1 diabetes: ongoing challenges, refined procedures, and long-term outcome", Rev Diabet Stud., 9:385-406 (2012).
Shaw, et al., "Global estimates of the prevalence of diabetes for 2010 and 2030", Diabetes Res. Clin. Pract. 87:4-14 (2010).
Stowell and Widlanski, "A new method for the phosphorylation of alcohols and phenols", Tetrahedron Lett., 36(11):1825-6 (1995).
Sussman, et al., "Porous implants modulate healing and induce shifts in local macrophage polarization in foreign body reaction", Ann. Biomed. Eng., 42 (7):1508-16 (2013).
Tuch, et al., "Safety and viability of microencapsulated human islets transplanted into diabetic humans", Diabetes Care, 32:1887-9 (2009).
Veiseh, et al., "Size- and shape-dependent foreign body immune response to materials implanted in rodents and non-human primates", Nat. Mater., 14 (6):643-51 (2015).
Ward, "A Review of the Foreign-body Response to Subcutaneously-implanted Devices: The Role of Macrophages and Cytokines in Biofouling and Fibrosis", J. Diabetes Sci. Technol., 2:768-777 (2008).
Wick, et al., "The immunology of fibrosis", Annu. Rev. Immunol., 31:107-35 (2013).
Wick, et al., "The immunology of fibrosis: innate and adaptive responses", Trends in Immunol., 31(3):110-19 (2010).
Williams, "On the mechanisms of biocompatibility", Biomaterials, 29:2941-53 (2008).
Wynn and Ramalingam, "Mechanisms of fibrosis: therapeutic translation for fibrotic disease", Nat. Med. 18:1028-40 (2012).
Zhang, et al., "Zwitterionic hydrogels implanted in mice resist the foreign-body reaction", Nat. Biotechnol., 31:553-6 (2013).
International Search Report for corresponding PCT application PCT/US2015/043495 dated Oct. 21, 2015.
Ahad, et al., "Surface modification of polymers for biocompatibility via exposure to extreme ultraviolet radiation", Society for Biomaterials, 3296-3310 (2013).
Hudalla, et al., "Immobilization of peptides with distinct biological activities onto stem cell culture substrates using orthogonal chemistries", Langmuir, 26(9):6449-6456 (2010).
Anderson, et al., "Conotoxins: Potential weapons from the sea", J. Bioterr. Biodef., 3:120 (2012).
Pedraza, et al., "Preventing hypoxia-induced cell death", PNAS, 109(11):4245-4250 (2012).
Yimin, et al., "Alginic Acid", 137-140. China Light Industry Press Ltd., 2008.

* cited by examiner

MODIFIED ALGINATES FOR ANTI-FIBROTIC MATERIALS AND APPLICATIONS

CROSS-REFERENCE TO RELATED APPLICATIONS

This application is a divisional of U.S. Ser. No. 14/817,084 filed Aug. 3, 2015, which claims priority to and benefit of U.S. Provisional Application No. 62/032,148, filed Aug. 1, 2014, and U.S. Provisional Application No. 62/180,415, filed on Jun. 16, 2015, which are incorporated herein by reference in their entirety.

STATEMENT REGARDING FEDERALLY SPONSORED RESEARCH

This invention was made with government support under Grants EB000244, EB000351, DE013023 and CA151884 awarded by the National Institutes of Health (NIH) and Grant W81XWH-13-1-0215 awarded by the Department of Defense (DOD). The government has certain rights in the invention.

FIELD OF THE INVENTION

The present invention relates to the use of alginates, chemically modified to enhance their biocompatibility and anti-fibrotic properties; to their use to coat or encapsulate materials, products, and devices, such as cells, implants, and medical devices; and to methods of treating diseases or disorders, including diabetes, by implantation of the modified alginates and materials coated or encapsulated with the modified alginates.

BACKGROUND OF THE INVENTION

The foreign body response is an immune-mediated reaction that impacts the fidelity of implanted biomedical devices (Anderson et al., *Semin. Immunol.* 20:86-100 (2008); Langer, *Adv. Mater.* 21:3235-3236 (2009); Ward, *J. Diabetes Sci. Technol. Online* 2:768-777 (2008); Harding & Reynolds, *Trends Biotechnol.* 32:140-146 (2014)). Macrophage recognition of biomaterial surfaces in these devices initiate a cascade of inflammatory events that result in the fibrous and collagenous encapsulation of these foreign materials (Anderson et al. (2008); Ward (2008); Harding & Reynolds (2014); Grainger, *Nat. Biotechnol.* 31:507-509 (2013); Williams, *Biomaterials* 29:2941-2953 (2008)). This encapsulation, over time, often leads to device failure and can result in discomfort for the recipient (Anderson et al. (2008); Harding & Reynolds (2014); Williams (2008)). These adverse outcomes emphasize the critical need for biomaterials that do not elicit foreign body responses to overcome this key challenge to long-term biomedical device function.

The foreign body response to implanted biomaterials is the culmination of inflammatory events and wound-healing processes resulting in implant encapsulation (Anderson et al. (2008)). The final pathological product of this response is fibrosis, which is characterized by the accumulation of excessive extracellular matrix at sites of inflammation and is a key obstacle for implantable medical devices as the cellular and collagenous deposition isolate the device from the host (Anderson et al. (2008); Wick et al., *Annu. Rev. Immunol.* 31:107-135 (2013); Wynn & Ramalingam, *Nat. Med.* 18:1028-1040 (2012)). This device isolation can interfere with sensing of the host environment, lead to painful tissue distortion, cut off nourishment (for implants containing living, cellular components), and ultimately lead to device failure. Materials commonly used for medical device manufacture today elicit a foreign body response that results in fibrous encapsulation of the implanted material (Langer (2009); Ward (2008); Harding & Reynolds (2014); Williams (2008); Zhang et al., *Nat. Biotechnol.* 31:553-556 (2013)). Overcoming the foreign body response to implanted devices could pave the way for implementing new medical advances, making the development of materials with both anti-inflammatory and anti-fibrotic properties a critical medical need (Anderson et al. (2008); Langer (2009); Harding & Reynolds (2014)).

Macrophages are a key component of material recognition and actively adhere to the surface of foreign objects (Anderson et al. (2008); Ward (2008); Grainger, *Nat. Biotechnol.* 31:507-509 (2013); Sussman et al., *Ann. Biomed. Eng.* 1-9 (2013) (doi:10.1007/s10439-013-0933-0)). Objects too large for macrophage phagocytosis initiate processes that result in the fusion of macrophages into foreign-body giant cells. These multi-nucleated bodies amplify the immune response by secreting cytokines and chemokines that result in the recruitment of fibroblasts that actively deposit matrix to isolate the foreign material (Anderson et al. (2008); Ward (2008); Rodriguez et al., *J. Biomed. Mater. Res. A* 89:152-159 (2009); Hetrick et al., *Biomaterials* 28:4571-4580 (2007)). This response has been described for materials of both natural and synthetic origins that encompass a wide range of physicochemical properties, including alginate, chitosan, dextran, collagen, hyaluronan, poly(ethylene glycol) (PEG), poly(methyl methacrylate) (PMMA), poly(2-hydroxyethyl methacrylate) (PHEMA), polyurethane, polyethylene, silicone rubber, Teflon, gold, titanium, silica, and alumina (Ward (2008); Ratner, *J. Controlled Release* 78:211-218 (2002)).

The transplantation of hormone- or protein-secreting cells from genetically non-identical members of the same species (i.e. allotransplantation) or from other species (i.e. xenotransplantion) is a promising strategy for the treatment of many diseases and disorders. Using alginate microcapsules to provide immunoisolation, hormone- or protein-secreting cells can be transplanted into a patient without the need for extensive treatment with immunosuppressant drugs. This principle has been successfully demonstrated by the transplantation of alginate-encapsulated pancreatic β-cells in diabetic rat models (Lim, F. and Sun, A. M. *Science.* 210, 908-910 (1980)). Methods of encapsulating biological material in alginate gels are described, for example, in U.S. Pat. No. 4,352,883 to Lim. In the Lim process, an aqueous solution containing the biological materials to be encapsulated is suspended in a solution of a water soluble polymer. The suspension is formed into droplets which are configured into discrete microcapsules by contact with multivalent cations such as $Ca^{2+}$. The surface of the microcapsules is subsequently crosslinked with polyamino acids, forming a semipermeable membrane around the encapsulated materials.

The Lim method employs conditions which are mild enough to encapsulate cells without adversely affecting their subsequent survival and function. The resulting alginate microcapsules are semipermeable, possessing sufficient porosity to permit nutrients, waste, and the hormones and/or proteins secreted from encapsulated cells to diffuse freely into and out of the microcapsules, and, when implanted into an animal host, the alginate microcapsules effectively isolate the encapsulated cells from the host's immune system. See also U.S. Pat. No. 7,807,150 to Vacanti, et al.

Many other synthetic materials have been tried, including block copolymers such as polyethyleneglycol-diacrylate polymers, polyacrylates, and thermoplastic polymers, as reported by U.S. Pat. No. 6,129,761 to Hubbell and by Aebischer, et al, J Biomech Eng. 1991 May 113(2):178-83. See Lesney Modern Drug Discovery 4(3), 45-46, 49, 50 (2001) for review of these materials.

Since Lim first reported on the transplantation of encapsulated cells, many other have tried to create "bioreactors" for cells that could maintain viability of the cells in the absence of vascularization, by diffusion of nutrients, gases and wastes through the encapsulating materials, and still protect the cells from the body's immune defenses against foreign cells and materials. Unfortunately, efforts to translate these therapies into human subjects have proven difficult. For example, alginate-encapsulated porcine islet cells transplanted into a human subject suffering from Type 1 diabetes initially demonstrated significant improvement and required decreased insulin dosing. However, by week 49, the patient's insulin dose retuned to pre-transplant levels (Elliot, R. B. et al. *Xenotransplantation.* 2007; 14(2): 157-161).

In some cases, it is desirable to elicit fibrosis, for example, when the cells are implanted as a bulking material, as described in U.S. Pat. No. 6,060,053 and as subsequently approved by the Food and Drug Administration for treatment of vesicoureteral reflux.

The diminished efficacy of the implanted cells over time is the result of fibroblastic overgrowth of the alginate capsules. The alginate gel matrix provokes an inflammatory response upon implantation, resulting in the encapsulation of the alginate matrix with fibrous tissue. The fibrous tissue on the alginate capsule surface reduces the diffusion of nutrients and oxygen to the encapsulated cells, causing them to die. No better results have been obtained with the other materials.

Therefore, it is an object of the invention to provide polymers suitable for coating products, devices, and surfaces where the polymers have greater long term biocompatibility following implantation of the products, devices, and surfaces.

It is also an object of the invention to provide polymers suitable for coating products, devices, and surfaces where the polymers have less foreign body response following implantation of the products, devices, and surfaces.

It is also an object of the invention to provide polymers suitable for encapsulation and implantation of cells where the polymers have greater long term biocompatibility following implantation.

It is also an object of the invention to provide polymers suitable for encapsulation and implantation of cells where the polymers have less foreign body response following implantation.

It is also an object of the invention to provide chemically modified, ionically crosslinkable alginates with improved biocompatibility and tailored physiochemical properties, including gel stability, pore size, and hydrophobicity/hydrophilicity.

It is also an object of the invention to provide chemically modified, ionically crosslinkable alginates with less foreign body response.

It is also an object of the invention to provide methods for the coating of products, devices, and surfaces using modified alginate polymers.

It is also an object of the invention to provide methods for the encapsulation of cells using modified alginate polymers.

It is also an object of the invention to provide methods for treating a disorder or disease in a human or animal patient by transplanting or implanting products, devices, and surfaces coated with a modified alginate polymer.

It is also an object of the invention to provide methods for treating a disorder or disease in a human or animal patient by transplanting exogenous biological material encapsulated in a modified alginate polymer.

It is also an object of the invention to provide high-throughput methods for the characterization of modified alginate polymers.

SUMMARY OF THE INVENTION

Alginates, chemically modified to tailor their biocompatibility and physical properties, have been developed. The modified alginates described herein provide enhanced properties relative to unmodified alginates. Moreover, based on the discovery that the starting materials, as well as chemically modified and reacted materials, must be exhaustively purified to remove contaminants prior to implantation to prevent encapsulation, these materials are less likely to elicit fibrous capsule formation following implantation.

In some embodiments, modified alginates are alginate polymers that contain one or more covalently modified monomers defined by Formula I Formula I

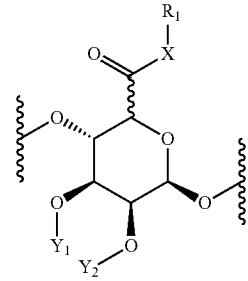

wherein,

X is oxygen, sulfur, or $NR_4$;

$R_1$ is hydrogen, or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_1$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group;

$Y_1$ and $Y_2$ independently are hydrogen or —$PO(OR_5)_2$; or $Y_2$ is absent, and $Y_1$, together with the two oxygen atoms to which $Y_1$ and $Y_2$ are attached form a cyclic structure as shown in Formula II Formula II

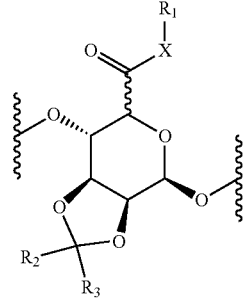

wherein; and $R_2$ and $R_3$ are, independently, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_2$ and $R_3$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and $R_4$ and $R_5$ are, independently, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_4$ and $R_5$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, modified alginates are alginate polymers that contain one or more covalently modified monomers defined by Formula I

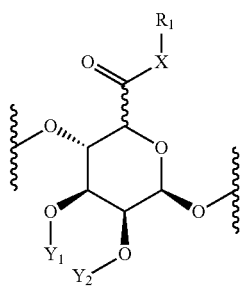

Formula I wherein,

X is oxygen, sulfur, or $NR_4$;

$R_1$ is, independently in the one or more modified monomers

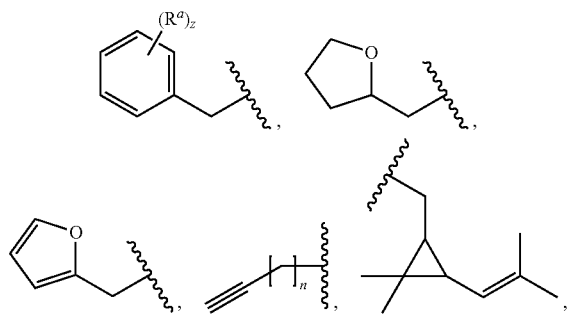

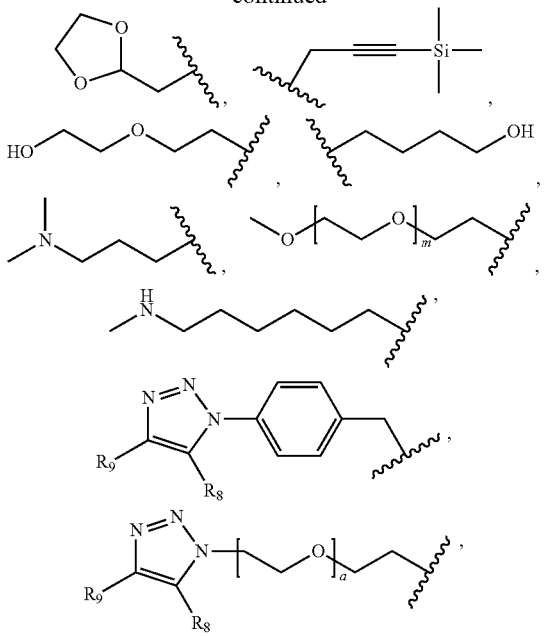

or —$R_6$—$R^b$, wherein a is an integer from 1 to 30, z is an integer from 0 to 5, n is an integer from 1 to 12, m is an integer from 3 to 16, and $R^a$ and $R^b$ are independently selected from alkoxy, amino, alkylamino, dialkylamino, hydroxy, alkenyl, alkynyl, substituted alkyl, substituted alkenyl, substituted alkynyl, phenyl, substituted phenyl, aryl, substituted aryl, heteroaryl, substituted heteroaryl, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or together with the carbon atom to which they are attached, form a 3- to 8-membered unsubstituted or substituted carbocyclic or heterocyclic ring;

wherein $Y_1$ and $Y_2$ independently are hydrogen or —$PO(OR_5)_2$; or $Y_2$ is absent, and $Y_1$, together with the two oxygen atoms to which $Y_1$ and $Y_2$ are attached form a cyclic structure as shown in Formula II

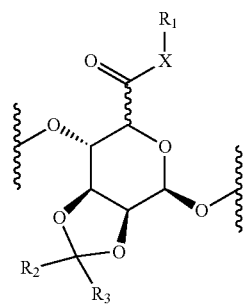

Formula II wherein $R_2$ and $R_3$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_2$ and $R_3$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and $R_4$, $R_5$, $R_6$, $R_8$, and $R_9$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, modified alginates are alginate polymers that contain one or more covalently modified monomers defined by Formula I

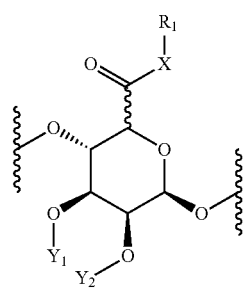

Formula I wherein,

X is oxygen, sulfur, or $NR_4$;

$R_1$ is, independently in the one or more modified monomers,

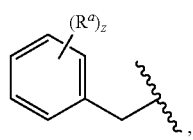

Formula X

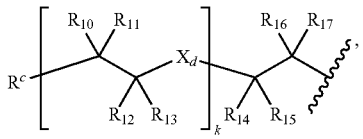

Formula XII

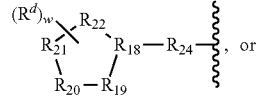

Formula XIV

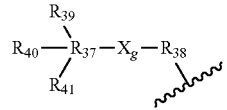

Formula XV wherein k is an integer from 1 to 10; wherein z is an integer from 0 to 5; wherein w is an integer from 0 to 4; wherein $X_d$ is absent, O or S;

wherein $R_{10}$, $R_{11}$, $R_{12}$, $R_{13}$, $R_{14}$, $R_{15}$, $R_{16}$, $R_{17}$, $R_{39}$, $R_{40}$, and $R_{41}$ are independently hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group;

wherein $R_{37}$ is C or Si;

wherein $X_g$ and $R_{38}$ are independently alkyl, substituted alkyl, alkenyl, substituted alkenyl, alkylene, substituted alkylene, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; and wherein $R^a$ and $R^c$ are independently alkoxy, amino, alkylamino, dialkylamino, hydroxy, alkenyl, alkynyl, substituted alkyl, substituted alkenyl, substituted alkynyl, phenyl, substituted phenyl, aryl, substituted aryl, heteroaryl, substituted heteroaryl, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or together with the carbon atom to which they are attached, form a 3- to 8-membered unsubstituted or substituted carbocyclic, heterocyclic ring or

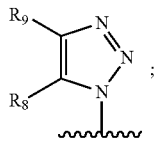

Formula XIII wherein $R_8$, $R_9$, or both are, independently, hydrogen, alkyl, substituted alkyl, alkoxy, amino, alkylamino, dialkylamino, hydroxy, alkenyl, alkynyl, substituted alkyl, substituted alkenyl, substituted alkynyl, carbonyl, substituted carbonyl, carbinol,

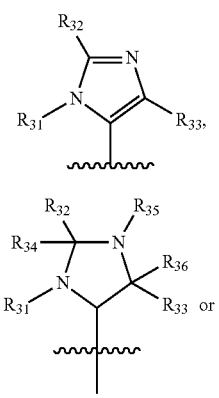

Formula VII

Formula VIII

Formula IX wherein $R_{31}$, $R_{32}$, $R_{33}$, $R_{34}$, $R_{35}$, and $R_{36}$ are, independently, hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group;

wherein y is an integer from 0 to 11; wherein $R^d$ and $R^e$ are each independently alkoxy, amino, alkylamino, dialkylamino, hydroxy, alkenyl, alkynyl, substituted alkyl, substituted alkenyl, substituted alkynyl, phenyl, substituted phenyl, aryl, substituted aryl, heteroaryl, substituted heteroaryl, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, and polypeptide group; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, $R_{22}$, and $R_{23}$ are independently C, O, N, or S, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ is independently $-(CR_{25}R_{25})_p-$ or $-(CR_{25}R_{25})_p-X_b-(CR_{25}R_{25})_q-$, wherein p and q are independently integers from 0 to 5, wherein $X_b$ is absent, $-O-$, $-S-$, $-SO_2-$, or $NR_4$, wherein each $R_{25}$ is independently absent, hydrogen, $=O$, $=S$, $-OH$, $-SH$, $-NR_4$, wherein $R_4$ is alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group;

wherein $R_8$, and $R_9$ are not both hydrogen; wherein at least one $R^b$ or $R^c$ is defined by Formula XIII; wherein $Y_1$ and $Y_2$ independently are hydrogen or $-PO(OR_5)_2$; or $Y_2$ is absent, and $Y_1$, together with the two oxygen atoms to which $Y_1$ and $Y_2$ are attached form a cyclic structure as shown in Formula II

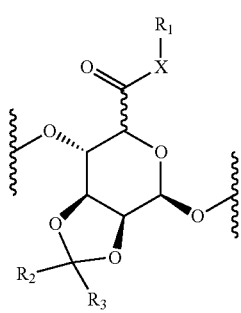

Formula II wherein $R_2$ and $R_3$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_2$ and $R_3$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and $R_4$ and $R_5$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, y in Formula IX is an integer from 0-3; $R^e$ is independently amino, hydroxyl, thiol, oxo, or substituted or unsubstituted $C_1$-$C_6$ alkyl, $C_1$-$C_6$ alkoxy, $C_1$-$C_6$ alkylamino, or $C_1$-$C_6$ alkylthio;

where $R_{18}$, $R_{19}$, $R_{20}$, $R_{21}$, $R_{22}$, and $R_{23}$ are independently C, O, N, or S, where the bonds between adjacent $R_{18}$ to $R_{23}$ are double or single according to valency, and where $R_{18}$ to $R_{23}$ are bound to none, one, or two hydrogens according to valency; and where $R_{24}$ is independently —$(CR_{25}R_{25})_p$— or —$(CR_{25}R_{25})_p$—$X_b$—$(CR_{25}R_{25})_q$—, where p and q are independently integers from 0 to 3, where $X_b$ is absent, —O—, —S—, —$SO_2$—, or $NR_4$, where each $R_{25}$ is independently absent, hydrogen, =O, =S, —OH, —SH, —$NR_4$, where $R_4$ is substituted or unsubstituted $C_1$-$C_6$ alkyl, $C_1$-$C_6$ alkoxy, $C_1$-$C_6$ alkylamino, or $C_1$-$C_6$ alkylthio.

In some embodiments, y in Formula IX is 2, $R_{18}$ is N, $R_{19}$, $R_{20}$, $R_{21}$, $R_{22}$, or $R_{23}$ is S, both $R^e$ are oxo and are bonded to the S, and all of the bonds between adjacent $R_{18}$ to $R_{23}$ are single.

In some embodiments, y in Formula IX is 2, both $R^e$ are oxo and are bonded to $R_{21}$, $R_{18}$ is N, $R_{21}$ is S, and all of the bonds between adjacent $R_{18}$ to $R_{23}$ are single.

In some embodiments, y in Formula IX is 2, both $R^e$ are oxo and are bonded to $R_{21}$, $R_{18}$ is N, $R_{21}$ is S, and all of the bonds between adjacent $R_{18}$ to $R_{23}$ are single, $X_b$ is absent, q is 0, p is 1, and each $R_{25}$ is hydrogen.

In some embodiments, y in Formula IX is 1, $R^e$ is amino, and three of the bonds between adjacent $R_{18}$ to $R_{23}$ are double and three of the bonds between adjacent $R_{18}$ to $R_{23}$ are single.

In some embodiments, y in Formula IX is 1, $R^e$ is amino and is bonded to $R_{21}$, and three of the bonds between adjacent $R_{18}$ to $R_{23}$ are double and three of the bonds between adjacent $R_{18}$ to $R_{23}$ are single.

In some embodiments, y in Formula IX is 1, $R^e$ is amino and is bonded to $R_{21}$, and three of the bonds between adjacent $R_{18}$ to $R_{23}$ are double and three of the bonds between adjacent $R_{18}$ to $R_{23}$ are single, $X_b$ is absent, p is 0 and q is 0.

In some embodiments, y in Formula IX is 0, $R_{19}$, $R_{20}$, $R_{21}$, $R_{22}$, or $R_{23}$ is O, and all of the bonds between adjacent $R_{18}$ to $R_{23}$ are single.

In some embodiments, y in Formula IX is 0, $R_{19}$ is O, and all of the bonds between adjacent $R_{18}$ to $R_{23}$ are single.

In some embodiments, y in Formula IX is 0, $R_{19}$ is O, all of the bonds between adjacent $R_{18}$ to $R_{23}$ are single, $X_b$ is oxygen, p is 1, q is 0 and each $R_{25}$ is hydrogen.

In some embodiments, $R_{19}$ and $R_{23}$ of Formula IX are O and all of the bonds between adjacent $R_{18}$ to $R_{23}$ are single.

In some embodiments, $R_{19}$ and $R_{23}$ of Formula IX are O, the bonds between $R_{18}$ and $R_{19}$, and between $R_{21}$ and $R_{22}$ are double bonds, and the rest of the bonds in the ring are single bonds.

In some embodiments, y in Formula IX is 1, $R^e$ is alkoxy and is bonded to $R_{19}$, $R_{20}$, $R_{21}$, $R_{21}$, $R_{22}$, or $R_{23}$, three of the bonds between adjacent $R_{18}$ to $R_{23}$ are double and three of the bonds between adjacent $R_{18}$ to $R_{23}$ are single.

In some embodiments, y in Formula IX is 1, $R^e$ is alkoxy and is bonded to $R_{19}$, three of the bonds between adjacent $R_{18}$ to $R_{23}$ are double and three of the bonds between adjacent $R_{18}$ to $R_{23}$ are single.

In some embodiments, y in Formula IX is 1, $R^e$ is methoxy, and is bonded to $R_{19}$, $R_{18}$ to $R_{23}$ are carbon atoms, three of the bonds between adjacent $R_{18}$ to $R_{23}$ are double and three of the bonds between adjacent $R_{18}$ to $R_{23}$ are single, $X_b$ is absent, p is 0 and q is 0.

In some embodiments, y in Formula IX is 1, $R^e$ is hydroxyl.

In some embodiments, y in Formula IX is 1 and $R^e$ is hydroxyl bonded at the position para- to the methylene group.

In some embodiments, y in Formula IX is 1, $R^e$ is Formula XIII shown below:

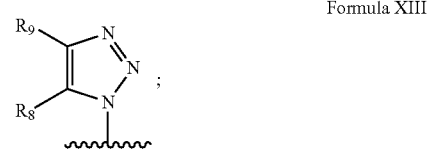

Formula XIII wherein $R_8$ is a substituted alkyl and $R_9$ is a dialkylamino, or $R_8$ is a dialkylamino and $R_9$ is a substituted alkyl, wherein the substituted alkyl is hydroxymethyl and the dialkylamino is N,N-diethylamino.

In some embodiments, y in Formula IX is 1, $R^e$ is Formula XIII, wherein $R_8$ is hydrogen and $R_9$ is Formula IX shown below:

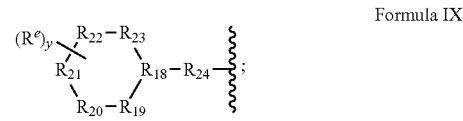

Formula IX or $R_8$ is Formula IX and $R_9$ is hydrogen. In some embodiments, y in Formula IX is 0, $R_{19}$, $R_{20}$, $R_{21}$, $R_{22}$, or $R_{23}$ is O, and all of the bonds between adjacent $R_{18}$ to $R_{23}$ are single. In some embodiments, y in Formula IX is 0, $R_{19}$ is O, and all of the bonds between adjacent $R_{18}$ to $R_{23}$ are single. In some embodiments, y in Formula IX is 0, $R_{19}$ is O, all of the bonds between adjacent $R_{18}$ to $R_{23}$ are single, $X_b$ is oxygen, p is 1, q is 0 and each $R_{25}$ is hydrogen.

In some embodiments, y in Formula IX is 1, $R^e$ is Formula XIII, wherein $R_8$ is hydrogen and $R_9$ is Formula VII or Formula VIII shown below:

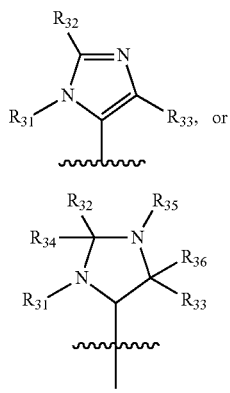

Formula VII

Formula VIII wherein $R_{31}$, $R_{32}$, $R_{33}$, $R_{34}$, $R_{35}$, and $R_{36}$ are, independently, hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments $R_{31}$ of Formula VII is alkyl. In some embodiments, $R_{31}$ is methyl.

In some embodiments $R_{31}$ of Formula VII is methyl, $R_{32}$ and $R_{33}$ are hydrogen.

In some embodiments, y in Formula IX is 1 and $R^e$ is hydroxyl bonded at the position para- to the methylene group.

In some embodiments of Formula XII, k is 1 and $R^c$ is hydroxyl.

In some embodiments of Formula XII, k is 1, $R^c$ is hydroxyl, and $X_d$ is absent.

In some embodiments of Formula XII, k is 1, $R^c$ is hydroxyl, $X_d$ is absent, and $R_{10}$—$R_{17}$ are hydrogen.

In some embodiments of Formula XII, $R^c$ is alkoxy.

In some embodiments of Formula XII, $R^c$ is methoxy and $X_d$ is O.

In some embodiments of Formula XII, $R^c$ is methoxy, $X_d$ is O, and $R_{10}$—$R_{17}$ are hydrogen.

In some embodiments of Formula XII, k is 2 and $R^c$ is alkylamino.

In some embodiments of Formula XII, k is 2, $R^c$ is methylamino, and $X_d$ is absent.

In some embodiments of Formula XII, k is 2, $R^c$ is methylamino, $X_d$ is absent, and $R_{10}$—$R_{17}$ are hydrogen.

In some embodiments of Formula XII, k is 3, $X_d$ is O and $R^c$ is Formula XIII shown below:

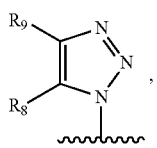

Formula XIII wherein $R_8$ and $R_9$ are alkyl.

In some embodiments of Formula XII, k is 3, $X_d$ is O, and $R^c$ is Formula XIII, wherein $R_8$ and $R_9$ are methyl.

In some embodiments of Formula XII, k is 3, $X_d$ is O and $R^c$ is Formula XIII, wherein $R_8$ is hydrogen, and $R_9$ is carbonyl, or $R_8$ is carbonyl, and $R_9$ is hydrogen.

In some embodiments of Formula XII, k is 3, $X_d$ is O and $R^c$ is Formula XIII, wherein $R_8$ is hydrogen, and $R_9$ is acetyl, or $R_8$ is acetyl, and $R_9$ is hydrogen.

In some embodiments of Formula XII, k is 3 and $R^c$ is Formula XIII, $R_8$ is hydrogen, and $R_9$ is Formula IX shown below:

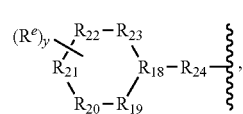

Formula IX or $R_8$ is hydrogen and $R_9$ is Formula IX.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 2, $R_{18}$ is N, $R_{19}$, $R_{20}$, $R_{21}$, $R_{22}$, or $R_{23}$ is S, both $R^e$ are oxo and are bonded to the S, and all of the bonds between adjacent $R_{18}$ to $R_{23}$ are single.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 2, both $R^e$ are oxo and are bonded to $R_{21}$, $R_{18}$ is N, $R_{21}$ is S, and all of the bonds between adjacent $R_{18}$ to $R_{23}$ are single.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 2, both $R^e$ are oxo and are bonded to $R_{21}$, $R_{18}$ is N, $R_{21}$ is S, and all of the bonds between adjacent $R_{18}$ to $R_{23}$ are single, $X_b$ is absent, q is 0, p is 1, and each $R_{25}$ is hydrogen.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 1, $R^e$ is amino, and three of the bonds between adjacent $R_{18}$ to $R_{23}$ are double and three of the bonds between adjacent $R_{18}$ to $R_{23}$ are single.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 1, $R^e$ is amino and is bonded to $R_{21}$, and three of the bonds between adjacent $R_{18}$ to $R_{23}$ are double and three of the bonds between adjacent $R_{18}$ to $R_{23}$ are single.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 1, $R^e$ is amino and is bonded to $R_{21}$, and three of the bonds between adjacent $R_{18}$ to $R_{23}$ are double and three of the bonds between adjacent $R_{18}$ to $R_{23}$ are single, $X_b$ is absent, p is 0 and q is 0.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 0, $R_{19}$, $R_{20}$, $R_{21}$, $R_{22}$, or $R_{23}$ is O, and all of the bonds between adjacent $R_{18}$ to $R_{23}$ are single.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 0, $R_{19}$ is O, and all of the bonds between adjacent $R_{18}$ to $R_{23}$ are single.

In some embodiments of Formula XII, k is 3 and R is Formula XIII, wherein $R_8$ is hydrogen, and $R_9$ is Formula IX, or $R_8$ is hydrogen and $R_9$ is Formula IX, wherein y in Formula IX is 0, $R_{19}$ is O, all of the bonds between adjacent $R_{18}$ to $R_{23}$ are single, $X_b$ is oxygen, p is 1, q is 0 and each $R_{25}$ is hydrogen.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 1, $R^e$ is alkoxy and is bonded to $R_{19}$, $R_{20}$, $R_{21}$, $R_{21}$, $R_{22}$, or $R_{23}$, three of the bonds between adjacent $R_{18}$ to $R_{23}$ are double and three of the bonds between adjacent $R_{18}$ to $R_{23}$ are single.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 1, $R^e$ is alkoxy and is bonded to $R_{19}$, three of the bonds between adjacent $R_{18}$ to $R_{23}$ are double and three of the bonds between adjacent $R_{18}$ to $R_{23}$ are single.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 1, $R^e$ is alkoxy such as methoxy, and is bonded to $R_{19}$, $R_{18}$ to $R_{23}$ are carbon atoms, three of the bonds between adjacent $R_{18}$ to $R_{23}$ are double and three of the bonds between adjacent $R_{18}$ to $R_{23}$ are single, $X_b$ is absent, p is 0 and q is 0.

In some embodiments, y in Formula XIV is 0, $R_{19}$, $R_{20}$, $R_{21}$, $R_{21}$, or $R_{22}$ is O, and, as valency permits, two of the bonds between adjacent $R_{18}$ to $R_{22}$ are double bonds, and three of the bonds between adjacent $R_{18}$ to $R_{22}$ are single bonds.

In some embodiments, y in Formula XIV is 0, $R_{19}$ is O, $R_{18}$, $R_{20}$, $R_{21}$ and $R_{22}$ are C, the bonds between $R_{18}$ and $R_{22}$, and between $R_{20}$ and $R_{21}$, are double bonds, and the rest of the bonds in the ring are single bonds.

In some embodiments, y in Formula XIV is 0, $R_{19}$ is O, $R_{18}$, $R_{20}$, $R_{21}$ and $R_{22}$ are C, the bonds between $R_{18}$ and $R_{22}$, and between $R_{20}$ and $R_{21}$, are double bonds, the rest of the bonds in the ring are single bonds, $X_b$ is absent, p is 1, q is 0, and each $R_{25}$ is hydrogen.

In some embodiments, y in Formula XIV is 0, $R_{19}$, $R_{20}$, $R_{21}$, or $R_{22}$ is O, and, the bonds between adjacent $R_{18}$ to $R_{22}$ are single bonds.

In some embodiments, y in Formula XIV is 0, $R_{19}$ is O, $R_{18}$, $R_{20}$, $R_{21}$ and $R_{22}$ are C, and the bonds between adjacent $R_{18}$ to $R_{22}$ are single bonds.

In some embodiments, y in Formula XIV is 0, $R_{19}$ is O, $R_{18}$, $R_{20}$, $R_{21}$ and $R_{22}$ are C, the bonds between adjacent $R_{18}$ to $R_{22}$ are single bonds, $X_b$ is absent, p is 1, q is 0, and each $R_{25}$ is hydrogen.

In some embodiments, y in Formula XIV is 0, $R_{19}$ and $R_{22}$ are O, and the bonds between adjacent $R_{11}$ to $R_{22}$ are single bonds.

In some embodiments, y in Formula XIV is 0, $R_{19}$ and $R_{22}$ are O, $R_{18}$, $R_{21}$ and $R_{22}$ are C, the bonds between adjacent $R_{18}$ to $R_{22}$ are single bonds.

In some embodiments, y in Formula XIV is 0, $R_{19}$ and $R_{22}$ are O, $R_{18}$, $R_{21}$ and $R_{22}$ are C, the bonds between adjacent $R_{18}$ to $R_{22}$ are single bonds, $X_b$ is absent, p is 1, q is 0, and each $R_{25}$ is hydrogen.

In some embodiments $R_{37}$ of Formula XV is Si, and $X_g$ is alkynyl.

In some embodiments $R_{37}$ of Formula XV is Si, $X_g$ is ethynyl, and $R_{38}$ is alkylene.

In some embodiments $R_{37}$ of Formula XV is Si, $X_g$ is ethynyl, $R_{38}$ is methylene, and $R_{39}$, $R_{40}$, and $R_{41}$ are alkyl.

In some embodiments $R_{37}$ of Formula XV is Si, $X_g$ is ethynyl, $R_{38}$ is methylene, and $R_{39}$, $R_{40}$, and $R_{41}$ are methyl.

Modified alginates can be either singularly modified alginate polymers or multiply modified alginate polymers. Singularly modified alginate polymers are alginate polymers that contain one or more covalently modified monomers, wherein substantially all of the covalently modified monomers possess the same covalent modification (i.e. the polymer contains one 'type' or species of covalently modified monomer). Multiply modified alginate polymers are alginate polymers that contain covalently modified monomers, wherein substantially all of the covalently modified monomers do not possess the same covalent modification (i.e. the polymer contains two or more 'types' or species of covalently modified monomers).

In some embodiments, the modified alginate polymer is a singularly modified alginate polymer. In some embodiments, the modified alginate polymer is one of the singularly modified alginate polymers shown below:

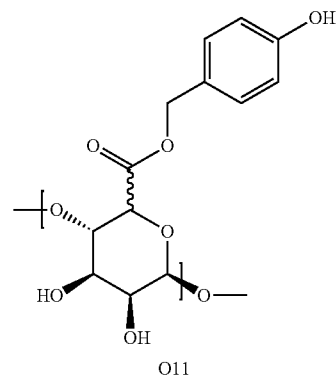

O11

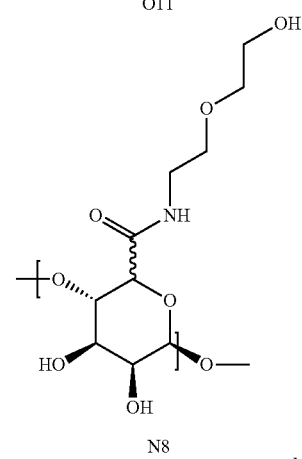

N8

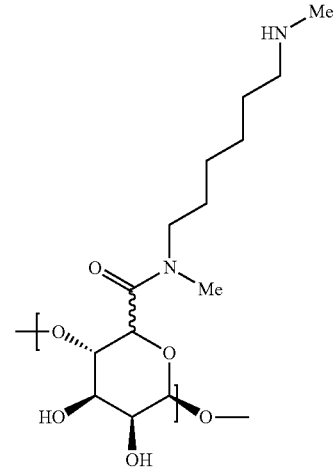

N7

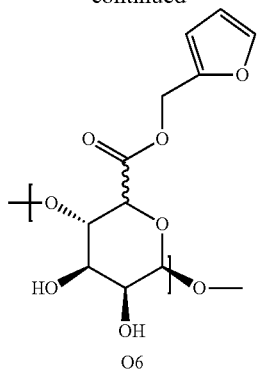
O6
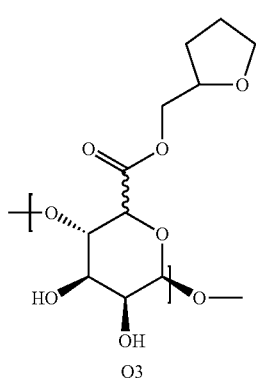
O3
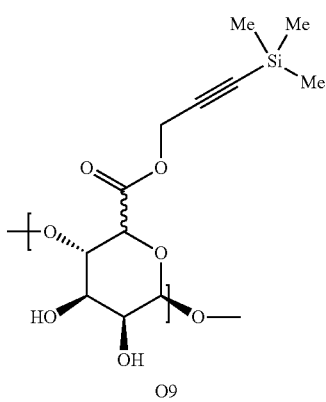
O9
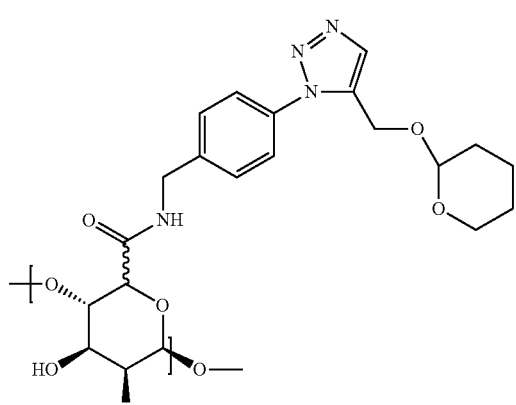
Z2-Y12
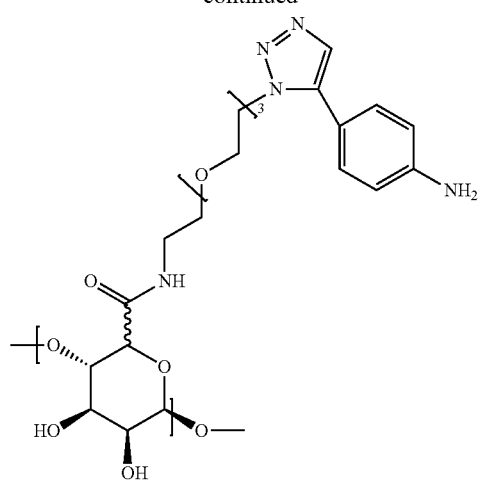
Z1-Y19
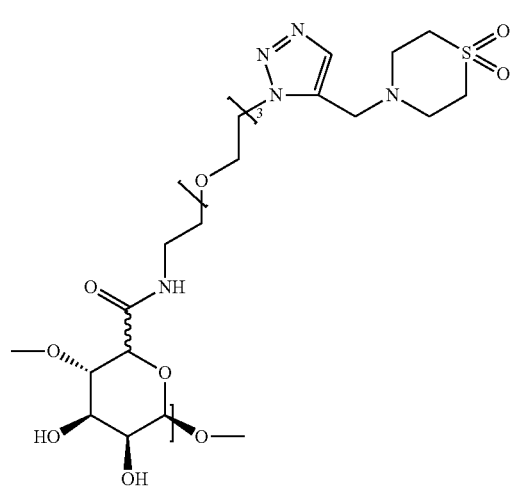
Z1-Y15
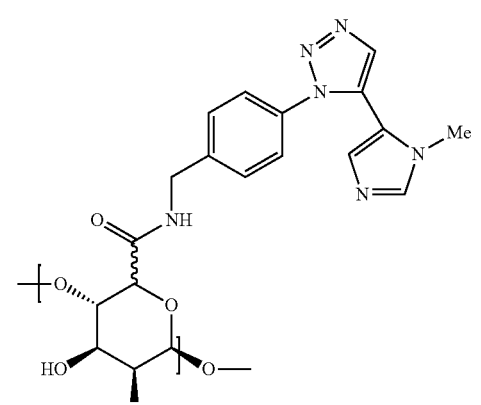
Z2-Y3

-continued

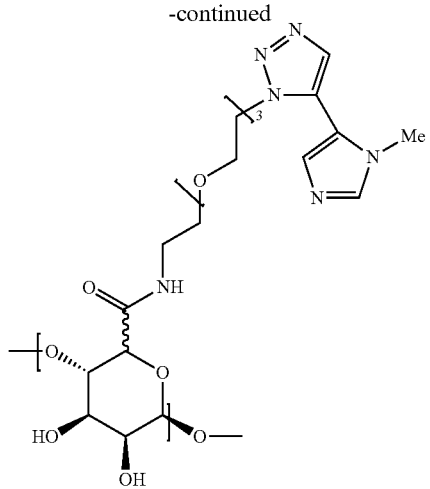
Z1-Y3

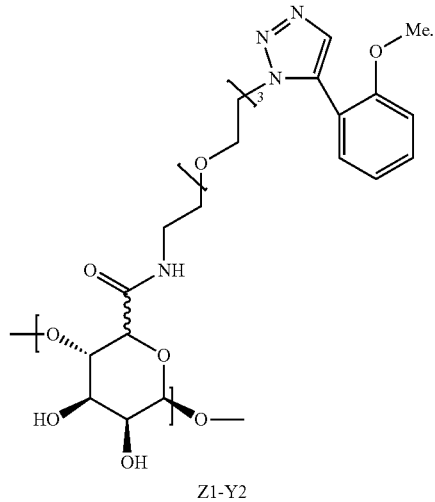
Z1-Y2

In preferred embodiments, the modified alginate polymer is a multiply modified alginate polymer possessing a polysaccharide backbone containing mannuronate monomers, guluronate monomers, a first species or type of covalently modified monomer defined by Formula I, and a second species or type of covalently modified monomer defined by Formula I. In some embodiments, the modified alginate polymer is one of the multiply modified alginate polymers shown below.

-continued

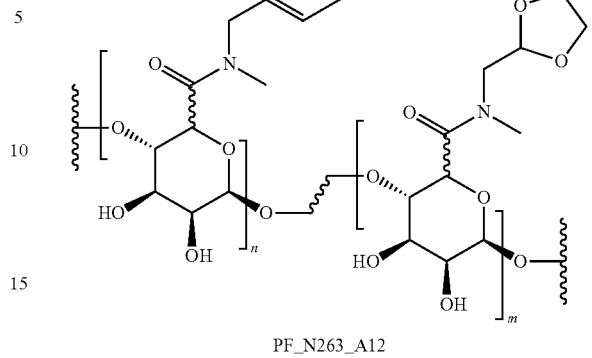
PF_N263_A12

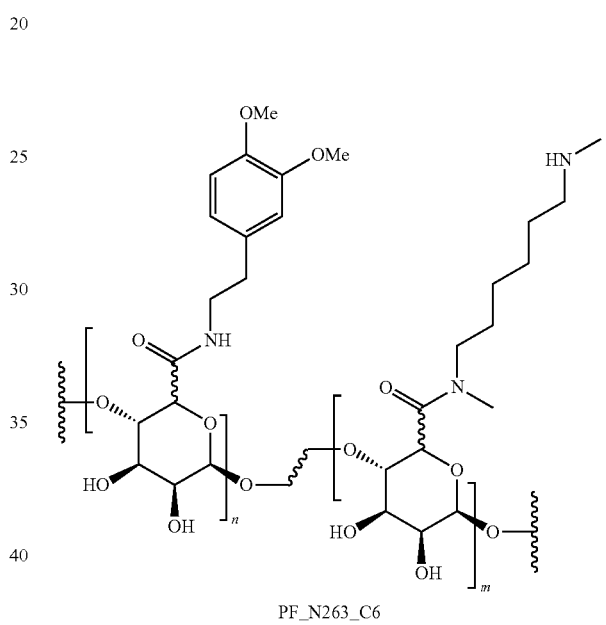
PF_N263_C6

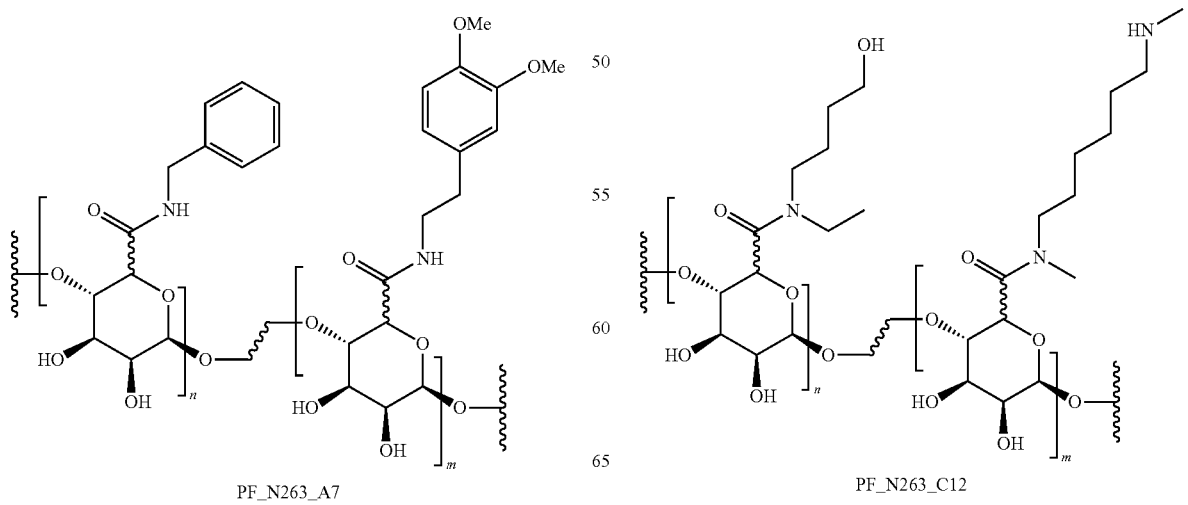

PF_N263_A7

PF_N263_C12

21
-continued
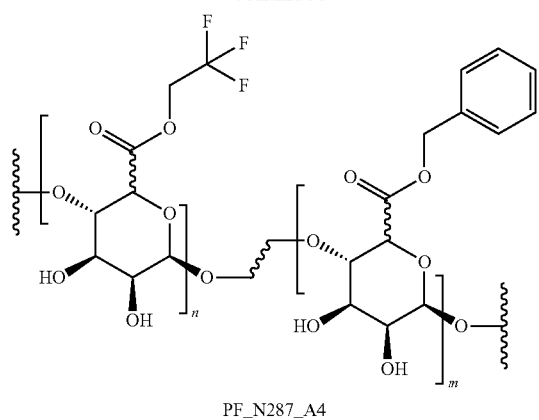
PF_N287_A4
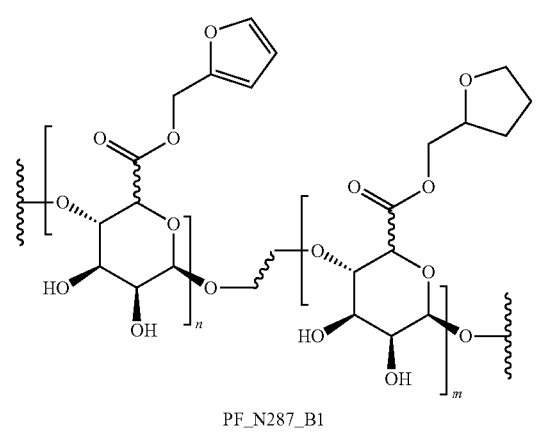
PF_N287_B1
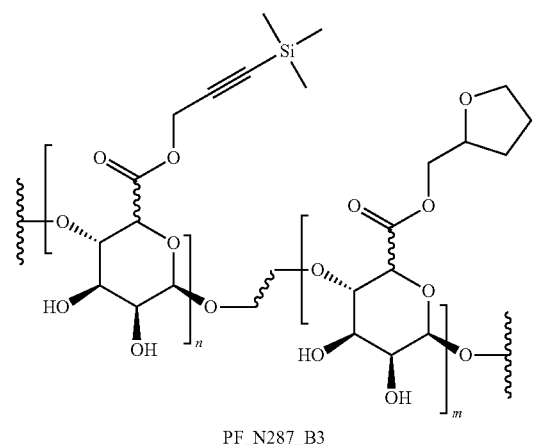
PF_N287_B3
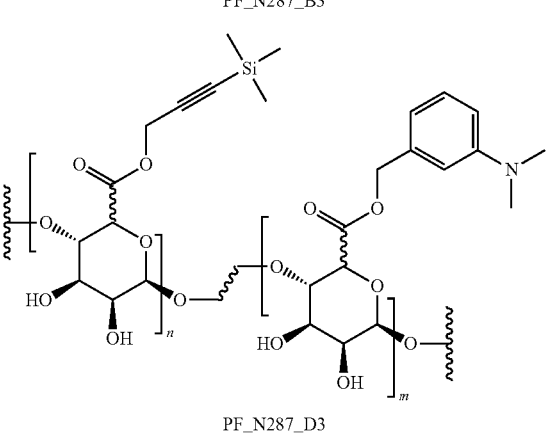
PF_N287_D3
22
-continued
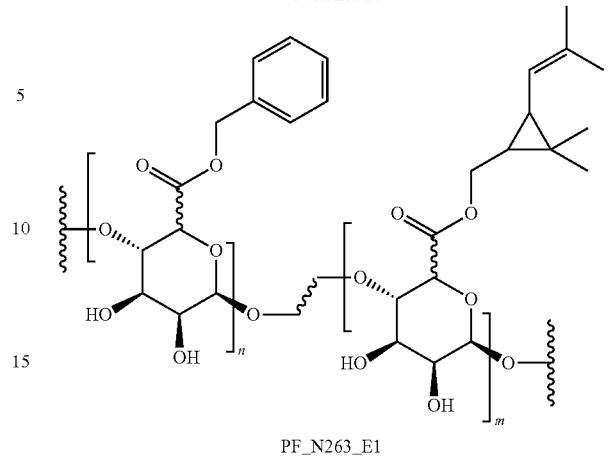
PF_N263_E1
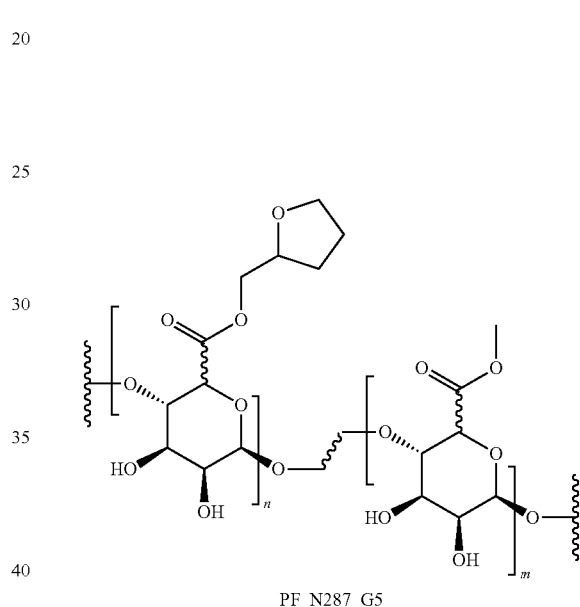
PF_N287_G5
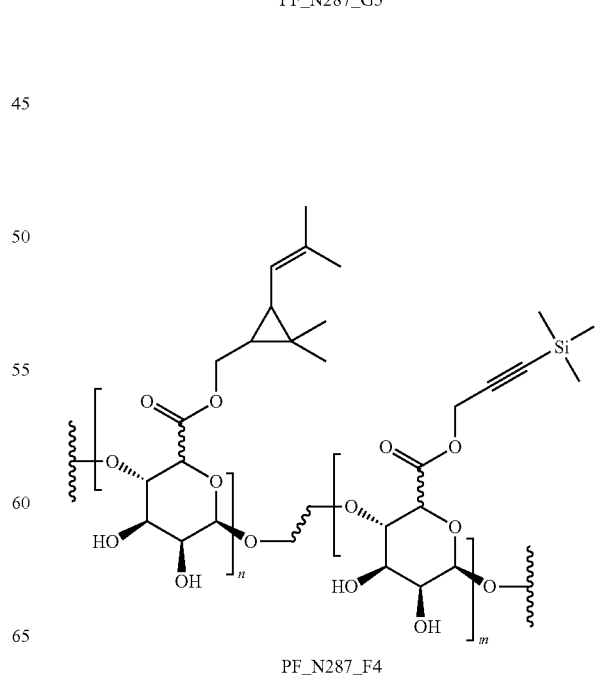
PF_N287_F4

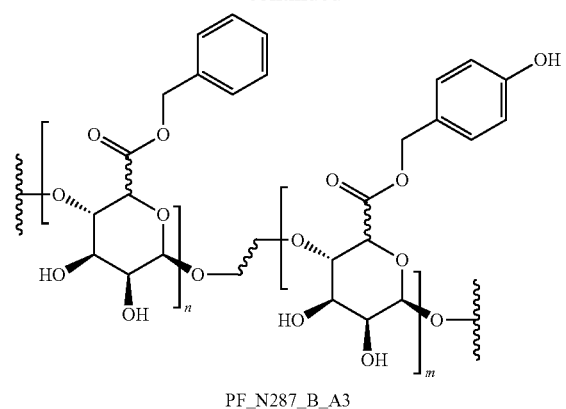
PF_N287_B_A3
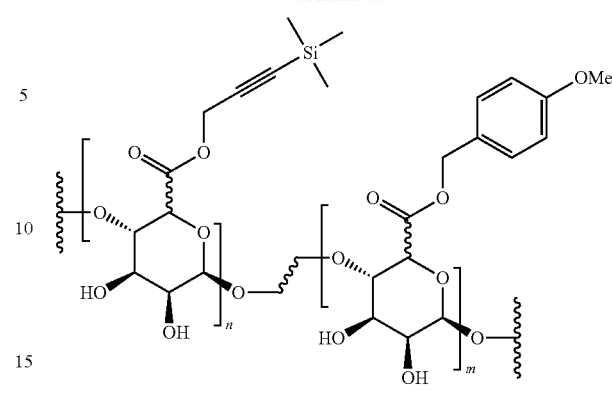
PF_N287_B_B8
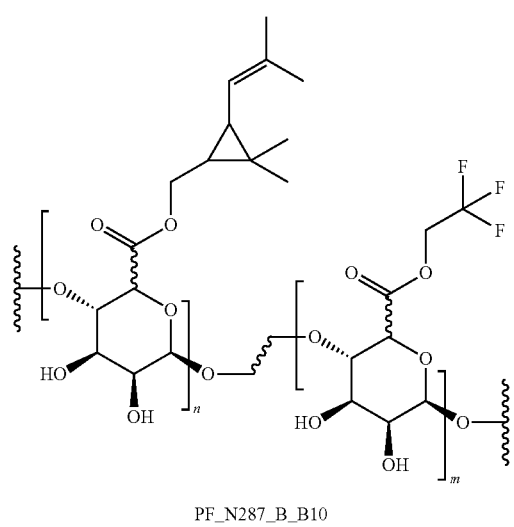
PF_N287_B_B10
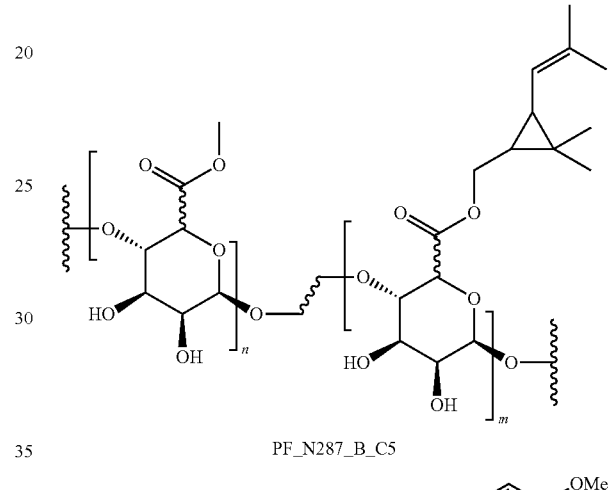
PF_N287_B_C5
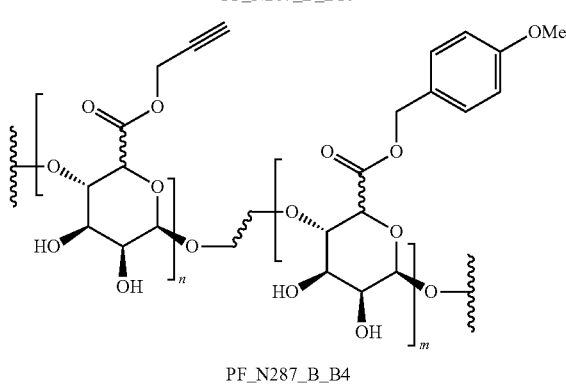
PF_N287_B_B4
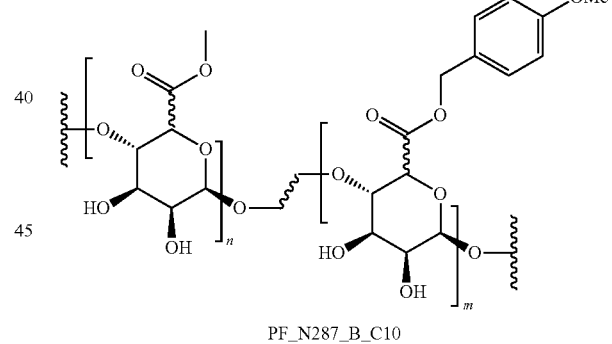
PF_N287_B_C10
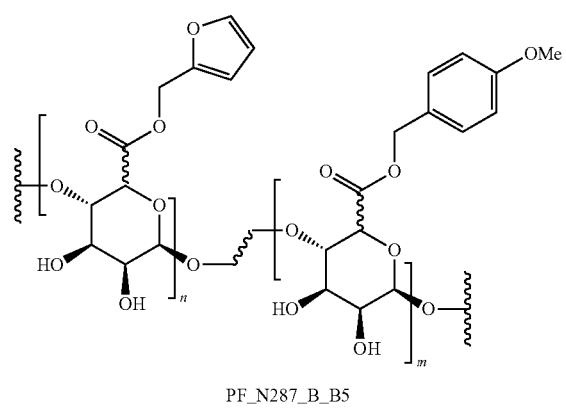
PF_N287_B_B5
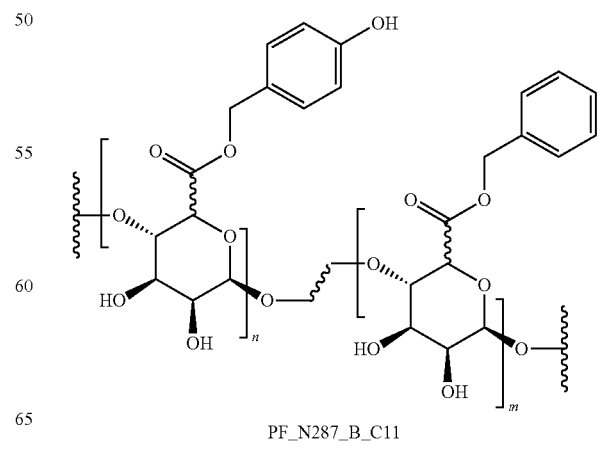
PF_N287_B_C11

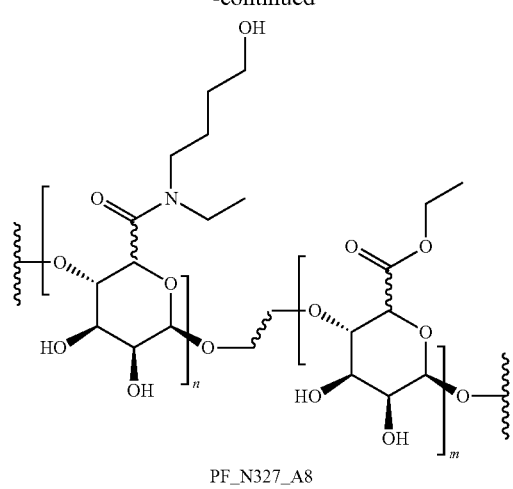
PF_N327_A8
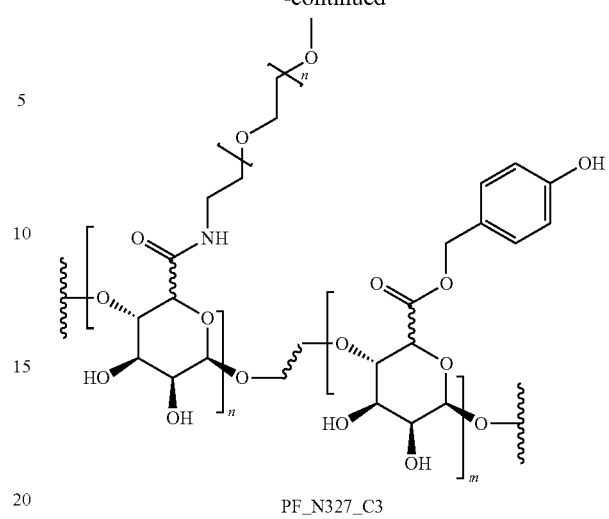
PF_N327_C3
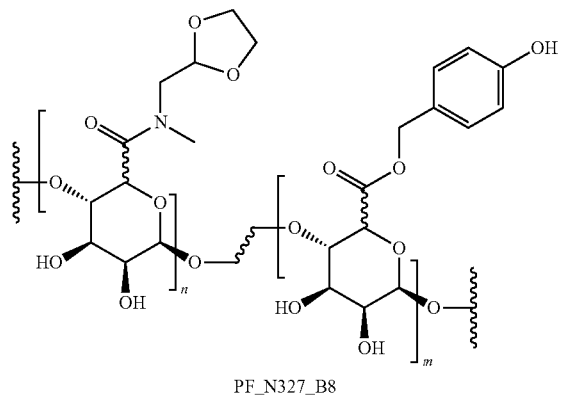
PF_N327_B8
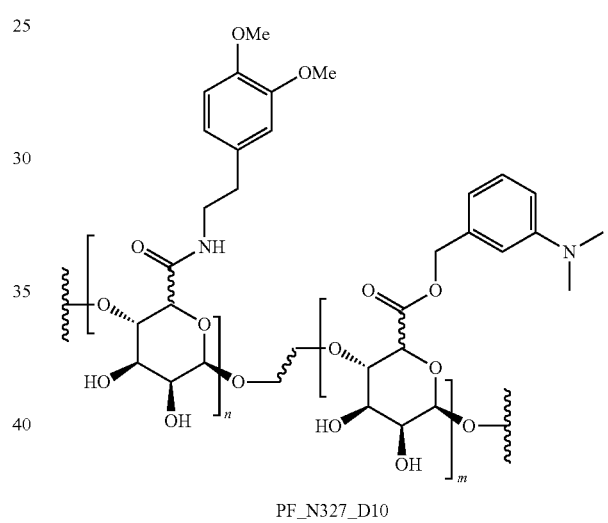
PF_N327_D10
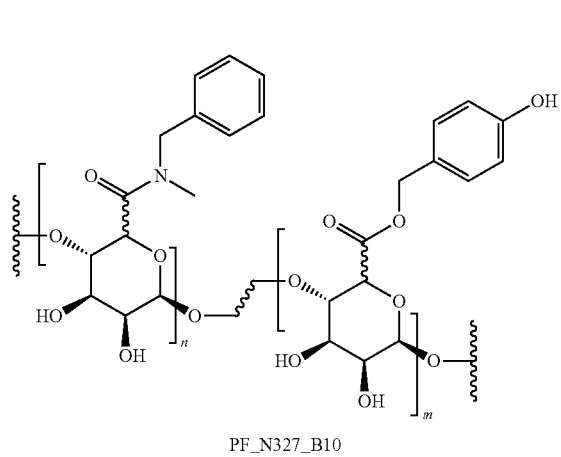
PF_N327_B10
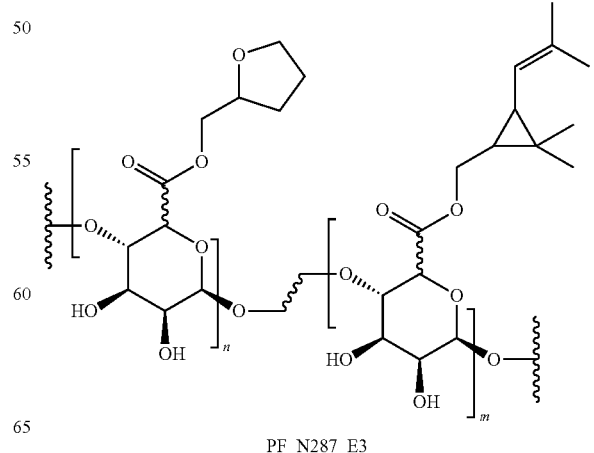
PF_N287_E3

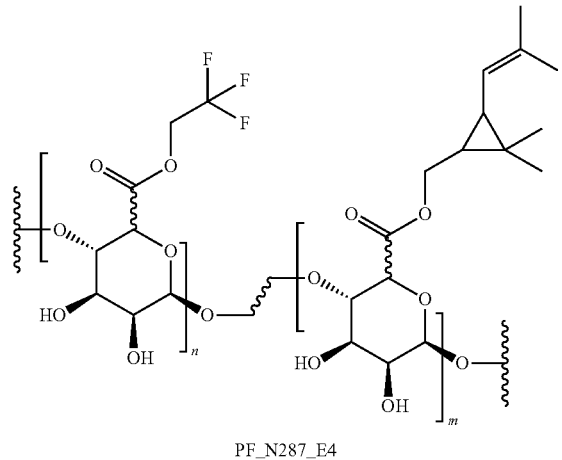
PF_N287_E4
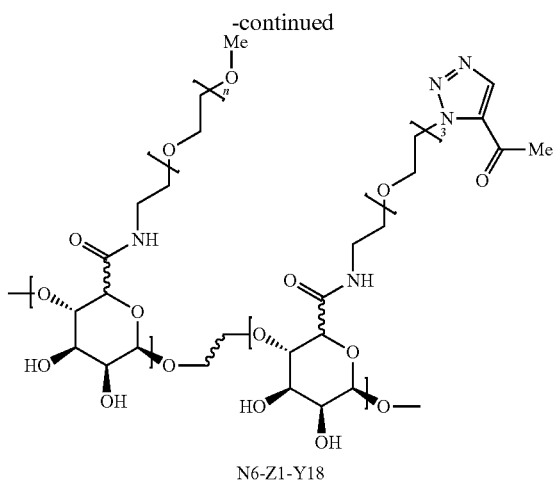
N6-Z1-Y18
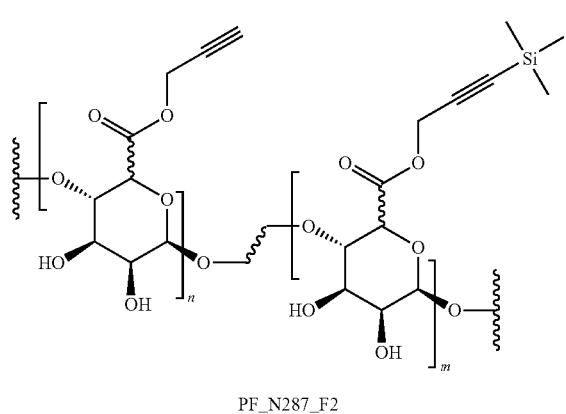
PF_N287_F2
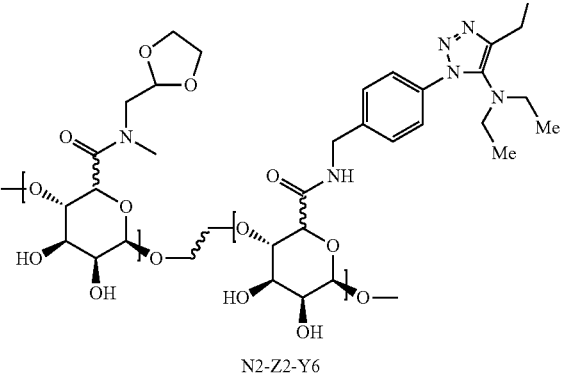
N2-Z2-Y6
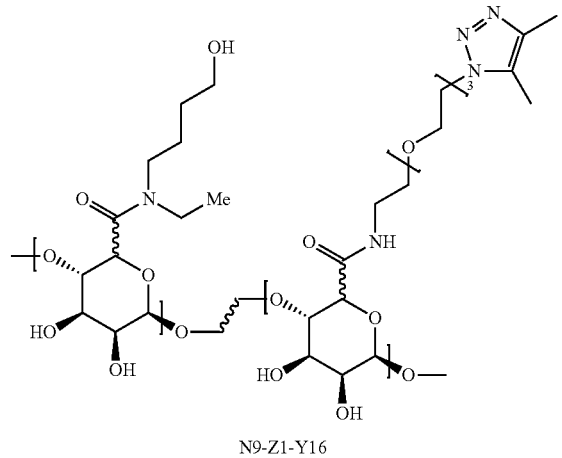
N9-Z1-Y16
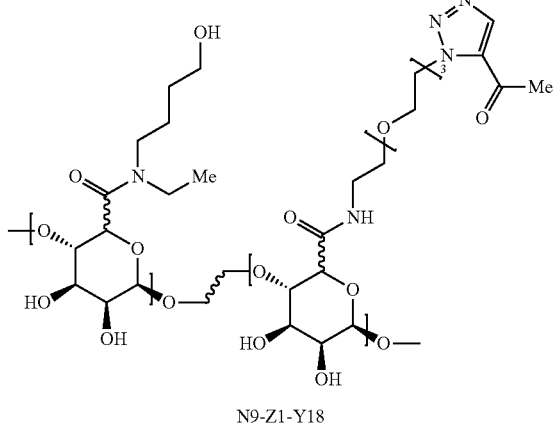
N9-Z1-Y18
In some embodiments, multiply modified alginates are alginate polymers that contain one or more covalently modified monomers having a structure according to Formula III

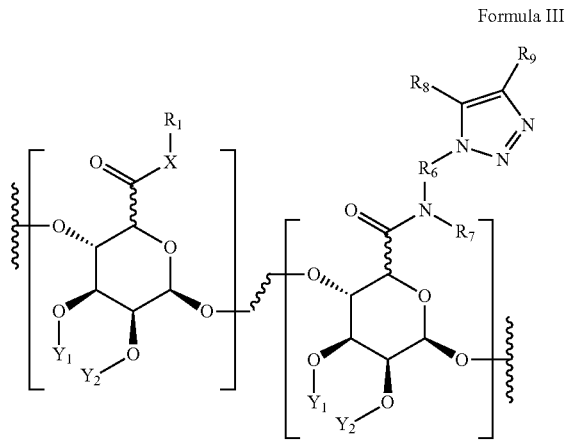

Formula III wherein

X is oxygen, sulfur, or $NR_4$;

$R_1$, $R_6$, $R_7$, $R_8$, and $R_9$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group;

wherein $Y_1$ and $Y_2$ independently are hydrogen or —$PO(OR_5)_2$; or $Y_2$ is absent, and $Y_1$, together with the two oxygen atoms to which $Y_1$ and $Y_2$ are attached form a cyclic structure as shown in Formula IV

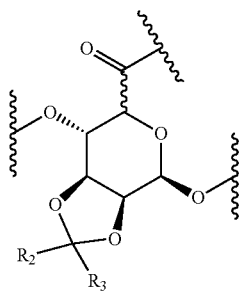

Formula IV wherein $R_2$ and $R_3$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_2$ and $R_3$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and $R_4$ and $R_5$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_4$ and $R_5$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, $R_8$, $R_9$, or both are, independently, hydrogen,

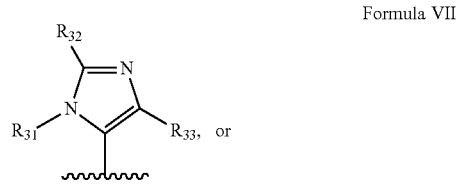

Formula VII

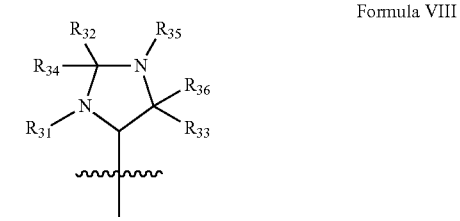

Formula VIII wherein $R_{31}$, $R_{32}$, $R_{33}$, $R_{34}$, $R_{35}$, and $R_{36}$ are, independently, hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, $R_1$ is (A)

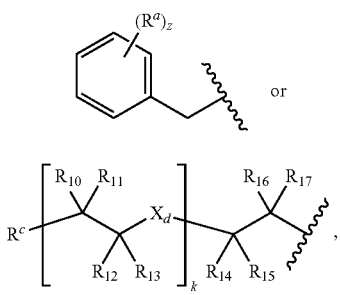

wherein k is independently an integer from 1 to 30; wherein z is an integer from 0 to 4; wherein $X_d$ is O or S; wherein $R_{10}$, $R_{11}$, $R_{12}$, $R_{13}$, $R_{14}$, $R_{15}$, $R_{16}$, and $R_{17}$ are independently hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; and wherein $R^a$ and $R^c$ are independently alkoxy, amino, alkylamino, dialkylamino, hydroxy, alkenyl, alkynyl, substituted alkyl, substituted alkenyl, substituted alkynyl, phenyl, substituted phenyl, aryl, substituted aryl, heteroaryl, substituted heteroaryl, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or together with the carbon atom to which they are attached, form a 3- to 8-membered unsubstituted or substituted carbocyclic, heterocyclic ring or

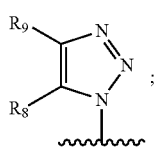

wherein $R_8$, $R_9$, or both are, independently, hydrogen,

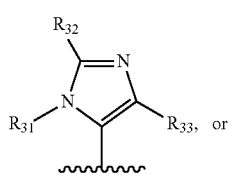

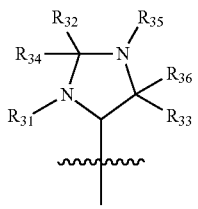

wherein $R_{31}$, $R_{32}$, $R_{33}$, $R_{34}$, $R_{35}$, and $R_{36}$ are, independently, hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, the modified alginates are alginate polymers that contain one or more covalently modified alginates units described by Formula I, Formula II, Formula III, or Formula IV, wherein for each formula $R_2$, $R_3$, $R_4$, $R_5$, $R_6$, $R_7$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and wherein $R_1$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, the modified alginates are alginate polymers that contain one or more covalently modified alginates units described by Formula I, Formula II, Formula III, or Formula IV, wherein for each formula $R_1$, $R_3$, $R_4$, $R_5$, $R_6$, $R_7$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and wherein $R_2$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, the modified alginates are alginate polymers that contain one or more covalently modified alginates units described by Formula I, Formula II, Formula III, or Formula IV, wherein for each formula $R_1$, $R_2$, $R_4$, $R_5$, $R_6$, $R_7$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and wherein $R_3$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, the modified alginates are alginate polymers that contain one or more covalently modified alginates units described by Formula I, Formula II, Formula III, or Formula IV, wherein for each formula $R_1$, $R_2$, $R_3$, $R_5$, $R_6$, $R_7$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and wherein $R_4$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, the modified alginates are alginate polymers that contain one or more covalently modified alginates units described by Formula I, Formula II, Formula III, or Formula IV, wherein for each formula $R_1$, $R_2$, $R_3$, $R_4$, $R_6$, $R_7$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and wherein $R_5$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, the modified alginates are alginate polymers that contain one or more covalently modified alginates units described by Formula I, Formula II, Formula III, or Formula IV, wherein for each formula $R_1$, $R_2$, $R_3$, $R_4$, $R_5$, $R_7$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and wherein $R_6$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, the modified alginates are alginate polymers that contain one or more covalently modified alginates units described by Formula I, Formula II, Formula III, or Formula IV, wherein for each formula $R_1$, $R_2$, $R_3$, $R_4$, $R_5$, $R_6$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and wherein $R_7$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, the modified alginates are alginate polymers that contain one or more covalently modified alginates units described by Formula I, Formula II, Formula III, or Formula IV, wherein for each formula $R_1$, $R_2$, $R_3$, $R_4$, $R_5$, $R_6$, $R_7$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and wherein $R_8$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, the modified alginates are alginate polymers that contain one or more covalently modified alginates units described by Formula I, Formula II, Formula III, or Formula IV, wherein for each formula $R_1$, $R_2$, $R_3$, $R_4$, $R_5$, $R_6$, $R_7$, and $R_8$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and wherein $R_9$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

Modified alginate polymers can contain any ratio of mannuronate monomers, guluronate monomers, and covalently modified monomers. In preferred embodiments, greater than 5%, greater than 10%, greater than 15%, greater than 20%, more preferably greater than 25%, and most preferably greater than 30%, of the monomers in the modified alginate polymer are covalently modified monomers.

In preferred embodiments, the modified alginate polymer can be ionically crosslinked to form hydrogels using a polyvalent ion, such as $Ca^{2+}$, $Sr^{2+}$, or $Ba^2$. The ability of modified alginates to form stable hydrogels in physiological conditions can be quantified using the hydrogel formation assay described herein. In preferred embodiments, the modified alginate polymer forms hydrogels such that the fluorescence intensity measured using the high throughput assay described herein is between 15,000 and 55,000, preferably between 20,000 and 55,000, more preferably between 25,000 and 55,000.

In preferred embodiments, the modified alginate is biocompatible, and induces a lower foreign body response than unmodified alginate. The biocompatibility of modified alginates can be quantitatively determined using in vitro and in vivo assays known in the field, including the in vivo biocompatibility assay described herein. In preferred embodiments, the modified alginate polymer is biocompatible such that the fluorescence response normalized to unmodified alginate measured using the in vivo biocompatibility assay described herein is less than 75%, 70%, 65%, 60%, 55%, or 50%. Also described are assays for the characterization of modified alginate polymers.

A high throughput assay useful to characterize the ability of modified alginate polymers to form hydrogels is also described. In some embodiments, the hydrogel formation assay described herein is used to quantify the stability of hydrogels formed from alginates or modified alginates. In preferred embodiments, the hydrogel formation assay described herein is used as a screening tool to identify modified alginates capable of forming stable hydrogels. The high throughput in vivo biocompatibility assay described herein is used to identify modified alginates which induce a lower foreign body response than unmodified alginate. Assays are also provided for quantifying the biocompatibility of modified alginates.

Further described herein are methods of coating medical products, devices, and surfaces using modified alginate polymers. In particular embodiments, the modified alginate polymers described herein are used to coat products, devices, and surfaces for use in methods of treating a disease or disorder in a human or animal patient. In some embodiments, a disease or disorder in a human or animal patient is treated by transplanting or implanting products, devices, and surfaces coated with a modified alginate polymer. In particular embodiments, a disease or disorder in a human or animal patient is treated by transplanting or implanting products, devices, and surfaces coated with a modified alginate polymer.

Further described herein are methods of encapsulating biological materials using modified alginate polymers. In particular embodiments, the modified alginate polymers described herein are used to encapsulate cells for use in methods of treating a disease or disorder in a human or animal patient. In some embodiments, a disease or disorder in a human or animal patient is treated by transplanting exogenous biological material encapsulated in a modified alginate polymer. In particular embodiments, a disease or disorder in a human or animal patient is treated by transplanting cells encapsulated in a modified alginate polymer. In a more particular embodiment, diabetes is treated by transplanting pancreatic islet cells encapsulated in a modified alginate polymer.

Cells suitable for encapsulation and transplantation are preferably secretory or metabolic cells (i.e., they secrete a therapeutic factor or metabolize toxins, or both) or structural cells (e.g., skin, muscle, blood vessel), or metabolic cells (e.g., they metabolize toxic substances). In some embodiments, the cells are naturally secretory, such as islet cells that naturally secrete insulin, or naturally metabolic, such as hepatocytes that naturally detoxify and secrete. In some embodiments, the cells are bioengineered to express a recombinant protein, such as a secreted protein or metabolic enzyme. Depending on the cell type, the cells may be organized as single cells, cell aggregates, spheroids, or even natural or bioengineered tissue.

DETAILED DESCRIPTION OF THE INVENTION

Figure 1:
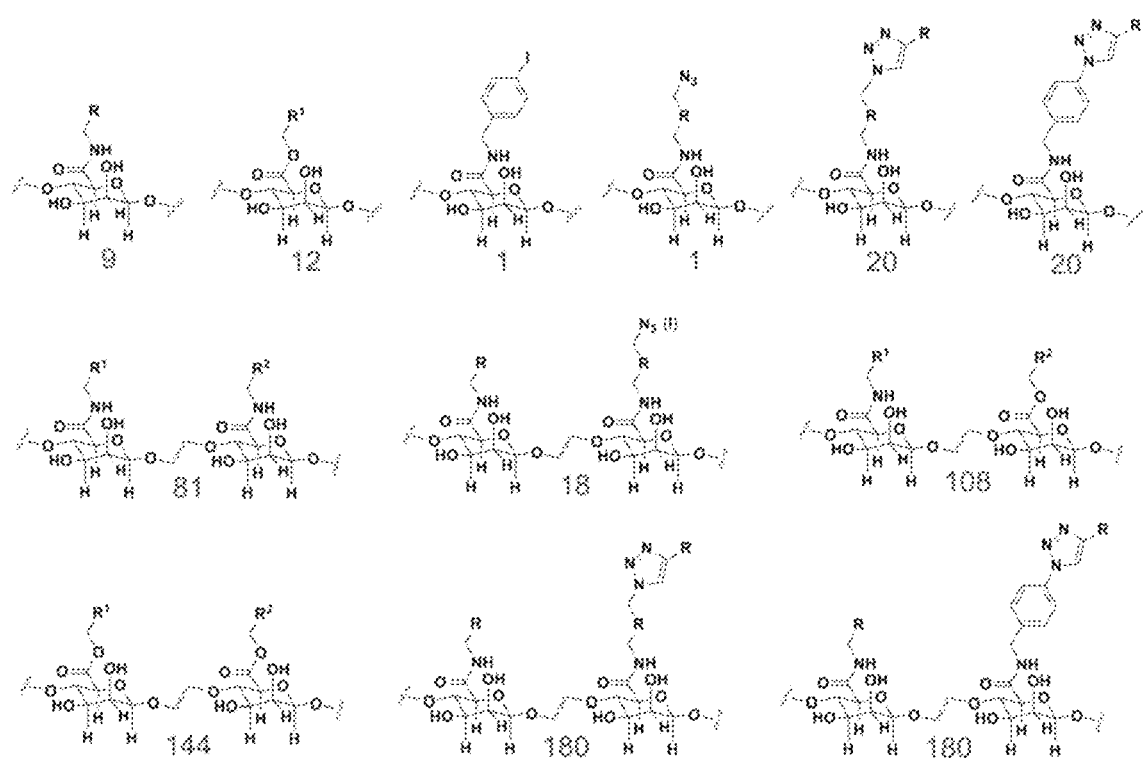
FIG. 1 shows the general structure of the modified alginates obtained using the combinatorial synthetic approach described in Example 1. The number of alginates prepared with each general structure is indicated below.
Figure 2:
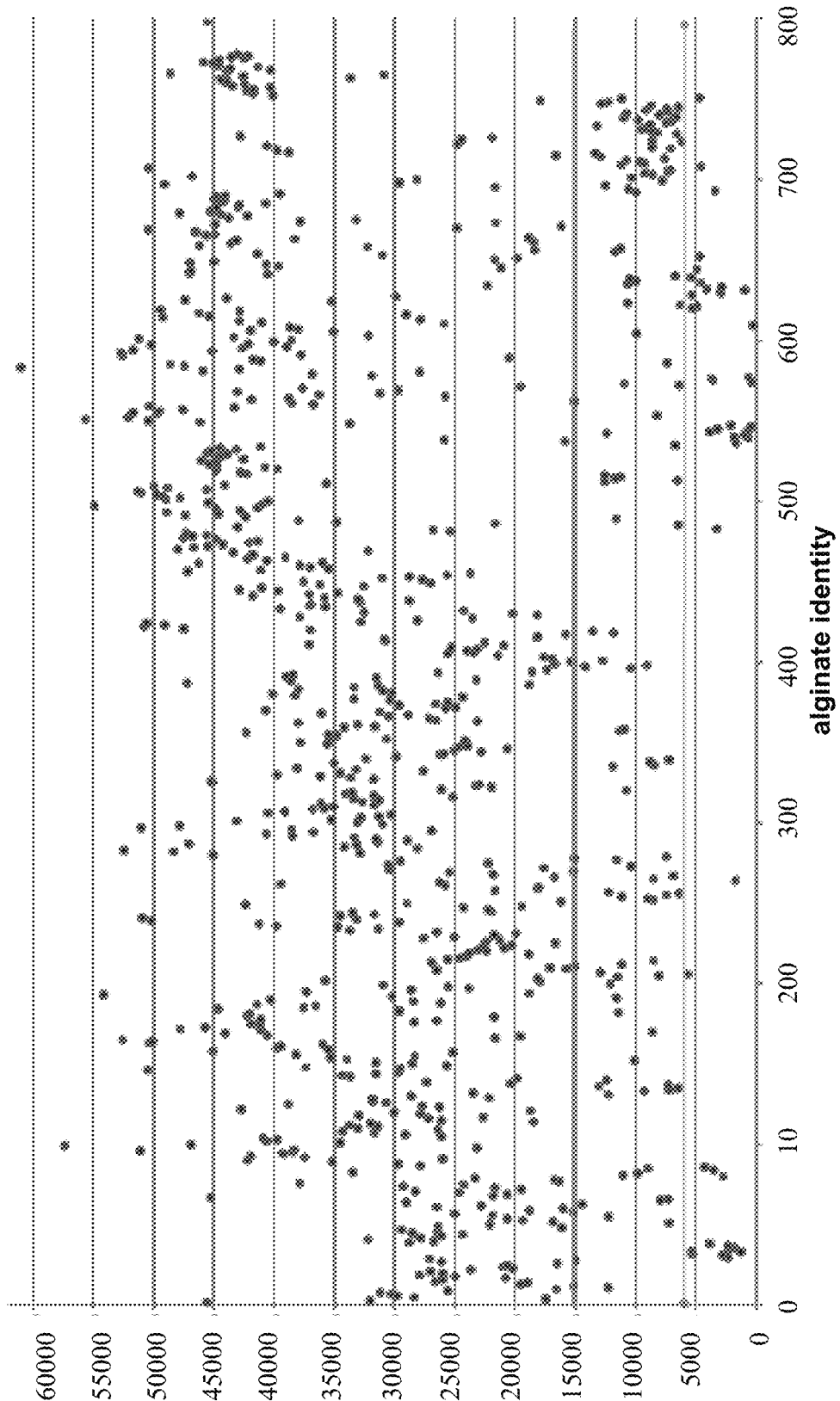
FIG. 2 is a plot obtained from the hydrogel formation assay described in Example 2. The average fluorescence intensity values measured for modified alginates are plotted. Modified alginates yielding fluorescence values below 15,000 were considered unusable for applications where hydrogel formation is critical (i.e. the encapsulation of cells).

Alginates are a class of linear polysaccharide copolymers formed from 1-4-glycosidically linked β-D-mannuronate (M) and its C-5 epimer α-L-guluronate (G). Alginates are naturally occurring biopolymers produced by a variety of organisms, including marine brown algae and at least two genera of bacteria (*Pseudomonas* and *Azotobacter*). Typically, commercial alginates are isolated from marine algae, including *Macrocystis pyrifera, Ascophyllum nodosum*, and various types of *Laminaria*.

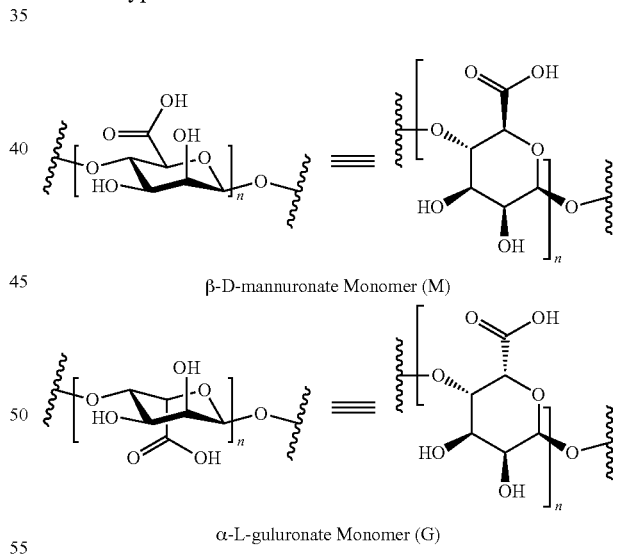

β-D-mannuronate Monomer (M)

α-L-guluronate Monomer (G)

Three types of primary structure define the polysaccharide backbone of alginates: homopolymeric regions of consecutive guluronate monomers (G-blocks), homopolymeric regions of consecutive mannuronate monomers (M-blocks), and regions containing alternating mannuronate and guluronate monomers (MG-blocks). The monomer blocks possess different conformations in solution, ranging from a flexible extended structure (M-blocks) to a rigid compact structure (G-blocks). In the case of G-blocks, the compact conformation facilitates the chelation of multivalent ions, notably $Ca^{2+}$ ions, such that G-blocks in one alginate chain can be ionically crosslinked with G-blocks in another alginate chain, forming stable gels. As a result, the proportion, length, and distribution of the monomer blocks influence the physiochemical properties of the alginate polymer.

In the case of commercially produced alginates obtained from algae, the molecular weight, primary structure, and overall molar ratio of uronic acid monomers (M/G ratio) in the alginate polymer depends on a number of factors, including the species producing the alginate, the time of year in which the species is collected, and the location and age of the algal body. As a result, alginates possessing a range of physiochemical properties, such as molecular weight and viscosity, are commercially available.

Alginates can be ionically crosslinked at room temperature and neutral pH to form hydrogels. The ability of alginates to form stable gels in physiologically compatible conditions renders alginate gels useful in a number of biomedical applications. For example, alginate gels have be used as a matrix for drug delivery to modulate the pharmacokinetics of therapeutic, diagnostic, and prophylactic agents.

I. Definitions

"Alginate", as used herein, is a collective term used to refer to linear polysaccharides formed from β-D-mannuronate and α-L-guluronate in any M/G ratio, as well as salts and derivatives thereof. The term "alginate", as used herein, encompasses any polymer having the structure shown below, as well as salts thereof.

otherwise providing a substrate or surface with a compound with the hydrophobic, polycationic polymer. The polymer can be covalently or non-covalently attached to the substrate or surface. In some embodiments, the polymer is non-covalently associated with the surface.

"Coating" as used herein refers to any temporary, semi-permanent or permanent layer, covering or surface. A coating can be applied as a gas, vapor, liquid, paste, semi-solid, or solid. In addition a coating can be applied as a liquid and solidified into a hard coating. Elasticity can be engineered into coatings to accommodate pliability, e.g. swelling or shrinkage, of the substrate or surface to be coated. Preferred coatings are modified alginate polymers disclosed herein.

"Independently", as used herein in the context of chemical formulae (and unless the context clearly indicates otherwise), means that each instance of the group referred to is chosen independently of the other instances of that group. For example, each instance of the group could be different from every other instance, some other instances, or no other instances of the group. Where multiple groups are referred to, "independently" means that each instance of each given group is chosen independently of the other instances of the respective group and that each of the groups are chosen independently of the other groups. For example, each instance of a first group could be different from every instance, some other instances, or no other instances of a second group (or third, or fourth, etc., group).

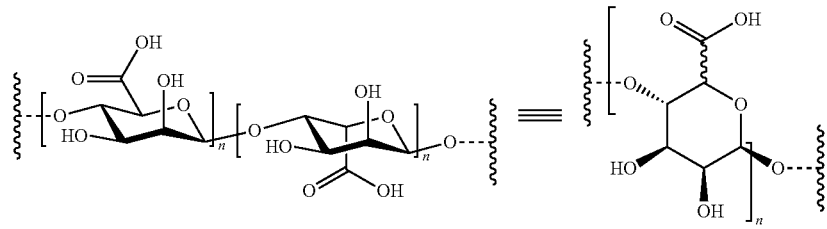

40

"Biocompatible", as used herein, refers to a material which performs its desired function when introduced into an organism without inducing significant inflammatory response, immunogenicity, or cytotoxicity to native cells, tissues, or organs. Biocompatibility, as used herein, can be quantified using the in vivo biocompatibility assay described herein in Example 5.

"Foreign Body Response", as used herein, refers to the immunological response of biological tissue to the presence of any foreign material in the tissue which can include protein adsorption, macrophages, multinucleated foreign body giant cells, fibroblasts, and angiogenesis.

"Chemically Modified Alginate" or "Modified Alginate", are used herein interchangeably, and refer to alginate polymers which contain one or more covalently modified monomers.

"Covalently Modified Monomer", as used herein, refers to a monomer which is an analog or derivative of a mannuronate and/or guluronate monomer obtained from a mannuronate and/or guluronate monomer via a chemical process.

"Contacting" as used herein in the context of coating refers to any way for coating a polymer, such as the modified alginate polymers disclosed herein, on a substrate or surface. Contacting can include, but is not limited to, intraoperative dip-coating, spraying, wetting, immersing, dipping, painting, bonding or adhering, stepwise surface derivatization, or "Component" as used herein in the context of medical products, such as medical devices, is a part of a product that is structurally integrated with that product. A component may be applied to a substrate or to the surface of a product, contained within the substance of the product, retained in the interior of the product, or any other arrangement whereby that part is an integral element of the structure of the product. As an example, the silicone covering surrounding the mechanical part of a pacemaker is a component of the pacemaker. A component may be the lumen of a product where the lumen performs some function essential to the overall function of the product. The lumen of a tissue expander port is a component of the tissue expander. A component can refer to a reservoir or a discrete area within the product specifically adapted for the delivery of a fluid to a surface of the product. A reservoir within an implantable drug delivery device is a component of that device.

The phrase "effective amount," as used herein in the context of a coating, generally refers to the amount of the coating applied to the implant in order to provide one or more clinically measurable endpoints, such as reduced foreign body response compared to an uncoated implant, an implant coated with an unmodified coating, or another suitable control. The phrase "effective amount," as used herein in the context of a cell, capsule, device, composition, or compound, refers to a nontoxic but sufficient amount of the cell, capsule, device, composition, or compound to provide the desired result. The exact amount required may vary from subject to subject, depending on the species, age, and general condition of the subject; the severity of the disease that is being treated; the particular cell, capsule, device, composition, or compound used; its mode of administration; and other routine variables. An appropriate effective amount can be determined by one of ordinary skill in the art using only routine experimentation.

"Surface" or "surfaces," as used herein, refers to any surface of any solid or semi-solid material, including glass, plastics, metals, polymers, and like. This includes surfaces constructed out of more than one material, including coated surfaces.

"Singularly Modified Alginate Polymer," as used herein, refers to modified alginates that contain one or more covalently modified monomers, wherein substantially all of the covalently modified monomers possess the same covalent modification (i.e. the polymer contains one 'type' or species of covalently modified monomer). Singularly modified alginate polymers include, for example, modified alginate polymers wherein substantially all of the monomers in the modified alginate polymer are represented by mannuronate monomers, guluronate monomers, and a covalently modified monomer defined by Formula I. Not all of the monomers are necessarily covalently modified.

"Capsule," as used herein, refers to a particle having a mean diameter of about 150 µm to about 5 cm, formed of a cross-linked hydrogel, having a cross-linked hydrogel core that is surrounded by one or more polymeric shells, having one or more cross-linked hydrogel layers, having a cross-linked hydrogel coating, or a combination thereof. The capsule may have any shape suitable for, for example, cell encapsulation. The capsule may contain one or more cells dispersed in the cross-linked hydrogel, thereby "encapsulating" the cells. Reference to "capsules" herein refers to and includes microcapsules unless the context clearly indicates otherwise. Preferred capsules have a mean diameter of about 150 µm to about 8 mm.

"Microcapsule" and "microgel," as used herein, are used interchangeably to refer to a particle or capsule having a mean diameter of about 150 µm to about 1000 µm.

"Biological material," as used herein, refers to any biological substance, including, but not limited to, tissue, cells, biological micromolecules, such as a nucleotides, amino acids, cofactors, and hormones, biological macromolecules, such as nucleic acids, polypeptides, proteins (for example enzymes, receptors, secretory proteins, structural and signaling proteins, hormones, ligands, etc.), polysaccharides, and/or any combination thereof.

"Cell," as used herein, refers to individual cells, cell lines, primary cultures, or cultures derived from such cells unless specifically indicated. "Culture," as used herein, refers to a composition including isolated cells of the same or a different type. "Cell line," as used herein, refers to a permanently established cell culture that will proliferate indefinitely given appropriate fresh medium and space, thus making the cell line "immortal." "Cell strain," as used herein, refers to a cell culture having a plurality of cells adapted to culture, but with finite division potential. "Cell culture," as used herein, is a population of cells grown on a medium such as agar.

Cells can be, for example, xenogeneic, autologous, or allogeneic. Cells can also be primary cells. Cells can also be cells derived from the culture and expansion of a cell obtained from a subject. For example, cells can also be stem cells or derived from stem cells. Cells can also be immortalized cells. Cells can also be genetically engineered to express a protein, nucleic acid, or other product.

"Mammalian cell," as used herein, refers to any cell derived from a mammalian subject.

"Autologous," as used herein, refers to a transplanted biological material, such as cells, taken from the same individual.

"Allogeneic," as used herein, refers to a transplanted biological material, such as cells, taken from a different individual of the same species.

"Xenogeneic," as used herein, refers to a transplanted biological material, such as cells, taken from a different species.

"Endocrine cell," as used herein, refers to a cell of the endocrine system. "Secreting endocrine cell," as used herein, refers to an endocrine cell that secretes one or more hormones.

"Islet cell," as used herein, refers to an endocrine cell derived from a mammalian pancreas. Islet cells include alpha cells that secrete glucagon, beta cells that secrete insulin and amylin, delta cells that secrete somatostatin, PP cells that secrete pancreatic polypeptide, or epsilon cells that secrete ghrelin. The term includes homogenous and heterogeneous populations of these cells. In preferred embodiments, a population of islet cells contains at least beta cells.

"Hormone-producing cell," as used herein, refers to a cell that produces one or more hormones. Preferred hormone-producing cells produce hormone in response to physiological stimulus, such as the physiological stimulus that cause secretion of the hormone from an endocrine cell that naturally secretes the hormone. Secreting endocrine cells, hormone-producing cells derived from stem cells, and cells genetically engineered to produce hormone are examples of hormone-producing cells.

"Insulin-producing cell," as used herein, refers to a cell that produces insulin. Preferred insulin-producing cells produce insulin in response to glucose levels. Islet beta cells, insulin-producing cells derived from stem cells, and cells genetically engineered to produce insulin are examples of insulin-producing cells.

"Transplant," as used herein, refers to the transfer of a cell, tissue, or organ to a subject from another source. The term is not limited to a particular mode of transfer. Encapsulated cells may be transplanted by any suitable method, such as by injection or surgical implantation.

"Primary cells," "primary cell lines," and "primary cultures," as used herein, are used interchangeably to refer to cells and cells cultures that have been derived from a subject and allowed to grow in vitro for a limited number of passages, that is, splittings, of the culture.

"Mesenchymal stem cell" or "MSC," as used herein, refer to multipotent stem cells present in or derived from mesenchymal tissue that can differentiate into a variety of cell types, including: osteoblasts, chondrocytes, and adipocytes.

"Derived from," as used herein, with respect to cells, refer to cells obtained from tissue, cell lines, or cells, which are then cultured, passaged, differentiated, induced, etc., to produce the derived cells. For example, induced pluripotent stem cells are derived from somatic cells.

"Pluripotency," as used herein, refers to the ability of cells to differentiate into multiple types of cells in an organism. By "pluripotent stem cells," it is meant cells that can self-renew and differentiate to produce all types of cells in an organism. By "multipotency" it is meant the ability of cells to differentiate into some types of cells in an organism but not all, typically into cells of a particular tissue or cell lineage.

"Multi-potent cells" and "adult stem cells," as used herein, refer to any type of stem cell that is not derived from an embryo or fetus and generally has a limited capacity to generate new cell types (referred to as "multipotency") and being committed to a particular lineage.

"Induced pluripotent stem cell," as used herein, encompasses pluripotent stem cells, that, like embryonic stem (ES) cells, can be cultured over a long period of time while maintaining the ability to differentiate into all types of cells in an organism, but that, unlike ES cells (which are derived from the inner cell mass of blastocysts), are derived from somatic cells.

For clarity of discussion herein, singularly modified alginates are defined using formulae illustrating the structure of the covalently modified monomers incorporated in the backbone and omitting the mannuronate and guluronate monomers. For example, a singularly modified alginate polymer composed of mannuronate monomers, guluronate monomers, and a covalently modified monomer defined by Formula I, wherein X is $NR_4$, $R_1$ is methyl, and $R_4$, $Y_1$, and $Y_2$ are hydrogen, is illustrated herein by the structure below.

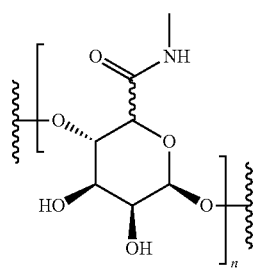

"Multiply Modified Alginate Polymer", as used herein, refers to modified alginates that contain covalently modified monomers, wherein substantially all of the covalently modified monomers do not possess the same covalent modification (i.e. the polymer contains two or more different 'types' or species of covalently modified monomers). Multiply modified alginate polymers include, for example, modified alginate polymers wherein substantially all of the monomers in the modified alginate polymer are represented by mannuronate monomers, guluronate monomers, and two or more different types of covalently modified monomers defined by Formula I. As used in this context, a 'type' or 'species' of covalently modified monomer refers to a covalent monomer defined by Formula I, wherein all possible variable positions are chemically defined. Not all the monomers are covalently modified.

For clarity of discussion herein, modified alginates are defined using formulae illustrating the covalently modified monomers incorporated in the backbone and omitting the mannuronate and guluronate monomers. For example, a multiply modified alginate polymer composed of mannuronate monomers, guluronate monomers, and two different types of covalently modified monomers, wherein the first type of covalently modified monomer is defined by Formula I, wherein X is $NR_4$, $R_1$ is methyl, and $R_4$, $Y_1$, and $Y_2$ are hydrogen and the second type of covalently modified monomer is defined by Formula I, wherein X is oxygen, $R_1$ is ethyl, and $Y_1$ and $Y_2$ are hydrogen, is illustrated by the structure below.

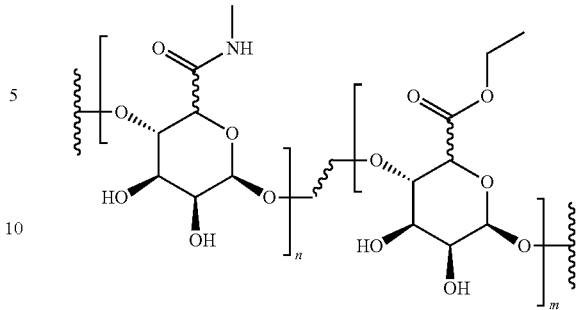

"Analog" and "Derivative," in the context of chemical compounds, are used herein interchangeably, and refer to a compound having a structure similar to that of a parent compound, but varying from the parent compound by a difference in one or more certain components. Analogs or derivatives differ from the parent compound in one or more atoms, functional groups, or substructures, which are replaced with other atoms, groups, or substructures. An analog or derivative can be imagined to be formed, at least theoretically, from the parent compound via some chemical or physical process. The terms analog and derivative encompass compounds which retain the same basic ring structure as the parent compound, but possess one or more different substituents on the ring(s). For example, analog or derivative of mannuronate or guluronate refers to compounds which retain the core of the monomer, e.g., the pyranose ring, but differ in or more substitutents on the ring.

"Mannuronate" and "Mannuronate Monomer", as used herein, refer to mannuronic acid monomers as well as salts thereof.

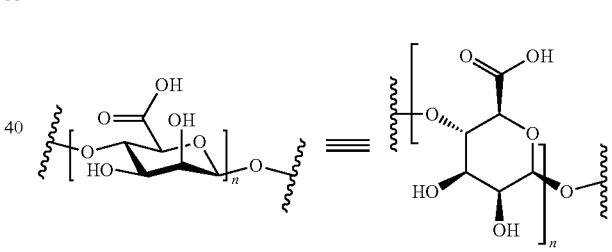

"Guluronate" and "Guluronate Monomer", as used herein, refer to guluronic acid monomers as well as salts thereof.

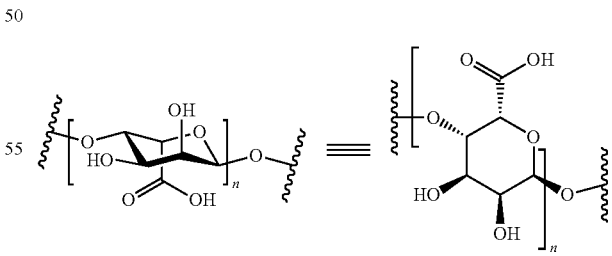

"Substantially", as used herein, specifies an amount of 95% or more, 96% or more, 97% or more, 98% or more, or 99% or more.

"Glass Transition Temperature" ($T_g$), as used herein, refers to the temperature at which a reversible transition is observed in amorphous materials from a hard and relatively brittle state into a molten or rubber-like state. $T_g$ values for alginate polymers can be experimentally determined using differential scanning calorimetry (DSC, heated and cooled at a rate of 10 K/min). In all cases herein, values of $T_g$ are measured using powder polymer samples.

"Click Chemistry", as used herein, refers to chemical reactions used to couple two compounds together which are high yielding, wide in scope, create only byproducts that can be removed without chromatography, are stereospecific, simple to perform, and can be conducted in easily removable or benign solvents. Examples of reactions which fulfill these criteria include the nucleophilic ring opening of epoxides and aziridines, non-aldol type carbonyl reactions, including the formation of hydrazones and heterocycles, additions to carbon-carbon multiple bonds, including Michael Additions, and cycloaddition reactions, such as a 1,3-dipolar cycloaddition reaction (i.e. a Huisgen cycloaddition reaction). See, for example, Moses, and Moorhouse, *Chem Soc. Rev.* 36:1249-1262 (2007); Kolb and Sharpless, *Drug Discovery Today.* 8(24):1128-1137 (2003); and Kolb et al., *Angew. Chem. Int. Ed.* 40:2004-2021 (2001).

"Polyvalent Cation", as used herein, refers to cations which have a positive charge greater than 1. Examples include, but are not limited to, $Ca^{2+}$, $Ba^{2+}$, and $Sr^{2+}$.

"Substituted", as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

"Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 41-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), preferably 20 or fewer, more preferably 10 or fewer, most preferably 6 or fewer. If the alkyl is unsaturated, the alkyl chain generally has from 2-30 carbons in the chain, preferably from 2-20 carbons in the chain, more preferably from 2-10 carbons in the chain. Likewise, preferred cycloalkyls have from 3-20 carbon atoms in their ring structure, preferably from 3-10 carbons atoms in their ring structure, most preferably 5, 6 or 7 carbons in the ring structure.

The terms "alkenyl" and "alkynyl" refer to unsaturated aliphatic groups analogous in length and possible substitution to the alkyls described above, but that contain at least one double or triple bond respectively.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —NO$_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, —CF$_3$; —CN; —NCOCOCH$_2$CH$_2$; —NCOCOCHCH; —NCS; and combinations thereof.

"Amino" and "Amine", as used herein, are art-recognized and refer to both substituted and unsubstituted amines, e.g., a moiety that can be represented by the general formula:

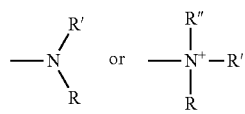

wherein, R, R', and R" each independently represent a hydrogen, substituted or unsubstituted alkyl, substituted or unsubstituted alkenyl, substituted or unsubstituted alkynyl, substituted or unsubstituted carbonyl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R") each independently represent a hydrogen atom, substituted or unsubstituted alkyl, a substituted or unsubstituted alkenyl, or —(CH$_2$)$_m$—R'''. Thus, the term 'alkylamine' as used herein refers to an amine group, as defined above, having a substituted or unsubstituted alkyl attached thereto (i.e. at least one of R, R', or R" is an alkyl group).

"Carbonyl", as used herein, is art-recognized and includes such moieties as can be represented by the general formula:

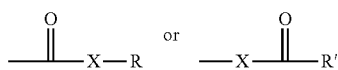

wherein X is a bond, or represents an oxygen or a sulfur, and R represents a hydrogen, a substituted or unsubstituted alkyl, substituted or unsubstituted alkenyl, substituted or unsubstituted alkynyl, —(CH$_2$)$_m$—R", or a pharmaceutical acceptable salt, R' represents a hydrogen, substituted or unsubstituted alkyl, substituted or unsubstituted alkenyl, substituted or unsubstituted alkynyl, or —(CH$_2$)$_m$—R"; R" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. In general, where the oxygen atom of the above formula is replaced by a sulfur atom, the formula represents a 'thiocarbonyl' group. Where X is sulfur and R or R' is not hydrogen, the formula represents a 'thioester'. Where X is sulfur and R is hydrogen, the formula represents a 'thiocarboxylic acid'. Where X is sulfur and R' is hydrogen, the formula represents a 'thioformate'. Where X is a bond and R is not hydrogen, the above formula represents a 'ketone'. Where X is a bond and R is hydrogen, the above formula represents an 'aldehyde'.

"Heteroalkyl", as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

"Alkoxy", "alkylamino", and "alkylthio" are used herein in their conventional sense, and refer to those alkyl groups attached to the remainder of the molecule via an oxygen atom, an amino group, or a sulfur atom, respectively.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, C$_1$-C$_{10}$ alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents as defined above for alkyl and aryl.

"Halogen", as used herein, refers to fluorine, chlorine, bromine, or iodine.

II. Modified Alginates

Described herein are alginate polymers that have been chemically modified to alter their biocompatibility and physical properties, as well as methods of making thereof.

A. Structure of Modified Alginate Polymers

Modified alginates contain one or more covalently modified monomers defined by Formula I

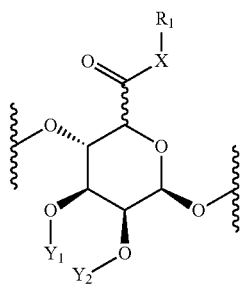

Formula I wherein,

X is oxygen, sulfur, or $NR_4$;

$R_1$ is hydrogen, or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_1$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group;

$Y_1$ and $Y_2$ independently are hydrogen or —$PO(OR_5)_2$; or $Y_2$ is absent, and $Y_2$, together with the two oxygen atoms to which $Y_1$ and $Y_2$ are attached form a cyclic structure as shown in Formula II

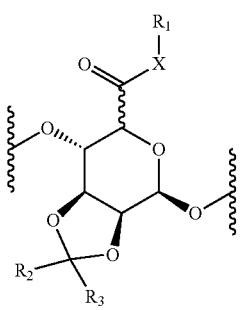

Formula II wherein; and $R_2$ and $R_3$ are, independently, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_2$ and $R_3$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and $R_4$ and $R_5$ are, independently, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_4$ and $R_5$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, the modified alginate polymer is a singularly modified alginate polymer. In specific embodiments, the singularly modified alginate polymer contains one or more covalently modified monomers defined by Formula I, wherein $R_1$ includes an azide group, an alkyne group, or a 1,2,3-triazole ring. In certain embodiments, the singularly modified alginate polymer contains one or more covalently modified monomers defined by Formula I, wherein X is not oxygen and $R_1$ is not an unsubstituted $C_1$-$C_{18}$ alkyl group, poly(ethylene glycol) chain, or cholesteryl moiety. In certain additional embodiments, the singularly modified alginate polymer contains one or more covalently modified monomers defined by Formula I, wherein X is not $NR_4$ and $R_1$ is not a substituted or unsubstituted $C_1$-$C_6$ alkyl group, or a poly(ethylene glycol) chain.

In alternative embodiments, the modified alginate polymer is a multiply modified alginate polymer. In preferred embodiments, the multiply modified alginate polymer possesses a polysaccharide backbone containing mannuronate monomers, guluronate monomers, a first species or type of covalently modified monomer defined by Formula I, and a second species or type of covalently modified monomer defined by Formula I. In other embodiments, the multiply modified alginate polymer possesses a polysaccharide backbone containing mannuronate monomers, guluronate monomers, and three or more different types of covalently modified monomers defined by Formula I.

In some embodiments, the multiply modified alginate polymer contains two different species of covalently modified monomers defined by Formula I, wherein in both species of monomer, X is NR$_4$. In other embodiments, the multiply modified alginate polymer contains two different species of covalently modified monomers defined by Formula I, wherein in both species of monomer, X is oxygen. In further embodiments, the multiply modified alginate polymer contains two different species of covalently modified monomers defined by Formula I, wherein in one species of monomer X is oxygen, and in the second species of monomer, X is NR$_4$.

In some embodiments, the multiply modified alginate polymer contains two different species of covalently modified monomers defined by Formula I, wherein in at least one species of monomer, R$_1$ includes one or more cyclic moieties. In preferred embodiments, the multiply modified alginate polymer contains two different species of covalently modified monomers defined by Formula I, wherein in at least one species of monomer, R$_1$ includes a phenyl ring, furan ring, oxolane ring, dioxolane ring, or a 1,2,3-triazole ring.

In certain embodiments, the multiply modified alginate polymer contains two different species of covalently modified monomers defined by Formula I, wherein in at least one species of monomer, R$_1$ includes one or more halogen moieties, an azide group, or an alkyne.

In preferred embodiments, the multiply modified alginate polymer is one of the multiply modified alginate polymers shown below.

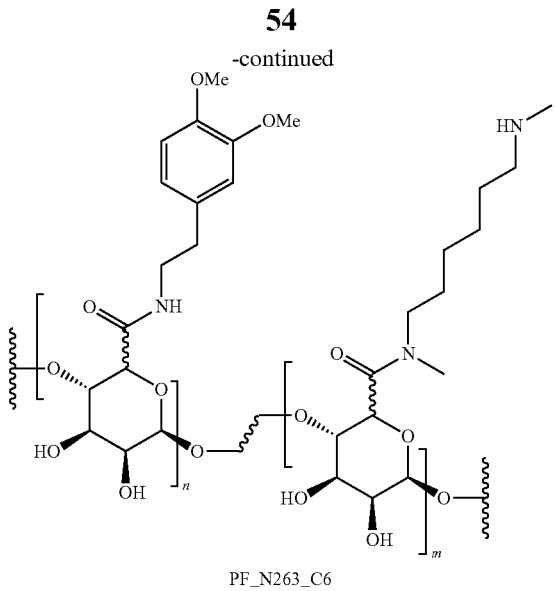

PF_N263_C6

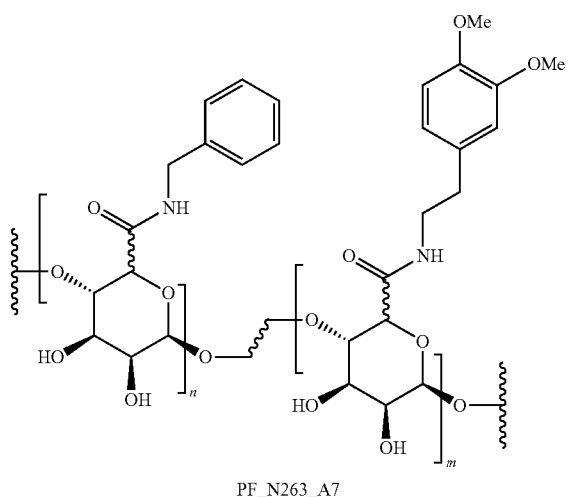

PF_N263_A7

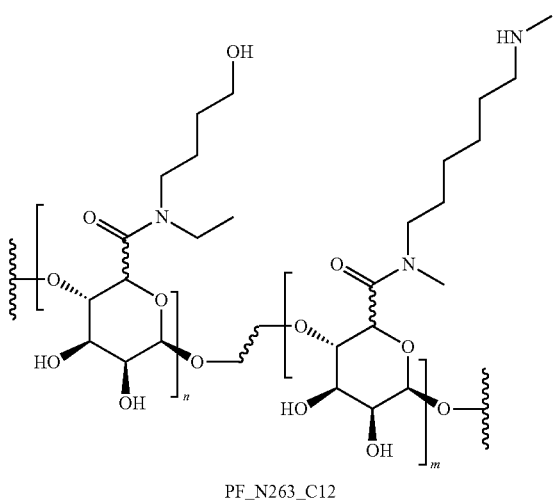

PF_N263_C12

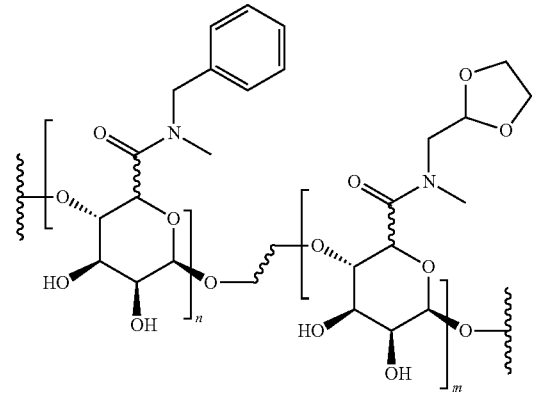

PF_N263_A12

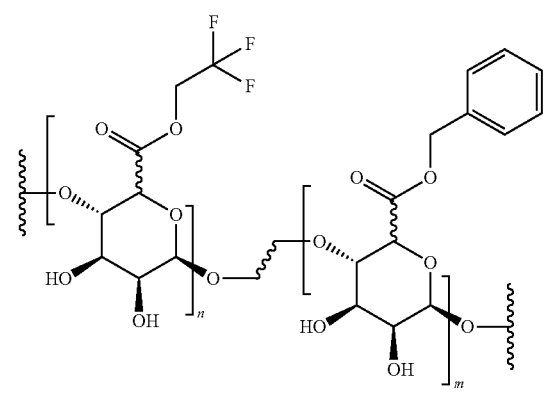

PF_N287_A4

-continued
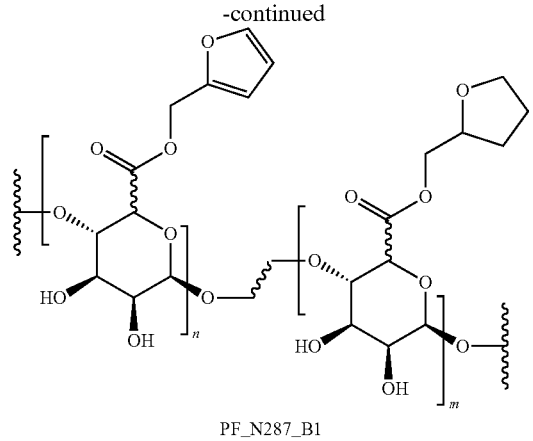
PF_N287_B1
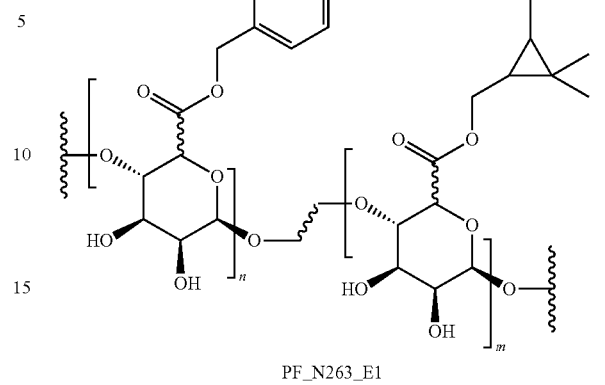
PF_N263_E1
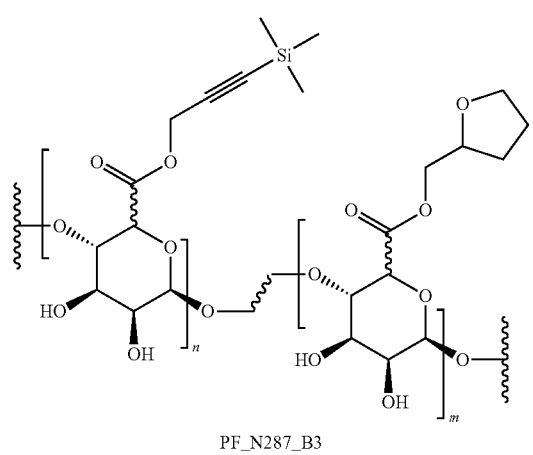
PF_N287_B3
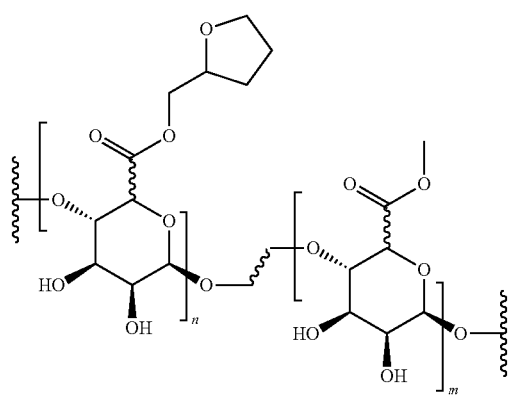
PF_N287_G5
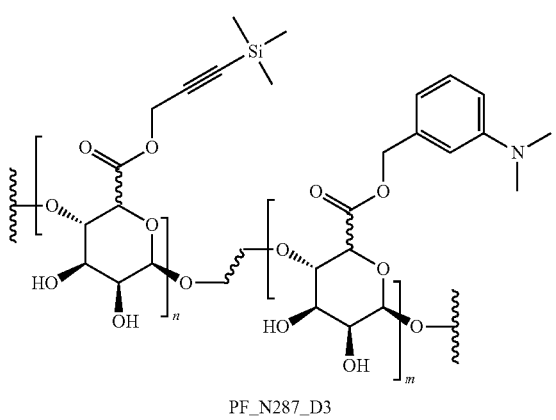
PF_N287_D3
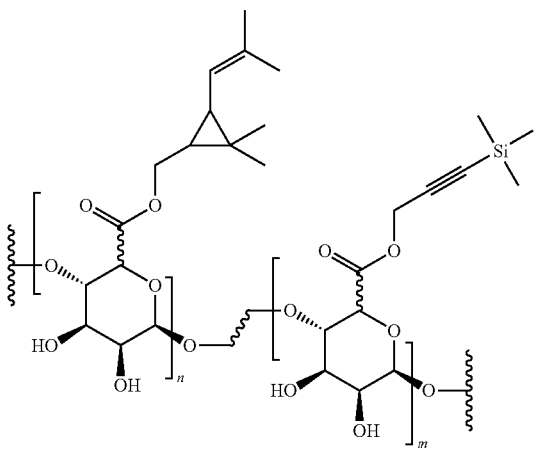
PF_N287_F4

-continued
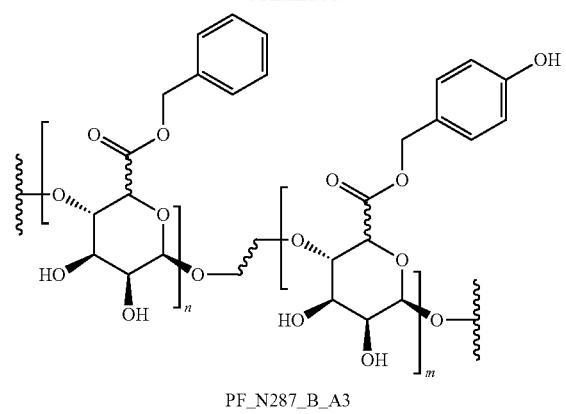
PF_N287_B_A3
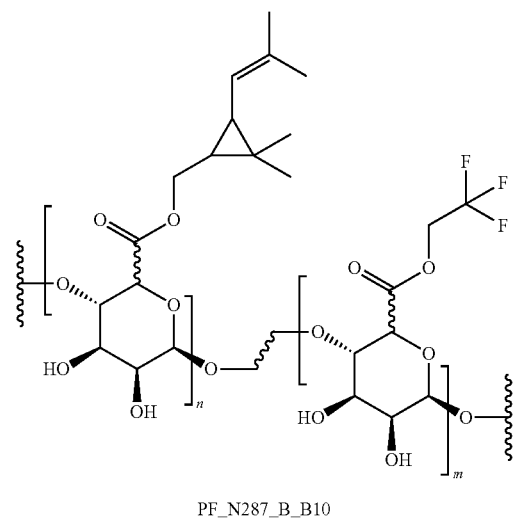
PF_N287_B_B10
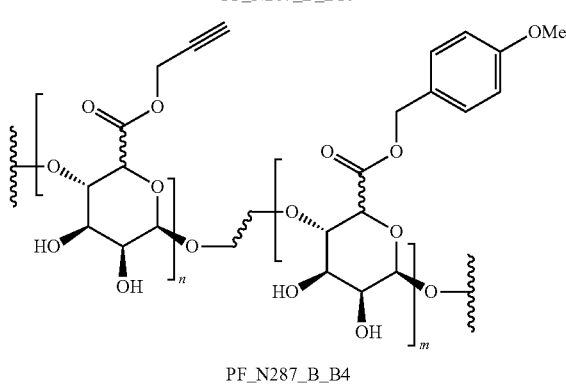
PF_N287_B_B4
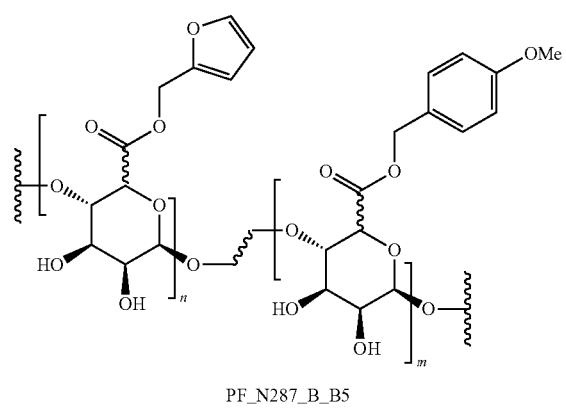
PF_N287_B_B5
-continued
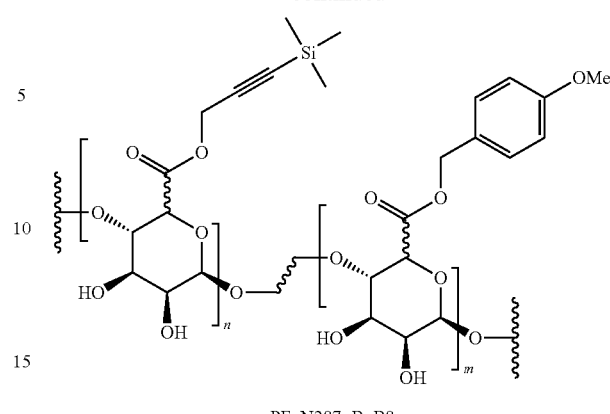
PF_N287_B_B8
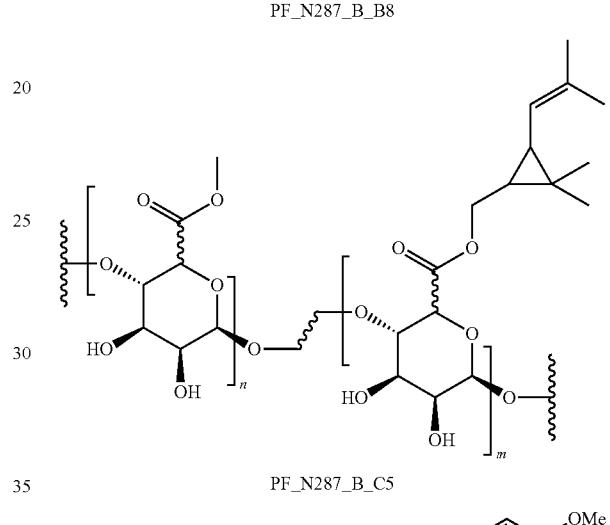
PF_N287_B_C5
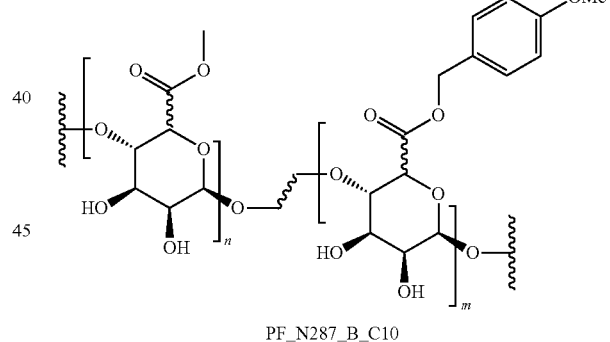
PF_N287_B_C10
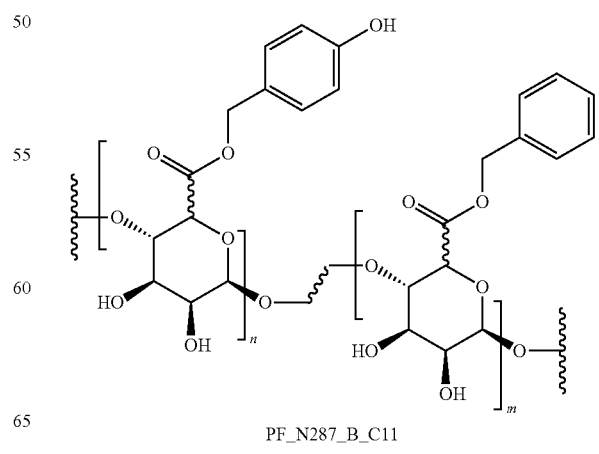
PF_N287_B_C11

-continued
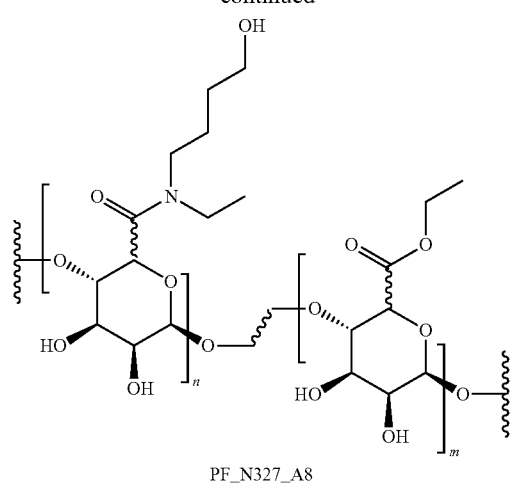
PF_N327_A8
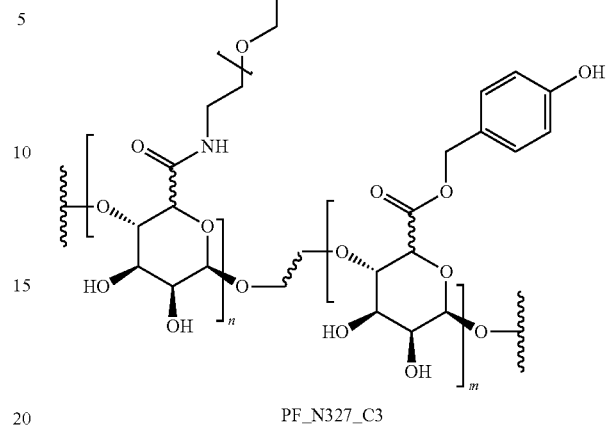
PF_N327_C3
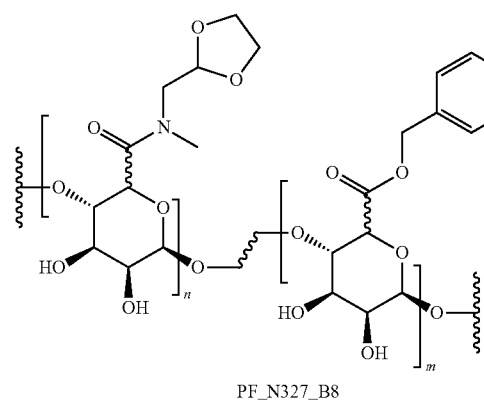
PF_N327_B8
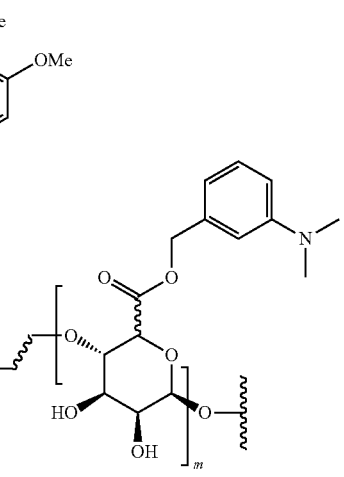
PF_N327_D10
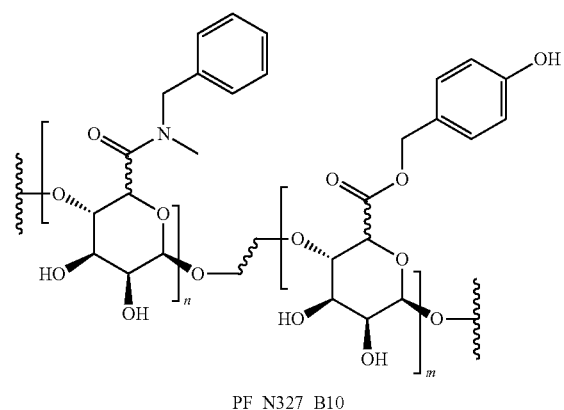
PF_N327_B10
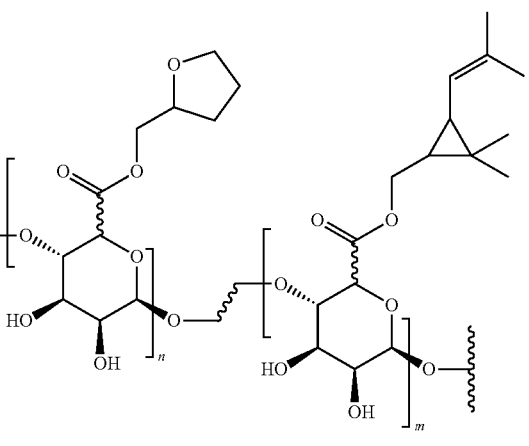
PF_N287_E3

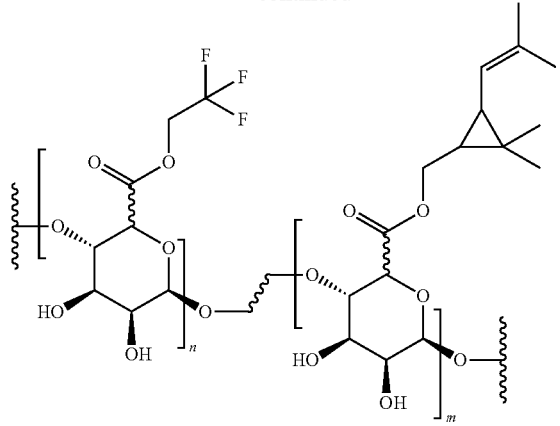

PF_N287_E4

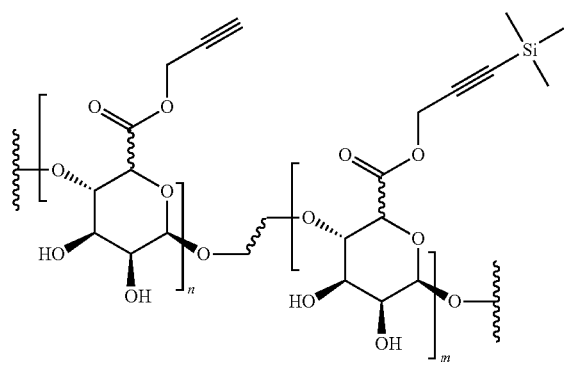

PF_N287_F2

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, or substituted or unsubstituted $C_1$-$C_{10}$ alkyl, $C_1$-$C_{10}$ alkoxy, $C_1$-$C_{10}$ alkylamino, $C_1$-$C_{10}$ alkylthio, $C_1$-$C_9$ alkyl, $C_1$-$C_9$ alkoxy, $C_1$-$C_9$ alkylamino, $C_1$-$C_9$ alkylthio, $C_1$-$C_8$ alkyl, $C_1$-$C_8$ alkoxy, $C_1$-$C_8$ alkylamino, $C_1$-$C_8$ alkylthio, $C_1$-$C_7$ alkyl, $C_1$-$C_7$ alkoxy, $C_1$-$C_7$ alkylamino, $C_1$-$C_7$ alkylthio, $C_1$-$C_6$ alkyl, $C_1$-$C_6$ alkoxy, $C_1$-$C_6$ alkylamino, $C_1$-$C_6$ alkylthio, $C_1$-$C_5$ alkyl, $C_1$-$C_5$ alkoxy, $C_1$-$C_5$ alkylamino, $C_1$-$C_5$ alkylthio, $C_1$-$C_4$ alkyl, $C_1$-$C_4$ alkoxy, $C_1$-$C_4$ alkylamino, $C_1$-$C_4$ alkylthio, $C_1$-$C_3$ alkyl, $C_1$-$C_3$ alkoxy, $C_1$-$C_3$ alkylamino, $C_1$-$C_3$ alkylthio, $C_1$-$C_2$ alkyl, $C_1$-$C_2$ alkoxy, $C_1$-$C_2$ alkylamino, $C_1$-$C_2$ alkylthio, $C_{10}$ alkyl, $C_{10}$ alkoxy, $C_{10}$ alkylamino, $C_{10}$ alkylthio, $C_9$ alkyl, $C_9$ alkoxy, $C_9$ alkylamino, $C_9$ alkylthio, $C_8$ alkyl, $C_8$ alkoxy, $C_8$ alkylamino, $C_8$ alkylthio, $C_7$ alkyl, $C_7$ alkoxy, $C_7$ alkylamino, $C_7$ alkylthio, $C_6$ alkyl, $C_6$ alkoxy, $C_6$ alkylamino, $C_6$ alkylthio, $C_8$ alkyl, $C_5$ alkoxy, $C_5$ alkylamino, $C_5$ alkylthio, $C_4$ alkyl, $C_4$ alkoxy, $C_4$ alkylamino, $C_4$ alkylthio, $C_3$ alkyl, $C_3$ alkoxy, $C_3$ alkylamino, $C_3$ alkylthio, $C_2$ alkyl, $C_2$ alkoxy, $C_2$ alkylamino, $C_2$ alkylthio, $C_1$ alkyl, $C_1$ alkoxy, $C_1$ alkylamino, or $C_1$ alkylthio.

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, or substituted or unsubstituted $C_1$-$C_{10}$ alkyl, $C_1$-$C_{10}$ alkoxy, $C_1$-$C_{10}$ alkylamino, or $C_1$-$C_{10}$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_1$-$C_9$ alkyl, $C_1$-$C_9$ alkoxy, $C_1$-$C_9$ alkylamino, or $C_1$-$C_9$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_1$-$C_8$ alkyl, $C_1$-$C_8$ alkoxy, $C_1$-$C_8$ alkylamino, or $C_1$-$C_8$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_1$-$C_7$ alkyl, $C_1$-$C_7$ alkoxy, $C_1$-$C_7$ alkylamino, or $C_1$-$C_7$ alkylthio.

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, or substituted or unsubstituted $C_1$-$C_6$ alkyl, $C_1$-$C_6$ alkoxy, $C_1$-$C_6$ alkylamino, or $C_1$-$C_6$ alkylthio.

In some embodiments, $R_1$ through $R_{17}$, $R_{31}$ through $R_{36}$, $R^a$, $R^b$, $R^c$, and $R^d$ are independently hydrogen, amino, hydroxyl, thiol, oxo, or substituted or unsubstituted $C_1$-$C_5$ alkyl, $C_1$-$C_5$ alkoxy, $C_1$-$C_5$ alkylamino, or $C_1$-$C_5$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_1$-$C_4$ alkyl, $C_1$-$C_4$ alkoxy, $C_1$-$C_4$ alkylamino, or $C_1$-$C_4$ alkylthio.

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, or substituted or unsubstituted $C_1$-$C_3$ alkyl, $C_1$-$C_3$ alkoxy, $C_1$-$C_3$ alkylamino, or $C_1$-$C_3$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_1$-$C_2$ alkyl, $C_1$-$C_2$ alkoxy, $C_1$-$C_2$ alkylamino, or $C_1$-$C_2$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_{10}$ alkyl, $C_{10}$ alkoxy, $C_{10}$ alkylamino, or $C_{10}$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_9$ alkyl, $C_9$ alkoxy, $C_9$ alkylamino, or $C_9$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_8$ alkyl, $C_8$ alkoxy, $C_8$ alkylamino, or $C_8$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_7$ alkyl, $C_7$ alkoxy, $C_7$ alkylamino, or $C_7$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_6$ alkyl, $C_6$ alkoxy, $C_6$ alkylamino, or $C_6$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_5$ alkyl, $C_5$ alkoxy, $C_5$ alkylamino, or $C_5$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_4$ alkyl, $C_4$ alkoxy, $C_4$ alkylamino, or $C_4$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_3$ alkyl, $C_3$ alkoxy, $C_3$ alkylamino, or $C_3$ alkylthio.

In some embodiments, $R_1$ through $R_{17}$, $R_{31}$ through $R_{36}$, $R^a$, $R^b$, $R^c$, $R^d$ and $R^e$ are independently hydrogen, amino, hydroxyl, thiol, oxo, or substituted or unsubstituted $C_2$ alkyl, $C_2$ alkoxy, $C_2$ alkylamino, or $C_2$ alkylthio.

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, or substituted or unsubstituted $C_1$ alkyl, $C_1$ alkoxy, $C_1$ alkylamino, or $C_1$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_1$-$C_{10}$ alkyl, $C_1$-$C_{10}$ alkoxy, $C_1$-$C_{10}$ alkylamino, $C_1$-$C_{10}$ alkylthio, $C_1$-$C_9$ alkyl, $C_1$-$C_9$ alkoxy, $C_1$-$C_9$ alkylamino, $C_1$-$C_9$ alkylthio, $C_1$-$C_8$ alkyl, $C_1$-$C_8$ alkoxy, $C_1$-$C_8$ alkylamino, $C_1$-$C_8$ alkylthio, $C_1$-$C_7$ alkyl, $C_1$-$C_7$ alkoxy, $C_1$-$C_7$ alkylamino, $C_1$-$C_7$ alkylthio, $C_1$-$C_6$ alkyl, $C_1$-$C_6$ alkoxy, $C_1$-$C_6$ alkylamino, $C_1$-$C_6$ alkylthio, $C_1$-$C_5$ alkyl, $C_1$-$C_5$ alkoxy, $C_1$-$C_5$ alkylamino, $C_1$-$C_5$ alkylthio, $C_1$-$C_4$ alkyl, $C_1$-$C_4$ alkoxy, $C_1$-$C_4$ alkylamino, $C_1$-$C_4$ alkylthio, $C_1$-$C_3$ alkyl, $C_1$-$C_3$ alkoxy, $C_1$-$C_3$ alkylamino, $C_1$-$C_3$ alkylthio, $C_1$-$C_2$ alkyl, $C_1$-$C_2$ alkoxy, $C_1$-$C_2$ alkylamino, $C_1$-$C_2$ alkylthio, $C_{10}$ alkyl, $C_{10}$ alkoxy, $C_{10}$ alkylamino, $C_{10}$ alkylthio, $C_9$ alkyl, $C_9$ alkoxy, $C_9$ alkylamino, $C_9$ alkylthio, $C_8$ alkyl, $C_8$ alkoxy, $C_8$ alkylamino, $C_8$ alkylthio, $C_7$ alkyl, $C_7$ alkoxy, $C_7$ alkylamino, $C_7$ alkylthio, $C_6$ alkyl, $C_6$ alkoxy, $C_6$ alkylamino, $C_6$ alkylthio, $C_5$ alkyl, $C_5$ alkoxy, $C_5$ alkylamino, $C_5$ alkylthio, $C_4$ alkyl, $C_4$ alkoxy, $C_4$ alkylamino, $C_4$ alkylthio, $C_3$ alkyl, $C_3$ alkoxy, $C_3$ alkylamino, $C_3$ alkylthio, $C_2$ alkyl, $C_2$ alkoxy, $C_2$ alkylamino, $C_2$ alkylthio, $C_1$ alkyl, $C_1$ alkoxy, $C_1$ alkylamino, or $C_1$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_1$-$C_{10}$ alkyl, $C_1$-$C_{10}$ alkoxy, $C_1$-$C_{10}$ alkylamino, or $C_1$-$C_{10}$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_1$-$C_9$ alkyl, $C_1$-$C_9$ alkoxy, $C_1$-$C_9$ alkylamino, or $C_1$-$C_9$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_1$-$C_8$ alkyl, $C_1$-$C_8$ alkoxy, $C_1$-$C_8$ alkylamino, or $C_1$-$C_8$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_1$-$C_7$ alkyl, $C_1$-$C_7$ alkoxy, $C_1$-$C_7$ alkylamino, or $C_1$-$C_7$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_1$-$C_6$ alkyl, $C_1$-$C_6$ alkoxy, $C_1$-$C_6$ alkylamino, or $C_1$-$C_6$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_1$-$C_5$ alkyl, $C_1$-$C_5$ alkoxy, $C_1$-$C_5$ alkylamino, or $C_1$-$C_5$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_1$-$C_4$ alkyl, $C_1$-$C_4$ alkoxy, $C_1$-$C_4$ alkylamino, or $C_1$-$C_4$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_1$-$C_3$ alkyl, $C_1$-$C_3$ alkoxy, $C_1$-$C_3$ alkylamino, or $C_1$-$C_3$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_1$-$C_2$ alkyl, $C_1$-$C_2$ alkoxy, $C_1$-$C_2$ alkylamino, or $C_1$-$C_2$ alkylthio.

In some embodiments, $R_1$ through $R_{17}$, $R_{31}$ through $R_{36}$, $R^a$, $R^b$, $R^c$, $R^d$ and $R^e$ are independently amino, hydroxyl, thiol, oxo, or substituted or unsubstituted $C_{10}$ alkyl, $C_{10}$ alkoxy, $C_{10}$ alkylamino, or $C_{10}$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_9$ alkyl, $C_9$ alkoxy, $C_9$ alkylamino, or $C_9$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_8$ alkyl, $C_8$ alkoxy, $C_8$ alkylamino, or $C_8$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_7$ alkyl, $C_7$ alkoxy, $C_7$ alkylamino, or $C_7$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_6$ alkyl, $C_6$ alkoxy, $C_6$ alkylamino, or $C_6$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_5$ alkyl, $C_5$ alkoxy, $C_5$ alkylamino, or $C_5$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_4$ alkyl, $C_4$ alkoxy, $C_4$ alkylamino, or $C_4$ alkylthio.

In some embodiments, $R_1$ through $R_{17}$, $R_{31}$ through $R_{36}$, $R^a$, $R^b$, $R^c$, $R^d$ and $R^e$ are independently amino, hydroxyl, thiol, oxo, or substituted or unsubstituted $C_3$ alkyl, $C_3$ alkoxy, $C_3$ alkylamino, or $C_3$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_2$ alkyl, $C_2$ alkoxy, $C_2$ alkylamino, or $C_2$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, or substituted or unsubstituted $C_1$ alkyl, $C_1$ alkoxy, $C_1$ alkylamino, or $C_1$ alkylthio.

Modified alginate polymers can be of any desired molecular weight. The weight average molecular weight of the alginates is preferably between 1,000 and 1,000,000 Daltons, more preferably between 10,000 and 500,000 Daltons as determined by gel permeation chromatography.

Modified alginate polymers can contain any ratio of mannuronate monomers, guluronate monomers, and covalently modified monomers. In some embodiments, greater than 2.5%, 5%, 7.5%, 10%, 12%, 14%, 15%, 16%, 18%, 20%, 22%, 24%, 25%, 26%, 28%, 30%, 32.5%, 35%, 37.5%, 40%, 45%, 50%, 55%, or 60% of the monomers in the modified alginate polymer are covalently modified monomers. Preferably greater than 10%, more preferably greater than 20%, and most preferably greater than 30% of the monomers in the modified alginate polymer are covalently modified monomers.

Modified alginate polymers can be produced incorporating covalently modified monomers possessing a range of different hydrogen bonding potentials, hydrophobicities/hydrophilicities, and charge states. The inclusion of covalently modified monomers into an alginate polymer alters the physiochemical properties of alginate polymer. Accordingly, the physiochemical properties of alginates can be tuned for desired applications by the selective incorporation of covalently modified monomers.

For example, the glass transition temperature ($T_g$), can be varied by the incorporation of covalently modified monomers. In some embodiments, the modified alginate polymer powder possess a $T_g$, as measured by differential scanning calorimetry (DSC), of greater than 50° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 160° C., 175° C., 190° C., or 200° C.

The hydrophobicity/hydrophilicity of alginates can be varied by the incorporation of hydrophobic and/or hydrophilic covalently modified monomers. In preferred embodiments, the modified alginate polymer contains one or more hydrophobic covalently modified monomers. The relative hydrophobicity/hydrophilicity of modified alginates can be quantitatively assessed by measuring the contact angle of a water droplet on a film of the modified alginate polymer using a goniometer. In some embodiments, the modified alginate has a contact angle of less than 90° (i.e. it is hydrophilic). In preferred embodiments, the modified alginate has a contact angle of more than 90° (i.e. it is hydrophobic). In some embodiments, the modified alginate has a contact angle of more than 95°, 100°, 105°, 110°, 115°, or 120°.

In embodiments used for cell encapsulation, the modified alginate polymer can be ionically crosslinked by a polyvalent cation such as $Ca^{2+}$, $Sr^{2+}$, or $Ba^{2+}$ to form hydrogels. The ability of modified alginates to form stable hydrogels in physiological conditions can be quantified using the hydrogel formation assay described in Example 2.

In some embodiments, the modified alginate polymer forms hydrogels such that the fluorescence intensity measured using the high throughput hydrogel formation assay described herein is greater than 10,000, 15,000, 20,000, 25,000, 30,000, 35,000, 40,000, 45,000, 50,000, or 55,000. In preferred embodiments, the modified alginate polymer forms hydrogels such that the fluorescence intensity measured using the high throughput hydrogel formation assay described herein is greater than 15,000. In preferred embodiments, the modified alginate polymer forms hydrogels such that the fluorescence intensity measured using the high throughput hydrogel formation assay described herein is between 15,000 and 55,000, preferably between 20,000 and 55,000, more preferably between 25,000 and 55,000.

In embodiments used for cell encapsulation, the modified alginate polymer forms a hydrogel with sufficient porosity to permit nutrients, waste, and the hormones and/or proteins secreted from encapsulated cells to diffuse freely into and out of the capsules, while simultaneously preventing the incursion of immune cells into the gel matrix. The porosity and surface area of modified alginate hydrogels can be measured using BET analysis. Prior to BET analysis, solvent and volatile impurities are removed by prolonged heating of the modified alginate gel under vacuum. Subsequently, the hydrogel samples are cooled under vacuum, for example by liquid nitrogen, and analyzed by measuring the volume of gas (typically $N_2$, Kr, $CO_2$, or Ar gas) adsorbed to the hydrogel at specific pressures. Analysis of the physisorption of the gas at variable pressures is used to characterize the total surface area and porosity of gels formed by the modified alginate polymers. The preferred method of determining hydrogel porosity is BET analysis.

In preferred embodiments, the modified alginate forms a hydrogel with sufficient porosity to permit nutrients, waste, and the hormones and/or proteins secreted from encapsulated cells to diffuse freely into and out of the capsules, while simultaneously preventing the incursion of immune cells into the gel matrix. In some embodiments, the porosity of the hydrogel formed by the modified alginate polymer is increased by 5%, 10%, 15%, or 20% relative to the porosity of a hydrogel formed from the unmodified alginate polymer. In alternative embodiments, the porosity of the hydrogel formed by the modified alginate polymer is decreased by 5%, 10%, 15%, or 20% relative to the porosity of a hydrogel formed from the unmodified alginate polymer.

In preferred embodiments used for cell encapsulation, the modified alginate is biocompatible. The biocompatibility of modified alginates can be quantitatively determined using the fluorescence-based in vivo biocompatibility assay described in Example 5. In this assay, cathepsin activity was measured using an in vivo fluorescence assay to quantify the foreign body response to the modified alginate.

In some embodiments, the modified alginate polymer is biocompatible such that the fluorescence response normalized to unmodified alginate measured using the in vivo biocompatibility assay described herein is less than 100%, 95%, 90%, 85%, 80%, 75%, 70%, 65%, 60%, 55%, 50%, 45%, or 40%. In preferred embodiments, the modified alginate polymer induces a lower foreign body response than unmodified alginate. This is indicated by fluorescence response normalized to unmodified alginate of less than 100%. In some embodiments, the modified alginate polymer is biocompatible such that the fluorescence response normalized to unmodified alginate measured using the in vivo biocompatibility assay described herein is less than 75%, more preferably less than 65%, and most preferably less than 50%.

B. Capsules and Particle Morphology

Capsules are particles having a mean diameter of about 150 μm to about 5 cm. The disclosed capsules can be formed of cross-linked hydrogel. Other than the encapsulated material, the capsules, for example, can be formed solely of cross-linked hydrogel, can have a cross-linked hydrogel core that is surrounded by one or more polymeric shells, can have one or more cross-linked hydrogel layers, can have a cross-linked hydrogel coating, or a combination thereof. The capsule may have any shape suitable for, for example, cell encapsulation. The capsule may contain one or more cells dispersed in the cross-linked hydrogel, thereby "encapsulating" the cells. Preferred capsules are formed of or include one or more of the disclosed modified alginates. Preferred capsules have a mean diameter of about 150 μm to about 8 mm.

The capsules can have any mean diameter from about 150 μm to about 5 cm. Preferably the capsules have a mean diameter that is greater than 1 mm, preferably 1.5 mm or greater. In some embodiments, the capsules can be as large as about 8 mm in diameter. For example, the capsule can be in a size range of about 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, or 1.5 mm to 2 mm.

The rate of molecules entering the capsule necessary for cell viability and the rate of therapeutic products and waste material exiting the capsule membrane can be selected by modulating capsule permeability. Capsule permeability can also be modified to limit entry of immune cells, antibodies, and cytokines into the capsule. Generally, as shown by the examples, known methods of forming hydrogel capsules can produce capsules the permeability of which limit entry of immune cells, antibodies, and cytokines into the capsule. Since different cell types have different metabolic requirements, the permeability of the membrane can be optimized based on the cell type encapsulated in the hydrogel. The diameter of the capsules is an important factor that influences both the immune response towards the cell capsules as well as the mass transport across the capsule membrane.

The growing recognition of the parameters driving fibrosis in vivo has been applied to the analysis of the performance of modified alginates. Intraperitoneal (IP) implantation of modified alginate capsules revealed that modified alginates may result in abnormally shaped capsules when crosslinked using conditions defined for unmodified alginates. These abnormally shaped capsules can complicate implementation and interpretation of modified alginate capsules implanted IP. In an effort to improve the capsule morphology, formulation methods for use with modified alginate microparticles were developed where modified alginates were blended with a small amount of high molecular weight alginate. Particles prepared from this mixture yielded particles with improved morphology and stability.

The unmodified alginate typically has a weight average molecular weight of about 50,000 Daltons to about 500,000 Daltons; however, unmodified alginates having molecular weights can also be used. In some embodiments, the weight average molecular weight is from about 50,000 to about 250,000 Daltons, more preferably from about 50,000 to about 150,000 Daltons. In some embodiments, the weight average molecular weight is about 100,000 Daltons.

In other embodiments, one or more additional hydrogel-forming polymers are used in combination with unmodified alginate or in place of unmodified alginate. Such polymers are known in the art. Examples include, but are not limited to, PEG, chitosan, dextran, hyaluronic acid, silk, fibrin, poly(vinyl alcohol) and poly(hydroxyl ethyl methacrylate).

For example, particles prepared from modified alginate 263_A12 microparticles formulated with barium and mannitol were compared to particles prepared from 263_A12 blended with a small amount of unmodified SLG100 alginate (16% by weight). The particles prepared from a mixture of modified alginate and unmodified alginate produced more homogenous microparticle populations in terms of shape and size as evaluated by scanning electron microscopy (SEM). Quantitative fluorescence analysis with prosense at several time points with modified alginates blended with SLG100 showed that several reformulated modified alginates display less inflammatory response at day 7 compared to the control alginate. Initial experiments with large capsules (1.5 mm diameter) were comparably clean capsules after 2 weeks in the IP space of immunocompetent C57BL6 mice. Subsequent experiments (Example 9) show that encapsulated human cells can achieve glucose-responsive, long-term glycemic correction (over 170 days) in an immune-competent diabetic animal with no immunosuppression. This result was accomplished using a modified alginate as disclosed to encapsulate the human cells. The resulting capsule mitigates immunological responses to human cell implants, effectively delaying the fibrotic deposition that leads to implant tissue necrosis. This formulation provided sufficient immunoprotection to enable long-term glycemic correction, in spite of the xenogeneic stimulation that these human cells manifest in an immunocompetent rodent recipient.

Because the disclosed modified alginates mediate the reduced fibrosis, capsules made of other materials but coated or encapsulated with the modified alginates is a useful form of capsule for achieving reduced fibrosis. This, the capsules can include capsules and particles made of a variety of materials that are then coated or encapsulated in alginate that is or included modified alginate.

The disclosed compositions may be fabricated into artificial organs, such as an artificial pancreas containing encapsulated islet cells. In some of these embodiments, the cells are encapsulated in a single hydrogel compartment. In other embodiments, the composition contains a plurality of encapsulated cells dispersed or encapsulated in a biocompatible structure.

C. Preparation of Modified Alginate Polymers

Modified alginates can be prepared through covalent modification of any available alginate polymer. Covalently modified monomers can be introduced into alginate polymers using a variety of synthetic procedures known in the art.

In some embodiments, mannuronate and guluronate monomers are covalently modified via esterification and/or amidation of their carboxylic acid moiety. In alternative embodiments, mannuronate and guluronate monomers are covalently modified via phosphorylation or acetal formation. Stoichiometric variation of the reactants during covalent modification can be used to vary the amount of covalently modified monomer incorporated into the modified alginate.

In addition to the reactions discussed below, alternative synthetic methodologies for the covalent modification of mannuronate and guluronate monomers are known in the art. (see, for example, March, "Advanced Organic Chemistry," 5$^{th}$ Edition, 2001, Wiley-Interscience Publication, New York).

1. Modification Via the Carboxylate Moiety of the Mannuronate and Guluronate Monomers Scheme 1.

Representative Reaction Conditions: i. HO—R$_1$, 2-Chloro-4,6-dimethoxy-1,3,5-triazine (CDMT), N-methyl morpholine (NMM); ii. HNR$_1$R$_7$, CDMT, NMM.

Mannuronate and guluronate monomers contain a carboxylic acid moiety which can serve as a point of covalent modification. In preferred embodiments, the carboxylic acid moiety present on one or more mannuronate and/or guluronate residues (1) are reacted as shown in Scheme 1.

Mannuronate and guluronate residues (A) can be readily esterified by a variety of methods known in the art, forming covalently modified monomer B. For example, using a Steglich Esterification, mannuronate and guluronate residues (A) can be esterified by reaction with any suitable alcohol (HO—R$_1$) in the presence of a carbodiimide (for example, N,N'-dicyclohexylcarbodiimide (DCC), N,N'-diisopropylcarbodiimide (DIC), or 1-ethyl-3-(3-dimethylaminopropyl) carbodiimide (EDC)) and dimethylaminopyridine (DMAP). In a preferred method, mannuronate and guluronate residues (A) were esterified by reaction with a large molar excess of an alcohol (HO—R$_1$) in the presence of 2-Chloro-4,6-dimethoxy-1,3,5-triazine (CDMT) and N-methyl morpholine (NMM). See, for example, Garrett, C.

E. et al. *Tetrahedron Lett.* 2002; 43(23): 4161-4164. Preferred alcohols for use as reagents in esterification include those shown below.

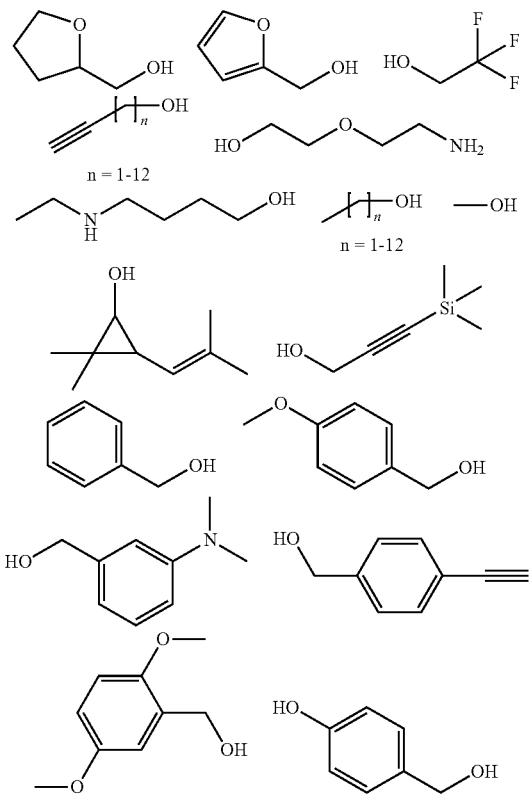

Mannuronate and guluronate residues (A) can also be covalently modified via amidation, forming modified monomer C. For example, mannuronate and guluronate residues (A) can amidated by reaction with any suitable amine ($R_1$—$NH_2$) in the presence of a carbodiimide and DMAP. In a preferred method, mannuronate and guluronate residues (A) were amidated by reaction with a stoichiometric amount of a suitable amine ($R_1$—$NH_2$) in the presence of CDMT and NMM. Preferred amines for use as reagents in amidation reactions include those shown below.

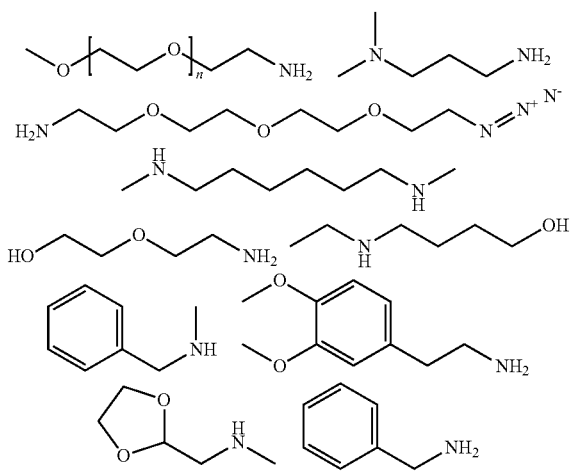

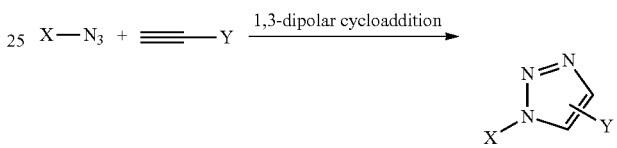

2. Modification of Mannuronate and Guluronate Monomers Via Click Chemistry

In some embodiments, mannuronate and guluronate monomers are covalently modified to introduce a functional group which can be further reacted via click chemistry.

In preferred embodiments, amidation and/or esterification is used to introduce a functional group which can further reacted using a 1,3-dipolar cycloaddition reaction (i.e. a Huisgen cycloaddition reaction). In a 1,3-dipolar cycloaddition reaction, a first molecule containing an azide moiety is reacted with a second molecule containing a terminal or internal alkyne. As shown below, the azide and the alkyne groups undergo an intramolecular 1,3-dipolar cycloaddition reaction, coupling the two molecules together and forming a 1,2,3-triazole ring.

$$X-N_3 + \equiv-Y \xrightarrow{\text{1,3-dipolar cycloaddition}}$$

The regiochemistry of 1,3-dipolar cycloadditions reaction can be controlled by addition of a copper(I) catalyst (formed in situ by the reduction of $CuSO_4$ with sodium ascorbate) or a ruthenium catalyst (such as Cp*RuCl($PPh_3$)$_2$, Cp*Ru (COD), or Cp*[$RuCl_4$]). For example, using a copper catalyst, azides and terminal alkynes can be reacted to exclusively afford the 1,4-regioisomers of 1,2,3-triazoles. Similarly, in the presence of a suitable ruthenium catalyst, azides can be reacted with internal or terminal alkynes to form exclusively the 1,5-regioisomers of 1,2,3-triazoles.

In some embodiments, amidation and/or esterification is used to form a covalently modified monomer containing an alkyne moiety. In these embodiments, the alkyne moiety present on the covalently modified monomer can be further reacted with a second molecule containing an azide functional group. Upon reaction, the azide and the alkyne groups undergo an intramolecular 1,3-dipolar cycloaddition reaction forming a 1,2,3-triazole ring, coupling the second molecule to the covalently modified monomer.

Examples of the alkyne-containing amidation/esterification reactant include $X_a$—$R_z$—C≡C—$R_x$; wherein $X_a$ is —OH or —$NH_2$; wherein $R_z$ is alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; and wherein $R_x$ is hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments,
(1) $R_z$ is hydrogen, (A)

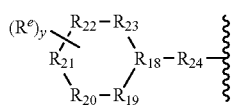

Formula IX wherein y is an integer from 1 to 11; wherein $R^e$ is independently alkoxy, amino, alkylamino, dialkylamino, hydroxy, alkenyl, alkynyl, substituted alkyl, substituted alkenyl, substituted alkynyl, phenyl, substituted phenyl, aryl, substituted aryl, heteroaryl, substituted heteroaryl, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, and polypeptide group; or together with the carbon atom to which they are attached, form a 3- to 8-membered unsubstituted or substituted carbocyclic or heterocyclic ring; wherein one instance of $R^e$ is or contains $X_a$; wherein $R_{18}$, $R_{19}$, $R_{20}$, $R_{21}$, $R_{22}$, and $R_{23}$ are independently C, O, N, or S, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ is independently —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —$SO_2$—, or $NR_4$, wherein each $R_{25}$ is independently absent, hydrogen, =O, =S, —OH, —SH, —$NR_4$, wherein $R_4$ is alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group;

(B) —$(CH_2)_s$—$R_{26}$, wherein s is an integer from 0 to 20; wherein $R_{26}$ is —$X_a$, —O—$R_{27}$, —S—$R_{27}$, —$(CH_2)_r$—$R_{27}$, —CO—$R_{27}$, or —$CHR_{28}R_{29}$, wherein r is an integer from 0 to 19; wherein $R_{27}$ is —$X_a$, —$(CH_2)_u$—$R_{30}$, wherein u is an integer from 0 to 18; wherein $R_{28}$ is —$(CH_2)_t$—$R_{30}$, $R_{29}$ is —$(CH_2)_v$—$R_{30}$, and t and v are integers from 0 to 18, wherein t and v together total 0 to 18; wherein $R_{30}$ is —$X_a$, methyl, —OH, —SH, or —COOH; or (C)

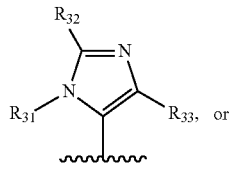

Formula VII

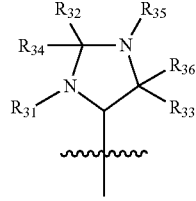

Formula VIII wherein $R_{31}$, $R_{32}$, $R_{33}$, $R_{34}$, $R_{35}$, and $R_{36}$ are, independently, hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; and wherein one instance of $R_{31}$, $R_{32}$, $R_{33}$, $R_{34}$, $R_{35}$, or $R_{36}$ is or contains $X_a$;

(2) $R_x$ is hydrogen, (A)

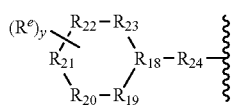

Formula IX wherein y is an integer from 0-11; wherein $R^e$ is independently alkoxy, amino, alkylamino, dialkylamino, hydroxy, alkenyl, alkynyl, substituted alkyl, substituted alkenyl, substituted alkynyl, phenyl, substituted phenyl, aryl, substituted aryl, heteroaryl, substituted heteroaryl, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, and polypeptide group; or together with the carbon atom to which they are attached, form a 3- to 8-membered unsubstituted or substituted carbocyclic or heterocyclic ring; wherein $R_{18}$, $R_{19}$, $R_{20}$, $R_{21}$, $R_{22}$, and $R_{23}$ are independently C, O, N, or S, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ is independently —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein X$_b$ is absent, —O—, —S—, —SO$_2$—, or NR$_4$, wherein each R$_{25}$ is independently absent, hydrogen, =O, =S, —OH, —SH, —NR$_4$, wherein R$_4$ is alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, C$_3$-C$_{20}$ cyclic, substituted C$_3$-C$_{20}$ cyclic, heterocyclic, substituted heterocyclic, aminoacid, poly(ethylene glycol), peptide, or polypeptide group;

(B) —(CH$_2$)$_s$—R$_{26}$, wherein s is an integer from 0 to 20; wherein R$_{26}$ is —O—R$_{27}$, —S—R$_{27}$, —(CH$_2$)$_r$—R$_7$, —CO—R$_{27}$, —CO—R$_{27}$, or —CHR$_{28}$R$_{29}$, wherein r is an integer from 0 to 19; wherein R$_{27}$ is —(CH$_2$)$_u$—R$_{30}$, wherein u is an integer from 0 to 18; wherein R$_{28}$ is —(CH$_2$)$_t$—R$_{30}$, R$_{29}$ is —(CH$_2$)$_v$—R$_{30}$, and t and v are integers from 0 to 18, wherein t and v together total 0 to 18; wherein R$_{30}$ is methyl, —OH, —SH, or —COOH; or (C)

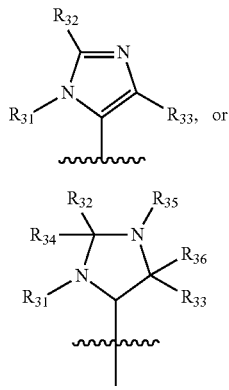

Formula VII

Formula VIII wherein R$_{31}$, R$_{32}$, R$_{33}$, R$_{34}$, R$_{35}$, and R$_{36}$ are, independently, hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, C$_3$-C$_{20}$ cyclic, substituted C$_3$-C$_{20}$ cyclic, heterocyclic, substituted heterocyclic, aminoacid, poly(ethylene glycol), peptide, or polypeptide group; and (3) wherein R$_z$ and R$_x$ are not both hydrogen.

Examples of the azide-containing second molecule include R$_w$—N$_3$, wherein R$_w$ is alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C$_3$-C$_{20}$ cyclic, substituted C$_3$-C$_{20}$ cyclic, heterocyclic, substituted heterocyclic, aminoacid, poly(ethylene glycol), peptide, or polypeptide group.

In some embodiments, R$_w$ is (A)

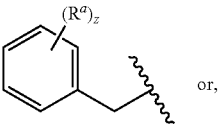

Formula X or,

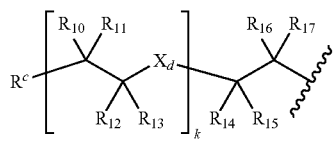

Formula XII wherein k are independently an integer from 1 to 30; wherein z is an integer from 0 to 4; wherein X$_d$ is O or S; wherein R$^a$ is independently alkoxy, amino, alkylamino, dialkylamino, hydroxy, alkenyl, alkynyl, substituted alkyl, substituted alkenyl, substituted alkynyl, phenyl, substituted phenyl, aryl, substituted aryl, heteroaryl, substituted heteroaryl, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, C$_3$-C$_{20}$ cyclic, substituted C$_3$-C$_{20}$ cyclic, heterocyclic, substituted heterocyclic, aminoacid, poly(ethylene glycol), peptide, or polypeptide group; or together with the carbon atom to which they are attached, form a 3- to 8-membered unsubstituted or substituted carbocyclic, or heterocyclic ring; and wherein R$_{10}$, R$_{11}$, R$_{12}$, R$_{13}$, R$_{14}$, R$_{15}$, R$_{16}$, R$_{17}$ are independently hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C$_3$-C$_{20}$ cyclic, substituted C$_3$-C$_{20}$ cyclic, heterocyclic, substituted heterocyclic, aminoacid, poly(ethylene glycol), peptide, or polypeptide group; or (B)

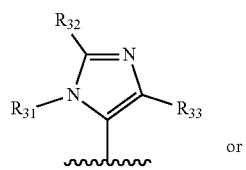

Formula VII or

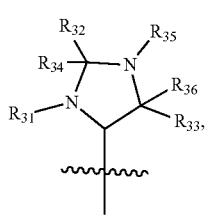

Formula VIII wherein $R_{31}$, $R_{32}$, $R_{33}$, $R_{34}$, $R_{35}$, and $R_{36}$ are, independently, hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In alternative embodiments, amidation and/or esterification is used to form a covalently modified monomer containing an azide moiety. In these embodiments, the azide moiety present on the covalently modified monomer can be further reacted with a second molecule containing a terminal or internal alkyne. Upon reaction, the azide and the alkyne groups undergo an intramolecular 1,3-dipolar cycloaddition reaction forming a 1,2,3-triazole ring, coupling the second molecule to the covalently modified monomer.

Examples of the azide-containing amidation/esterification reactant include $X_c$—$R_w$—$N_3$, where $X_c$ is —OH or —NH$_2$ and $R_w$ is alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, $X_c$ is not —NH$_2$ and $R_w$ is not —CH$_2$—Ar— or —CH$_2$—CH$_2$—(O—CH$_2$—CH$_2$)$_3$—.

In some embodiments, $R_w$ is (A)

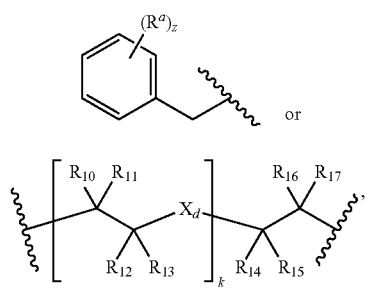

Formula X or

Formula XI wherein k are independently an integer from 1 to 30; wherein z is an integer from 0 to 4; wherein $X_d$ is O or S; wherein $R^a$ is independently alkoxy, amino, alkylamino, dialkylamino, hydroxy, alkenyl, alkynyl, substituted alkyl, substituted alkenyl, substituted alkynyl, phenyl, substituted phenyl, aryl, substituted aryl, heteroaryl, substituted heteroaryl, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or together with the carbon atom to which they are attached, form a 3- to 8-membered unsubstituted or substituted carbocyclic, or heterocyclic ring; wherein one instance of $R^a$ is or contains $X_c$; wherein $R_{10}$, $R_{11}$, $R_{12}$, $R_{13}$, $R_{14}$, $R_{15}$, $R_{16}$, $R_{17}$ are independently hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; and wherein one instance of $R_{10}$, $R_{11}$, $R_{12}$, $R_{13}$, $R_{14}$, $R_{15}$, $R_{16}$, or $R_{17}$ is or contains $X_c$; or (B)

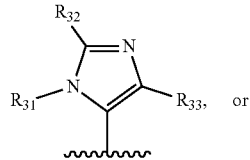

Formula VII

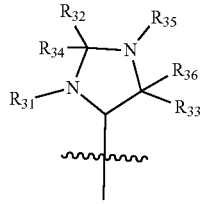

Formula VIII wherein $R_{31}$, $R_{32}$, $R_{33}$, $R_{34}$, $R_{35}$, and $R_{36}$ are, independently, hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; and wherein one instance of $R_{31}$, $R_{32}$, $R_{33}$, $R_{34}$, $R_{35}$, or $R_{36}$ is or contains $X_c$.

Examples of the alkyne-containing second molecule include $R_z$—C≡C—$R_x$, wherein $R_z$ and $R_x$ are, independently, hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, $R_z$ and $R_x$ are independently hydrogen, (A)

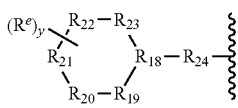

Formula IX wherein y is an integer from 0 to 11; wherein $R^e$ is independently alkoxy, amino, alkylamino, dialkylamino, hydroxy, alkenyl, alkynyl, substituted alkyl, substituted alkenyl, substituted alkynyl, phenyl, substituted phenyl, aryl, substituted aryl, heteroaryl, substituted heteroaryl, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, and polypeptide group; or together with the carbon atom to which they are attached, form a 3- to 8-membered unsubstituted or substituted carbocyclic or heterocyclic ring; wherein $R_{18}$, $R_{19}$, $R_{20}$, $R_{21}$, $R_{22}$, and $R_{23}$ are independently C, O, N, or S, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ is independently —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —$SO_2$—, or $NR_4$, wherein each $R_{25}$ is independently absent, hydrogen, =O, =S, —OH, —SH, —$NR_4$, wherein $R_4$ is alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group;

(B) —$(CH_2)_s$—$R_{26}$, wherein s is an integer from 0 to 20; wherein $R_{26}$ is —O—$R_{27}$, —S—$R_{27}$, —$(CH_2)_r$—$R_{27}$, —CO—$R_{27}$, or —$CHR_{28}R_{29}$, wherein r is an integer from 0 to 19; wherein $R_{27}$ is —$(CH_2)_u$—$R_{30}$, wherein u is an integer from 0 to 18; wherein $R_{28}$ is —$(CH_2)_t$—$R_{30}$, $R_{29}$ is —$(CH_2)_v$—$R_{30}$, and t and v are integers from 0 to 18, wherein t and v together total 0 to 18; wherein $R_{30}$ is methyl, —OH, —SH, or —COOH; or (C)

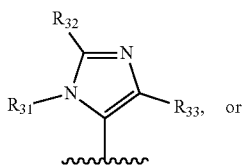

Formula VII

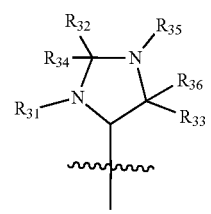

Formula VIII wherein $R_{31}$, $R_{32}$, $R_{33}$, $R_{34}$, $R_{35}$, and $R_{36}$ are, independently, hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; and wherein $R_z$ and $R_x$ are not both hydrogen.

In some embodiments, the azide moiety can be added to a covalently modified monomer containing a leaving group, such as I, Br, OTs, OMs. In some embodiments, amidation and/or esterification is used to form the covalently modified monomer containing the leaving group. Examples of the leaving group-containing amidation/esterification reactant include $X_c$—$R_w$-L, where $X_c$ is —OH or —$NH_2$, L is the leaving group, and $R_w$ is alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, $X_c$ is not —$NH_2$ and $R_w$ is not —$CH_2$—Ar— or —$CH_2$—$CH_2$—(O—$CH_2$—$CH_2$)$_3$—.

In some embodiments, $R_w$ is (A)

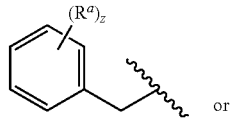

Formula X or

Formula XI

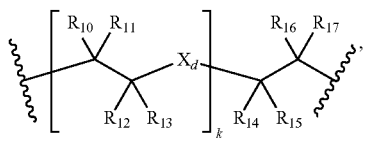

wherein k are independently an integer from 1 to 30; wherein z is an integer from 0 to 4; wherein $X_d$ is O or S; wherein $R^a$ is independently alkoxy, amino, alkylamino, dialkylamino, hydroxy, alkenyl, alkynyl, substituted alkyl, substituted alkenyl, substituted alkynyl, phenyl, substituted phenyl, aryl, substituted aryl, heteroaryl, substituted heteroaryl, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or together with the carbon atom to which they are attached, form a 3- to 8-membered unsubstituted or substituted carbocyclic, or heterocyclic ring; wherein one instance of $R^a$ is or contains $X_c$; wherein $R_{10}$, $R_{11}$, $R_{12}$, $R_{13}$, $R_{14}$, $R_{15}$, $R_{16}$, $R_{17}$ are independently hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; and wherein one instance of $R_{10}$, $R_{11}$, $R_{12}$, $R_{13}$, $R_{14}$, $R_{15}$, $R_{16}$, or $R_{17}$ is or contains $X_c$; or (B)

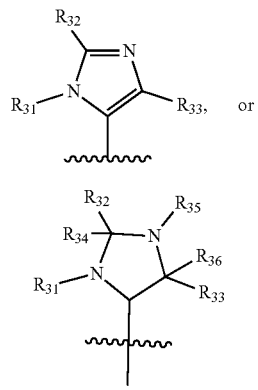

Formula VII

Formula VIII wherein $R_{31}$, $R_{32}$, $R_{33}$, $R_{34}$, $R_{35}$, and $R_{36}$ are, independently, hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; and wherein one instance of $R_{31}$, $R_{32}$, $R_{33}$, $R_{34}$, $R_{35}$, or $R_{36}$ is or contains $X_c$.

In some embodiments, $X_c$ is not —$NH_2$ and $R_w$ is not —$CH_2$—Ar— or —$CH_2$—$CH_2$—(O—$CH_2$—$CH_2$)$_3$—.

In preferred embodiments, amidation is used to form a covalently modified monomer containing an azide moiety. Subsequently, the azide moiety present on the covalently modified monomer is reacted with a second molecule containing a terminal or internal alkyne, forming a 1,2,3-triazole ring and coupling the second molecule to the covalently modified monomer.

As shown in Scheme 2, different strategies can be employed to prepare covalently modified monomers containing an azide moiety.

Scheme 2.

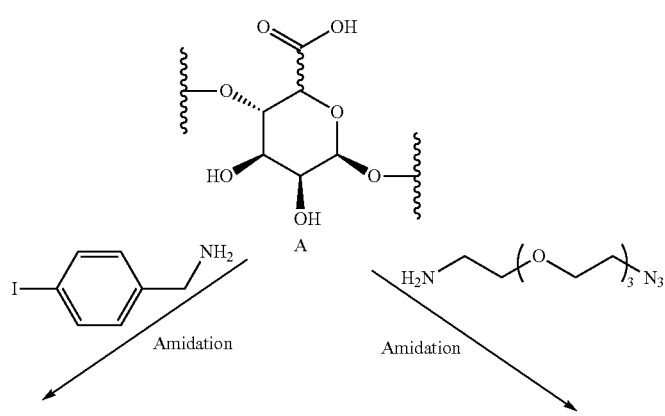

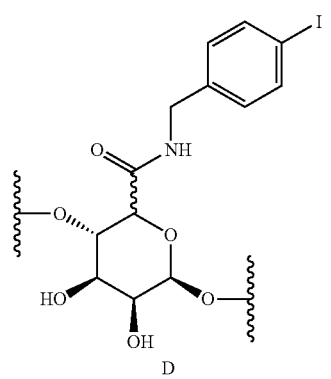

D

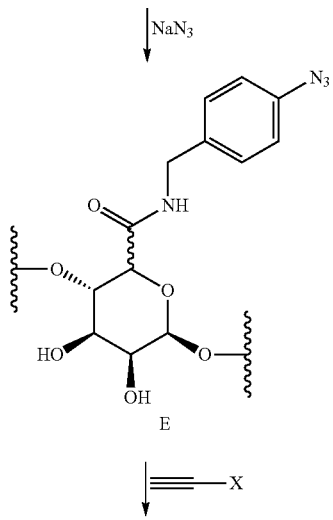

E

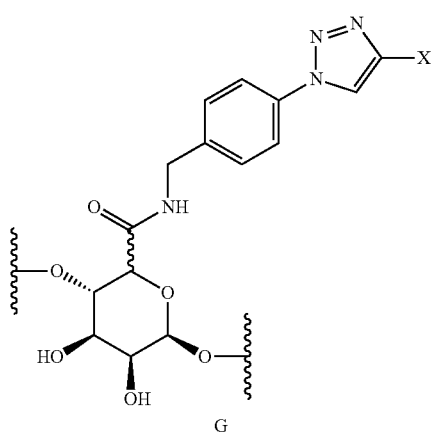

G

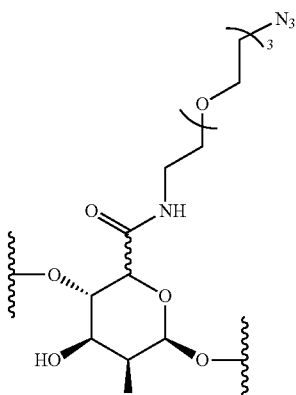

F

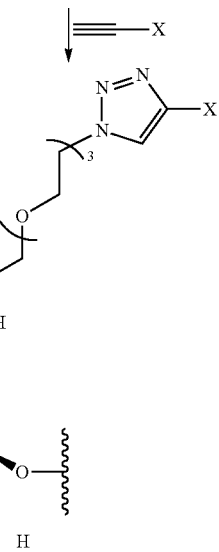

H

For example, mannuronate and guluronate residues (A) can amidated by reaction with an amine substituted with an azide moiety (for example, 11-Azido-3,6,9-trioxaundecan-1-amine) in the presence of a carbodiimide and DMAP, forming azide-functionalized modified monomer F in a single synthetic step. Alternatively, mannuronate and guluronate residues (A) can amidated by reaction with an amine substituted with any moiety which can be readily transformed into an azide. For example, mannuronate and guluronate residues can be amidated by reaction with 4-iodobenzylamine in the presence of a carbodiimide and DMAP, forming iodo-functionalized monomer D. The iodine moiety can then be readily converted to the azide, for example by treatment with sodium azide.

Subsequently, the azide-functionalized monomers can be reacted with a molecule containing an alkyne functionality. For example, azide-functionalized monomers F and E can be reacted with a molecule containing a terminal alkyne functionality in the presence of a copper(I) catalyst (formed in situ by the reduction of $CuSO_4$ with sodium ascorbate), forming covalently modified monomers G and H.

Preferred alkynes for use as reagents in 1,3-dipolarcycloaddition reactions include those shown below.

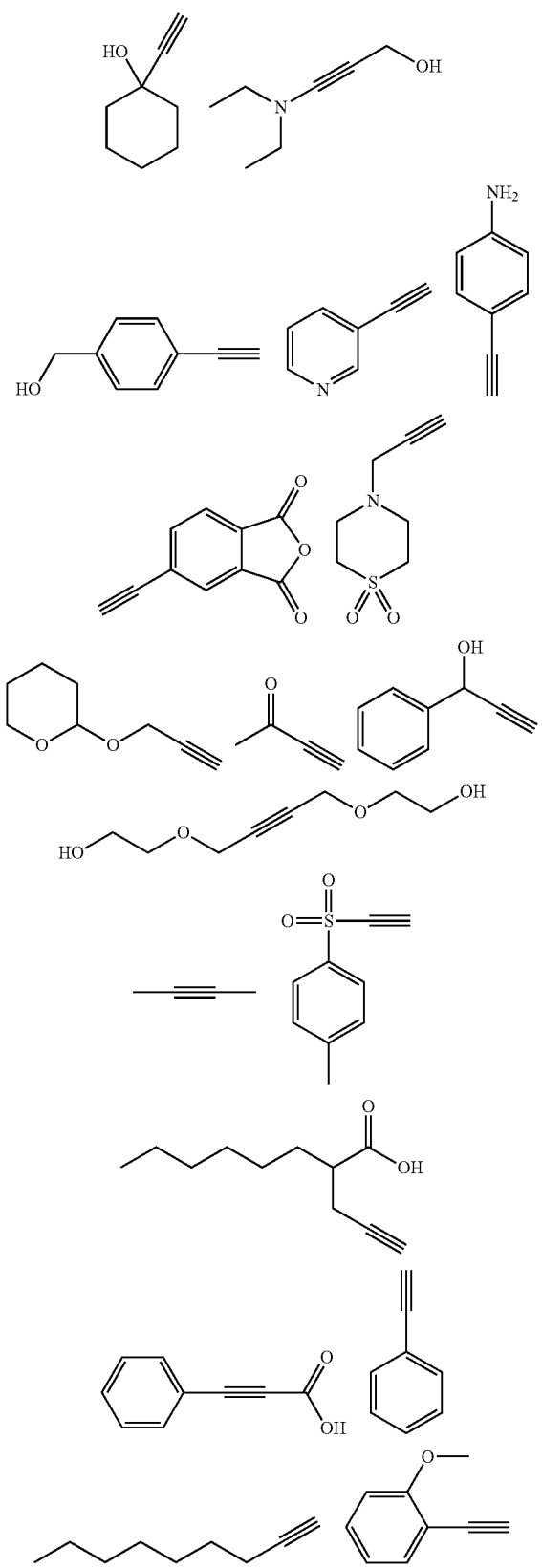

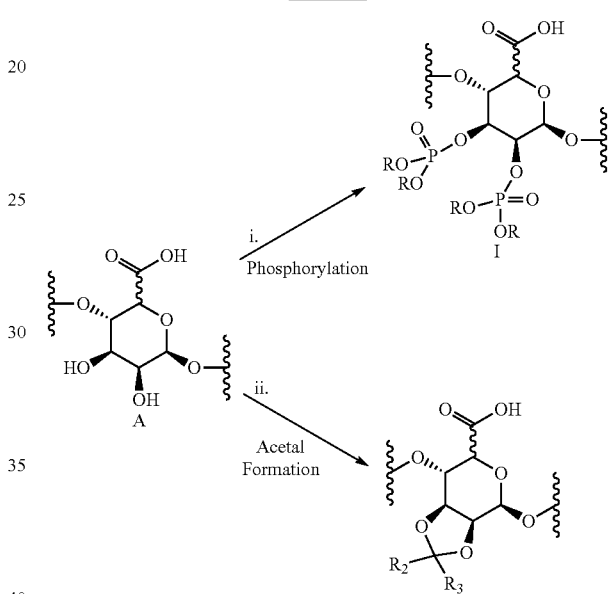

3. Modification Via the Hydroxyl Moiety of the Mannuronate and Guluronate Monomers Mannuronate and guluronate monomers contain hydroxyl moieties which can serve as a point of covalent modification. In preferred embodiments, the hydroxyl moieties of mannuronate and guluronate residues (1) are reacted as shown in Scheme 3.

Representative Reaction Conditions: i. I—PO(OR$_5$)$_2$, pyridine; ii. R$_2$—CO—R$_3$, H$^+$.

Mannuronate and guluronate residues (A) can be phosphorylated by a variety of methods known in the art, forming covalently modified monomer I. For example, mannuronate and guluronate residues can be phosphorylated by reaction with I—PO(OR$_5$)$_2$ in the presence of pyridine (Stowell, J. K. and Widlanski, T. S. *Tetrahedron Let.* 1995; 36(11): 1825-1826.).

Mannuronate and guluronate residues (A) can also be converted to a cyclic acetal using procedures known in the art. For example, a cyclic acetal can be formed by reaction of mannuronate and guluronate residues with any suitable ketone (R$_2$—CO—R$_3$) in acidic conditions.

4. Methods for Preparing Multiply Modified Alginate Polymers

In the case of singularly modified alginate polymers, only a single reaction or sequence of reactions is performed, introducing one type of covalently modified monomer.

In the case of multiply modified alginate polymers, one or more reactions are performed to introduce multiple different types of covalently modified monomers into the modified alginate polymer. In some embodiments, multiply modified alginate polymers are prepared using multiple sequential synthetic reactions. For example, the multiply modified alginate polymer shown below can be prepared using two sequential reactions: (1) amidation of mannuronate and guluronate monomers with methylamine in the presence of CDMT and NMM; and (2) esterification of mannuronate and guluronate residues with ethanol in the presence of CDMT and NMM.

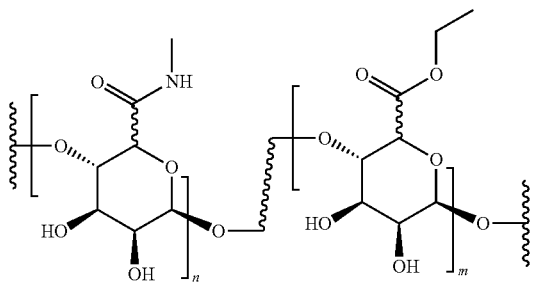

In alternative embodiments, multiply modified alginate polymers can be prepared using a 'one-pot' synthesis. In these embodiments, multiple covalently modified monomers are introduced into the alginate polymer in a single synthetic step. For example, the multiply modified alginate polymer shown above can alternatively be prepared in a single synthetic step by reacting an alginate polymer with methylamine and ethanol in the presence of CDMT and NMM.

Any type or form of modified alginate, any type or form of alginate modification, and any type or form of reagent for modifying alginate can be, independently and in any combination, specifically included or excluded in any of the disclosed modified alginates, alginate modifications, reagents for alginate modifications, methods, and kits, and in any context, combination, or use. For example, any type or form of esterification reagent, amidation reagent, click reagent, alkyne-containing reagent, azide-containing reagent, phosphorylating reagent, and ketone reagent, such as those described above and in the examples, can be, independently and in any combination, specifically included or excluded from use to modify alginates, and any alginate modifications and any modified alginates that include or are based on such reagents can be, independently and in any combination, specifically included or excluded in any of the disclosed modified alginates, alginate modifications, reagents for alginate modifications, methods, and kits, and in any context, combination, or use.

As another example, any of the reagents described in Table 2 can be, independently and in any combination, specifically included or excluded from use to modify alginates, and any alginate modifications and any modified alginates that include or are based on the reagents described in Table 2 can be, independently and in any combination, specifically included or excluded in any of the disclosed modified alginates, alginate modifications, reagents for alginate modifications, methods, and kits, and in any context, combination, or use. For example, all of the reagents described in Table 2 in combination but excluding reagent Y3 can be specifically included or excluded from use to modify alginates, and any alginate modifications and any modified alginates that include or are based on all the reagents described in Table 2 in combination but excluding reagent Y3 can be specifically included or excluded in any of the disclosed modified alginates, alginate modifications, reagents for alginate modifications, methods, and kits, and in any context, combination, or use.

As another example, any modified alginate, alginate modification, or reagents for alginate modification described in U.S. Patent Application No. 20120308650 can be, independently and in any combination, specifically included or excluded. U.S. Patent Application Publication No. 20120308650 is hereby incorporated herein by reference in its entirety, and specifically for its description of modified alginates, alginate modifications, and reagents for alginate modifications. Any of the R group substituents for any of the R groups described herein can be, independently and in any combination, specifically included or excluded as an option or as the choice for the respective R group.

D. Purification of Alginates

Commercial alginates are generally obtained from algae. Crude alginates from seaweed contain numerous contaminants, including polyphenols, proteins, and endotoxins (de Vos, P, et al. *Biomaterials* 2006; 27: 5603-5617). The presence of these impurities has been shown to limit the biocompatibility of implanted alginates.

To optimize the biocompatibility of the chemically modified alginates described herein, a rigorous purification methodology was developed to eliminate potentially irritating impurities. In preferred embodiments, ultra-pure low viscosity alginate (UPVLVG, FMC Biopolymer) was used as a substrate for covalent modification. Following each covalent modification, the modified alginates were filtered through modified silica columns, for example cyano-modified silica columns, aimed at capturing bulk organic impurities. Finally, after covalent modification of the alginate polymer is complete, the modified alginates are dialyzed to remove any remaining small-molecule or low molecular weight impurities. In a preferred method, the modified alginates are dialyzed against 10,000 molecular weight cut-off (MWCO) membrane to remove any remaining small-molecule impurities.

The purity of the modified alginates can be determined by $^1$H NMR analysis. In such an analysis, the $^1$H NMR spectra of the modified alginate polymer is collected, and peaks corresponding to the modified alginate polymer and to any impurities are integrated to determine the relative quantity of each species in the sample. In some embodiments, the purity of the modified alginate polymer, as determined by $^1$H NMR, is greater than 90%, 91%, 92%, 93%, 94%, 95%, 96%, 97%, 98%, or 99%. In preferred embodiments, purity of the modified alginate polymer, as determined by $^1$H NMR, is greater than 90%, more preferably greater than 95%.

III. Biological Materials

Biological material for encapsulation in the disclosed alginates can be any biological substance. For example, the biological material can be tissue, cells, biological micromolecules, or biological macromolecules. Examples of biological macromolecules include nucleotides, amino acids, cofactors, and hormones. Examples of biological macromolecules include nucleic acids, polypeptides, proteins, and polysaccharides. Examples of proteins include enzymes, receptors, secretory proteins, structural proteins, signaling proteins, hormones, and ligands. Any class, type, form, or particular biological material can be used together with any other classes, types, forms, or particular biological materials.

A. Cells

The cell type chosen for encapsulation in the disclosed compositions depends on the desired therapeutic effect. The cells may be from the patient (autologous cells), from another donor of the same species (allogeneic cells), or from another species (xenogeneic). Xenogeneic cells are easily accessible, but the potential for rejection and the danger of possible transmission of viruses to the patient restricts their clinical application. Any of these types of cells can be from natural sources, stem cells, derived cells, or genetically engineered cell.

In some embodiments, the cells secrete a therapeutically effective substance, such as a protein or nucleic acid. In some embodiments, the cells produce a metabolic product. In some embodiments, the cells metabolize toxic substances. In some embodiments, the cells form structural tissues, such as skin, bone, cartilage, blood vessels, or muscle. In some embodiments, the cells are natural, such as islet cells that naturally secrete insulin, or hepatocytes that naturally detoxify. In some embodiments, the cells are genetically engineered to express a heterologous protein or nucleic acid and/or overexpress an endogenous protein or nucleic acid.

Types of cells for encapsulation in the disclosed compositions include cells from natural sources, such as cells from xenotissue, cells from a cadaver, and primary cells; stem cells, such as embryonic stem cells, mesenchymal stem cells, and induced pluripotent stem cells; derived cells, such as cells derived from stem cells, cells from a cell line, reprogrammed cells, reprogrammed stem cells, and cells derived from reprogrammed stem cells; and genetically engineered cells, such as cells genetically engineered to express a protein or nucleic acid, cells genetically engineered to produce a metabolic product, and cells genetically engineered to metabolize toxic substances.

Types of cells for encapsulation in the disclosed compositions include hepatocytes, islet cells, parathyroid cells, endocrine cells, cells of intestinal origin, cells derived from the kidney, and other cells acting primarily to synthesize and secret, or to metabolize materials. A preferred cell type is a pancreatic islet cell or other insulin-producing cell. Hormone-producing cells can produce one or more hormones, such as insulin, parathyroid hormone, anti-diuretic hormone, oxytocin, growth hormone, prolactin, thyroid stimulating hormone, adrenocorticotropic hormone, follicle-stimulating hormone, lutenizing hormone, thyroxine, calcitonin, aldosterone, cortisol, epinephrine, glucagon, estrogen, progesterone, and testosterone. Genetically engineered cells are also suitable for encapsulation according to the disclosed methods. In some embodiments, the cells are engineered to produce one or more hormones, such as insulin, parathyroid hormone, anti-diuretic hormone, oxytocin, growth hormone, prolactin, thyroid stimulating hormone, adrenocorticotropic hormone, follicle-stimulating hormone, lutenizing hormone, thyroxine, calcitonin, aldosterone, cortisol, epinephrine, glucagon, estrogen, progesterone, and testosterone. In some embodiments, the cells are engineered to secrete blood clotting factors (e.g., for hemophilia treatment) or to secrete growth hormones. In some embodiments, the cells are contained in natural or bioengineered tissue. For example, the cells for encapsulation are in some embodiments a bioartificial renal glomerulus. In some embodiments, the cells are suitable for transplantation into the central nervous system for treatment of neurodegenerative disease.

Cells can be obtained directly from a donor, from cell culture of cells from a donor, or from established cell culture lines. In the preferred embodiments, cells are obtained directly from a donor, washed and implanted directly in combination with the polymeric material. The cells are cultured using techniques known to those skilled in the art of tissue culture.

Cell viability can be assessed using standard techniques, such as histology and fluorescent microscopy. The function of the implanted cells can be determined using a combination of these techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. For example, pancreatic islet cells and other insulin-producing cells can be implanted to achieve glucose regulation by appropriate secretion of insulin. Other endocrine tissues and cells can also be implanted.

The site, or sites, where cells are to be implanted is determined based on individual need, as is the requisite number of cells. For cells replacing or supplementing organ or gland function (for example, hepatocytes or islet cells), the mixture can be injected into the mesentery, subcutaneous tissue, retroperitoneum, properitoneal space, and intramuscular space.

The amount and density of cells encapsulated in the disclosed compositions, such as capsules and microcapsules, will vary depending on the choice of cell, hydrogel, and site of implantation. In some embodiments, the single cells are present in the hydrogel at a concentration of $0.1 \times 10^6$ to $4 \times 10^6$ cells/ml, preferred $0.5 \times 10^6$ to $2 \times 10^6$ cells/mi. In other embodiments, the cells are present as cell aggregates. For example, islet cell aggregates (or whole islets) preferably contain about 1500-2000 cells for each aggregate of 150 µm diameter, which is defined as one islet equivalent (IE). Therefore, in some embodiments, islet cells are present at a concentration of 100-10000 IE/ml, preferably 200-3,000 IE/ml, more preferably 500-1500 IE/ml.

1. Islet Cells and Other Insulin-Producing Cells

In preferred embodiments, the disclosed compositions contain islet cells or other insulin-producing cells. Methods of isolating pancreatic islet cells are known in the art. Field et al., *Transplantation* 61:1554 (1996); Linetsky et al., *Diabetes* 46:1120 (1997). Fresh pancreatic tissue can be divided by mincing, teasing, comminution and/or collagenase digestion. The islets can then be isolated from contaminating cells and materials by washing, filtering, centrifuging or picking procedures. Methods and apparatus for isolating and purifying islet cells are described in U.S. Pat. No. 5,447,863 to Langley, U.S. Pat. No. 5,322,790 to Scharp et al., U.S. Pat. No. 5,273,904 to Langley, and U.S. Pat. No. 4,868,121 to Scharp et al. The isolated pancreatic cells may optionally be cultured prior to microencapsulation, using any suitable method of culturing islet cells as is known in the art. See e.g., U.S. Pat. No. 5,821,121 to Brothers. Isolated cells may be cultured in a medium under conditions that helps to eliminate antigenic components. Insulin-producing cells can also be derived from stem cells and cell lines and can be cells genetically engineered to produce insulin.

2. Genetically Engineered Cells

In some embodiments, the disclosed compositions contain cells genetically engineered to produce a protein or nucleic acid (e.g., a therapeutic protein or nucleic acid). In these embodiments, the cell can be, for example, a stem cell (e.g., pluripotent), a progenitor cell (e.g., multipotent or oligopotent), or a terminally differentiated cell (i.e., unipotent). Any of the disclosed cell types can be genetically engineered. The cell can be engineered, for example, to contain a nucleic acid encoding, for example, a polynucleotide such miRNA or RNAi or a polynucleotide encoding a protein. The nucleic acid can be, for example, integrated into the cells genomic DNA for stable expression or can be, for example, in an expression vector (e.g., plasmid DNA). The polynucleotide or protein can be selected based on the disease to be treated (or effect to be achieved) and the site of transplantation or implantation. In some embodiments, the polynucleotide or protein is anti-neoplastic. In other embodiments, the polynucleotide or protein is a hormone, growth factor, or enzyme.

B. Hormones

Hormones to be included in the disclosed capsules or, most preferably, produced from cells encapsulated in the disclosed capsules can be any home of interest.

Examples of endocrine hormones include Anti-diuretic Hormone (ADH), which is produced by the posterior pituitary, targets the kidneys, and affects water balance and blood pressure; Oxytocin, which is produced by the posterior pituitary, targets the uterus, breasts, and stimulates uterine contractions and milk secretion; Growth Hormone (GH), which is produced by the anterior pituitary, targets the body cells, bones, muscles, and affects growth and development; Prolactin, which is produced by the anterior pituitary, targets the breasts, and maintains milk secretions; Thyroid Stimulating Hormone (TSH), which is produced by the anterior pituitary, targets the thyroid, and regulates thyroid hormones; Adrenocorticotropic Hormone (ACTH), which is produced by the anterior pituitary, targets the adrenal cortex, and regulates adrenal cortex hormones; Follicle-Stimulating Hormone (FSH), which is produced by the anterior pituitary, targets the ovaries/testes, and stimulates egg and sperm production; Lutenizing Hormone (LH), which is produced by the anterior pituitary, targets the ovaries/testes, and stimulates ovulation and sex hormone release; Thyroxine, which is produced by the thyroid, targets the body cells, and regulates metabolism; Calcitonin, which is produced by the thyroid, targets the adrenal cortex, and lowers blood calcium; Parathyroid Hormone, which is produced by the parathyroid, targets the bone matrix, and raises blood calcium; Aldosterone, which is produced by the adrenal cortex, targets the kidney, and regulates water balance; Cortisol, which is produced by the adrenal cortex, targets the body cells, and weakens immune system and stress responses; Epinephrine, which is produced by the adrenal medulla, targets the heart, lungs, liver, and body cells, and affects primary "fight or flight" responses; Glucagon, which is produced by the pancreas, targets the liver body, and raises blood glucose level; Insulin, which is produced by the pancreas, targets body cells, and lowers blood glucose level; Estrogen, which is produced by the ovaries, targets the reproductive system, and affects puberty, menstrual, and development of gonads; Progesterone, which is produced by the ovaries, targets the reproductive system, and affects puberty, menstrual cycle, and development of gonads; and Testosterone, which is produced by the adrenal gland, testes, targets the reproductive system, and affects puberty, development of gonads, and sperm.

IV. Assays for the Characterization of Modified Alginate Polymers

The covalent modification of alginate polymers alters the physiochemical properties and biological compatibility of the alginate polymer.

In some embodiments, a hydrogel formation assay is used to quantify the stability of hydrogels formed from alginates or modified alginates. In preferred embodiments, the hydrogel formation assay is used as a screening tool to identify modified alginates capable of forming stable hydrogels.

In vivo assays can be useful to characterize the biocompatibility of modified alginate polymers. In some embodiments, the high throughput in vivo biocompatibility assay described herein is used to identify modified alginates which induce a lower foreign body response than unmodified alginate.

Further described herein is an in vivo method for quantifying the biocompatibility of modified alginates.

The assays can be used to assess the suitability and biocompatibility of both modified and unmodified alginates for certain applications.

A. High Throughput Hydrogel Formation Assay

Covalent modification of the alginates affects the physical properties of the alginate, including the ability of the alginate to form hydrogels suitable for the encapsulation of cells and biomolecules.

The gel-forming assay exploits the ability of hydrogels to trap fluorescent compounds, and differentially retain the fluorophores upon washing based on the stability of the hydrogel. In this assay, a hydrogel formed by ionically crosslinking a candidate modified alginate in aqueous solution containing a dissolved fluorophore. A variety of fluorophores can be used in this assay. In preferred embodiments, the fluorophores possess emission maxima between 480 and 750 nm. In preferred embodiments, the fluorophore is a rhodamine dye possessing an emission maximum between 550 and 600 nm.

After crosslinking, the hydrogel is repeatedly washed with water. Candidate modified alginates which do not efficiently crosslink are washed away along with any fluorophore present. Modified alginates which efficiently crosslink retain the fluorophore during washes. Accordingly, by measuring the fluorescence of modified alginate hydrogels after washing, modified alginates capable of forming stable hydrogels can be readily identified.

In some embodiments, the relative fluorescence intensity values measured for a modified alginate are compared relative to fluorescence levels measured for the negative control and unmodified alginate to determine if the modified alginate is capable of forming hydrogels. In alternative embodiments, the hydrogel formation assay described herein is used to quantify the stability of hydrogels formed from alginates or modified alginates. In these embodiments, the fluorescence intensity measured for a modified alginate is used to indicate the stability of the hydrogel formed by the alginate.

In preferred embodiments, the modified alginate polymer forms hydrogels such that the fluorescence intensity measured using the high throughput hydrogel formation assay described herein is greater than 10,000, 15,000, 20,000, 25,000, 30,000, 35,000, 40,000, 45,000, 50,000, or 55,000. In preferred embodiments, the modified alginate polymer forms hydrogels such that the fluorescence intensity measured using the high throughput hydrogel formation assay described herein is greater than 15,000. In preferred embodiments, the modified alginate polymer forms hydrogels such that the fluorescence intensity measured using the high throughput hydrogel formation assay described herein is between 15,000 and 55,000, more preferably between 25,000 and 55,000.

B. High Throughput In Vivo Biocompatibility Assay

Current biocompatibility analysis methods are slow and require histological analysis. Described herein is a high throughput in vivo biocompatibility assay, useful for assessing the relative biocompatibility of alginate polymers.

In the high throughput in vivo biocompatibility assay described herein, modified alginate polymers and an unmodified alginate control are injected in an array format on the back of an animal test subject to facilitate high-throughput screening. In preferred embodiments, the animal test subject is a mouse. After injection, cathepsin activity at the point of injection of the modified alginates was compared to cathepsin activity at the point of injection the unmodified alginate to compare the foreign body response to the implanted alginates using in vivo fluorescence imaging. In preferred embodiments, the biocompatibility of the materials was assessed at 14 days post injection using in vivo fluorescence imaging.

In preferred embodiments, the high throughput in vivo biocompatibility assay described herein is used to identify modified alginates which induce a lower foreign body response than unmodified alginate. The fluorescence intensity measured at the implantation site of modified alginates was compared with the fluorescence intensity measured at the implantation site of an unmodified alginate. In preferred embodiments, modified alginates exhibiting smaller fluorescence intensity at the implantation site than the fluorescence intensity measured at the implantation site of unmodified alginates were qualitatively characterized as biocompatible. Conversely, modified alginates exhibiting greater fluorescence intensity at the implantation site than the fluorescence intensity measured at the implantation site of unmodified alginates were characterized as not biocompatible.

The high throughput in vivo biocompatibility assay described above can also be used to characterize the ability of modified alginates to form mechanically stable hydrogels in vivo. In preferred embodiments, the in vivo stability of the alginate gels was assessed at 28 days post injection.

In preferred embodiments, modified alginates gels which remained at the site of injection after 28 days were characterized as capable of forming mechanically stable hydrogels in vivo. Conversely, modified alginate gels which were not present at the site of injection after 28 days were deemed to not capable of forming mechanically stable hydrogels in vivo.

C. In Vivo Screening of Modified Alginates to Quantify biocompatibility

Further described herein is an in vivo method for quantifying the biocompatibility of modified alginates.

In this method, a modified alginate polymers is injected on the back of an animal test subject. In preferred embodiments, the animal test subject is a mouse. After injection, cathepsin activity at the point of injection of the modified alginates was measured using in vivo fluorescence assay. In preferred embodiments, the fluorescence assay was conducted at 7 days post injection using in vivo fluorescence imaging. In preferred embodiments, the fluorescence intensity was measured and normalized to the fluorescence response measured using unmodified alginate in order to quantify the biocompatibility of the modified alginates.

In preferred embodiments, the modified alginate polymer induces a lower foreign body response than unmodified alginate (i.e. the fluorescence response normalized to unmodified alginate is less that 100%). In some embodiments, the modified alginate polymer is biocompatible such that the fluorescence response normalized to unmodified alginate measured using the in vivo biocompatibility assay described herein is less than 95%, 90%, 85%, 80%, 75%, 70%, 65%, 60%, 55%, 50%, 45%, or 40%. In preferred embodiments, the modified alginate polymer is biocompatible such that the fluorescence response normalized to unmodified alginate measured using the in vivo biocompatibility assay described herein is less than 75%, more preferably less than 65%, and most preferably less than 50%.

V. Methods of Use

Alginates are used in a variety of applications in the food, pharmaceutical, cosmetic, agriculture, printing, and textile industries. Alginates are widely employed in the food industry as thickening, gelling, stabilizing, bodying, suspending, and emulsifying agents. Alginates can be used as a matrix to control the delivery of therapeutic, prophylactic, and/or diagnostic agents. Alginates can be incorporated in pharmaceutical compositions as excipients, where they can act as viscosifiers, suspension agents, emulsifiers, binders, and disintigrants. Alginate also used as a dental impression material, component of wound dressings, and as a printing agent. One of ordinary skill in the art will recognize that the modified alginates disclosed herein can be used in any application for which alginates are currently employed.

It is specifically contemplated that modified alginates described herein can be used in applications where improved biocompatibility and physical properties (such as being anti-fibrotic), as compared to commercially available alginates, are preferred.

A. Encapsulation of Cells

Alginate can be ionically cross-linked with divalent cations, in water, at room temperature, to form a hydrogel matrix. See, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete capsules by contact with multivalent cations, then the surface of the capsules is crosslinked with polyamino acids to form a semipermeable membrane around the encapsulated materials.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e.g., $R_3N+$--\/\/\/--$+NR_3$ can also be used. Aqueous solutions of the salts of these cations are added to the polymers to form soft, highly swollen hydrogels and membranes. The higher the concentration of cation or the higher the valence, the greater the degree of cross-linking of the polymer. Concentrations from as low as 0.005 M have been demonstrated to cross-link the polymer. Higher concentrations are limited by the solubility of the salt.

The preferred anions for cross-linking of polymers containing basic sidechains to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

In a preferred method, cells are encapsulated in a modified alginate polymer. In a preferred embodiment, modified alginate capsules are fabricated from solution of modified alginate containing suspended cells using the encapsulator (such as an Inotech encapsulator). In some embodiments, modified alginates are ionically crosslinked with a polyvalent cation, such as $Ca^{2+}$, $Ba^{2+}$, or $Sr^{2+}$. In particularly preferred embodiments, the modified alginate is crosslinked using $BaCl_2$. In some embodiments, the capsules are further purified after formation. In preferred embodiments, the capsules are washed with, for example, HEPES solution, Krebs solution, and/or RPMI-1640 medium.

Cells can be obtained directed from a donor, from cell culture of cells from a donor, or from established cell culture lines. In the preferred embodiments, cells are obtained directly from a donor, washed and implanted directly in combination with the polymeric material. The cells are cultured using techniques known to those skilled in the art of tissue culture. In the preferred embodiment, the cells are autologous—i.e., derived from the individual into which the cells are to be transplanted, but may be allogeneic or heterologous.

Cell attachment and viability can be assessed using scanning electron microscopy, histology, and quantitative assessment with radioisotopes. The function of the implanted cells can be determined using a combination of the above-techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. For example, islet cells of the pancreas may be delivered in a similar fashion to that specifically used to implant hepatocytes, to achieve glucose regulation by appropriate secretion of insulin to cure diabetes. Other endocrine tissues can also be implanted. Studies using labeled glucose as well as studies using protein assays can be performed to quantitate cell mass on the polymer scaffolds. These studies of cell mass can then be correlated with cell functional studies to determine what the appropriate cell mass is. In the case of chondrocytes, function is defined as providing appropriate structural support for the surrounding attached tissues.

This technique can be used to provide multiple cell types, including genetically altered cells, within a three-dimensional scaffolding for the efficient transfer of large number of cells and the promotion of transplant engraftment for the purpose of creating a new tissue or tissue equivalent. It can also be used for immunoprotection of cell transplants while a new tissue or tissue equivalent is growing by excluding the host immune system.

Examples of cells which can be implanted as described herein include chondrocytes and other cells that form cartilage, osteoblasts and other cells that form bone, muscle cells, fibroblasts, and organ cells. As used herein, "organ cells" includes hepatocytes, islet cells, cells of intestinal origin, cells derived from the kidney, and other cells acting primarily to synthesize and secret, or to metabolize materials. A preferred cell type is a pancreatic islet cell.

The polymeric matrix can be combined with humoral factors to promote cell transplantation and engraftment. For example, the polymeric matrix can be combined with angiogenic factors, antibiotics, antiinflammatories, growth factors, compounds which induce differentiation, and other factors which are known to those skilled in the art of cell culture.

For example, humoral factors could be mixed in a slow-release form with the cell-alginate suspension prior to formation of implant for transplantation. Alternatively, the hydrogel could be modified to bind humoral factors or signal recognition sequences prior to combination with isolated cell suspension.

The techniques described herein can be used for delivery of many different cell types to achieve different tissue structures. In the preferred embodiment, the cells are mixed with the hydrogel solution and injected directly into a site where it is desired to implant the cells, prior to hardening of the hydrogel. However, the matrix may also be molded and implanted in one or more different areas of the body to suit a particular application. This application is particularly relevant where a specific structural design is desired or where the area into which the cells are to be implanted lacks specific structure or support to facilitate growth and proliferation of the cells.

The site, or sites, where cells are to be implanted is determined based on individual need, as is the requisite number of cells. For cells having organ function, for example, hepatocytes or islet cells, the mixture can be injected into the mesentery, subcutaneous tissue, retroperitoneum, properitoneal space, and intramuscular space. For formation of cartilage, the cells are injected into the site where cartilage formation is desired. One could also apply an external mold to shape the injected solution. Additionally, by controlling the rate of polymerization, it is possible to mold the cell-hydrogel injected implant like one would mold clay. Alternatively, the mixture can be injected into a mold, the hydrogel allowed to harden, then the material implanted.

B. Coating Products and Surfaces

Medical products can be coated with the disclosed modified alginate polymers using a variety of techniques, examples of which include spraying, dipping, and brush coating. Polymer coatings are typically applied to the surface to be coated by dissolving a polymer in an appropriate, preferably organic solvent, and applying by spraying, brushing, dipping, painting, or other similar technique. The coatings are deposited on the surface and associate with the surfaces via non-covalent interactions. The coated products and surfaces that result are specifically contemplated and disclosed.

In some embodiments, the surface may be pretreated with an appropriate solution or suspension to modify the properties of the surface, and thereby strengthen the non-covalent interactions between the modified surface and the coating.

The polymer solution is applied to a surface at an appropriate temperature and for a sufficient period of time to form a coating on the surface, wherein the coating is effective in forming an anti-fibrotic surface. Typical temperatures include room temperature, although higher temperatures may be used. Typical time periods include 5 minutes or less, 30 minutes or less, 60 minutes or less, and 120 minutes or less. In some embodiments the solution can be applied for 120 minutes or longer to form a coating with the desired anti-fibrotic activity. However, preferably shorter time periods are used. Anti-fibrotic activity can be measured in any of the ways disclosed herein or known in the art. Preferably the anti-fibrotic activity can be the foreign body response determined as described herein.

The disclosed modified alginate polymers can be covalently or non-covalently associated with the products, devices, and surfaces. For those embodiments where the modified alginate polymer is covalently associated with the product, device, or surface, the polymer can be attached to the product, device, or surface by, for example, functionalizing the product, device, or surface with a reaction functional group, such as a nucleophilic group, and reacting the nucleophilic group with a reaction functional group on the polymer, such as an electrophilic group. Alternatively, the polymer can be functionalized with a nucleophilic group which is reacted with an electrophilic group on the product, device, or surface.

In particular embodiments, the modified alginate polymer is non-covalently associated with the product, device, or surface. The polymer can be applied to the product, device, or surface by spraying, wetting, immersing, dipping, painting, bonding or adhering or otherwise providing a product, device, or surface with a compound with the modified alginate polymer. In one embodiment, the polymer is applied by spraying, painting, or dipping or immersing. For example, a polymer paint can be prepared by dissolving the modified alginate polymer in a suitable solvent (generally aqueous), and optionally sonicating the solution to ensure the polymer is completely dissolved. The product, device, or surface to be coated can be immersed in the polymer solution for a suitable period of time, e.g., 5 seconds, followed by drying, such as air drying. The procedure can be repeated as many times as necessary to achieve adequate coverage. The thickness of the coating is generally from about 1 nm to about 1 cm, preferably from about 10 nm to 1 mm, more preferably from about 100 nm to about 100 microns.

The coating can be applied at the time the product, device, or surface is manufactured or can be applied subsequent to manufacture of the product, device, or surface. In some embodiments, the coating is applied to the product, device, or surface immediately prior to use of the product, device, or surface. This is referred to an intraoperative coating. "Immediately prior", as used herein, mean within 1, 2, 5, 10, 15, 20, 30, 45, 60, 75, 90, 120, 150, 180 minutes or greater of implantation or use. In some embodiments, the product, device, or surface is coated at the hospital, e.g., in the operating room, with 20, 15, 10, or 5 minutes of implantation or use. Coating immediately prior to use may overcome limitations of products, devices, and surfaces coated at the time of manufacture, such as damage of the coating during storage and/or transportation of the product, device, or surface and/or decrease in the efficacy of the coating over time as the coating is exposed to environmental conditions, which may be harsh (e.g., high temps, humidity, exposure to UV light, etc.).

The coated medical products can be used for the known uses and purposes of uncoated or differently coated forms of the medical products.

1. Medical Products

Medical products useful for coating include any types of medical devices used, at least in part, for implantation in the body of a patient. Examples include, but are not limited to, implants, implantable medical products, implantable devices, catheters and other tubes (including urological and biliary tubes, endotracheal tubes, wound drain tubes, needle injection catheters, peripherably insertable central venous catheters, dialysis catheters, long term tunneled central venous catheters peripheral venous catheters, short term central venous catheters, arterial catheters, pulmonary catheters, Swan-Ganz catheters, urinary catheters, peritoneal catheters), vascular catheter ports, blood clot filters, urinary devices (including long term urinary devices, tissue bonding urinary devices, artificial urinary sphincters, urinary dilators), shunts (including ventricular or arterio-venous shunts, stent transplants, biliary stents, intestinal stents, bronchial stents, esophageal stents, ureteral stents, and hydrocephalus shunts), balloons, pacemakers, implantable defibrillators, orthopedic products (including pins, plates, screws, and implants), transplants (including organs, vascular transplants, vessels, aortas, heart valves, and organ replacement parts), prostheses (including breast implants, penile prostheses, vascular grafting prostheses, heart valves, artificial joints, artificial larynxes, otological implants, artificial hearts, artificial blood vessels, and artificial kidneys), aneurysm-filling coils and other coil devices, transmyocardial revascularization devices, percutaneous myocardial revascularization devices, tubes, fibers, hollow fibers, membranes, blood containers, titer plates, adsorber media, dialyzers, connecting pieces, sensors, valves, endoscopes, filters, pump chambers, scalpels, needles, scissors (and other devices used in invasive surgical, therapeutic, or diagnostic procedures), and other medical products and devices intended to have anti-fibrotic properties. The expression "medical products" is broad and refers in particular to products that come in contact with blood briefly (e.g., endoscopes) or permanently (e.g., stents).

Useful medical products are balloon catheters and endovascular prostheses, in particular stents. Stents of a conventional design have a filigree support structure composed of metallic struts. The support structure is initially provided in an unexpanded state for insertion into the body, and is then widened into an expanded state at the application site. The stent can be coated before or after it is crimped onto a balloon. A wide variety of medical endoprostheses or medical products or implants for highly diverse applications and are known. They are used, for example, to support vessels, hollow organs, and ductal systems (endovascular implants), to attach and temporarily affix tissue implants and tissue transplants, and for orthopedic purposes such as pins, plates, or screws.

The modified alginate polymers can be applied to, absorbed into, or coupled to, a variety of different substrates and surfaces. Examples of suitable materials include metals, metallic materials, ceramics, polymers, fibers, inert materials such as silicon, and combinations thereof.

Suitable polymeric materials include, but are not limited to, styrene and substituted styrenes, ethylene, propylene, poly(urethane)s, acrylates and methacrylates, acrylamides and methacrylamides, polyesters, polysiloxanes, polyethers, poly(orthoester), poly(carbonates), poly(hydroxyalkanoate)s, copolymers thereof, and combinations thereof.

Substrates can be in the form of, or form part of, films, particles (nanoparticles, microparticles, or millimeter diameter beads), fibers (wound dressings, bandages, gauze, tape, pads, sponges, including woven and non-woven sponges and those designed specifically for dental or ophthalmic surgeries), sensors, pacemaker leads, catheters, stents, contact lenses, bone implants (hip replacements, pins, rivets, plates, bone cement, etc.), or tissue regeneration or cell culture devices, or other medical devices used within or in contact with the body.

Implants coated with modified alginate polymer coatings are described herein. "Implants" are any object intended for placement in the body of a mammal, such as a human, that is not a living tissue. Implants are a form of medical product. Implants include naturally derived objects that have been processed so that their living tissues have been devitalized. As an example, bone grafts can be processed so that their living cells are removed, but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components. The term "implant" can be applied to the entire spectrum of medical devices intended for placement in a human body or that of a mammal, including orthopedic applications, dental applications, ear, nose, and throat ("ENT") applications, and cardiovascular applications.

In some embodiments, "implant" as used herein refers to a macroscopic composition including a device for implantation or a surface of a device for implantation and a modified alginate polymer coating. In these embodiments, the term "implant" does not encompass nanoparticles and/or microparticles. "Macroscopic" as used herein generally refers to devices, implants, or compositions that can be viewed by the unaided eye.

Examples of implantable medical devices and medical devices and mechanical structures that can use a bio-compatible coating include, but are not limited to, stents, conduits, scaffolds, cardiac valve rings, cardiovascular valves, pacemakers, hip replacement devices, implanted sensor devices, esophageal stents, heart implants, bio-compatible linings for heart valves, dialysis equipment and oxygenator tubing for heart-lung by-pass systems.

In general, a stent is a device, typically tubular in shape, that is inserted into a lumen of the body, such as a blood vessel or duct, to prevent or counteract a localized flow constriction. The purpose of a stent, in some cases, is to mechanically prop open a bodily fluid conduit. Stents are often used to alleviate diminished blood flow to organs and extremities in order to maintain adequate delivery of oxygenated blood. The most common use of stents is in coronary arteries, but they are also widely used in other bodily conduits, such as, for example, central and peripheral arteries and veins, bile ducts, the esophagus, colon, trachea, large bronchi, ureters, and urethra. Frequently, stents inserted into a lumen are capable of being expanded after insertion or are self-expanding. For example, metal stents are deployed into an occluded artery using a balloon catheter and expanded to restore blood flow. For example, stainless steel wire mesh stents are commercially available from Boston Scientific, Natick, Mass.

In some embodiments, the implant is an orthopedic implant. An "orthopedic implant" is defined as an implant which replaces bone or provides fixation to bone, replaces articulating surfaces of a joint, provides abutment for a prosthetic, or combinations thereof or assists in replacing bone or providing fixation to bone, replacing articulating surfaces of a joint, providing abutment for a prosthetic, and combinations thereof.

Orthopedic implants can be used to replace bone or provide fixation to bone, replace articulating surfaces of a joint, provide abutment for a prosthetic, or combinations thereof or assist in replacing bone or providing fixation to bone, replacing articulating surfaces of a joint, providing abutment for a prosthetic, including dental applications, and combinations thereof.

Suitable orthopedic implants include, but are not limited to, wire, Kirschner wire, bone plates, screws, pins, tacs, rods, nails, nuts, bolts, washers, spikes, buttons, wires, fracture plates, reconstruction and stabilizer devices, endo- and exoprostheses (articulating and non-articulating), intraosseous transcutaneous prostheses, spacers, mesh, implant abutments, anchors, barbs, clamps, suture, interbody fusion devices, tubes of any geometry, scaffolds, and combinations thereof.

In other embodiments, the implant is an ear, nose, and/or throat ("ENT") implant. Exemplary ENT implants include, but are not limited to, ear tubes, endotracheal tubes, ventilation tubes, cochlear implants and bone anchored hearing devices.

In other embodiments, the implant is a cardiovascular implant. Exemplary cardiovascular implants are cardiac valves or alloplastic vessel wall supports, total artificial heart implants, ventricular assist devices, vascular grafts, stents, electrical signal carrying devices such as pacemaker and neurological leads, defibrillator leads, and the like.

Implants can be prepared from a variety of materials. In some embodiments, the material is biocompatible. In some embodiments, the material is biocompatible and non-biodegradable. Exemplary materials include metallic materials, metal oxides, polymeric materials, including degradable and non-degradable polymeric materials, ceramics, porcelains, glass, allogeneic, xenogenic bone or bone matrix; genetically engineered bone; and combinations thereof.

Suitable metallic materials include, but are not limited to, metals and alloys based on titanium (such as nitinol, nickel titanium alloys, thermo-memory alloy materials), stainless steel, tantalum, palladium, zirconium, niobium, molybdenum, nickel-chrome, or certain cobalt alloys including cobalt-chromium and cobalt-chromium-nickel alloys such as ELGILOY® and PHYNOX®. Useful examples include stainless steel grade 316 (SS 316L) (comprised of Fe, <0.3% C, 16-18.5% Cr, 10-14% Ni, 2-3% Mo, <2% Mn, <1% Si, <0.45% P, and <0.03% S), tantalum, chromium molybdenum alloys, nickel-titanium alloys (such as nitinol) and cobalt chromium alloys (such as MP35N, ASTM Material Designation: 35Co-35Ni-20Cr-10Mo). Typical metals currently in use for stents include SS 316L steel and MP35N. See also, "Comparing and Optimizing Co—Cr Tubing for Stent Applications," Poncin, P, Millet, C., Chevy, J, and Profit, J. L., Materials & Processes for Medical Devices Conference, August 2004, ASM International.

Suitable ceramic materials include, but are not limited to, oxides, carbides, or nitrides of the transition elements such as titanium oxides, hafnium oxides, iridium oxides, chromium oxides, aluminum oxides, and zirconium oxides. Silicon based materials, such as silica, may also be used.

Suitable polymeric materials include, but are not limited to, polystyrene and substituted polystyrenes, polyethylene, polypropylene, polyacetylene, polystyrene, TEFLON®, poly(vinyl chloride) (PVC), polyolefin copolymers, poly(urethane)s, polyacrylates and polymethacrylates, polyacrylamides and polymethacrylamides, polyesters, polysiloxanes, polyethers, poly(orthoester), poly(carbonates), poly(hydroxyalkanoate)s, polyfluorocarbons, PEEK®, Teflon® (polytetrafluoroethylene, PTFE), silicones, epoxy resins, Kevlar®, Dacron® (a condensation polymer obtained from ethylene glycol and terephthalic acid), nylon, polyalkenes, phenolic resins, natural and synthetic elastomers, adhesives and sealants, polyolefins, polysulfones, polyacrylonitrile, biopolymers such as polysaccharides and natural latex, collagen, cellulosic polymers (e.g., alkyl celluloses, etc.), polysaccharides, poly(glycolic acid), poly(L-lactic acid) (PLLA), a polydioxanone (PDA), or racemic poly(lactic acid), polycarbonates, (e.g., polyamides (nylon); fluoroplastics, carbon fiber, and blends or copolymers thereof.

The polymer can be covalently or non-covalently associated with the surface; however, in particular embodiments, the polymer is non-covalently associated with the surface. The polymer can be applied by a variety of techniques in the art including, but not limited to, spraying, wetting, immersing, dipping, such as dip coating (e.g., intraoperative dip coating), painting, or otherwise applying a hydrophobic, polycationic polymer to a surface of the implant.

A surface of a product adapted for use in a medical environment can be capable of sterilization using autoclaving, biocide exposure, irradiation, or gassing techniques, like ethylene oxide exposure. Surfaces found in medical environments include the inner and outer aspects of various instruments and devices, whether disposable or intended for repeated uses.

2. Hydrogels

Medical products can also be made of or using hydrogels. The disclosed modified alginate polymers can form hydrogels for this and other purposes. Products made of other hydrogels can also be coated with the disclosed modified alginate polymers. Thus, the disclosed modified alginate polymers can be used as a coating on a product or surface or can be used as the product itself. Hydrogels are three-dimensional, hydrophilic, polymeric networks capable of imbibing large amounts of water or biological fluids (Peppas et al. *Eur. J. Pharm. Biopharm.* 2000, 50, 27-46). These networks are composed of homopolymers or copolymers, and are insoluble due to the presence of chemical crosslinks or physical crosslinks, such as entanglements or crystallites. Hydrogels can be classified as neutral or ionic, based in the nature of the side groups. In addition, they can be amorphous, semicrystalline, hydrogen-bonded structures, supermolecular structures and hydrocolloidal aggregates (Peppas, N. A. Hydrogels. In: *Biomaterials science: an introduction to materials in medicine*; Ratner, B. D., Hoffman, A. S., Schoen, F. J., Lemons, J. E., Eds; Academic Press, 1996, pp. 60-64; Peppas et al., *Eur. J. Pharm. Biopharm.* 2000, 50, 27-46). Hydrogels can be prepared from synthetic or natural monomers or polymers. Preferred hydrogels herein are the disclosed modified alginate polymers.

Hydrogels can be prepared from synthetic polymers such as poly(acrylic acid) and its derivatives [e.g. poly(hydroxyethyl methacrylate) (pHEMA)], poly(N-isopropylacrylamide), poly(ethylene glycol) (PEG) and its copolymers and poly(vinyl alcohol) (PVA), among others (Bell and Peppas, *Adv. Polym. Sci.* 122:125-175 (1995); Peppas et al., *Eur. J. Pharm. Biopharm.* 50:27-46 (200); Lee and Mooney, *Chem. Rev.* 101:1869-1879 (2001)). Hydrogels prepared from synthetic polymers are in general non-degradable in physiologic conditions.

Hydrogels can also be prepared from natural polymers including, but not limited to, polysaccharides, proteins, and peptides. The disclosed modified alginate polymers are a preferred example. These networks are in general degraded in physiological conditions by chemical or enzymatic means.

In some embodiments, the hydrogel is non-degradable under relevant in vitro and in vivo conditions. Stable hydrogel coatings are necessary for certain applications including central venous catheters coating, heart valves, pacemakers and stents coatings. In other cases, hydrogel degradation may be a preferential approach such as in tissue engineering constructs.

In some embodiments, the hydrogel can be formed by dextran. Dextran is a bacterial polysaccharide, consisting essentially of $\alpha$-1,6 linked D-glucopyranose residues with a few percent of $\alpha$-1,2, $\alpha$-1,3, or $\alpha$-1,4-linked side chains. Dextran is widely used for biomedical applications due to its biocompatibility, low toxicity, relatively low cost, and simple modification. This polysaccharide has been used clinically for more than five decades as a plasma volume expander, peripheral flow promoter and antithrombolytic agent (Mehvar, R. *J. Control. Release* 2000, 69, 1-25). Furthermore, it has been used as macromolecular carrier for delivery of drugs and proteins, primarily to increase the longevity of therapeutic agents in the circulation. Dextran can be modified with vinyl groups either by using chemical or enzymatic means to prepare gels (Ferreira et al. Biomaterials 2002, 23, 3957-3967).

Dextran-based hydrogels prevent the adhesion of vascular endothelial, smooth muscle cells, and fibroblasts (Massia, S. P.; Stark, J. *J. Biomed. Mater. Res.* 2001, 56, 390-399. Ferreira et al. 2004, *J. Biomed. Mater. Res.* 68A, 584-596) and dextran surfaces prevent protein adsorption (Österberg et al. *J. Biomed. Mat. Res.* 1995, 29, 741-747).

As described herein, the disclosed modified alginate polymers can be used to encapsulate cells. In some embodiments, the encapsulated cells can be fabricated into a macrodevice. For example, in some embodiments, cells encapsulated in modified alginate hydrogel can be coated onto a surface, such as a planar surface. In some embodiments, capsules containing cells can be adhered to tissue of a subject using a biocompatible adhesive. In other embodiments, capsules containing cells can be coated onto a medical device suitable for implantation.

C. Treatment of Diseases or Disorders

Encapsulated cells can be transplanted into a patient in need thereof to treat a disease or disorder. In some embodiments, the encapsulated cells are obtained from a genetically non-identical member of the same species. In alternative embodiments, the encapsulated cells are obtained from a different species than the patient. In preferred embodiments, hormone- or protein-secreting cells are encapsulated and transplanted into a patient to treat a disease or disorder.

In preferred embodiments, the disease or disorder is caused by or involves the malfunction hormone- or protein-secreting cells in a patient. In a preferred embodiment, the disease or disorder is diabetes.

Medical products, devices, and surfaces coated with a modified alginate polymer can be transplanted or implanted into a patient in need thereof to treat a disease or disorder.

The disclosed capsules, products, devices, and surfaces can remain substantially free of fibrotic effects, or can continue to exhibit a reduced foreign body response, for 2 weeks, 3 weeks, 4 weeks, 5 weeks, 6 weeks, 7 weeks, 8 weeks, 9 weeks, 10 weeks, 2 months, 3 months, 4 months, 5 months, 6 months, 7 months, 8, months, 9 months, 10 months, 11 months, 1 year, 2 years, or longer after administration or implantation.

The disclosed capsules, products, devices, and surfaces can be administered or implanted alone or in combination with any suitable drug or other therapy. Such drugs and therapies can also be separately administered (i.e., used in parallel) during the time the capsules, products, devices, and surfaces are present in a patient. Although the disclosed capsules, products, devices, and surfaces reduce fibrosis and immune reaction to the capsules, products, devices, and surfaces, use of anti-inflammatory and immune system suppressing drugs together with or in parallel with the capsules, products, devices, and surfaces is not excluded. In preferred embodiments, however, the disclosed capsules, products, devices, and surfaces are used without the use of anti-inflammatory and immune system suppressing drugs. In preferred embodiments, fibrosis remains reduced after the use, concentration, effect, or a combination thereof, of any anti-inflammatory or immune system suppressing drug that is used falls below an effective level. For example, fibrosis can remain reduced for 2 weeks, 3 weeks, 4 weeks, 5 weeks, 6 weeks, 7 weeks, 8 weeks, 9 weeks, 10 weeks, 2 months, 3 months, 4 months, 5 months, 6 months, 7 months, 8, months, 9 months, 10 months, 11 months, 1 year, 2 years, or longer after the use, concentration, effect, or a combination thereof, of any anti-inflammatory or immune system suppressing drug that is used falls below an effective level.

The present invention will be further understood by reference to the following non-limiting examples.

EXAMPLES

Example 1: Combinatorial Synthesis of Chemically Modified Alginates

The determinate parameters governing material biocompatibility are poorly understood. Accordingly, the rational design and synthesis of modified alginates possessing improved biocompatibility is challenging. In an effort to identify modified alginates with improved biocompatibility and physical properties, a combinatorial approach was used to prepare a library of modified alginates possessing a range of covalent modifications.

1. General Combinatorial Strategy

A pool of twelve alcohols, nine amines, two amines used to introduce an azide moiety (one amine containing an azide moiety and one amine containing an iodide moiety to be converted to an azide moiety subsequent to amidation), and nineteen alkynes with a range of different chemical structures, hydrophobicities/hydrophilicities, hydrogen-bonding potentials, and charge states were selected as reagents for the combinatorial synthesis of modified alginates. With the knowledge that impurities present in alginate polymers have been shown to limit the biocompatibility of implanted alginates, ultra-pure, low viscosity alginate (UPLVG, FMC Biopolymers) was selected as a starting material for modification experiments.

Alkynes Used as Reagents for 1,3-Dipolar Cycloaddition

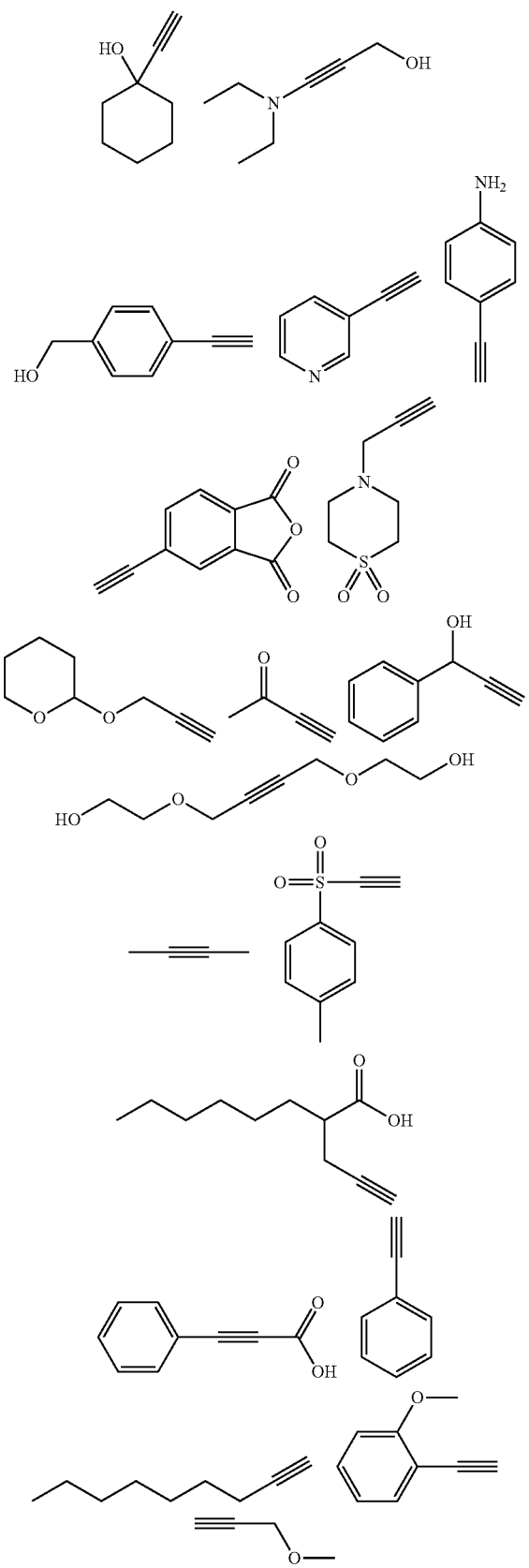

Alcohols Used as Reagents for Esterification

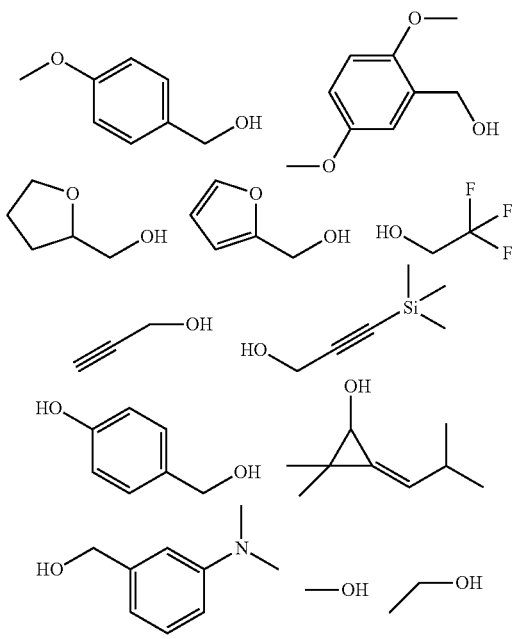

Amines used as Reagents for Amidation

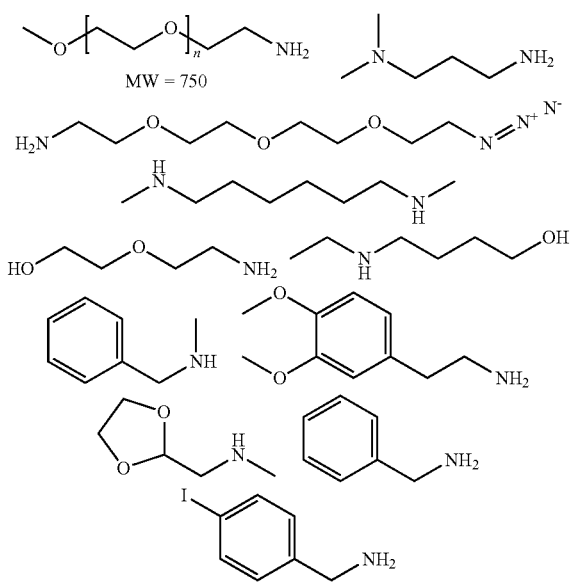

Amines Used as Reagents to Introduce Azide Moieties

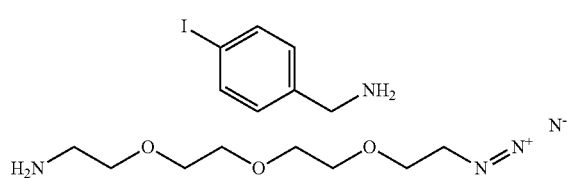

Unmodified alginate polymer was covalently modified by reaction with one, two, or three the esters, amines, and/or alkynes shown above in a combinatorial fashion. FIG. 1 shows the general structure of the modified alginates obtained using this method.

2. Representative Reaction Conditions

Due to the parallel and combinatorial nature of the modification process, synthetic reactions were performed using a robotic core module. UPLVG alginate was selected as a starting material for modification experiments. In the first combinatorial reaction, the unmodified alginate was reacted with one of the alcohols, amines, and amines used to introduce an azide moiety in the presence of 2-Chloro-4,6-dimethoxy-1,3,5-triazine (CDMT) and N-methyl morpholine (NMM). In a second combinatorial step, each of the modified alginate polymers formed above was reacted with another of the alcohols, amines, or amines used to introduce an azide moiety in the presence of 2-Chloro-4,6-dimethoxy-1,3,5-triazine (CDMT) and N-methyl morpholine (NMM). In a final combinatorial step, all members of the library which were reacted with an amine used to introduce an azide moiety were further functionalized using a 1,3-dipolar cycloaddition reaction. Those members of the library which had been reacted with 4-iodobenzylamine were first reacted with sodium azide to convert the iodide moieties to azide moieties. Subsequently, all members of the library which were reacted with an amine used to introduce an azide moiety were reacted with one of the alkynes used as reagents for 1,3-dipolar cycloaddition in the presence of $CuSO_4$/sodium ascorbate.

To optimize the biocompatibility of the chemically modified alginates, a rigorous purification methodology was developed to eliminate potentially irritating impurities. Following each covalent modification, the modified alginates were filtered through a cyano-modified silica column aimed at capturing bulk organic impurities. Finally, after completing all covalent modification steps, the modified alginates were dialyzed against 10,000 MWCO membrane to remove any remaining small-molecule or low molecular weight impurities.

The purity of the modified alginates was determined by $^1$H NMR analysis. The $^1$H NMR spectra of each modified alginate polymer was collected, and peaks corresponding to the modified alginate polymer and to any impurities were integrated to determine the relative quantity of each species in the sample.

Example 2: High Throughput Screening of Modified Alginates Using a Hydrogel Formation Assay Covalent modification of the alginates affects the physical properties of the alginate, including the ability of the alginate to form hydrogels suitable for the encapsulation of cells and biomolecules. To eliminate modified alginates that have lost their ability to form hydrogels and to further focus our screening efforts on stronger candidates, a fluorescence-based crosslinking assay was used to quantify the ability of modified alginates to form hydrogels.

The hydrogel formation assay described herein exploits the ability of hydrogels to trap fluorescent compounds, and differentially retain the fluorophores upon washing based on the stability of the hydrogel. Each of the modified alginates prepared using the combinatorial approach described in Example 1 was dissolved in water. A rhodamine dye that fluoresces at 580 nm was added to each sample. The modified alginate sample was then crosslinked by the addition of a barium or calcium salt, for example $BaCl_2$, to induce formation of a hydrogel. After incubation for 10 minutes, each sample was washed repeatedly with water. The fluorescence intensity of each sample was measured using a fluorimeter.

Each modified alginate was screened three times, and the results obtained in the three trials were averaged. The average fluorescence intensity values for each modified alginate were compared to the fluorescence levels of the negative control (water) and unmodified alginate (UPLVG). Modified alginates yielding fluorescence values below the negative control were considered unusable for applications where hydrogel formation is critical (i.e. the encapsulation of cells).

Example 3: In Vitro Screening of Modified Alginates for Biocompatibility

The cytotoxicity of the modified alginate polymers on HeLa cells was evaluated to screen for biocompatibility in vitro. The modified alginates identified in Example 2 as capable of forming hydrogels were loaded into wells of 96-well plates which were coated with poly-L-lysine. Unmodified alginate and saline were also loaded into wells of 96-well plates which were coated with poly-L-lysine as controls. A 100 mM $BaCl_2$ crosslinking solution was dispensed in all of the wells of the 96-well plate. The excess crosslinker was then aspirated. HeLa cells were seeded into the wells and incubated for 3 days at 37° C. in a humidified chamber.

A cell viability assay using 3-(4,5-Dimethylthiazol-2-yl)-2,5-diphenyltetrazolium bromide (MTT) was performed, in which the media was aspirated from all wells and 100 µl of DMEM media without phenol red and 10 µl MTT (5 mg/ml) were added to all of the wells of the 96-well plate. The plate was incubated for 4 hours at 37° C. in a humidified chamber. After incubation, 85 µl of solution was aspirated and 100 µl DMSO was added. Purple formazan crystals form during the assay in proportion to the number of viable HeLa cells present in each well. The contents of each well were pipetted up and down to solubilize the formazan crystals prior to measurement. The plate was incubated at 37° C. for 10 minutes after which the bubbles from agitation were removed. The plate was read using a UV/Vis plate reader at 540 nm with a reference at 700 nm. The viability was normalized to cells seeded in wells with no alginate.

Figure 3:
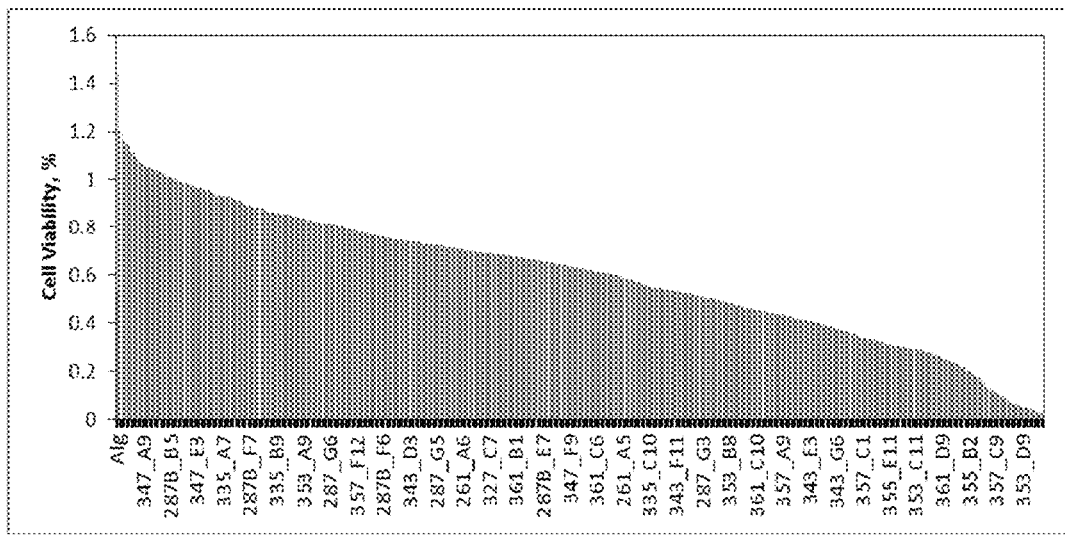
FIG. 3 is a plot showing the effect of selected modified alginates on HeLa cell line viability as compared to the positive control (no alginate). Alginate (Alg) has a viability of 53%. Several polymers are shown to be more cytotoxic than Alg, however, the majority of the library performs as well or better than Alg.

The results of the cell viability are shown in FIG. 3, which plots the effect of selected modified alginates on HeLa cell line viability as compared to the positive control (no alginate). Alginate (Alg) has a viability of 53%. The assay identified modified alginate polymers which displayed decreased cytotoxicity relative to unmodified alginate. These were selected for further analysis.

Example 4: High Throughput In Vivo Screening of Modified Alginates to Assess Biocompatibility Current biocompatibility analysis methods are slow and require histological analysis. In order to screen the large numbers of modified alginates prepared using the combinatorial synthetic methods described herein, a high throughput in vivo biocompatibility assay was used to assess the relative biocompatibility of alginate polymers.

1. High Throughput In Vivo Screening Protocol 8-12 week old male SKH1 mice were obtained from Charles River Laboratories (Wilmington, Mass.). The mice were maintained at the animal facilities of Massachusetts Institute of Technology, accredited by the American Association of Laboratory Animal care, and were housed under standard conditions with a 12-hour light/dark cycle. Both water and food were provided ad libitum.

Injections were performed in accordance with ISO 10993-6: 2001. Prior to injection all materials were sterilized via 0.22 µm filtration. The mice were anesthetized via isoflurane inhalation at a concentration of 1-4% isoflurane/balance $O_2$ to minimize movement. Their backs were scrubbed with 70% isopropyl alcohol and the animals were injected with modified alginates in an array format on the animals' back for high-throughput screening. Six injections were made in each mouse with one of the injections being an unmodified alginate control. Injection volumes were 100 µl.

On days 1, 3, 7, 14, 21, and 28 post-injection, host cell activity in response to the implantation of modified alginates was imaged kinetically using fluorescent whole animal imaging. 24 hours before in vivo fluorescence imaging, 2 nmol of ProSense-680 (VisEn Medical, Woburn, Mass., excitation wavelength 680±10 nm, emission 700±10 nm) dissolved in 150 µl sterile PBS was injected into the tail vein of each mouse to image cathepsin activity.

In vivo fluorescence imaging was performed with an IVIS-Spectrum measurement system (Xenogen, Hopkinton, Mass.). The animals were maintained under inhaled anesthesia using 1-4% isoflurane in 100% oxygen at a flow rate of 2.5 L/min. A binning of 8×8 and a field of view of 13.1 cm were used for imaging. Exposure time and f/stop—the relative size of the opening of the aperture—were optimized for each acquired image. Data were acquired and analyzed using the manufacturer's proprietary Living Image 3.1 software. All images are presented in fluorescence efficiency, which is defined as the ratio of the collected fluorescent intensity to an internal standard of incident intensity at the selected imaging configuration. Regions of interest (ROIs) were designated around the site of each injection.

Biocompatibility of the materials was examined 14 days post injection. The fluorescence intensity measured at the implantation site of modified alginates was compared with the fluorescence intensity measured at the implantation site of and unmodified alginates. Modified alginates exhibiting smaller fluorescence intensity at the implantation site than the fluorescence intensity measured at the implantation site of unmodified alginates were characterized as biocompatible. Modified alginates exhibiting greater fluorescence intensity at the implantation site than the fluorescence intensity measured at the implantation site of unmodified alginates were characterized as not biocompatible.

The in vivo stability of the alginate gels was assessed at 28 days post injection. Modified alginates which remained at the site of injection after 28 days were characterized as capable of forming mechanically stable hydrogels in vivo. Modified alginates which were not present at the site of injection after 28 days were deemed to not capable of forming mechanically stable hydrogels in vivo, and were classified as 'failures'.

Modified alginates characterized as both biocompatible and capable of forming mechanically stable hydrogels in vivo were identified as 'hits', and selected for further study.

2. Validation of the High Throughput In Vivo Screening Protocol

In order to validate the high throughput in vivo screening assay described above, modified alginates were subcutaneously injected into mice in an array format and crosslinked in situ as described above. Mice were imaged on days 1, 3, 7, 14, 21, and 28 post-injection using fluorescent, whole animal imaging, and tissue samples were collected after imaging for histological analysis. To obtain tissue samples for histological analysis, mice were euthanized via $CO_2$ asphyxiation and the injected biomaterial and surrounding tissue were excised. The tissues were then fixed in 10% formalin, embedded in paraffin, cut into 5 μm sections, and stained using hematoxylin and eosin (H&E) for histological analysis by a board certified pathologist.

Fibrosis was rated on a scale where a zero involved no fibrosis, a one indicated partial coverage with one to two layers of fibrosis, a two is designated a thicker fibrotic layer that nearly covered the implant, and a three denoted concentric fibrotic coverage of the polymer. Both polymorphonuclear (PMN) cells and macrophages were rated on a scale where no observed cells were indicated with a zero, scattered cells scored a one, numerous cells clustering on the sides of the polymer scored a two, and numerous cells surrounding the material resulted in a three. Both the histological score and fluorescence response normalized to alginate were examined for the whole library and materials that outperformed unmodified alginate were judged to be biocompatible. This corresponds to a normalized fluorescent signal of <100% and a fibrosis score of <3.

Data captured using whole animal imaging was demonstrated to displayed similar temporal trends in cellular recruitment of phagocytes to the biomaterials compared to histological analysis. Accordingly, the high throughput in vivo screening method described above was validated.

Example 5: In Vivo Screening of Modified Alginates to Quantify

Biocompatibility 8-12 week old male SKH1 mice were obtained from Charles River Laboratories (Wilmington, Mass.). The mice were maintained at the animal facilities of Massachusetts Institute of Technology, accredited by the American Association of Laboratory Animal care, and were housed under standard conditions with a 12-hour light/dark cycle. Both water and food were provided ad libitum.

Injections were performed in accordance with ISO 10993-6: 2001. Prior to injection all materials were sterilized via 0.22 m filtration. The mice were anesthetized via isoflurane inhalation at a concentration of 1-4% isoflurane/balance $O_2$ to minimize movement. Their backs were scrubbed with 70% isopropyl alcohol and the animals were injected with a modified alginate. The injection volume was 100 μl.

Cathepsin activity was measured 7 days post injection using an in vivo fluorescence assay to quantify the foreign body response to the modified alginate. 24 hours before in vivo fluorescence imaging, 2 nmol of ProSense-680 (VisEn Medical, Woburn, Mass., excitation wavelength 680±10 nm, emission 700±10 nm) dissolved in 150 μl sterile PBS was injected into the tail vein of each mouse to image cathepsin activity.

In vivo fluorescence imaging was performed with an IVIS-Spectrum measurement system (Xenogen, Hopkinton, Mass.). The animals were maintained under inhaled anesthesia using 1-4% isoflurane in 100% oxygen at a flow rate of 2.5 L/min. A binning of 8×8 and a field of view of 13.1 cm were used for imaging. Exposure time and f/stop—the relative size of the opening of the aperture—were optimized for each acquired image. Data were acquired and analyzed using the manufacturer's proprietary Living Image 3.1 software. All images are presented in fluorescence efficiency, which is defined as the ratio of the collected fluorescent intensity to an internal standard of incident intensity at the selected imaging configuration. Regions of interest (ROIs) were designated around the site of each injection.

Figure 4:
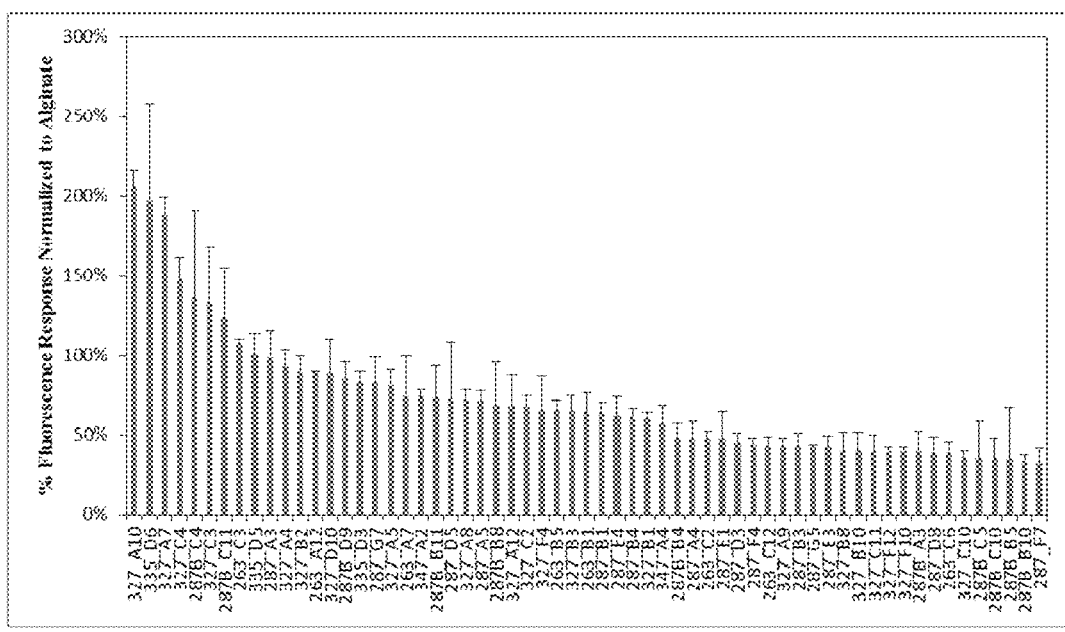
FIG. 4 is a plot obtained using the in vivo method described in Example 5, which quantifies the biocompatibility of selected modified alginates. The fluorescence response obtained for the modified alginates using the in vivo method described in Example 5 was normalized to the fluorescence response measured using unmodified alginate in order to quantify the biocompatibility of the modified alginates in terms of % fluorescence response.

Fluorescence images were captured 7 days post-injection illustrating relative cathepsin activity at the point of injection of selected modified alginates. The fluorescence intensity was measured and normalized to the fluorescence response measured using unmodified alginate in order to quantify the biocompatibility of the modified alginates. The results obtained for selected modified alginates are included in FIG. 4.

Example 6: Treatment of Diabetes in STZ-Induced Diabetic Mice

The transplantation of biocompatible alginate-encapsulated beta cells offers potential as a treatment for diabetes. Pancreatic rat islet cells were encapsulated using fourteen biocompatible modified alginate polymers identified using the assays detailed above (including PF_N287_B_B4, PF_N287_F2, PF_N287_G3, PF_N287_B3, PF_N287_B1, PF_N287_A4, PF_N287_B1, PF_N287_E3, PF_N263_C12, PF_N63_A12, PF_N287_E1, PF_N287_D3, PF_N263_A7, and PF_N263_C6). Alginate-encapsulated islets capsules were fabricated from 750 μl of a 4% (w/v) solution of each modified alginate in deionized water containing suspended 1,000 islets suspended using the Inotech encapsulator (Inotech) set to a voltage of 1.05 kV, a vibration of 1225 Hz, and a flow rate of 10-25 ml/min with a 300 μm nozzle. Alginate was crosslinked in a 20 mM $BaCl_2$ solution. After encapsulation, the capsules were washed twice with HEPES solution, four times with Krebs solution, and twice with RPMI-1640 medium.

The encapsulated rat islet cells were transplanted into STZ induced diabetic mice. Prior to transplantation, the mice were anesthetized under continuous flow of 1-4% isofluorane with oxygen at 0.5 L/min. A shaver with size #40 clipper blade will be used to remove hair to reveal an area of about 2 cm×2 cm on ventral midline of the animal abdomen. The entire shaved area was aseptically prepared with a minimum of 3 cycles of scrubbing with povidine, followed by rinsing with 70% alcohol. A final skin paint with povidine was also applied. The surgical site was draped with sterile disposable paper to exclude surrounding hair from touching the surgical site. A sharp surgical blade was used to cut a 0.5-0.75 cm midline incision through the skin and the linea alba into the abdomen. A sterile plastic pipette was used to transfer the alginate capsules into the peritoneal cavity. The abdominal muscle was closed by suturing with 5-0 Ethicon black silk or PDS-absorbable 5.0-6.0 monofilament absorbable thread. The external skin layer was closed using wound clips. These wound clips were removed 7-10 d post-surgery after complete healing was confirmed.

Blood glucose levels in the STZ induced diabetic mice were monitored daily for between 20 and 30 days post-transplantation using a drop of blood obtained by scrubbing the tail with 70% isopropyl alcohol and making a superficial cut on the skin of the tail to produce a drop of blood. Mice were restrained during sampling in a rotating tail injector.

Figure 5:
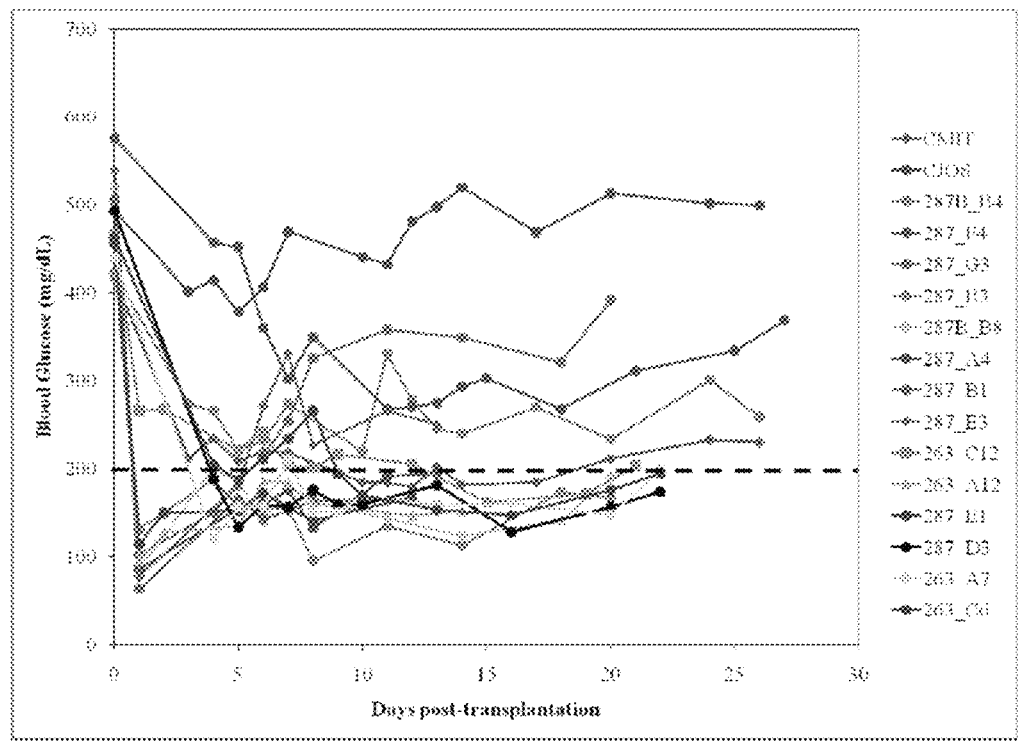
FIG. 5 is a plot detailing the blood glucose level of mice transplanted with rat islets encapsulated in selected modified alginates as well as two different unmodified alginates (CMIT and CJOS). The dashed line represents normoglycemia in mice. At 5 days post-implantation, 287_F4, CJOS, 287_B4, 263_C12, and CMIT are above the dashed line while the others are below the line. At 20 5 days post-implantation, the lines are, from top to bottom: CJOS, 287_G3, 287_F4, 287B_B4, CMIT, 287B_B8, 263_C12, 263_C6, 287_B3, 287_D3, and 263_A7.

The blood glucose levels in the STZ induced diabetic mice following islet transplantation are shown in FIG. 5. The dashed black line represents normoglycemia in mice. Pancreatic rat islet cells that were encapsulated in modified alginates were able to reduce the blood glucose levels in all cases, and in some cases, were even able to induce normoglycemia.

Example 7: Particles Prepared from Mixture of Modified Alginate(s) and Unmodified Alginate The growing recognition of the parameters driving fibrosis in vivo has been applied to the analysis of the performance of modified alginates. Intraperitoneal (IP) implantation of modified alginate capsules revealed that modified alginates may result in abnormally shaped capsules when crosslinked using conditions defined for unmodified alginates. These abnormally shaped capsules can complicate implementation and interpretation of modified alginate capsules implanted IP. In an effort to improve the capsule morphology, formulation methods for use with modified alginate microparticles were developed where modified alginates were blended with a small amount of high molecular weight alginate. Particles prepared from this mixture yielded particles with improved morphology and stability.

A 6% solution of modified alginate (w/w) was combined 1:1 by volume with a 1.15% solution of unmodified alginate (w/w). After mixing, capsules are formed by following this solution through an electrostatic droplet generator, followed by crosslinking of the polymer in a 20 mM aqueous barium chloride solution.

Figure 6:
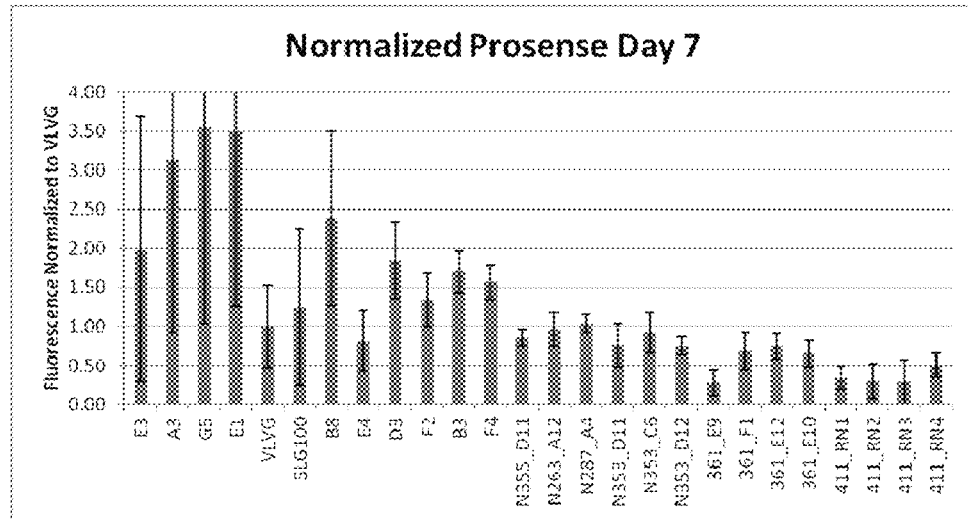
FIG. 6 is a bar graph showing inflammatory response (as measured by fluorescence normalized to VLVG) as a function of modified alginate (combined with unmodified alginate).

Particles prepared from modified alginate 263_A12 microparticles formulated with barium and mannitol were compared to particles prepared from 263_A12 blended with a small amount of unmodified SLG100 alginate (16% by weight). The particles prepared from a mixture of modified alginate and unmodified alginate produced more homogenous microparticle populations. Quantitative fluorescence analysis with prosense at several time points with modified alginates blended with SLG100 was performed. The results are shown in FIG. 6. Several reformulated modified alginates displayed less inflammatory response at day 7 compared to the control alginate. Initial experiments with large capsules (1.5 mm diameter) show comparably clean capsules after 2 weeks in the IP space of immunocompetent C57BL6 mice.

Data collected to date with these controlled capsules indicates that reformulation and capsule morphology can have a significant effect on inflammation as measured by prosense. An improved inflammation response is observed in some polymers (FIG. 6), while others are impacted negatively.

Example 8: Demonstration of Anti-Fibrotic Activity of Modified Alginates

In this example, a chemical modification approach was taken to mitigate the immune recognition of alginate microspheres in preclinical fibrosis models, including NHPs, which are relevant to translation in humans. The lead materials evade immune recognition and fibrosis in the IP space of both C57BL/6 mice and cynomolgus macaques. This alginate blocks macrophage adhesion, stunting activation of the foreign body response and providing insight to the surface properties necessary to overcome the fibrosis of implanted materials.

I. Methods
  A. Alginate Chemical Modification
    1. Alginate Amidation
    Alginate (Pronova UPVLVG from NovaMatrix, 1 eq., 100 mg=0.52 mmol of COOH available for reaction) was dissolved as a 2% Alginate solution in a 3:2 water:acetonitrile mixture (5 ml total volume). Amine (N1 to N9, Z1, Z2) (1 eq, Sigma Aldrich or TCI America) was then added to the mixture along with the coupling agent 2-chloro-4,6-dimethoxy-1,3,5-triazine (CDMT, 0.5 eq., 45 mg, Sigma Aldrich) and 4-Methylmorpholine (NMM, 1 eq., 56 µl, Sigma Aldrich). The mixture was stirred at 55° C. overnight and the solvent was removed under reduced pressure. The resulting solid was dissolved in water and filtered through cyano modified silica gel (Silicycle) to remove insoluble precipitate. The resulting solution was then dialyzed against a 10,000 MWCO dialysis membrane overnight with DI water to further purify the polymer. The resulting solution was then lyophilized to get purified compound.

2. Alginate Esterification
    Alginate (Pronova UPVLVG from NovaMatrix, 1 eq., 100 mg=0.52 mmol of COOH available for reaction) was dissolved as a 2% Alginate solution in a 3:2 water:alcohol (O1 to O12) mixture (5 ml total volume). The coupling agent 2-chloro-4,6-dimethoxy-1,3,5-triazine (CDMT, 0.5 eq., 45 mg, Sigma Aldrich) and 4-Methylmorpholine (NMM, 1 eq., 56 µl, Sigma Aldrich) was then added and the mixture was stirred at 55° C. overnight. The next day the solvent was removed under reduced pressure. The resulting solid was dissolved in water and filtered through cyano modified silica gel (Silicycle) to remove insoluble precipitate. The resulting solution was then dialyzed against a 10,000 MWCO dialysis membrane overnight with DI water to further purify the polymer. The resulting solution was then lyophilized to get purified compound.

3. Huisgen Cycloaddition ("Click")
    In a second step, alginates reacted with Z2 were dissolved in a solution of water:methanol 1:1 (5 ml total). Sodium azide (0.25 eq., 19 mg, Sigma Aldrich), sodium L-ascorbate (0.05 eq., 19 mg, Sigma Aldrich), trans-N,N'-Dimethylcyclohexane-1,2-diamine (0.25 eq., typically 20 µl, Sigma Aldrich), Copper(I)-Iodide (0.5 eq., 10 mg, Sigma Aldrich) were added as coupling agents. Then 0.51 mmol of the respective Alkyne (Y1 to Y20) was added and the mixture was stirred at 55° C. overnight. The solvent was removed under reduced pressure. The resulting solid was dissolved in water and filtered through cyano modified silica gel to remove insoluble precipitate. The clear solution was lyophilized and dissolved in 5 ml of water and dialyzed. The resulting solution was then dialyzed against a 10,000 MWCO dialysis membrane overnight with DI water to further purify the polymer. The resulting solution was then lyophilized to get purified compound.

In a second step, alginates reacted with Z1 were dissolved in a solution of water:methanol 1:1 (5 ml total). Tris[(1-benzyl-1H-1,2,3-triazol-4-yl)methyl]amine (TBTA, 0.2 eq., 50 mg, Sigma Aldrich), Trietylamine (0.25 eq, typically 15 µl, Sigma Aldrich), Copper(I)-Iodide (0.25 eq., 5 mg, Sigma Aldrich) were added as coupling agents. Then 0.51 mmol of the respective Alkyne was added and the mixture was stirred at 55° C. overnight. The solvent was removed under reduced pressure. The resulting solid was dissolved in water and filtered through cyano modified silica gel to remove insoluble precipitate. The clear solution was lyophilized, dissolved in 5 ml of water and dialyzed. The resulting solution was then dialyzed against a 10,000 MWCO dialysis membrane overnight with DI water to further purify the polymer. The resulting solution was then lyophilized to get purified compound.

4. Optimized Syntheses for Preparation of Z2-Y12, Z1-Y15 and Z1-Y19:
      Z2-Y12 Amine:
      10 g of 2-(2-Propynyloxy) tetrahydopyran (1 eq. 71.36 mmol) was added to a solution of 5.1 g Sodium azide (1.1 eq, 78.5 mmol), 1.41 g Sodium ascorbate (0.1 eq, 7.14 mmol), 2.29 ml Trans-N—N'-Dimethylcyclohexane-1,2-diamine (0.25 eq, 17.83 mmol), 3.4 g Copper(I)-iodide (0.025 eq, 17.83 mmol) in 75 ml methanol. To this mixture 19.97 g of 4 Iodobenzylamide HCl was added. The reaction was stirred overnight at 55° C. The solvent was removed under reduced pressure. The crude reaction was purified by liquid chromatography with dichloromethane:ultra (22% MeOH in DCM with 3% NH$_4$OH) mixture 0%→40% on silica gel. The product was then reacted with alginate as described below.

Z1-Y15 Amine:

3.5 g of 4-Propagylthiomorpholine 1,1-Dioxide (1 eq. 20 mmol) was added to a solution of 2.5 g TBTA (0.2 eq, 4 mmol), 750 µl Triethylamine (0.5 eq, 10 mmol), 250 mg Copper(I)-iodide (0.06 eq, 1.3 mmol) in 50 ml methanol. The mixture was cooled to 0° C. and 5.25 ml of 11-Azido-3,6,9-trioxaundecan-1-amine (1 eq, 20 mmol) was added. The reaction was stirred overnight at 55° C. The solvent was removed under reduced pressure. The crude reaction was purified by liquid chromatography with dichloromethane:ultra (22% MeOH in DCM with 3% NH$_4$OH) mixture 0%->100% on a C18 column. The product was then reacted with alginate as described below.

Z1-Y19 Amine:

3 g of 4-Ethynylaniline (1 eq. 20.2 mmol) was added to a solution of 2.5 g TBTA (0.2 eq, 4 mmol), 750 µl Triethylamine (0.5 eq, 10.1 mmol), 250 mg Copper(I)-iodide (0.06 eq, 1.31 mmol) in 50 ml methanol. The mixture was cooled to 0° C. and 5.25 ml of 11-Azido-3,6,9-trioxaundecan-1-amine (1 eq, 20 mmol) was added. The reaction was stirred overnight at 55° C. The solvent was removed under reduced pressure. The crude reaction was purified by liquid chromatography with dichloromethane:ultra (22% MeOH in DCM with 3% NH$_4$OH) mixture 0%→30% on a cyano functionalized silica column. The product was then reacted with alginate as described below.

Alginate Reaction:

1.5 g of UPVLVG (1 eq) was dissolved in 45 ml of water and 675 mg of 2-Chloro-4,6-dimethoxy-1,3,5-triazine (CDMT, 0.5 eq) and 840 µl of N-Methylmorpholine (NMM, 1 eq) was added. Then 7.65 mmol of the Z2-Y12, Z1-Y15, or Z1-Y19 amine was dissolved in 22.5 ml acetonitrile and added to the mixture. The reaction was stirred overnight at 55° C. The solvent was removed under reduced pressure and the solid was dissolved in water. The solution was filtered through a pad of cyano functionalized silica and the water was removed under reduced pressure to concentrate the solution. It was then dialyzed against a 10,000 MWCO membrane in DI water overnight. The water was removed under reduced pressure to give the functionalized alginate.

B. Capsule Formation

An electrostatic droplet generator was set up as follows: an ES series 0-100 KV, 20 Watt high voltage power generator (Gamma ES series, Gamma High Voltage Research, FL, USA) is connected to the top and bottom of a blunt tipped needle (SAI Infusion Technologies, IL, USA). This needle is attached to a 5 mL lure lock syringe (BD, NJ, USA) which is clipped to a syringe pump (Pump 11 Pico Plus, Harvard Apparatus, MA, USA) that is oriented vertically. The syringe pump pumps alginate out into a glass dish containing a 20 mM barium 5% mannitol solution (Sigma Aldrich, MO, USA). The settings of the PicoPlus syringe pump are 12.06 mm diameter and 0.2 mL/min flow rate. After the capsules are formed, they are then collected and then washed with hepes buffer (NaCl 15.428 g, KCl 0.70 g, MgCl2*6H2O 0.488 g, 50 mL of hepes (IM) buffer solution (Gibco, Life Technologies, California, USA) in 2 L of DiH2O) 4 times. The alginate capsules are left overnight at 4° C. The capsules are then washed 2 times in 0.8% saline and kept at 4° C. until use.

Solubilizing alginates: SLG20 (NovaMatrix, Sandvika, Norway) was dissolved at 1.4% weight to volume in 0.8% saline. SLG100 (NovaMatrix, Sandvika, Norway) was dissolved at 1.2% weight to volume in 0.8% saline. UPVLVG (NovaMatrix, Sandvika, Norway) was dissolved at 5% weight to volume in 0.8% saline. All modified alginates were initially dissolved at 5% weight to volume in 0.8% saline. Modifies were then blended with 3% weight to volume SLG100, dissolved in 0.8% saline (see Table 1 for ratios).

Forming different sized capsules: for 300 µm diameter capsules, a 30 gauge blunt tipped needle (SAI Infusion Technologies) was used with a voltage of 7-8 kV. For 500 µm diameter capsules, a 25 gauge blunt tipped needle (SAI Infusion Technologies) was used with a voltage of 5-7 kV. For 1.5 mm capsules, an 18 gauge blunt tipped needle (SAI Infusion Technologies) was used with a voltage of 5-7 kV.

TABLE 1

Modified Alginate to SLG100 blended volume ratios

| Modified Alginate | % Volume Modified Solution | % Volume SLG100 |
|---|---|---|
| 361_E9 | 70 | 30 |
| 411_RN8 | 80 | 20 |
| 411_OH6 | 60 | 40 |
| 411_OH9 | 60 | 40 |
| 411_OH11 | 50 | 50 |
| 411_OH3 | 80 | 20 |
| 411_RZA15 | 80 | 20 |
| 411_RZA2 | 50 | 50 |
| 411_RZA19 | 70 | 30 |
| 411_RN7 | 80 | 20 |
| VLVG/SLG100* | 80 | 20 |

Table 1 Legend:
Modified alginates are blended with SLG100 to make capsules. Modified alginate and SLG100 are drawn into a 5 mL syringe and thoroughly vortexed before encapsulation. Different modified alginates require a different percent volume of SLG100 added to make spherical capsules.
*VLVG/SLG100 is a control blend. The unmodified VLVG is blended with SLG100.

C. Transplantation of the Hydrogel Capsules and Other Material Spheres

All animal protocols were approved by the MIT Committee on Animal Care, and all surgical procedures and post-operative care was supervised by MIT Division of Comparative Medicine veterinary staff. Immune-competent male C57BL/6 mice (Jackson Laboratory, Bar Harbor, Me.) were anesthetized with 3% isoflurane in oxygen and had their abdomens shaved and sterilized using betadine and isopropanol. A 0.5 mm incision was made along the midline of the abdomen and the peritoneal lining was exposed using blunt dissection. The peritoneal wall was then grasped with forceps and a 0.5-1 mm incision was made along the linea alba. A desired volume of capsules were then loaded into a sterile pipette and transplanted into the peritoneal cavity through the incision. The incision was then closed using 5-0 taper tipped polydioxanone (PDS II) absorbable sutures. The skin was then closed over the incision using a wound clip and tissue glue. Preoperatively, all mice also received a 0.05 mg/kg dose of buprenorphine subcutaneously as a pre-surgical analgesic, along with 0.3 mL of 0.9% saline subcutaneously to prevent dehydration.

D. Retrieval of Cells, Tissues, and Materials

At desired time points post-transplantation, as specified in figures and results, mice were euthanized by CO$_2$ administration, followed by cervical dislocation. In certain instances, 5 ml of ice cold PBS was first injected in order perform an intraperitoneal lavage to rinse out and collect free-floating intraperitoneal immune cells. An incision was then made using the forceps and scissors along the abdomen skin and peritoneal wall, and intraperitoneal lavage volumes were pipetted out into fresh 15 ml falcon tubes (each prepared with 5 ml of RPMI cell culture media). Next, a wash bottle tip was inserted into the abdominal cavity. KREBS buffer was then used to wash out all material capsules from the abdomen and into petri dishes for collection. After ensuring all the capsules were washed out or manually retrieved, if fibrosed directly to intraperitoneal tissues, they were transferred into 50 mL conical tubes for downstream processing and imaging. After intraperitoneal lavage and capsule retrieval, remaining fibrosed intraperitoneal tissues were also excised for downstream FACS and expression analyses.

E. Imaging of the Retrieved Material Capsules

For phase contrast imaging, retrieved materials were gently washed using Krebs buffer and transferred into 35 mm petri dishes for phase contrast microscopy using an Evos XI microscope (Advanced Microscopy Group).

F. ProSense Assay

Female SKH1 mice (6 weeks old) were utilized for this assay. 100 ul of capsules were resuspended in 200 ul of saline, and injected subcutaneously into the mouse on the left side of upper back. The mice were feeded on AIN-93G purified rodent diet (TD 94045, Harlan) to minimize the fluorescent background after injection. Six days later, 100 ul (4 nmol) of ProSence 750 FAST (NEV11171, PerkinElmer Inc.) per mouse was injected intravenously via tail vein. At day 7 (i.e., 24 hours post the ProSense 750 FAST intravenous administration), the mice were scanned by IVIS Spectrum system (Xenogen, Caliper LifeScience). The mice were anesthetized using 3% isofluorane in oxygen and maintained at the same rate throughout the procedure, and the settings of the IVIS Spectrum system were Exposure=7.50, Binning=Medium, FStop=2, Excitation=605 and Emission=660. The images were analyzed with LivingImage Software, and the right side of upper back on the same mouse was used as control during the signal quantification.

G. Cell Staining and Confocal Immunofluorescence

Retrieved samples were stored in 4% paraformaldehyde overnight (diluted in 1×PBS). Samples were then washed in Krebs Buffer (7.889 g NaCl, 0.35 g KCl, 5.958 g HEPES (Sigma-Aldrich, Montana, USA), 0.163 g KH2PO4, 0.144 g MGSO4*H2O in 1000 mLs of DiH2O). Samples were washed with 10 mLs of PBS. PBS was aspirated and 20 mL of 1% Triton X-100 (Sigma-Aldrich, Montana, USA) solution was used to permeabilize cells. Samples were incubated for 10 minutes at room temperature. Samples were then incubated in 15 mLs of 1% albumin solution (Sigma-Aldrich, Montana, USA), diluted in 1×PBS for 30 minutes at room temperature. 3 mLs of antibody solution (1:200 CD68 488 Anti Mouse (BioLegend California, USA), 1:200 Anti-Mouse Actin, α-Smooth Muscle-Cy3(Sigma-Aldrich, Montana, USA), 1:30 Phalloidin anti mouse 647 (Life Technologies, California, USA), DAPI (NucBlue Live Cell Stain ReadyProbes, Life Technologies, California, USA) 2 drops per mL) all diluted in 1% albumin solution was added to each sample. Samples were incubated in staining solution for 45 minutes at room temperature. Staining solution was then aspirated. Samples were then washed twice with 20 mLs of 0.1% tween 20 solution (Sigma-Aldrich, Montana, USA), diluted in 1×PBS. Samples were then washed twice with 20 mLs of 1×PBS. Samples were then transferred to a 24 well glass bottom plate. Excess PBS was aspirated and 1 mL of 50% glycerol solution (Sigma-Aldrich, Montana, USA) was added. A Zeiss LSM 700 system with ZEN microscope software was used to image and analyze the stained samples. Obtained images where adjusted linearly for presentation using Photoshop (Adobe Inc. Seattle, Wash.).

H. Protein Extraction

Cells on retrieved capsules were lysed by sonication for 30 seconds on 30 seconds off cycle three times at 70% amplitude (QSonica Sonicator, Model #Q125, QSonica LLC) on ice in NP40 cell lysis buffer (Cat #FNN0021, Invitrogen) at the ratio of 100 ul capsules to 200 ul lysis buffer, with 100 mM PMSF and 1× protease inhibitors (Halt Protease inhibitor single-use cocktail, Cat. #78430, Thermo Scientific). Lysates were centrifuged for 20 min at 12000 rpm at 4° C.; the supernatant which contains proteins was aspirated in a fresh tube kept on ice. The pellets were washed with the same volume of lysis buffer (i.e. the pellet of 100 ul capsules were washed with 200 ul lysis buffer), and then centrifuged for 20 min at 12000 rpm at 4° C., combined the supernatant with the previous one. The proteins were stored at −80° C. for future use.

I. Elispot (Mouse Cytokine Array)

This assay was accomplished with Proteome Profiler Mouse Cytokine Array Panel A kit (Cat #ARY006, R&D system). For each membrane, 200 ul of protein solution was mixed with 100 ul of sample buffer (array buffer 4) and 1.2 ml of block buffer (array buffer 6), then added with 15 ul of reconstituted Mouse Cytokine Array Panel A Detection Antibody Cocktail and incubated at room temperature for 1 hour. The array membrane was incubated with block buffer (array buffer 6) for 2 hours on a rocking platform shaker in the meantime, and then the block buffer was aspirated, the prepared sample/antibody mixture was added onto the membrane and incubated overnight at 4° C. on a rocking platform shaker. The membrane was washed with 20 ml of 1× wash buffer for 10 minutes on a rocking platform shaker for three time and rinsed with deionized water once, then was probed with Fluorophore-conjugated streptavidin (1:5,000 dilution, Cat #926-32230, Li-Cor) at room temperature for 30 minutes on a rocking platform shaker, washed with wash buffer for three times and rinsed with deionized water once again as in above steps. Antibody-antigen complexes were visualized using Odyssey Detection (Li-Cor, Serial No. ODY-2329) at 800 nm wavelengths. The densities of the spots were analyzed by Image J software.

J. Western Blotting 12 ul of protein solution mixed with 1× loading buffer (SDS-Sample buffer, Cat.#BP-111R, Boston BioProducts) for each lane was boiled at 95° C. for 20 min and electrophoresed on SDS polyacrylamide gels (Any Kd 15-well comb mini-gel, Biorad, Cat #456-9036), and 3 ul of Precision Plus Protein Dual Xtra Stands (Cat #161-0377, Bio-rad) was used as ladder to indicate the position of the bands, and then blotted onto nitrocellulose membranes (Biorad, Cat. #162-0213). Blots were probed with anti-αSmooth Muscle actin antibody (1:400 dilution, Rabbit polyclonal to alpha smooth muscle Actin; Cat. #ab5694, AbCam) and anti-βactin antibody (1:4000 dilution, Monoclonal Anti-β-Actin antibody produced in mouse; Cat #A1978, Sigma Aldirch) as a loading control followed by Donkey Anti-Rabbit (1 to 15,000 dilution, Cat #926-32213, Li-Cor) and Goat Anti-Mouse (1 to 15,000 dilution, Cat #926-68070, Li-Cor) Fluorophore-conjugated secondary antibodies. Antibody-antigen complexes were visualized using Odyssey Detection (Li-Cor, Serial No. ODY-2329) at 700 and 800 nm wavelengths. The densities of the bands were analyzed by Image J software.

K. NanoString Analysis

RNAs for mock-transplanted (MT) controls, or for 500 or 1,500 μm alginate capsule-bearing mice (n=5/group) were isolated from tissue samples taken at various time points after transplantation. Respective RNAs were quantified, diluted to the appropriate concentration (100 ng/μl), and then 500 ng of each sample was processed according to NanoString manufacturer protocols for expression analysis via our customized multiplexed 53-gene mouse macrophage subtyping panel. RNA levels (absolute copy numbers) were obtained following nCounter (NanoString Technologies Inc., Seattle, Wash.) quantification, and group samples were analyzed using nSolver analysis software (NanoString Technologies Inc., Seattle, Wash.).

L. FACS Analysis

Single-cell suspensions of freshly excised tissues were prepared using a gentleMACS Dissociator (Miltenyi Biotec, Auburn, Calif.) according to the manufacturer's protocol. Single-cell suspensions were prepared in PEB dissociation buffer (1×PBS, pH 7.2, 0.5% BSA, and 2 mM EDTA) and suspensions were passed through 70 μm filters (Cat. #22363548, Fisher Scientific, Pittsburgh, Pa.). All tissue and material sample-derived, single-cell populations were then subjected to red blood cell lysis with 5 ml of 1×RBC lysis buffer (Cat. #00-4333, eBioscience, San Diego, Calif., USA) for 5 min at 4° C. The reaction was terminated by the addition of 20 ml of sterile 1×PBS. The cells remaining were centrifuged at 300-400 g at 4° C. and resuspended in a minimal volume (~50 μl) of eBioscience Staining Buffer (cat. #00-4222) for antibody incubation. All samples were then co-stained in the dark for 25 min at 4° C. with two of the fluorescently tagged monoclonal antibodies specific for the cell markers CD68 (1 μl (0.5 μg) per sample; CD68-Alexa647, Clone FA-11, Cat. #11-5931, BioLegend), Ly-6G (Gr-1) (1 μl (0.5 μg) per sample; Ly-6G-Alexa-647, Clone RB6-8C5, Cat. #108418, BioLegend), CD11b (1 μl (0.2 μg) per sample; or CD11b-Alexa-488, Clone M1/70, Cat. #101217, BioLegend). Two ml of eBioscience Flow Cytometry Staining Buffer (cat. #00-4222, eBioscience) was then added, and the samples were centrifuged at 400-500 g for 5 min at 4° C. Supernatants were removed by aspiration, and this wash step was repeated two more times with staining buffer. Following the third wash, each sample was resuspended in 500 μl of Flow Cytometry Staining Buffer and run through a 40 μm filter (Cat. #22363547, Fisher Scientific) for eventual FACS analysis using a BD FACSCalibur (cat. #342975), BD Biosciences, San Jose, Calif., USA). For proper background and laser intensity settings, unstained, single antibody, and IgG (labeled with either Alexa-488 or Alexa-647, BioLegend) controls were also run.

M. Intravital Imaging

For intravital imaging, SLG20 hydrogels of 500 μm and 1500 μm sizes were loaded with Qdot 605 (Life technologies, Grand Island, N.Y.) and surgically implanted into C57BL/6-Tg(Csf1r-EGFP-NGFR/FKBP1A/TNFRSF6) 2Bck/J mice as described above. After 7 days post transplantation, the mice were placed under isoflurane anesthesia and a small incision was made at the site of the original surgery to expose beads. The mice were placed on an inverted microscope and imaged using a 25×, N.A. 1.05 objective on an Olympus FVB-1000 MP multiphoton microscope at an excitation wavelength of 860 nm. Z-stacks of 200 μm (10 μm steps) were acquired at 2-minute intervals for time series of 20-45 minutes depending on the image. The mice were kept under constant isoflurane anesthesia and monitored throughout the imaging session. Obtained images were analyzed using Velocity 3D Image Analysis Software (Perkin Elmer, Waltham, Mass.).

N. Confocal Raman Spectroscopy

Sample Preparation:

A drop of hydrogel capsules with buffer solution was dried on the quartz coverslip (043210-KJ, Alfa Aesar). In order to remove the salt from dried buffer solution, a drop of distilled water was gently applied on top of the dried sample and immediately absorbed by a tissue. By doing that, dried hydrogel capsules are prepared for Raman mapping.

Instrumentation:

A custom-built NIR confocal Raman microscopy system was previously reported (Kang et al., Combined confocal Raman and quantitative phase microscopy system for biomedical diagnosis. Biomed. Opt. Exp. 2(9):2484-2492 (2011); Kang et al., Measuring uptake dynamics of multiple identifiable carbon nanotube species via high-speed confocal Raman imaging of live cells. Nano Letters 12(12):6170-6174 (2012)). Briefly, a 785 nm wavelength Ti: Sapphire laser (3900S, Spectra-Physics) was used for sample excitation. The collimated beam was filtered by a band pass filter (BPF, LL01-785-12.5, Semrock) and redirected to the dual axes galvanometer mirrors. High-speed XY scanning was performed by the galvanometer mirrors (CT-6210, Cambridge Technology). A 1.2 NA water immersion objective lens (Olympus UPLSAPO60XWIR 60X/1.20) was used to both focus the laser light onto the sample and to collect the back-scattered light. A piezo actuator combined with a differential micrometer (DRV517, Thorlabs) was used to perform the coarse and fine adjustments, respectively, of the sample focus. A flip mirror was placed after the tube lens so that the sample focal plane from the incoherent transmission source can be observed using a video camera with 75× magnification. The back-scattered Raman light from the sample passes through two dichroic mirrors (DM1: Semrock LPD01-785RU-25, DM2: Semrock LPD01-785RU-25×36× 1.1) and was collected by a multi-mode fiber (Thorlabs M14L01). The collected signal was delivered to the spectrograph (Holospec f/1.8i, Kaiser Optical Systems) and detected by a thermoelectric-cooled, back-illuminated and deep depleted CCD (PIXIS: 100BR_eXcelon, Princeton Instruments). LabView 8.6 software (National Instruments), data acquisition board (PCI-6251, National Instruments) and MATLAB 2013 software (Mathworks) were used to control the system, acquire the data, and analyze the data.

Raman Spectroscopy Measurement:

60 mW of 785 nm laser power was focused to a micron spot size and used to raster scan the hydrogel samples. 30×30 spectra were acquired from 45 μm×45 μm area with an integration time 1.0 s/pixel. The total measurement time was approximately 15 minutes.

Data Processing:

Two Raman images are generated based on the intensities of two Raman bands. These Raman images are resized and overlaid as red and green colors on top of corresponding bright field image from the same area.

II. Polymer and Compound Characterization

N7: $^1$H (400 MHz; $D_2O$): 3.10-4.10 (m, alginate protons), 4.20 (2H, s, $H_2N$—$CH_2$-Ph), 4.40-5.20 (m, alginate protons), 7.41 (2H, m, Phenyl), 7.49 (3H, m, Phenyl)

IR (ATR): 3234, 1579, 1465, 1407, 1368, 1078, 810, 692, 517.

N8: $^1$H (400 MHz; $D_2O$): 3.00-3.20 (m, alginate protons), 3.60 (8H, m, ethoxy), 3.60-5.10 (m, alginate protons).

IR (ATR): 3233, 2927, 2358, 1591, 1405, 1318, 1022, 945, 810.

O3: $^1$H (400 MHz; D$_2$O): 1.90-2.10 (m, 4H, Furfuryl), 3.23 (m, 2H, Furfuryl) 3.26-4.00 (m, alginate protons), 4.03 (3H, m, O—CH2-C[furfuryl]), 4.10-5.20 (m, alginate protons)

IR (ATR): 3202, 3070, 2344, 1711, 1594, 1398, 1021, 715, 549

O6: $^1$H (400 MHz; D$_2$O): 3.60-4.52 (m, alginate protons), 4.59 (2H, m, O—CH2-C[furfuryl]), 4.6-5.2 (m, alginate protons), 6.45 (2H, m, CH—CH=CH—O Furfuryl), 7.53 (1H, m, CH—CH=CH—O Furfuryl).

IR (ATR): 3232, 2360, 1614, 1410, 1028, 538.

O9: $^1$H (400 MHz; D$_2$O): 0.20 (s, 9H, Furfuryl,) 3.10-5.20 (m, alginate protons).

IR (ATR): 3310, 2939, 2360, 1592, 1406, 1316, 1081, 1020, 902, 770.

O11: $^1$H (400 MHz; D$_2$O): 3.05-4.50 (m, alginate protons), 4.52 (2H, s, O—CH2-Ph), 4.52-5.2 (m, alginate protons), 6.88 (2H, m, Phenyl), 7.26 (2H, m, Phenyl).

IR (ATR): 3370, 3089, 1597, 1517, 1454, 1235, 1207, 989, 835, 801, 561.

Z1-Y2: $^1$H (400 MHz; D$_2$O): 3.05-3.40 (m, alginate protons), 3.40-3.66 (16H, m, ethoxy), 3.75 (3H, s, methoxy) 3.8-5.1 (m, alginate protons), 7.19 (1H, m, Phenyl), 7.50 (1H, m, Phenyl), 7.94 (1H, m, Phenyl), 8.00 (1H, m, Phenyl), 8.49 (1H, s, triazole).

IR (ATR): 3144, 2922, 1592, 1400, 1329 1019, 943.

Z1-Y15: $^1$H (400 MHz; D$_2$O): 3.07 (4H, s, N—CH$_2$—CH$_2$—S), 3.17-3.40 (m, alginate protons), 3.46 (4H, s, N—CH$_2$—CH$_2$—S), 3.50-3.70 (16H, m, ethoxy), 3.7-5.2 (m, alginate protons), 8.08 (1H, s, triazole).

IR (ATR):3268, 2933, 2250, 1602, 1409, 1292, 1119, 1023, 946.

Z1-Y19: $^1$H (400 MHz; D$_2$O): 3.05-3.40 (m, alginate protons), 3.40-3.66 (16H, m, ethoxy), 4.4-5.1 (m, alginate protons), 6.96 (2H, m, Phenyl), 7.63 (3H, m, Phenyl), 8.23 (1H, s, triazole).

IR (ATR): 3234, 2929, 2361, 1593, 1406, 1317 1024, 947, 810.

Z2-Y12: $^1$H (400 MHz; D$_2$O): 1.57-1.78 (m, 6H, pyran), 3.10-4.40 (m, alginate protons), 4.48 (4H, m, pyran), 4.50-5.10 (m, alginate protons), 7.56 (2H, m, Phenyl), 7.76 (3H, m, Phenyl), 8.51 (1H, s, triazole).

IR (ATR): 3235, 2933, 2111, 1592, 1405, 1290, 1023, 946.

N4-N2: $^1$H (400 MHz; D$_2$O): 2.72 (s, 3H, N—CH$_3$ Dioxolane) 2.77 (s, 3H, N—CH$_3$ Benzyl), 3.36 (2H, d, N—CH$_2$-Dioxolane), 3.55-4.20 (m, alginate protons), 4.22 (2H, m, N—CH$_2$-Ph), 4.50-5.10 (m, alginate protons), 5.19 (1H, m, CH2-CH—O Dioxolane), 7.51 (5H, m, Phenyl).

IR (ATR): 3250, 2894, 1601, 1409, 1127, 1088, 1029, 946.

O3-O10: $^1$H (400 MHz; D$_2$O): 1.60-2.20 (m, 4H, Tetrahydrofurfuryl), 3.55-5.10 (m, alginate protons), 3.78 (2H, m, CH$_2$—CH$_2$—O Tetrahydrofurfuryl), 3.85 (3H, s, COO—CH$_3$), 4.13-4.30 (3H, m, N—CH$_2$— Tetrahydrofurfuryl).

IR (ATR): 3448, 2926, 2111, 1618, 1420, 1290, 1096, 948, 904.

N9-O8: $^1$H (400 MHz; D$_2$O): 1.28 (m, 3H, N—CH$_2$—CH$_3$), 1.32 (m, 3H, O—CH$_2$—CH$_3$), 1.63 (m, 3H, N—CH$_2$—CH$_2$—CH$_2$—OH) 1.74 (m, 3H, N—CH$_2$—CH$_2$—CH$_2$—OH), 3.09-3.40 (m, 6H, CH$_3$—CH$_2$—N—CH$_2$—CH$_2$—CH$_2$—OH), 3.55-5.10 (m, alginate protons), 4.06 (m, 3H, O—CH$_2$—CH$_3$).

IR (ATR): 3422, 1709, 1655, 1611, 1474, 1395, 1042, 798.

Small Molecule Preparations:

Z2-Y12 amine:

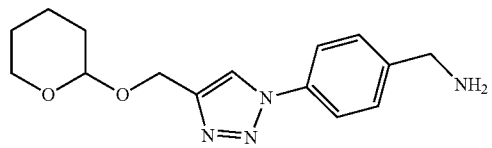

$^1$H (400 MHz; MeOD): 1.57 (m, 4H, pyran), 1.72 (m, 1H, pyran), 1.82 (m, 1H, pyran) 3.58 (m, 1H, pyran), 3.87 (s, 1H, NH$_2$—CH$_2$—Ph), 3.92 (m, 1H, pyran), 4.68 (d, 1H, J=12 Hz, O—CH$_2$-triazole), 4.79 (m, 1H, O—CH—O pyran), 4.97 (d, 1H, J=12 Hz, O—CH2-triazole), 7.54 (m, 2H, aromatic), 7.80 (m, 2H, aromatic), 8.49 (s, 1H, triazole).

$^{13}$C (400 MHz; MeOD): 20.3 (CH$_2$ pyran), 26.5 (CH$_2$ pyran), 31.5 (CH$_2$ pyran), 46.1 (NH$_2$CH$_2$), 61.0 (O—CH$_2$—C), 63.3 (CH$_2$—O pyran), 99.5 (O—CH—O pyran), 121.6 (CH aromatic), 123.17 (CH triazole), 129.9 (CH aromatic), 137.1 (Cq-N aromatic), 144.9 (Cq-C aromatic), 146.9 (C triazole).

High resolution MS: M+1=289.1665+3.1 ppm.

Z1-Y15 amine:

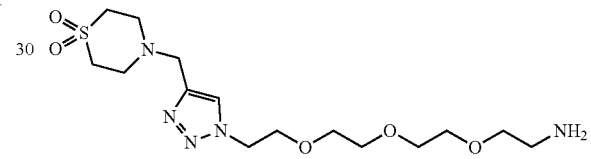

$^1$H (400 MHz; D$_2$O): 2.86 (2H, s, NH$_2$), 3.01 (4H, m, N—CH$_2$—CH$_2$—S), 3.10 (4H, m, N—CH$_2$—CH$_2$—S), 3.55 (2H, t, J=5.2 Hz, NH$_2$—CH$_2$), 3.61 (8H, m, PEG) 3.85 (2H, s, Thiomorpholine-CH$_2$-Triazole), 3.90 (2H, m, J=5.2 Hz, N—CH$_2$—CH$_2$—O), 4.59 (t, 2H, J=5.2, N—CH$_2$—CH$_2$—O), 7.99 (1H, s, triazole).

$^{13}$C (400 MHz; MeOH): 41.7 (NH$_2$—CH$_2$), 51.42 (N—CH$_2$), 51.48 (N—CH$_2$ Thiomorpholine) 52.1 (S—CH$_2$ Thiomorpholine) 52.4 (Thiomorpholine-CH$_2$-Triazole), 70.4-72.1 (m, PEG), 126.0 (CH triazole), 144.5 (C triazole).

High resolution MS: M+1=392.1968-6.1 ppm.

Z1-Y19 amine:

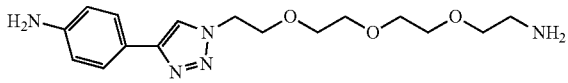

$^1$H (400 MHz; MeOD): 2.79 (t, 2H, J=5.2 Hz, NH$_2$—CH$_2$), 3.46 (t, 2H, J=5.2, NH$_2$—CH$_2$—CH$_2$), 3.53 (m, 4H, PEG), 3.61 (m, 4H, PEG), 3.91 (t, 2H, J=5.2, N—CH$_2$—CH$_2$—O), 4.58 (t, 2H, J=5.2, N—CH$_2$—CH$_2$—O) 6.76 (m, 2H, aromatic), 7.54 (m, 2H, aromatic), 8.14 (s, 1H, triazole).

$^{13}$C (400 MHz; MeOD): 41.6 (NH$_2$—CH$_2$), 51.4 (N—CH$_2$), 70.3-71.9 (m, PEG), 116.4 (CH aromatic), 121.1 (Cq-C), 121.5 (CH triazole), 127.7 (CH aromatic), 149.4 (C—NH$_2$ aromatic), 149.5 (C triazole).

High resolution MS: M+1=336.2036-8.3 ppm.

III. Results

The amines and alcohols listed in Table 2 were used to prepare the modified alginates. In the first combinatorial reaction, UPLVG alginate was reacted with one of the compounds in Table 2 in the presence of 2-Chloro-4,6-dimethoxy-1,3,5-triazine (CDMT) and N-methyl morpholine (NMM). In order to prepare multiply modified alginates, the first step was repeated using a different alcohol or amine from Table 2. Alginates modified with amine Z2 were then reacted with sodium azide to prepare the corresponding azide-modified alginate. These alginates, along with alginates modified with amine Z1, were then reacted with one of the alkynes listed in Table 2 in the presence of $CuSO_4$ and sodium ascorbate in order to prepare tetrazole-modified alginates.

Following each covalent modification, the modified alginates were filtered through a cyano-modified silica column to capture bulk organic impurities. Finally, after completing all covalent modification steps, the modified alginates were dialyzed against 10,000 MWCO membrane to remove any remaining small-molecule or low molecular weight impurities.

The purity of the modified alginates was determined by $^1H$ NMR analysis. The $^1H$ NMR spectra of each modified alginate polymer was collected, and peaks corresponding to the modified alginate polymer and to any impurities were integrated to determine the relative quantity of each species in the sample.

TABLE 2

Chemical modifications of the 73 capsule formulations

| Alginate # | Modifications |
|---|---|
| 1 | O1-O7 |
| 2 | O3-O10 |
| 3 | O1-O11 |
| 4 | O9-O12 |
| 5 | O3-O7 |
| 6 | Z2-Y8 |
| 7 | Z1-Y20 |
| 8 | SLG100 |
| 9 | Z2-Y16 |
| 10 | Z2-Y13 |
| 11 | Z2-Y17 |
| 12 | O5 |
| 13 | O7-O9 |
| 14 | Z2-Y15 |
| 15 | O8 |
| 16 | O4-O1 |
| 17 | Z2-Y4 |
| 18 | N9-Z1-Y16 |
| 19 | Z1-Y4 |
| 20 | VLVG |
| 21 | Z1-Y6 |
| 22 | Z2-Y11 |
| 23 | N1 |
| 24 | N9 |
| 25 | Z2-Y3 |
| 26 | N6-Z1-Y18 |
| 27 | O9-O2 |
| 28 | Z2-Y2 |
| 29 | Z1-Y7 |
| 30 | O4-O7 |
| 31 | N4-N2 |
| 32 | Z1-Y8 |
| 33 | Z2-Y16 |
| 34 | V/S |
| 35 | Z2 |
| 36 | Z1-Y14 |
| 37 | O9-O3 |
| 38 | N2-Z2-Y6 |
| 39 | N2 |
| 40 | O5-O9 |
| 41 | Z2-Y15 |
| 42 | Z1-Y18 |
| 43 | O7 |

TABLE 2-continued

Chemical modifications of the 73 capsule formulations

| Alginate # | Modifications |
|---|---|
| 44 | Z1-Y12 |
| 45 | N9-Z1-Y18 |
| 46 | O10 |
| 47 | Z2-Y7 |
| 48 | Z1-Y10 |
| 49 | N6 |
| 50 | Z2-Y13 |
| 51 | O12 |
| 52 | N3 |
| 53 | O4 |
| 54 | Z1-Y11 |
| 55 | Z1-Y17 |
| 56 | Z1-Y1 |
| 57 | Z1-Y9 |
| 58 | Z2-Y6 |
| 59 | SLG20 |
| 60 | N5 |
| 61 | Z1-Y3 |
| 62 | Z2-Y5 |
| 63 | Z1 |
| 64 | O6 |
| 65 | Z1-Y15 |
| 66 | Z1-Y2 |
| 67 | N8 |
| 68 | Z1-Y19 |
| 69 | O3 |
| 70 | Z2-Y12 |
| 71 | N7 |
| 72 | O9 |
| 73 | O11 |

Figure 7:
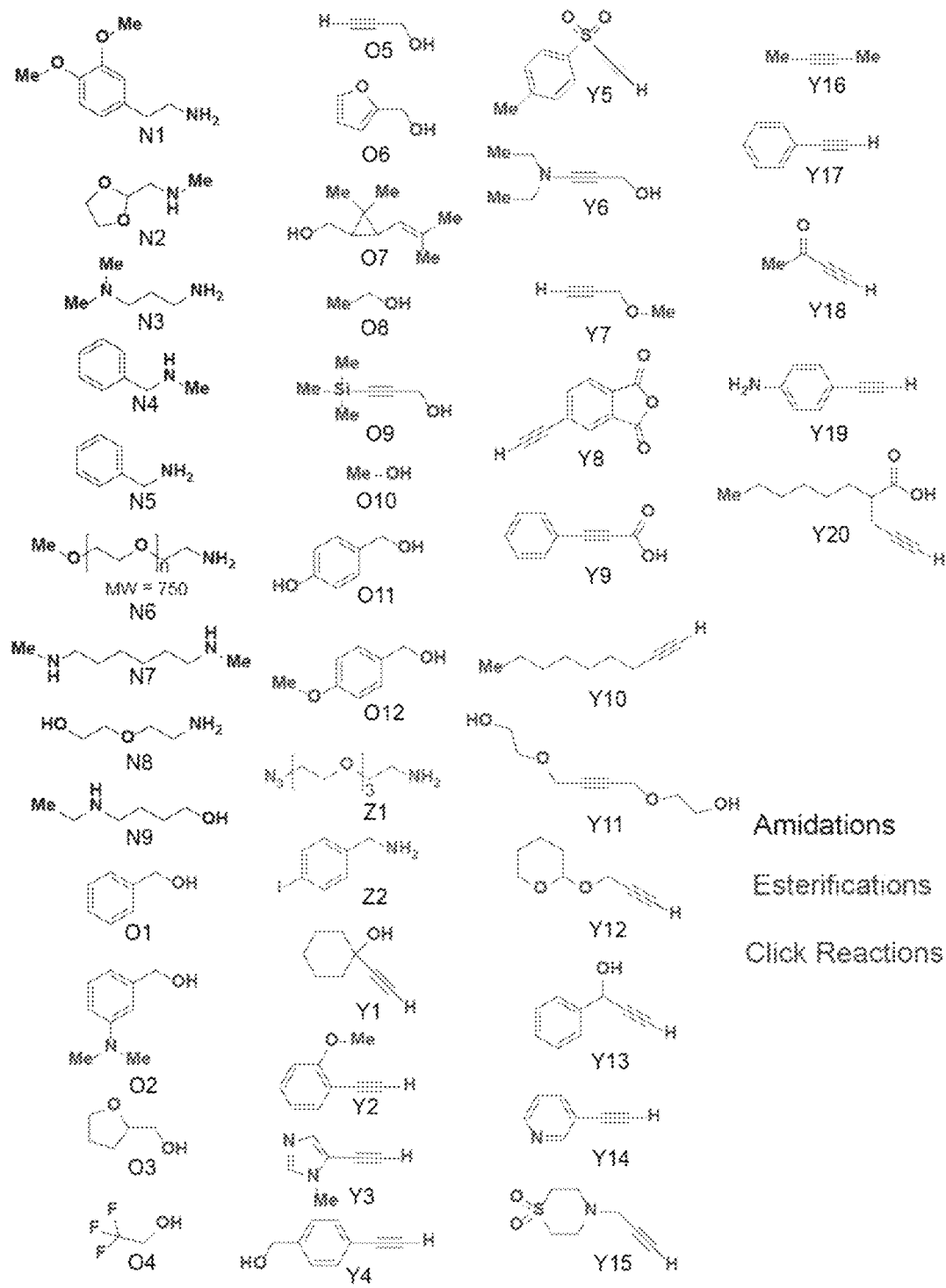
FIG. 7 is a diagram of the structures of amines, alcohols, azides, and alkynes used for the chemical modification of alginate. "N" designation indicates amidation reagents, "O" designations indicate esterification reagents, and "Y" designations indicate click reagents.
Figure 9:
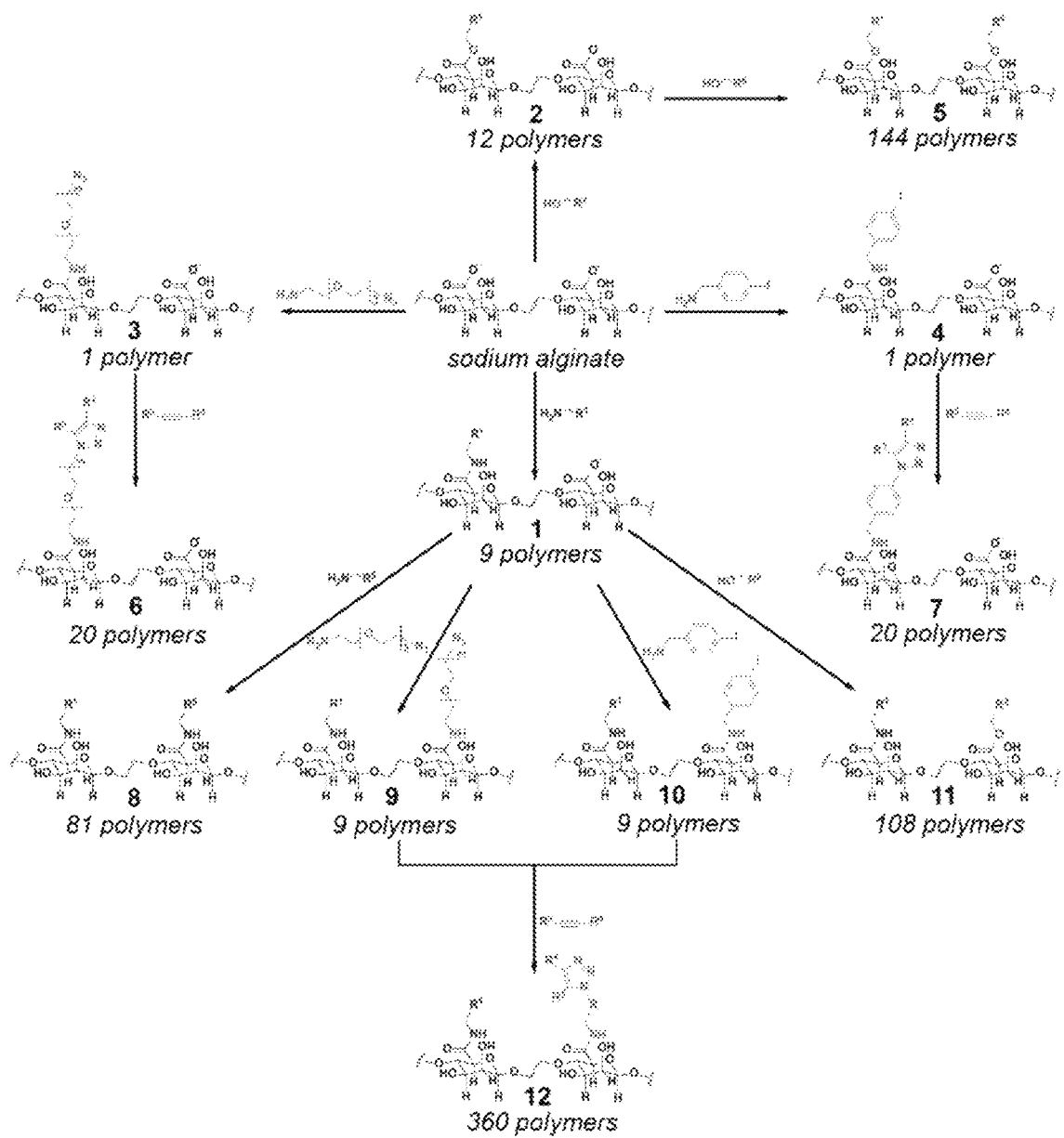
FIG. 9 is a diagram of the scheme for the synthesis of 774 alginate analogues.
Figure 11:
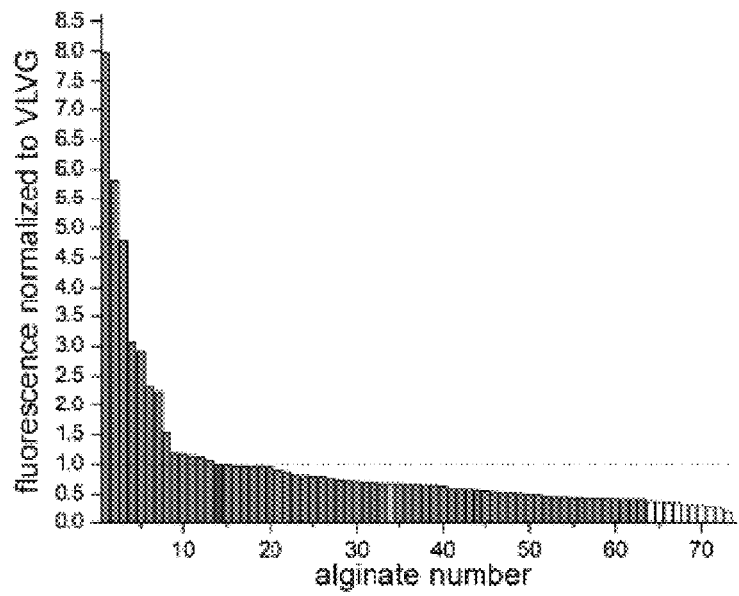
FIG. 11 is a graph showing secondary cathepsin evaluation of 70 top modified alginates from the initial screen formulated as 300 μm capsules. Data normalized to the fluorescence of VLVG capsules. The ten alginate analogue capsules with the lowest cathepsin levels are on the right with lighter shading.

A. Chemical Modification of Alginate Curtails the Foreign Body Response in C57BL/6 Mice The physicochemical parameters governing anti-fibrotic properties are currently poorly understood, making rationally designed approaches challenging (Williams, *Biomaterials* 29:2941-2953 (2008)). To better understand which structural features are germane to anti-fibrotic properties, a pool of diverse chemical compounds was selected that can modify latent functionalities and properties on the polymeric alginate backbone (FIG. 7). A 774-membered alginate analogue library was constructed with a variety of amines, alcohols, azides, and alkynes (FIG. 9). Of the 774 alginate analogues, 35 analogues resulted in unacceptably low yields and 634 alginates were determined to be capable of gelation after modification. These alginates were then evaluated as bulk hydrogels in a subcutaneous high-throughput mouse to measure levels of acute inflammation (Tables 3-7). 200 alginate analogues displayed lower levels of cathepsin activity than the control alginate UPVLVG, the alginate used as the starting material for the library synthesis. Component designations refer to the components of Table 2 and FIG. 7. This assay monitors neutrophil activation subcutaneously with an imaging agent which yields increased fluorescence in response to increased neutrophil-mediated cathepsin activity. Two hundred analogues displayed fluorescent levels that were lower than the base unmodified, ultrapure VLVG alginate (FIG. 11).

Figure 12:
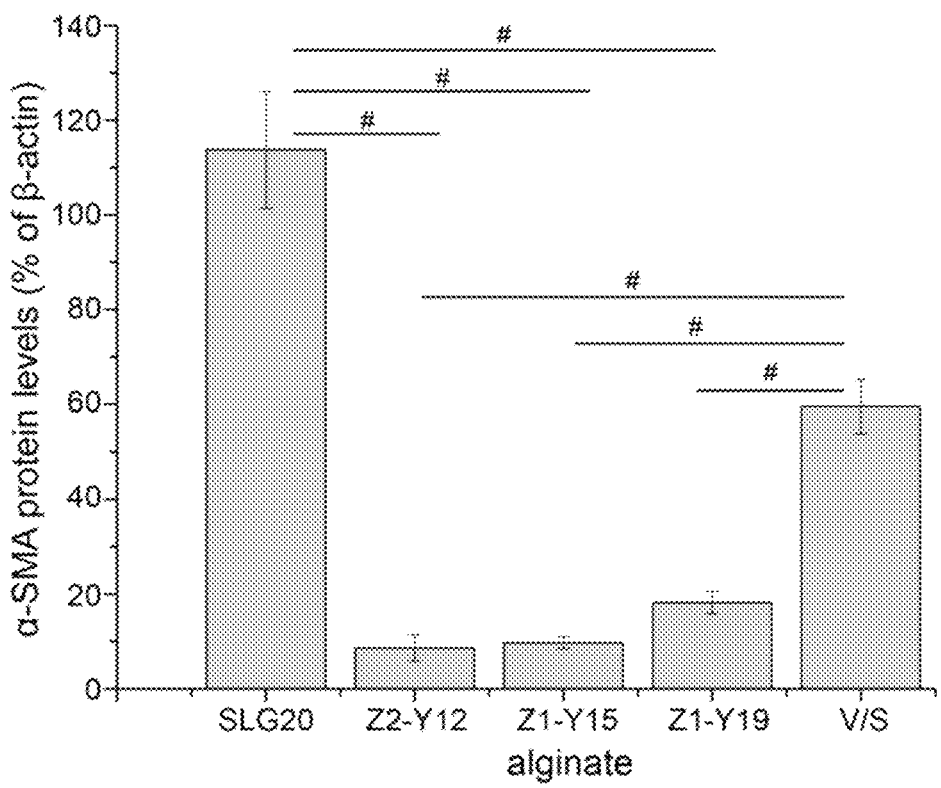
FIG. 12 is a graph of cytokine panel analysis (Elispot) of protein extracted from 300 μm capsules of the top ten alginate analogue capsules and control alginate capsules (SLG20, V/S) retrieved from the IP space of C57BL/6 mice after 14 days. For each cohort n=5. # indicate a significance difference between the means with p<0.01.

Since microcapsules have been the preferred alginate geometry in both drug delivery and cell encapsulation applications, 70 of the top 200 performing polymers (Table 2) from the initial screen were fabricated into 300 µm capsules and re-evaluated in the subcutaneous inflammation assay (FIG. 12). Using chemically-modified alginate proved problematic in constructing microspheres, and good capsule morphology was restored by blending a small amount of ultrapure SLG100 alginate with the alginate analogue solution.

TABLE 3

Cathepsin Activity of Singularly Modified Alginate Polymers

| Moiety | Cathepsin Activity | Moiety | Cathepsin Activity | Moiety | Cathepsin Activity |
|---|---|---|---|---|---|
| N8  | 3.69 | Z2-Y16 | 1.37 | Z1-Y4  | 0.48 |
| N9  | 0.76 | Z2-Y10 | 1.37 | Z1-Y6  | 0.50 |
| N3  | 1.14 | Z2-Y14 | 1.00 | Z1-Y17 | 0.58 |
| N6  | 1.37 | Z2-Y5  | 1.14 | Z1-Y1  | 0.82 |
| N4  | 1.37 | Z2-Y12 | 0.84 | Z1-Y2  | 0.48 |
| N5  | 2040 | Z2-Y7  | 1.37 | Z1-Y11 | 0.64 |
| N2  | 0.96 | Z2-Y6  | 0.71 | Z1-Y10 | 0.54 |
| N1  | 1.57 | Z2-Y8  | 0.97 | Z1-Y12 | 0.84 |
| N7  | 0.39 | Z2-Y20 | 1.57 | Z1-Y13 | 0.76 |
| O6  | —    | Z2-Y3  | 1.37 | Z1-Y16 | 0.92 |
| O12 | 0.81 | Z2-Y18 | 1.37 | Z1-Y9  | 0.60 |
| O11 | —    | Z2-Y2  | 2.17 | Z1-Y14 | 0.79 |
| O5  | 1.17 | Z2-Y4  | 1.60 | Z1-Y15 | 0.82 |
| O3  | 1.17 | Z2-Y17 | 1.60 | Z1-Y7  | 0.66 |
| O4  | 0.96 | Z2-Y1  | 1.77 | Z1-Y5  | 0.42 |
| O9  | 0.82 | Z2-Y11 | 1.60 | Z1-Y20 | 0.50 |
| O7  | 0.72 | Z2-Y9  | 0.8  | Z1-Y3  | 0.42 |
| O8  | 0.96 | Z2-Y13 | 1.57 | Z1-Y18 | 0.56 |
| O2  | 0.97 | Z2-Y15 | 0.91 | Z1-Y19 | 0.54 |
| O1  | 1.17 | Z2-Y19 | —    | Z1-Y8  | 0.58 |
| O10 | 0.69 |        |      |        |      |

TABLE 4

Cathepsin Activity of Multiply Modified Alginate Polymers

|     | N8   | N9   | N3    | N6   | N4    | N5   | N2    | N1    | N7   |
|-----|------|------|-------|------|-------|------|-------|-------|------|
| N7  | —    | —    | 0.20  | —    | —     | —    | —     | —     | —    |
| N9  | 0.51 | —    | —     | —    | 0.42  | 0.54 | 0.92  | —     | 1.37 |
| N4  | 1.37 | 0.48 | 2.40  | —    | −1.14 | —    | 2.17  | 0.76  | 1.17 |
| N2  | —    | 0.81 | —     | —    | 0.86  | 0.80 | −2.40 | —     | —    |
| N6  | —    | 0.60 | —     | —    | —     | —    | —     | 0.91  | 1.37 |
| N8  | 0.87 | 0.97 | —     | —    | —     | 1.17 | 0.86  | —     | 0.97 |
| O3  | 0.71 | 0.88 | 0.60  | 0.72 | 0.6   | 0.58 | 0.58  | 0.64  | 0.76 |
| O2  | 0.63 | 0.99 | 0.78  | 0.69 | 0.91  | 0.64 | 0.75  | 0.72  | 1.17 |
| O10 | 1.17 | 0.72 | 0.95  | 0.78 | 0.92  | 0.88 | 0.82  | 0.88  | 0.69 |
| O1  | 0.97 | 0.91 | 0.80  | 0.76 | 0.92  | 0.89 | 0.88  | 0.88  | 0.75 |
| O8  | 0.87 | 0.92 | 0.81  | 0.93 | 0.78  | 0.80 | 0.84  | 0.81  | 0.89 |
| O12 | 0.76 | 0.88 | 0.79  | 0.87 | 0.81  | 0.75 | 0.82  | 0.75  | 0.76 |
| O9  | 0.88 | 0.92 | 1.17  | 0.85 | 0.84  | 0.78 | 1.17  | 1.17  | 0.89 |
| O7  | 1.17 | 0.97 | 0.99  | 0.96 | 1.17  | 1.17 | 1.17  | 0.84  | 1.37 |
| O4  | 0.89 | 0.71 | 1.17  | 0.78 | 1.37  | 1.14 | 0.76  | 0.91  | 1.60 |
| O5  | —    | 0.88 | 0.54  | 0.96 | 0.96  | 1.37 | 0.60  | 0.69  | 1.17 |
| O11 | 1.00 | 1.37 | —     | 1.17 | 1.17  | —    | 0.75  | 0.69  | 1.17 |
| N1  | 2.57 | 1.77 | —     | 1.17 | —     | 0.56 | —     | −0.50 | 1.17 |
| N3  | 1.37 | 1.17 | −0.82 | 0.75 | —     | —    | 1.57  | —     | —    |
| N5  | 0.75 | 1.60 | 0.69  | 1.60 | —     | —    | 0.63  | —     | 0.24 |
| O6  | 0.75 | —    | 0.63  | —    | 0.69  | 0.89 | 0.82  | 0.81  | —    |

TABLE 5

Cathepsin Activity of Multiply Modified Alginate Polymers

|        | N2   | N1   | N3   | N4   | N5   | N7   | N9   | N8   | N6   |
|--------|------|------|------|------|------|------|------|------|------|
| Z2-Y16 | 1.14 | —    | 1.17 | 0.60 | 0.75 | 1.17 | 1.37 | 1.57 | 0.93 |
| Z2-Y10 | —    | —    | 1.37 | 1.37 | —    | 1.17 | 1.37 | 1.14 | 1.37 |
| Z2-Y14 | —    | —    | —    | —    | 1.60 | 1.97 | 1.77 | 1.77 | 1.77 |
| Z2-Y5  | 1.37 | 1.17 | 0.96 | 1.37 | 0.87 | 0.93 | 0.86 | 0.66 | 0.66 |
| Z2-Y12 | 1.37 | 1.77 | 1.37 | 1.37 | 1.97 | 1.17 | 1.14 | 0.96 | 0.88 |
| Z2-Y7  | 0.75 | 0.66 | 0.99 | 0.76 | 0.81 | —    | 0.96 | 0.79 | 0.96 |
| Z2-Y6  | 0.78 | 1.37 | 0.97 | 0.84 | 0.92 | —    | 0.82 | 0.54 | 0.97 |
| Z2-Y8  | —    | 1.17 | —    | —    | 1.37 | 1.14 | 1.37 | 1.37 | 1.37 |
| Z2-Y20 | 0.51 | 1.37 | 0.56 | 0.44 | 0.58 | 1.37 | 1.60 | 0.46 | 1.37 |
| Z2-Y3  | 0.79 | 1.17 | 0.69 | 0.94 | 0.92 | 1.57 | 1.37 | 1.37 | 2.00 |
| Z2-Y18 | 1.37 | 0.93 | 1.37 | 1.14 | 1.37 | 0.82 | 1.57 | 1.57 | 1.37 |
| Z2-Y2  | 1.37 | 0.86 | 0.82 | 1.17 | 1.57 | 1.37 | 1.37 | 1.57 | 1.60 |
| Z2-Y4  | 1.14 | 1.37 | 1.37 | —    | 1.37 | 1.17 | 1.60 | 1.60 | 1.97 |
| Z2-Y17 | 1.37 | —    | 1.37 | 1.17 | 0.94 | 1.37 | 1.00 | 1.17 | 1.37 |
| Z2-Y1  | 1.17 | —    | 1.37 | 0.92 | —    | 0.93 | 0.80 | 1.37 | 1.37 |
| Z2-Y11 | 0.95 | 1.37 | 1.37 | —    | —    | 1.37 | —    | —    | —    |
| Z2-Y9  | 0.72 | 0.84 | 0.92 | 0.69 | —    | 0.75 | 1.77 | 1.37 | 1.37 |
| Z2-Y13 | 1.37 | 1.37 | 1.60 | 0.75 | 1.37 | 1.37 | —    | 1.57 | 1.77 |
| Z2-Y15 | 1.57 | 1.17 | 1.00 | —    | —    | 1.57 | —    | —    | —    |
| Z2-Y19 | —    | —    | —    | —    | —    | —    | —    | —    | —    |

TABLE 6

Cathepsin Activity of Multiply Modified Alginate Polymers

|        | N1   | N4   | N7   | N3   | N2   | N8   | N5   | N9   | N6   |
|--------|------|------|------|------|------|------|------|------|------|
| Z1-Y4  | 0.63 | 0.51 | 1.17 | 0.51 | 0.60 | 1.37 | 1.37 | 1.37 | 1.17 |
| Z1-Y6  | 1.17 | 0.88 | 1.17 | 0.84 | 0.75 | 0.87 | 0.75 | 1.57 | 0.99 |
| Z1-Y17 | 0.72 | 0.78 | 0.91 | 0.58 | 0.79 | 0.56 | 0.76 | 0.81 | 0.69 |
| Z1-Y1  | 0.63 | 0.58 | 1.17 | 0.50 | 0.54 | 0.50 | 0.50 | 1.17 | 1.17 |
| Z1-Y2  | 1.00 | 1.37 | 1.17 | 1.37 | 1.37 | 1.37 | 1.37 | 1.37 | 1.37 |
| Z1-Y11 | 1.00 | 1.37 | 1.37 | 1.37 | 1.37 | 1.00 | 1.17 | 1.34 | 1.37 |
| Z1-Y10 | 1.14 | 1.00 | 1.37 | 1.37 | 1.14 | 1.37 | 1.37 | 0.97 | 1.37 |
| Z1-Y12 | 1.37 | 1.17 | 1.37 | 1.37 | 1.37 | 1.17 | 1.37 | 1.17 | 1.17 |
| Z1-Y13 | 1.14 | 0.99 | 1.14 | 1.37 | 1.17 | 1.17 | 1.17 | 1.17 | 1.17 |
| Z1-Y16 | 1.37 | 1.14 | 1.17 | 1.37 | 1.17 | 1.00 | 1.17 | 0.97 | 0.96 |
| Z1-Y9  | 0.97 | 0.94 | 0.94 | 0.97 | 0.93 | 0.84 | 0.96 | 0.87 | 0.84 |
| Z1-Y14 | 0.89 | 0.99 | 0.85 | 0.88 | 1.17 | 0.76 | 0.78 | 0.85 | 0.86 |
| Z1-Y15 | 0.94 | 0.92 | 0.99 | 0.89 | 1.17 | 1.17 | 1.37 | 0.89 | 1.37 |
| Z1-Y7  | 1.37 | 0.77 | 1.00 | 0.76 | 1.37 | 0.76 | 0.75 | 1.14 | 1.17 |
| Z1-Y5  | 1.14 | 0.99 | 1.17 | 0.96 | 1.00 | 1.37 | 1.57 | 1.17 | 1.17 |
| Z1-Y20 | 0.75 | 0.84 | 1.14 | 0.97 | 1.14 | 1.37 | 1.17 | 0.81 | 0.79 |
| Z1-Y3  | 1.37 | 1.17 | 0.86 | 1.17 | 1.37 | 1.37 | 0.94 | 0.58 | 0.96 |
| Z1-Y18 | 0.75 | 0.82 | —    | 0.77 | —    | —    | —    | 0.63 | 0.63 |
| Z1-Y19 | 1.17 | —    | 0.99 | —    | —    | —    | —    | —    | 1.17 |
| Z1-Y8  | —    | 1.17 | 1.00 | 0.94 | 0.92 | 0.94 | 1.14 | 1.37 | 0.97 |

TABLE 7

Cathepsin Activity of Multiply Modified Alginate Polymers

|  | O6 | O12 | O11 | O5 | O3 | O4 | O9 | O7 | O8 | O2 | O1 | O10 |
|---|---|---|---|---|---|---|---|---|---|---|---|---|
| O7 | 1.37 | 1.17 | — | 1.37 | 1.17 | 0.99 | 1.37 | 1.37 | 1.17 | 1.37 | 1.37 | 1.14 |
| O9 | 1.14 | 1.37 | — | 1.37 | 1.37 | 1.37 | 1.17 | 1.17 | 1.37 | 1.14 | 1.77 | 1.14 |
| O1 | 0.86 | 0.82 | 1.37 | 1.17 | 1.37 | 0.92 | 0.97 | 0.97 | 1.37 | 0.97 | 1.17 | 1.17 |
| O2 | 1.14 | 0.97 | 1.17 | 1.00 | 0.95 | — | 0.89 | 0.76 | 0.91 | 0.76 | 0.92 | 0.72 |
| O6 | 1.37 | — | — | 0.90 | — | 0.99 | 1.37 | 1.17 | 0.85 | 0.79 | 0.78 | 1.37 |
| O12 | 0.99 | 1.77 | 0.89 | 1.37 | 1.37 | 1.17 | 0.75 | 0.96 | — | — | — | 1.37 |
| O3 | 0.95 | 1.60 | 1.37 | — | — | 1.17 | 0.87 | 0.80 | 1.14 | — | 0.93 | 0.97 |
| O5 | — | 1.97 | — | — | — | 1.00 | — | — | 1.17 | — | 0.79 | 0.94 |
| O11 | — | 1.17 | 0.95 | — | — | — | — | — | — | 1.17 | 1.37 | 1.14 |
| O4 | — | 1.37 | — | — | — | — | — | — | 0.94 | 0.92 | 0.97 | 1.14 |
| O10 | — | 1.57 | 0.88 | 0.99 | 0.96 | 1.17 | — | 1.17 | — | 0.80 | 1.17 | 1.37 |
| O8 | — | 1.57 | — | 0.71 | 0.72 | 0.85 | 0.80 | 0.92 | 1.37 | 0.69 | 1.37 | 1.14 |

All modified microcapsule formulations required this blending, capsules made from a blended solution of unmodified alginates VLVG and SLG100 (V/S) and the conventional SLG20 capsule formulation served as controls. Of the 70 formulated alginate microcapsules, an improved inflammation response was observed with several polymers (FIG. 12). The top 10 modified microcapsules displayed inflammation levels of 10-40% lower than the control alginates. To see if these lower levels of acute inflammation translated into lower levels of fibrosis, the implant sites of these top 10 alginates were sampled, sectioned, and processed histologically after 28 days. Three modified alginates, Z2-Y12, Z1-Y15, and Z1-Y19, displayed minimal fibrotic overgrowth with capsules able to fully detach from the surrounding tissue.

To test if the subcutaneous results translate into other implantation sites, 300 μm capsules of the top 10 lead modified alginates were implanted in the intraperitoneal (IP) space of C57BL/6 mice. Capsules were retrieved after 14 days and evaluated for the accumulation of cellular and fibrotic tissue. Phase contrast imaging of retrieved control capsules show a robust fibrotic response, with a white fibrous collagenous deposition observed on the capsules with brown capsule clumping. By comparison, the top ten lead modified alginates show varying degrees of fibrosis, with the modified alginates Z2-Y12, Z1-Y15, and Z1-Y19 showing almost no fibrous deposition and emerging as materials with anti-fibrotic properties.

Cellular staining and confocal microscopy of the Z2-Y12, Z1-Y15, and Z1-Y19 capsules showed little to no presence of macrophages (CD68), myofibroblasts (SMA) or general cellular deposition (DAPI). The conventional microcapsule alginate, however, showed significant quantities of these cell populations on the retrieved capsules. Cellular deposition is a key mechanistic component of material recognition and an initiator of collagenous deposition, and the absence of cells on the capsule surface is a further illustration of the anti-fibrotic properties of these modified alginates. To confirm these results, the SMA levels of Z2-Y12, Z1-Y15, Z1-Y19, and the control capsules quantified by Western Blotting. 40 different cytokines from protein samples extracted from the retrieved microcapsules were also profiled. The cytokine profile of Z2-Y12 microcapsules show the lowest cytokine levels of all tested samples, indicative of an overall lower inflammatory response. Importantly, retrieved Z2-Y12 capsules had low protein levels of TNF-α, IL-13, IL-6, G-CSF, GM-CSF, IL-4, CCL2, and CCL4 which are known mediators of the foreign body response and fibrosis (Rodriguez et al., *J. Biomed. Mater. Res. A* 89:152-159 (2009)). Quantification of seventy nine RNA sequences of known inflammation factors and immune cell markers isolated from retrieved capsules also support lower levels of inflammation for Z2-Y12 implants. The RNA profile in the surrounding IP fluid and fat tissue of Z2-Y12 implanted mice also more closely resembled mock treatment than mice implanted with control capsules, further demonstrating the lower inflammatory potential of this material.

B. Anti-Fibrotic Alginates Show Lower Macrophage Adhesion

Figure 8:
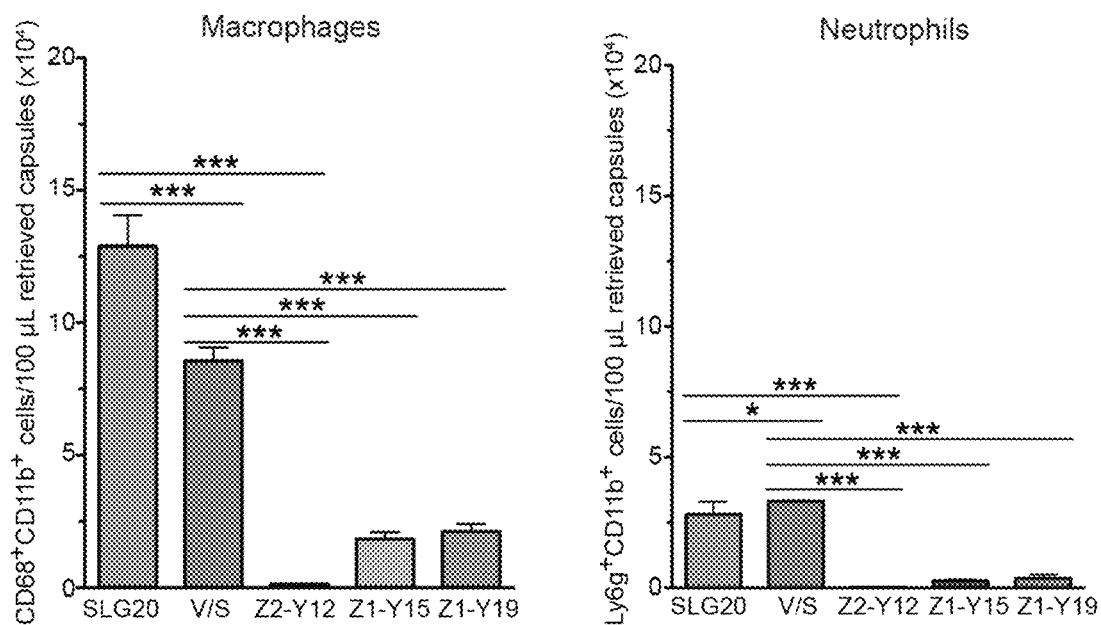
FIG. 8 is a graph of FACS analysis of macrophages (CD11b+, CD68+) and neutrophils (CD11b+, Ly6 g+) isolated from Z2-Y12, Z1-Y15, Z1-Y19, SLG20, and V/S capsules retrieved after 14 days in the IP space of C57BL/6 mice. ***=p<0 0001, ns=not significant.

FACS analysis was performed on retrieved capsules after 14 days IP to characterize the different immune populations that are recruited to Z2-Y12 capsules compared to control capsules (FIG. 8). Z2-Y12 capsules displayed significantly lower percentages of macrophage and neutrophil populations, suggesting that Z2-Y12 capsules may be interfering with either the recruitment of immune cell populations or amplification of an inflammatory response. To see if lower macrophage recruitment was evident in vivo, IP intra-vital imaging was performed 7 days after implantation of fluorescent Z2-Y12 capsules in MAFIA mice (where macrophages express GFP) and compared them to fluorescent SLG20 capsules. SLG20 capsules show a large population of macrophages actively aggregating at the surface of these capsules, an indication of foreign-body giant cell formation and a clear step towards fibrosis. Z2-Y12 capsules by comparison showed much lower levels of macrophages near the capsules and there was no visible macrophage aggregation.

The lack of immune cell recruitment/activation to the surface of Z2-Y12 capsules is consistent with the chemical modification of the polymer chains creating differential surfaces. Confocal raman spectroscopic mapping was performed to determine the distribution of the Z2-Y12 chemical modification in the microcapsule. Strikingly, the diagnostic raman signature for the tetrahydropyranyl modification had a higher intensity at the surface of the microcapsule than at the core. Freeze-fracture cryo-SEM was then performed on Z2-Y12 microcapsules to examine both the surface and core topography of the alginate analogue microspheres and compare them to the control capsule formulations. Z2-Y12 capsules display a more variable porosity throughout the capsule core compared to either the blended control or conventional SLG20 capsules, with pores ranging from 1 μm to 10 μm in size. The surface features between the different capsule formulations are quite distinct; the surface of Z2-Y12 capsules show fewer cratered features. These surface differences are likely created by interactions at the boundary layer between the modified polymer chains and the surrounding aqueous solution.

C. Z2-Y12, Z1-Y15, and Z1-Y19 Resist Fibrosis in Non-Human Primates

The lead materials, Z2-Y12, Z1-Y15, and Z1-Y19, were advanced into primate studies to test their anti-fibrotic properties in a NHP model. Previous reports from our lab have established that spheroid size is also a key parameter in mitigating fibrosis, with larger spheres (>1 mm) displaying anti-fibrotic properties. 1.5 mm capsules of the conventional SLG20 capsules and the new Z2-Y12, Z1-Y15, and Z1-Y19 formulated capsules were separately transplanted into non-human primates (n=3 each) using a minimally invasive laparoscopic procedure. Capsules were retrieved by IP lavage at 2 and 4 weeks, with one primate from each cohort allowed to continue for 6 months. By 14 days post-transplant, SLG20 1.5 mm capsules were also largely free and not embedded in tissue at 2 weeks as well. However, numerous capsules were fibrosed and clumped together. The 1.5 mm Z2-Y12, Z1-Y15, and Z1-Y19 retained a high retrieval rate and minimal embedding into the surrounding tissue. At both 2 and 4 weeks Z2-Y12, Z1-Y15, and Z1-Y19 capsules displayed significantly reduced fibrotic responses in phase contrast imaging compared to 1.5 mm SLG20 capsules. Confocal imaging and FACS analysis of retrieved capsules showed large 1.5 mm SLG20 capsules had more extensive immune macrophage and fibrosis-associated activated myofibroblast coverage, consistent with the visible fibrotic overgrowth seen in the phase contrast imaging.

To investigate whether increasing capsule size and/or the modified chemistries would maintain improved anti-fibrotic activity over a longer period of time, confocal staining was also performed on capsules retrieved from NHPs after 6 months. SLG20 capsules showed significant and extensive fibrotic overgrowth, while Z2-Y12 capsules were still clean, showing no associated macrophages or myofibroblasts. FACS analysis displayed similar results with a lower macrophage composition associated with retrieved Z2-Y12 capsules.

The combination of both increased capsule size (1.5 mm) and modified (Z2-Y12) chemistry substantially improved biocompatibility even at the 6 month time point. Large 1.5 mm Z2-Y12 capsules looked to have minimal (almost non-existent) levels of fibrosis throughout all time points, indicating that anti-fibrotic effects of large capsule size synergize with those of modified Z2-Y12 chemistry.

The results in this example demonstrate that chemical modification of one of the most widely used biomaterials, alginate, produces hydrogels that are able to resist foreign body reactions in both rodents and non-human primates. The lead alginate analogues, Z2-Y12, Z1-Y15, and Z1-Y19, show minimal recognition by macrophages and other immune cells, low levels of inflammatory cytokines, and almost no visible fibrous deposition in both rodents and non-human primates even after 6 months (Z2-Y12). The distribution of the Z2-Y12 chemical modification results in a unique hydrogel surface that inhibits macrophage adhesion, effectively mitigating the foreign body response to the biomaterial. The results show that chemical modification of existing biomaterials is a viable strategy to overcome their foreign body responses. These are the first biomaterials to resist the foreign body response in non-human primates and their versatility as alginate-based materials allows its use in multiple biomedical applications.

Example 9: Demonstration of Anti-Fibrotic Activity of Modified Alginates Encapsulating Human Cells in Immunocompetent Animals This example demonstrates the anti-fibrotic properties of the modified alginates encapsulating human cells, which are implanted in robust immunocompetent STZ C57BL/6J mice for a long period of time. The encapsulated human cells are actively secreting xenogeneic substances including, but not limited to, proteins. The xenogeneic substances should elicit an intense immune response from the mice. Therefore, this test represents a severe immune challenge to the implanted modified alginates. Nonetheless, the implanted modified alginates resist foreign body responses and shield the encapsulated human cells from host foreign body responses for long periods of time. As a result, the beneficial effects of the human cells are exerted for long periods of time. This example describes testing of modified alginates encapsulating human cells secreting insulin for their ability to reduce blood glucose levels and maintain normoglycemia in STZ-induced diabetic mice. The implants reduce blood glucose levels and maintain normoglycemia long-term in the STZ C57BL/6J mice without the need for immune suppressants.

Diabetes is a global epidemic afflicting over 300 million people (Shaw et al., Diabetes Res. Clin. Pract. 87:4-14 (2010)). While a rigorous regimen of blood glucose monitoring coupled with daily injections of exogenous insulin remains the leading treatment for type one diabetics, patients still suffer ill effects due to the challenges associated with daily compliance (Pickup et al., N. Engl. J. Med. 366:1616-1624 (2012)). In addition, the regulation of insulin secretion by the beta cells of the pancreatic islets of Langerhans in response to blood glucose level is a highly dynamic process, which is imperfectly simulated by periodic insulin injections (Robertson et al., N. Engl. J. Med. 350:694-705 (2004)). The transplantation of donor tissue, either in the form of a pancreas transplantation or infusion of cadaveric islets, are currently implemented clinically as one strategy to achieve insulin independence for type 1 diabetics (Shapiro et al., N. Engl. J. Med. 355:1318-1330 (2006); Shapiro et al., N. Engl. J. Med. 343:230-238 (2000); Qi et al., Acta Diabetologica 51:833-843 (2014)). This approach has been limited due to two major drawbacks: (1) the limited supply of available donor tissue, and (2) the adverse effects associated with a lifetime of immunosuppression (Hirshberg et al., Current Diabetes Reports 7:301-303 (2007); Gibly et al., Diabetologia, 54:2494-2505 (2011); O'Sullivan et al., Endocrine Reviews 32:827-844 (2011)). Methods to relieve the need for life long immunosuppression must be developed to allow for the broadest clinical implementation (Hirshberg et al., Current Diabetes Reports 7:301-303 (2007); Shapiro et al., The Review of Diabetic Studies: RDS 9:385-406 (2012); Vogel et al., Diabetologia 56:1605-1614 (2013)).

Cell encapsulation is a promising technology that overcomes the need of immunosuppression by protecting therapeutic tissues from host rejection (Dolgin, Nat. Med. 20:9-11 (2014); Jacobs-Tulleneers-Thevissen et al., Diabetologia 56:1605-1614 (2013)). The most commonly investigated method for islet encapsulation therapy is the formulation of isolated islets into alginate microspheres (Jacobs-Tulleneers-Thevissen et al., Diabetologia 56:1605-1614 (2013); Scharp et al., Advanced Drug Delivery Reviews 67-68:35-73 (2014)). Clinical evaluation of this technology in diabetic patients with cadaveric human islets has only achieved glycemic correction for short periods (Jacobs-Tulleneers-Thevissen et al., Diabetologia 56:1605-1614 (2013); Basta et al., Diabetes Care 34:2406-2409 (2011); Calafiore et al., Diabetes Care 29:137-138, (2006)). Implants from these studies are characterized by strong immune-mediated foreign body responses that result in fibrotic deposition, nutrient isolation, and donor tissue necrosis (de Groot et al., Journal of Surgical Research 121:141-150 (2004); Tuch et al., Diabetes Care 32:1887-1889 (2009)). Similar results are observed with encapsulated xenogeneic islets and pancreatic progenitor cells in preclinical diabetic mouse or non-human primate models, where both the therapeutic efficacy (Hirshberg et al., Current Diabetes Reports 7:301-303 (2007)) of encapsulated cadaveric human islets and pig islets is hampered by immunological responses (Elliot et al., Transplantation Proceedings 37:3505-3508 (2005); Omer et al., Diabetes 52:69-75 (2003); Schneider et al., Diabetes 54:687-693 (2005)).

A major contributor to the performance of encapsulated cell implants is the immune response to the biomaterials used for cell encapsulation (Lim et al., Science 210:908-910 (1980); Jacobs-Tulleneers-Thevissen et al., Diabetologia 56:1605-1614 (2013); Scharp et al., Advanced Drug Delivery Reviews 67-68:35-73 (2014)). Immune-mediated foreign body responses to implanted materials commonly lead to tissue capsule formation that results in implant failure (King et al., Journal of Biomedical Materials Research 57:374-383 (2001)). When implanted into the intraperitoneal space of non-human primates or rodents with robust immune systems such as C57BL/6J, (King et al., Journal of Biomedical Materials Research 57:374-383 (2001); Dang et al., Biomaterials 32, 4464-4470 (2011)) alginate microspheres elicit foreign body reactions and fibrosis (King et al., Journal of Biomedical Materials Research 57:374-383 (2001); Dang et al., Biomaterials 32:4464-4470 (2011)).

Figure 13:
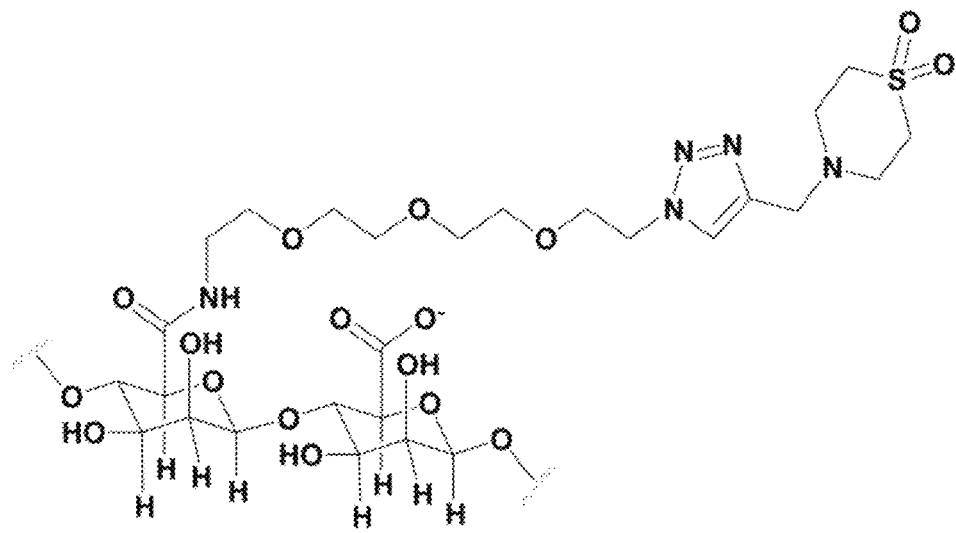
FIG. 13 is a chemical structure of triazole-thiomorpholine dioxide (TMTD) alginate.
Figure 14:
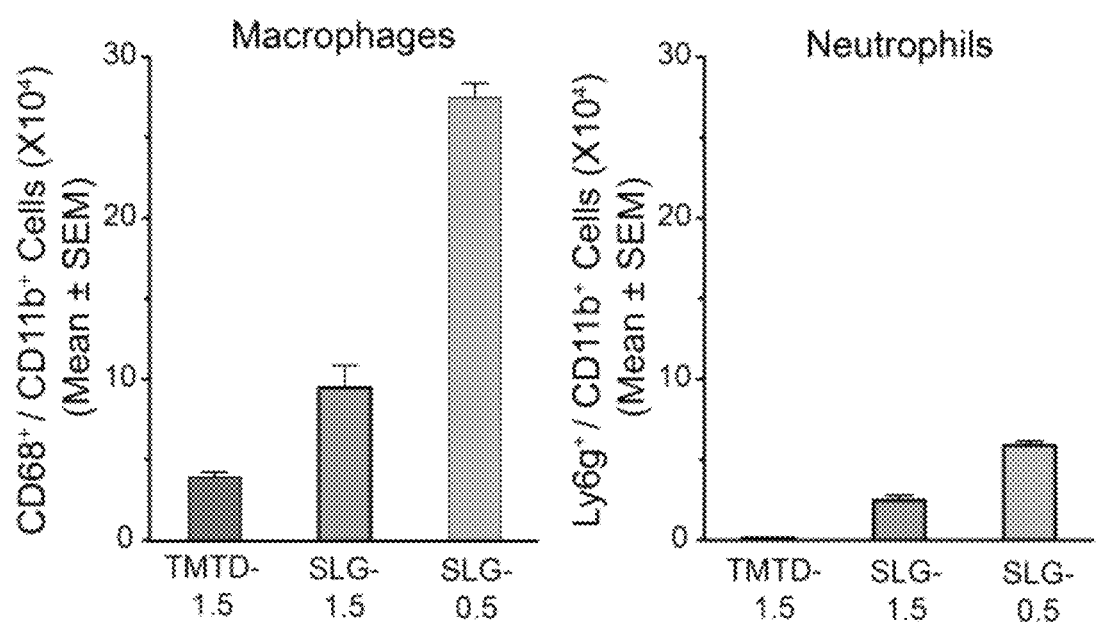
FIG. 14 is graphs of FACS analysis of encapsulated human cell implants retrieved after 14 days IP in C57BL/6 showing macrophages and neutrophils.
Figure 15:
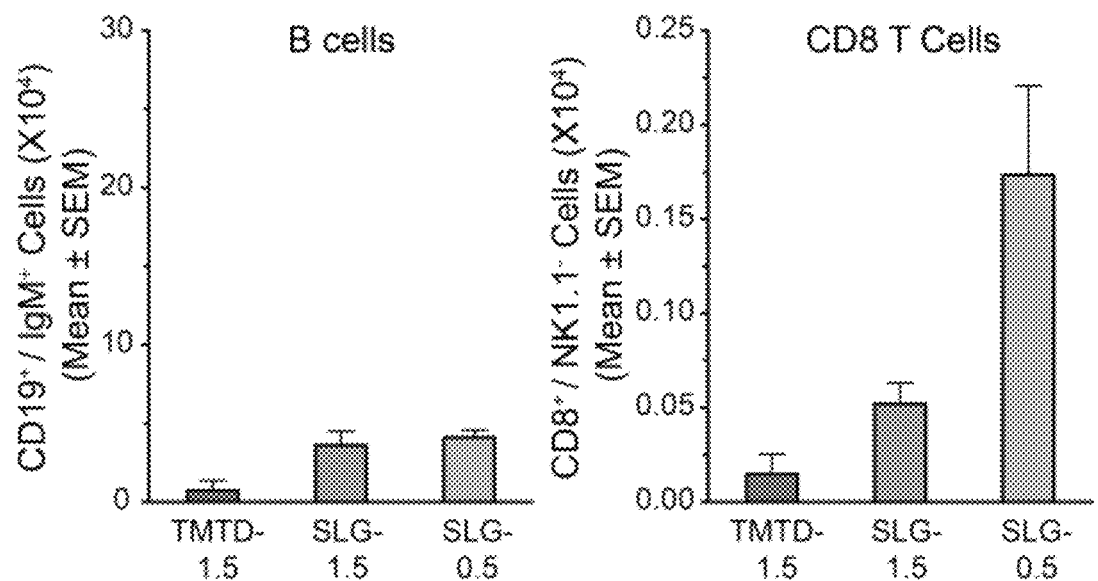
FIG. 15 is graphs of FACS analysis of encapsulated human cell implants retrieved after 14 days IP in C57BL/6 showing B cells and CD8 T cells.
Figure 16:
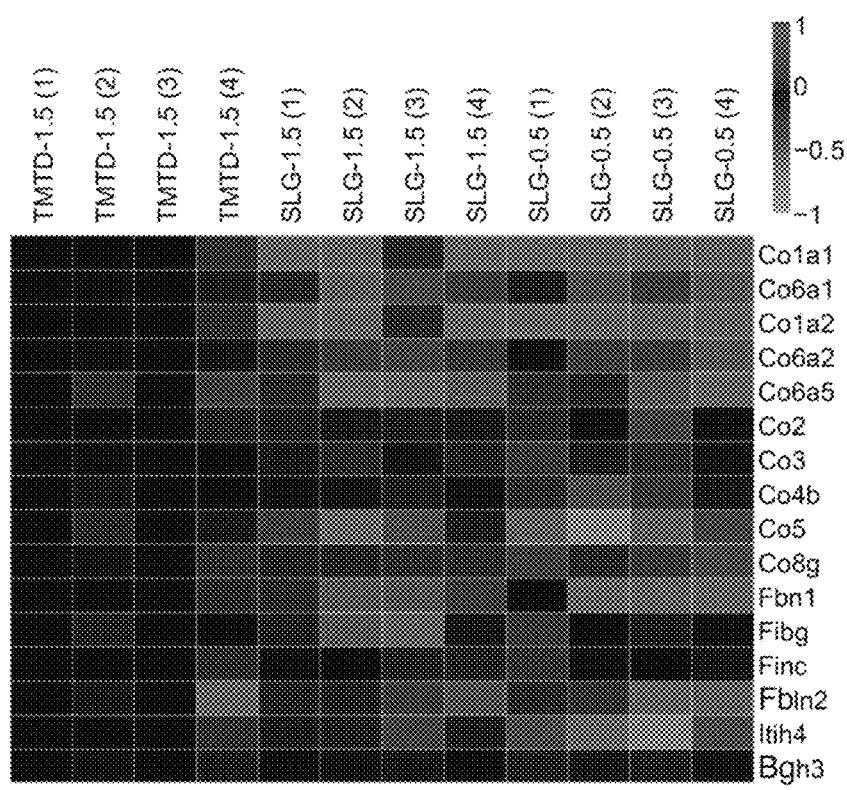
FIG. 16 is a heat map of proteomic quantification of proteins detected in protein isolates from implants retrieved from the STZ-C57BL/6J. Each column in the heatmap is an individual STZ-C57BL/6 mouse from the respective cohort.

A large library of chemically modified alginates was recently developed and evaluated for their potential to resist implant rejection in both rodent and non-human primate models. This example extends that work to show that triazole-thiomorpholine dioxide (TMTD; FIG. 13) alginate-encapsulating human cells were able to mitigate foreign body responses in immune-competent C57BL/6 mice (FIGS. 14 through 16). As a result, the TMTD alginate-encapsulating human cells are able to provide long-term glycemic correction and glucose-responsiveness. These results demonstrate that these new materials can be used to provide long term, glycemic correction through implantation of microencapsulated human cell, thus improving therapeutic effect of such implanted cells.

This example demonstrates the successful use potential of encapsulated human cells in immunocompetent animals for the restoration of normoglycemia without immune suppression. This shows the expectation that the disclosed modified alginates can be used to encapsulate cells and coat material and keep immune reactions to the cells and materials at bay in subjects in which they are implanted. To ensure proper biocompatibility assessment in these studies an immunocompetent streptozotocin-induced diabetic C57BL/6 mouse model was used because this strain is known to produce a strong fibrotic and foreign body response similar to observations made in human patients (Kolb et al., J. Respir. Cell. Mol. Biol. 27:141-150 (2002)). Formulations that have shown glycemic correction utilizing other tissue sources, such as conventional microencapsulation with alginate (Lim et al., Science 210; 908-910 (1980); Calafiore et al., Diabetes Care 29:137-138, (2006)) and larger sphere formulations (Veiseh et al., Nat. Mater., DOI: 10.1038/NMAT4290), were unable to support glycemic correction with human cells.

All materials were implanted intraperitoneally and retrieved at specified times from immunocompetent streptozotocin induced diabetic C57BL/6 or B6.129S6-Ccr6tm1 (EGFP)Irw/J mice in accordance with approved protocols and federal guidelines. Sample processing, staining, FACS, and imaging were performed as detailed in below.

I. Materials

All chemicals were obtained from Sigma-Aldrich (St. Louis, Mo.) and cell culture reagents from Life Technologies (Grand Island, N.Y.), unless otherwise noted. Antibodies: Alexa Fluor 488-conjugated anti-mouse CD68 (Cat. #137012, Clone FA-11) and Alexa Fluor 647-conjugated anti-mouse Ly-6G/Ly-6C (Gr-1) (Cat. #137012, Clone RB6-8C5) were purchased from BioLegend Inc. (San Diego, Calif.). Cy3-conjugated anti-mouse alpha smooth muscle actin antibody was purchased from Sigma Aldrich (St. Louis Mo.). Filamentous actin (F-actin)-specific Alexa Fluor 488-conjugated Phalloidin was purchased from Life Technologies (Grand Island, N.Y.). Anti-Glucagon cat #ab82270, Anti-insulin cat #ab7842, Goat Anti-Guinea pig IgG H&L conjugated Alexa Fluor® 488 cat #ab150185, and Goat Anti-Mouse IgG H&L conjugated Alexa Fluor® 594 cat #ab150116 were purchased from abcam (Cambridge, Mass.). Anti-human C-peptide cat #GN-1D4 was purchased from Developmental Studies Hybridoma Bank (University of Iowa, Iowa City, Iowa). A sampling of the spheres used in this study was submitted for endotoxin testing by a commercial vendor (Charles River, Wilmington, Mass.) and the results showed that spheres contained <0.05 EU/ml of endotoxin levels.

II. Methods

A. Fabrication of Alginate Hydrogel Capsules and Cell Encapsulation

All buffers were sterilized by autoclave and alginate solutions were sterilized by filtration through a 0.2 um filter. After solutions were sterilized, aseptic processing was implemented by performing capsule formation in a type II class A2 biosafety cabinet to maintain sterility of manufactured microcapsules/spheres for subsequent implantation. The hydrogel capsules following the protocol described in Example 8.

To solubilize alginates, SLG20 (NovaMatrix, Sandvika, Norway) was dissolved at 1.4% weight to volume in 0.8% saline. TMTD alginate was initially dissolved at 5% weight to volume in 0.8% saline, and then blended with 3% weight to volume SLG100 (also dissolved in 0.8% saline) at a volume ratio of 80% TMTD alginate to 20% SLG100.

For formation of 0.5 mm spheres were generated with a 25 G blunt needle, a voltage of 5 kV and a 200 µl/min flow rate. For formation of 1.5 mm spheres, an 18 gauge blunt tipped needle (SAI Infusion Technologies) was used with a voltage of 5-7 kV.

Cultured human cells were used for encapsulation. Immediately prior to encapsulation, the cultured human cell clusters were centrifuged at 1,400 rpm for 1 minute and washed with Ca-free Krebs-Henseleit (KH) Buffer (4.7 mM KCl, 25 mM HEPES, 1.2 mM $KH_2PO_4$, 1.2 mM $MgSO_4$× $7H_2O$, 135 mM NaCl, pH≈7.4, ≈290 mOsm). After washing, the human cells were centrifuged again and all supernatant was aspirated. The human cell pellet was then re-suspended in the SLG20 or TMTD alginate solutions (described above) at cluster densities of 1,000, 250, and 100 clusters per 0.5 ml alginate solution. Spheres were crosslinked using a $BaCl_2$ gelling solution and their sizes were controlled as described above. Immediately after crosslinking, the encapsulated human cell clusters were washed 4 times with 50 mL of CMRLM media and cultured overnight in a spinner flask at 37° C. prior to transplantation. Due to an inevitable loss of human cell clusters during the encapsulation process, the total number of encapsulated clusters were recounted post-encapsulation.

B. Transplantation Surgeries

All animal protocols were approved by the MIT Committee on Animal Care, and all surgical procedures and post-operative care was supervised by MIT Division of Comparative Medicine veterinary staff. Immune-competent male STZ-induced diabetic C57BL/6 mice (Jackson Laboratory, Bar Harbor, Me.) or male B6.129S6-Ccr6tm1(EGFP)Irw/J mice (Jackson Laboratory, Bar Harbor, Me.) were anesthetized with 3% isoflurane in oxygen and had their abdomens shaved and sterilized using betadine and isopropanol. Preoperatively, all mice also received a 0.05 mg/kg dose of buprenorphine subcutaneously as a pre-surgical analgesic, along with 0.3 mL of 0.9% saline subcutaneously to prevent dehydration. A 0.5 mm incision was made along the midline of the abdomen and the peritoneal lining was exposed using blunt dissection. The peritoneal wall was then grasped with forceps and a 0.5-1 mm incision was made along the linea alba. A desired volume of spheres (all materials without islets, as well as SLG20 spheres encapsulating rat islets) were then loaded into a sterile pipette and implanted into the peritoneal cavity through the incision. The incision was then closed using 5-0 taper-tipped polydioxanone (PDS II) absorbable sutures. The skin was then closed over the incision using a wound clip and tissue glue.

C. Blood Glucose Monitoring

To create insulin-dependent diabetic mice, healthy C57BL/6 mice were treated with Streptozotocin (STZ) by the vendor (Jackson Laboratory, Bar Harbor, Me.) prior to shipment to MIT. The blood glucose levels of all the mice were retested prior to transplantation. Only mice whose non-fasted blood glucose levels were above 400 mg/dL for two consecutive days were considered diabetic and underwent transplantation.

Blood glucose levels were monitored three times a week following transplantation of islet-containing alginate capsules. A small drop of blood was collected from the tail vein using a lancet and tested using a commercial glucometer (Clarity One, Clarity Diagnostic Test Group, Boca Raton, Fla.). Mice with unfasted blood glucose levels below 200 mg/dL were considered normoglycemic. Monitoring continued until experimental time points had been reached, at which point they were euthanized and the spheres were retrieved.

D. Human c-Peptide Monitoring

Human c-peptide levels were monitored every three weeks following transplantation of human cell-containing alginate capsules. Mice were fasted for 1 hour before blood collection, at which point approximately 100-150 µL of blood was collected retro-orbitally into a serum collection tube. Collected blood was centrifuged for 10 minutes at 13000 rpm, serum was removed, and stored at 20° C. until assayed. Serum was assayed for human c-peptide using the Alpco human c-peptide kit (Catalog #: 80-CPTHU-E10) according to the manufacturer's instructions.

E. Retrieval of Cells, Tissues and Materials

Retrieval of cells, tissues and materials was performed as described above in Example 8.

F. Imaging of the Retrieved Material Spheres

For phase contrast imaging of retrieved materials was performed following the protocol described in Example 8.

For bright-field imaging of retrieved materials, samples were gently washed using Krebs buffer and transferred into 35 mm petri dishes for bright-field imaging using a Leica Stereoscopic microscope.

G. Confocal Immunofluorescence

Immunofluorescence imaging was used to determine immune populations attached to spheres. Materials were retrieved from mice and fixed overnight using 4% paraformaldehyde at 4° C. Samples were then washed twice with KREBS buffer, permeabilized for 30 min using a 0.1% Triton X100 solution, and subsequently blocked for 1 hour using a 1% bovine serum albumin (BSA) solution. Next, the spheres were incubated for 1 hour in an immunostaining cocktail solution consisting of DAPI (500 nM), specific marker probes (1:200 dilution) in BSA. After staining, spheres were washed three times with a 0.1% Tween 20 solution and maintained in a 50% glycerol solution. Spheres were then transferred to glass bottom dishes and imaged using an LSM 700 point scanning confocal microscope (Carl Zeiss Microscopy, Jena Germany) equipped with 5 and 10× objectives. Obtained images were adjusted linearly for presentation using Photoshop (Adobe Inc. Seattle, Wash.).

H. Proteomic Analysis

1. Reduction, Alkylation and Tryptic Digestion

Retrieved samples were suspended in urea cell lysis buffer (8 M urea, Tris pH 8.0) and incubated at 4° C. overnight. Equivalent amounts of protein were reduced (10 mM dithiothreitol, 56° C. for 45 min) and alkylated (50 mM iodoacetamide, room temperature in the dark for 1 h). Proteins were subsequently digested with trypsin (sequencing grade, Promega, Madison, Wis.), at an enzyme/substrate ratio of 1:50, at room temperature overnight in 100 mM ammonium acetate pH 8.9. Trypsin activity was quenched by adding formic acid to a final concentration of 5%. Peptides were desalted using C18 SpinTips (Protea, Morgantown, W. Va.) then lyophilized and stored at −80° C.

2. TMT Labeling

Peptides were labeled with TMT 6plex (Thermo) per manufacturer's instructions. Lyophilized samples were dissolved in 70 µL ethanol and 30 µl of 500 mM triethylammonium bicarbonate, pH 8.5, and the TMT reagent was dissolved in 30 µl of anhydrous acetonitrile. The solution containing peptides and TMT reagent was vortexed, incubated at room temperature for 1 h. Samples labeled with the six different isotopic TMT reagents were combined and concentrated to completion in a vacuum centrifuge. For the first analysis samples were labeled using the TMT 6plex channels as follows: 126—RZA 1.5 mm 250 biological replicate 1; 127—RZA 1.5 mm 250 biological replicate 2; 128—SLG20 1.5 mm 250 biological replicate 1; 129—SLG20 1.5 mm 250 biological replicate 2; 130—SLG20 500 µm 250 biological replicate 1; and 131—SLG20 5001 µm 250 biological replicate 2. For the second analysis samples were labeled using the TMT 6plex channels as follows: 126—RZA 1.5 mm 250 biological replicate 3; 127—RZA 1.5 mm 250 biological replicate 4; 128—SLG20 1.5 mm 250 biological replicate 3; 129—SLG20 1.5 mm 250 biological replicate 4; 130—SLG20 500 µm 250 biological replicate 3; and 131—SLG20 500 µm 250 biological replicate 4.

3. LC-MS/MS

Peptides were then loaded on a precolumn and separated by reverse phase HPLC (Thermo Easy nLC 1000) over a 140 minute gradient before nanoelectrospray using a QExactive mass spectrometer (Thermo). The mass spectrometer was operated in a data-dependent mode. The parameters for the full scan MS were: resolution of 70,000 across 350-2000 m/z, AGC $3e^6$, and maximum IT 50 ms. The full MS scan was followed by MS/MS for the top 10 precursor ions in each cycle with a NCE of 32 and dynamic exclusion of 30 s. Raw mass spectral data files (.raw) were searched using Proteome Discoverer (Thermo) and Mascot version 2.4.1 (Matrix Science). Mascot search parameters were: 10 ppm mass tolerance for precursor ions; 0.8 Dathe fragment ion mass tolerance; 2 missed cleavages of trypsin; fixed modification was carbamidomethylation of cysteine; variable modification was methionine oxidation. TMT quantification was obtained using Proteome Discoverer and isotopically corrected per manufacturer's instructions.

I. Histological Processing for H&E and Masson's Trichrome Staining

Retrieved materials were fixed overnight using 4% paraformaldehyde at 4° C. After fixation, alginate sphere or retrieved tissue samples were washed using 70% alcohol. The materials were then mixed with 4 degrees calcium-cooled Histogel (VWR, CA #60872-486). After the molds hardened, the blocks were processed for paraffin embedding, sectioning and staining according to standard histological methods.

J. Histological Immunostaining

Paraffin embedded sectioned samples were stained for the following: human insulin (Anti-insulin cat #ab7842, abcam), human c-peptide (C-peptide cat #GN-1D4, Developmental Studies Hybridoma Bank, University of Iowa), human glucagon (Anti-Glucagon cat #ab82270, abcam). Cellular nuclei were stained with DAPI (cat #D1306, Life Technologies).

Paraffin slides were deparaffinized through subsequent incubations in the following solvents (Xylene 5 min 2×100% ETOH 2 min×2 95% 2 min×2 70% 2 min×2 d-water). Antigen retrieval was done by incubating sections for 30 min in ice cooled PBS, and then blocking with 3% horse serum to block for 30 min. Antibody mixtures were then applied as follows: Primary A—Mix together Glucagon 1 to 200 and c-peptide 1 to 500. Primary B—Mix together Human insulin 1 to 500 and glucagon 1 to 200, incubate for 2 hours and then Wash in PBS 10 min×4. Secondary A—Add anti-mouse AF594 1 to 500 and anti-rat AF488 1 to 500. Secondary B—Add anti-guinea pig AF488 1 to 500 with anti-mouse AF594 1 to 500 incubate for 30 min then wash 10 min 4×. Slides were then stained with DAPI and coverslips mounted using prolong gold antifade (Life Technologies, Carlsbad, Calif.).

K. Western Blotting

Protein was extracted directly from materials for western blot analysis. For protein analyses, retrieved materials were prepared by immersing materials in Pierce RIPA buffer (Cat. #89901, Thermo Scientific) with protease inhibitors (Halt Protease inhibitor single-use cocktail, Cat. #78430, Thermo Scientific) on ice, and then lysed by sonication (for 30 seconds on, 30 seconds off, twice at 70% amplitude). Samples were then subjected to constant agitation for 2 hours at 4° C. Lysates were then centrifuged for 20 min at 12,000 rpm at 4° C., and protein-containing supernatants were collected in fresh tubes kept on ice. In samples from fat tissue, an excess of fat (a top layer on the supernatant) was first removed before supernatant transfer. 20 µg protein (quantified by BCA assay, Pierce BCA protein assay kit, Cat. #23225, Thermo Scientific) for each lane was boiled at 95° C. for 5 min and electrophoresed on SDS-polyacrylamide gels (Any kD 15-well comb mini-gel, Biorad, Cat. #456-9036) and then blotted onto nitrocellulose membranes (Biorad, Cat. #162-0213). Blots were probed with anti-αSmooth Muscle actin antibody (1:400 dilution, Rabbit polyclonal to alpha smooth muscle actin; Cat. #ab5694, AbCam), anti-PDX1 antibody (1:1000 dilution, Rabbit polyclonal to pancreatic & duodenal homeobox 1; Cat. #06-1379, EMD Millipore), and anti-β-actin antibody (1:4000 dilution, monoclonal anti-β-actin antibody produced in mouse; Cat. #A1978, Sigma Aldrich) as a loading control followed by donkey anti-rabbit (1:15,000 dilution, Cat. #926-32213, Li-Cor) and goat anti-mouse (1:15,000 dilution, Cat. #926-68070, Li-Cor) fluorophore-conjugated secondary antibodies. Antibody-antigen complexes were visualized using Odyssey detection (Li-Cor, Serial No. ODY-2329) at 700 and 800 nm wavelengths.

L. FACS Analysis

Single-cell suspensions of freshly excised tissues were prepared using a gentleMACS Dissociator (Miltenyi Biotec, Auburn, Calif.) according to the manufacturer's protocol. Single-cell suspensions were prepared in a passive PEB dissociation buffer (IX PBS, pH 7.2, 0.5% BSA, and 2 mM EDTA) and suspensions were passed through 70 µm filters (Cat. #22363548, Fisher Scientific, Pittsburgh, Pa.). This process removed the majority of cells adhered to the surface (>90%). All tissue and material sample-derived, single-cell populations were then subjected to red blood cell lysis with 5 ml of 1×RBC lysis buffer (Cat. #00-4333, eBioscience, San Diego, Calif., USA) for 5 min at 4° C. The reaction was terminated by the addition of 20 ml of sterile 1×PBS. The cells remaining were centrifuged at 300-400 g at 4° C. and resuspended in a minimal volume (~50 µl) of eBioscience Staining Buffer (cat. #00-4222) for antibody incubation. All samples were then co-stained in the dark for 25 min at 4° C. with two of the fluorescently tagged monoclonal antibodies specific for the cell markers CD68 (1 µl (0.5 µg) per sample; CD68-Alexa647, Clone FA-11, Cat. #11-5931, BioLegend), Ly-6G (Gr-1) (1 µl (0.5 µg) per sample; Ly-6G-Alexa-647, Clone RB6-8C5, Cat. #108418, BioLegend), CD11b (1 µl (0.2 µg) per sample; or CD11b-Alexa-488, Clone M1/70, Cat. #101217, BioLegend), CD19 (1 µl (0.2 µg) per sample; CD19-Alexa-647, Clone HIB19, Cat. #302222, BioLegend), or IgM (1 µl (0.2 µg) per sample; IgM-FITC, Clone RMM-1, Cat. #406505, BioLegend), CD8 (1 µl (0.2 µg) per sample, BioLegend). Two ml of eBioscience Flow Cytometry Staining Buffer (cat. #00-4222, eBioscience) was then added, and the samples were centrifuged at 400-500 g for 5 min at 4° C. Supernatants were removed by aspiration, and this wash step was repeated two more times with staining buffer. Following the third wash, each sample was resuspended in 500 µl of Flow Cytometry Staining Buffer and run through a 40 µm filter (Cat. #22363547, Fisher Scientific) for eventual FACS analysis using a BD FACSCalibur (cat. #342975), BD Biosciences, San Jose, Calif., USA). For proper background and laser intensity settings, unstained, single antibody, and IgG (labeled with either Alexa-488 or Alexa-647, BioLegend) controls were also run.

M. Intravital Imaging

For intravital imaging, human cell-containing hydrogels of 0.5 mm and 1.5 mm sizes were fabricated with Qdot 605 (Life technologies, Grand Island, N.Y.) and surgically implanted into B6.129S6-Ccr6$^{tm1(EGFP)Irw}$/J mice as described above.

After 14 days post implantation, the mice were placed under isoflurane anesthesia and a small incision was made at the site of the original surgery to expose beads. The mice were placed on an inverted microscope and imaged using a 25×, N.A. 1.05 objective on an Olympus FVB-1000 MP multiphoton microscope at an excitation wavelength of 860 nm. Z-stacks of 200 µm (10 µm steps) were acquired at 2-minute intervals for time series of 20-45 minutes depending on the image. The mice were kept under constant isoflurane anesthesia and monitored throughout the imaging session. Obtained images were analyzed using Velocity 3D Image Analysis Software (Perkin Elmer, Waltham, Mass.).

N. In Vivo Glucose Challenges (GSIS)

Mice were fasted overnight (12 hours) prior to glucose challenge. On the day of the challenge, fasting blood glucose levels were measured and then mice were injected via tail-vein with a 30 g/L solution of glucose at a dose of 200 mg/kg. Blood glucose was then monitored every 15 minutes for 2 hours.

O. Pancreas Removal and Insulin Quantification

After 174 days, mice treated with human cells encapsulated in TMTD-alginate were euthanized and the pancreas of each mouse removed. Each pancreas was weighed and then placed into vial with a stainless steel ball while keeping samples frozen in liquid nitrogen. A volume of 3 ml of acid ethanol was added to each vial and samples were homogenized on a GenoGrinder at 1000 rpm at 1 min increments until tissue was pulverized. Sample vials are held by aluminum blocks that can be placed in liquid nitrogen between each cycle to keep it cold. Vials were then centrifuged at 2400 rpm at 4° C. for 30 min. The supernatant (now containing insulin) was removed and stored, while the vial is filled with more acid ethanol and vortexed. The vials were left overnight shaking at 4° C. Again, vials were centrifuged at 2400 rpm at 4° C. for 30 min and the supernatant was collected and added to the previously stored supernatant. Acid ethanol was again added to the vials, vortexed, incubated overnight, centrifuged, and supernatant collected and combined. Supernatant solution was evaporated using a Genevac EZ-2 plus. Samples were stored at −80° C. until used. Prior to insulin quantification, samples were resuspended in PBS and quantified using a mouse insulin ELISA kit (Alpco catalog #: 80-INSMS-E10) according to manufacturer's instructions. This same procedure was repeated for healthy, wild type C57BL/6 mice and a STZ treated C57BL/6 mice.

P. Statistical Analysis

Data are expressed as mean±SEM, and N=5 mice per time point and per treatment group. For Rat studies N=3 per treatment. These sample sizes were chosen based on previous literature. All animals were included in analyses except in instances of unforeseen sickness or morbidity. Animal cohorts were randomly selected. Investigators were not blind to performed experiments. FACS data was analyzed for statistical significance either by unpaired, two-tailed t-test, or one-way ANOVA with Bonferroni multiple comparison correction, unless indicated otherwise, as implemented in GraphPad Prism 5; *: $p<0.05$, : $p<0.001$, and *: $p<0.0001$.

Quantified data shown are group mean values±SEM.

II. Results

A. TMTD Alginate Mitigates Immunological Responses to Encapsulated Human Cells.

It has been recently demonstrated that microsphere size can have a beneficial impact on resisting immunological responses to implanted alginates, with spheres of 1.5 mm diameters and larger and TMTD alginates, mitigating fibrotic responses in both rodents and non-human primates (Veiseh et al. in press and Vegas et al. submitted). The chemical structure of TMTD is shown in FIG. 13.

To evaluate the immune responses to these spheres, encapsulated human cells were implanted IP into C57BL/6 mice and were retrieved after 14 days. Cells associated with the outside of the spheres were isolated and analyzed by FACS (FIGS. 14 and 15). Statistically significant lower levels of macrophages, neutrophils, B cells, and CD8+ T cells were measured for TMTD alginate encapsulated human cells (formulation 3) compared to SLG20 controls (formulation 1, 2). Implants retrieved after 80-90 days in STZ-C57BL/6J mice revealed that TMTD alginate spheres had much lower levels of fibrotic deposition. Immunofluorescence staining of these retrieved spheres for cellular deposition (DAPI, F-actin) and myofibroblasts (α-SMA) showed significantly lower levels of cellular deposition on TMTD alginate spheres. Proteomic analysis of these protein extracts detected 18 collagen isoforms, and 10 out of the 18 detected collagen proteins were significantly reduced in TMTD alginate transplants further showing that these materials are able to mitigate fibrotic responses (FIG. 16).

Figure 10:
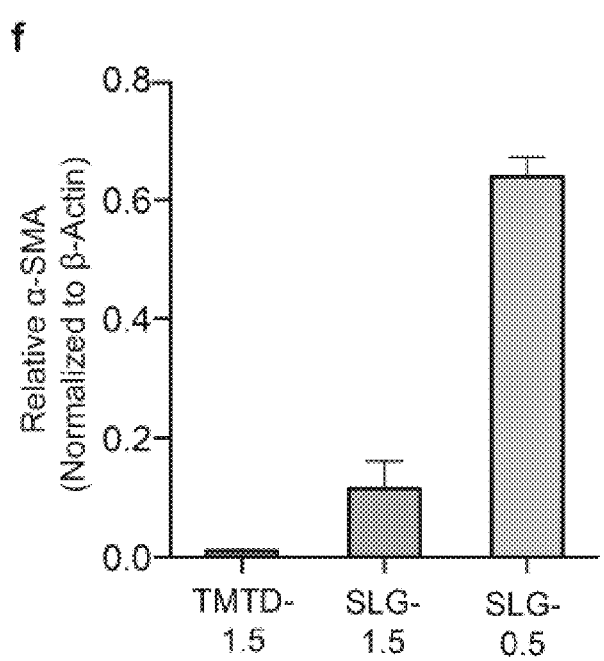
FIG. 10 is a graph of Western blot quantification of α-SMA protein isolated from implants retrieved from the STZ-C57BL/6J.

Western blot quantification of α-SMA protein extracted from the retrieved implants is consistent with lower fibrosis levels on TMTD spheres (FIG. 10).

Finally, consistent with these results, histological processing and immunostaining of TMTD encapsulated human clusters retrieved after over 90 days from STZ-C57BL/6 mice revealed cell clusters with positive co-localized staining of mature human cell markers human insulin and c-peptide. Minimal to no co-localized staining was observed between human c-peptide and glucagon or human insulin and glucagon, consistent with the human cells retaining their differentiation state through the entire study.

The ability of TMTD alginate spheres to provide immunoisolation of the encapsulated human cells was next characterized. Freeze-fracture cryogenic scanning electron microscopy (cryo-SEM) of the spheres display a heterogeneous pore structure with pore sizes ranging from submicron to 1-3 μm in size, a range capable of preventing permeation by cells and large proteins. Intravital imaging of transplanted spheres after 14 days in B6.129S6-Ccr6tm1 (EGFP)Irw/J mice (where T, B, and dendritic cells express EGFP) showed localization of CCR6+ cells to regions of spheres containing human cells, but an inability of these cells to make contact and initiate cytotoxic events.

B. Encapsulation of Human Cells with Triazole-Thiomorpholine Dioxide (TMTD) Alginate Enables Glycemic Correction in STZ-C57BL/6J.

To investigate the potential of microencapsulation of human cells to provide glycemic correction, cells were used in three different formulations: (1) 500 μm alginate microcapsules conventionally used for islet encapsulation (Lim et al., *Science* 210:908-910 (1980); Calafiore et al., Diabetes Care 29:137-138 (2006)), (2) 1.5 mm alginate spheres (Veiseh et al. in press), and (3) 1.5 mm TMTD alginate spheres. Each of these formulations was transplanted in streptozotocin (STZ) treated C57BL/6J mice at three different doses of human cell clusters and evaluated for their ability to restore normoglycemia. Naked, non-encapsulated human cells are unable to provide glycemic correction in this diabetic model regardless of implantation site.

Encapsulation into 500 j m barium alginate microcapsules is a commonly implemented formulation for islet transplantation (Lim et al., *Science* 210, 908-910 (1980); Calafiore, et al., Diabetes Care 29:137-138, (2006)). Mice transplanted with human cells encapsulated in 500 μm microcapsules showed the lowest levels of glycemic control, with only the highest dose of transplanted clusters able to restore normoglycemia for 15 days. Human cells encapsulated in 1.5 mm alginate spheres performed better than the 500 μm microcapsule formulation with normoglycemia maintained for 20-30 days for the two higher doses, consistent with earlier results obtained using rat islets (Veiseh et al. in press). Sustained normoglycemia was achieved for over 70 days with 1.5 mm TMTD alginate spheres at all three doses tested. Robust human c-peptide levels were measured at 21, 43, and 63 days during the course of this study, consistent with human cell function, with TMTD alginate spheres showing the highest levels of human c-peptide.

C. Encapsulated Human Cells Support Sustained Normoglycemia and Glucose Responsiveness in STZ-C57BL/6J.

To evaluate the capacity of TMTD alginate encapsulated human cell transplants to sustain normoglycemia, a cohort of transplanted diabetic mice was tracked for 6 months. Transplanted mice successfully maintained glycemic correction over the 6-month period, and 5 closely matched the blood glucose levels of wild type C57BL/6J mice tracked over a similar period. In addition, robust human c-peptide levels over 100 pmol/L were recorded at multiple points throughout the study. A glucose challenge was also performed on these mice 150 days post-transplantation, and encapsulated human cells restored normoglycemia comparably to wild type mice. Host pancreas insulin levels for each cohort were also analyzed to confirm the successful STZ treatment and a lack of endogenous pancreas cell regeneration. Human cells implants retrieved after 6 months displayed no signs of fibrotic overgrowth, with little collagenous and cellular deposition evident on the capsule. Since spheres retrieved after 3 months showed minimal levels of fibrosis, this indicates that TMTD alginate mitigates immunological responses by altering the immune recognition/activation kinetics.

The results show that encapsulated human cells can achieve glucose-responsive, long-term glycemic correction (over 170 days) in an immune-competent diabetic animal with no immunosuppression. This result was accomplished by implementing a novel TMTD alginate formulation that mitigates immunological responses to human cell implants, effectively delaying the fibrotic deposition that leads to implant tissue necrosis. This formulation provided sufficient immunoprotection to enable long-term glycemic correction, in spite of the xenogeneic stimulation that these human cells manifest in an immunocompetent rodent recipient. These result support the expectation that human cells encapsulated in the disclosed modified alginates can provide insulin independence for patients suffering from type 1 diabetes. These result support the expectation that human cells encapsulated in the disclosed modified alginates can provide products produced by the encapsulated cells to patients for long periods of time.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An implant that is not a living tissue, wherein all or a portion of the implant is coated with a modified alginate comprising one or more covalently modified monomers defined by Formula I

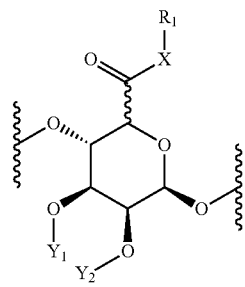

Formula I wherein
X is oxygen, sulfur, or NR$_4$,
R$_1$ is, independently, hydrogen, alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C$_3$-C$_{20}$ cyclic, substituted C$_3$-C$_{20}$ cyclic, heterocyclic, substituted heterocyclic, amino acid, poly(ethylene glycol), peptide, or polypeptide group, wherein R$_1$ is, independently in at least one covalently modified monomer

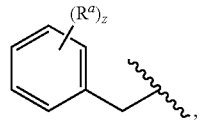

Formula X

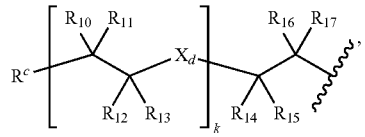

Formula XII or —R$_6$—R$^b$ wherein for compounds of Formula X and XII
z is an integer from 0 to 5,
k is an integer from 1 to 10,
X$_d$ is absent, O or S,
R$_{10}$, R$_{11}$, R$_{12}$, R$_{13}$, R$_{14}$, R$_{15}$, R$_{16}$, and R$_{17}$ are independently hydrogen, alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C$_3$-C$_{20}$ cyclic, substituted C$_3$-C$_{20}$ cyclic, heterocyclic, substituted heterocyclic, amino acid, poly(ethylene glycol), peptide, or polypeptide group, wherein R$^a$ and R$^c$ are independently alkoxy, alkylamino, dialkylamino, hydroxy, alkenyl, alkynyl, substituted alkyl, substituted alkenyl, substituted alkynyl, aryl, substituted aryl, heteroaryl, substituted heteroaryl, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, polyaryl, substituted polyaryl, C$_3$-C$_{20}$ cyclic, substituted C$_3$-C$_{20}$ cyclic, heterocyclic, substituted heterocyclic, amino acid, poly(ethylene glycol), peptide, or polypeptide group, or together with the carbon atom to which they are attached, form a 3- to 8-membered unsubstituted or substituted carbocyclic, heterocyclic ring or Formula XIII

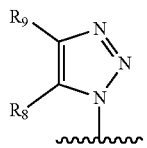

wherein $R_8$, $R_9$, or both are, independently, hydrogen, alkyl, substituted alkyl, alkoxy, amino, alkylamino, dialkylamino, hydroxy, alkenyl, alkynyl, substituted alkyl, substituted alkenyl, substituted alkynyl, carbonyl, substituted carbonyl, carbinol, Formula VII

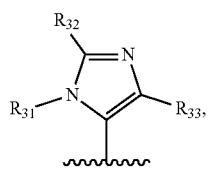

Formula VIII

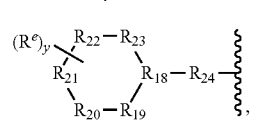

or

Formula IX

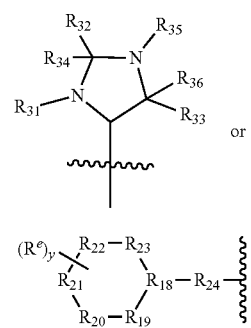

wherein $R_{31}$, $R_{32}$, $R_{33}$, $R_{34}$, $R_{35}$, and $R_{36}$ are, independently, hydrogen, alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, amino acid, poly(ethylene glycol), peptide, or polypeptide group, wherein y is an integer from 0 to 11, wherein $R^e$ is independently alkoxy, alkylamino, dialkylamino, hydroxy, alkenyl, alkynyl, substituted alkyl, substituted alkenyl, substituted alkynyl, aryl, substituted aryl, heteroaryl, substituted heteroaryl, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, amino acid, poly(ethylene glycol), peptide, and polypeptide group, or together with the carbon atom to which they are attached, form a 3- to 8-membered unsubstituted or substituted carbocyclic or heterocyclic ring, wherein $R_{18}$, $R_{19}$, $R_{20}$, $R_{21}$, $R_{22}$, and $R_{23}$ are independently C, O, N, or S, wherein the bonds between adjacent $R_{18}$ to $R_{23}$ are double or single according to valency, and wherein $R_{18}$ to $R_{23}$ are bound to none, one, or two hydrogens according to valency, and wherein $R_{24}$ is independently —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —SO_2—, or $NR_4'$, wherein each $R_{25}$ is independently absent, hydrogen, =O, =S, —OH, —SH, —$NR_4'$, wherein $R_4'$ is alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, $R_8$ and $R_9$ are not both hydrogen, wherein at least one $R^a$ or $R^c$ is defined by Formula XIII, wherein $Y_1$ and $Y_2$ independently are hydrogen or —PO($OR_5$)$_2$, or $Y_2$ is absent, and $Y_1$, together with the two oxygen atoms to which $Y_1$ and $Y_2$ are attached form a cyclic structure as shown in Formula II Formula II

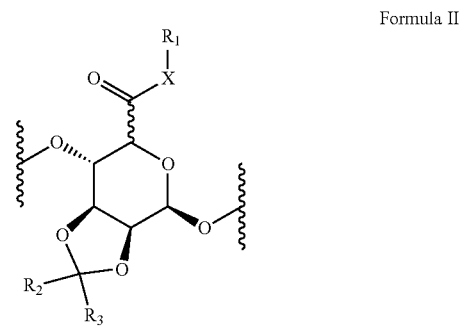

wherein $R_2$ and $R_3$ are, independently, hydrogen, alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, amino acid, poly(ethylene glycol), peptide, or polypeptide group, or $R_2$ and $R_3$, together with the carbon atom to which they are attached, form a 3- to 8-membered unsubstituted or substituted carbocyclic or heterocyclic ring, and $R_4$ and $R_5$ are, independently, hydrogen, alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, amino acid, poly(ethylene glycol), peptide, or polypeptide group, and for —$R_6$—$R^b$, $R_6$ is alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted C3-C20 cyclic, heterocyclic, substituted heterocyclic, amino acid, poly(ethylene glycol), peptide, or polypeptide group, and wherein $R_b$ is

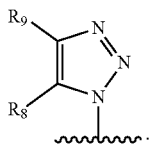

Formula XIII

2. The implant of claim 1, wherein
$R_1$ is, independently in the one or more covalently modified monomers,

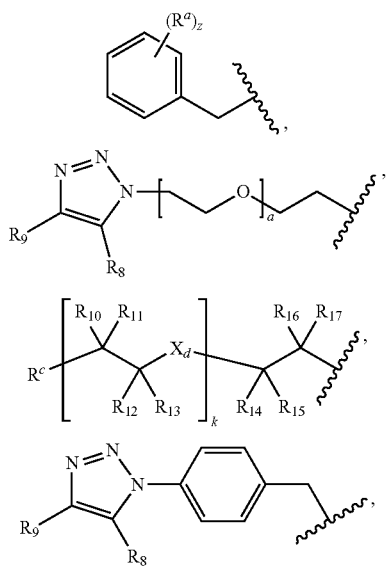

or $-R_6-R^b$, wherein a is an integer between 1 and 30, inclusive.

3. The implant of claim 2, wherein
$R_6$ is $-CH_2$-aryl- or $-CH_2-CH_2-(O-CH_2-CH_2)_3-$,
$R_4$ is hydrogen,
$R_8$ is hydrogen, methyl, or $-CH_2-OH$, and
$R_9$ is methyl, $-COCH_3$, $-CH_2-N(CH_2-CH_3)_2$,

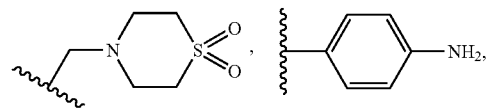

4. The implant of claim 3, wherein $R_8$ is hydrogen, and $R_9$ is

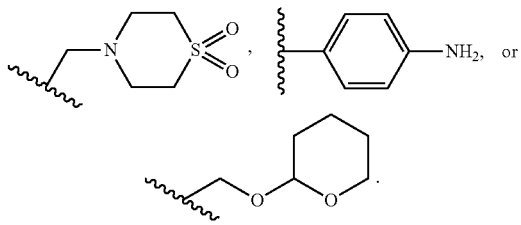

5. The implant of claim 1, wherein $R_8$ is hydrogen, and $R_9$ is

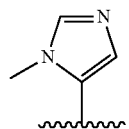

methyl, $-COCH_3$, or $-CH_2-N(CH_2-CH_3)_2$.

6. The implant of claim 1, wherein
X is oxygen or $NR_4$, and wherein $R_4$ is hydrogen, methyl, or $-CH_2-CH_3$.

7. The implant of claim 1, wherein the one or more covalently modified monomers is

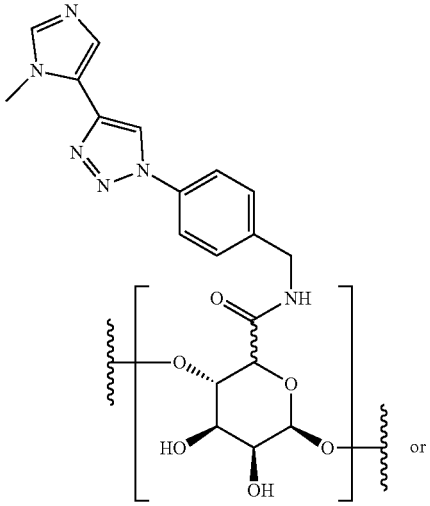

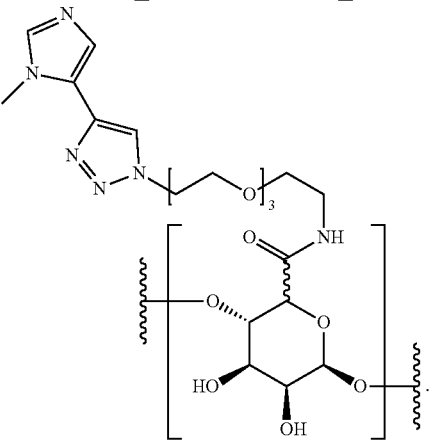

8. The implant of claim 1, wherein $Y_1$ and $Y_2$ are hydrogen.

9. The implant of claim 1, wherein the one or more covalently modified monomers are selected from the group consisting of

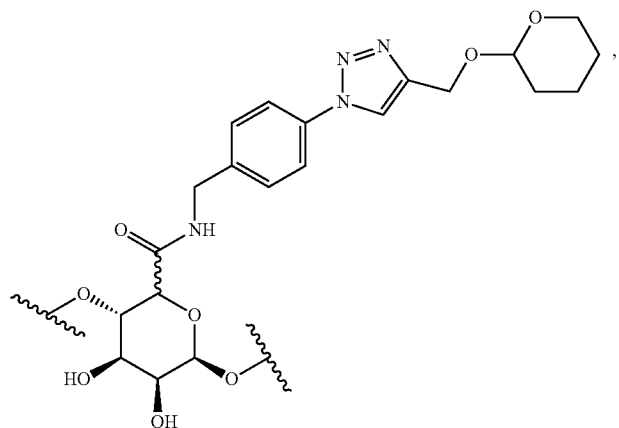

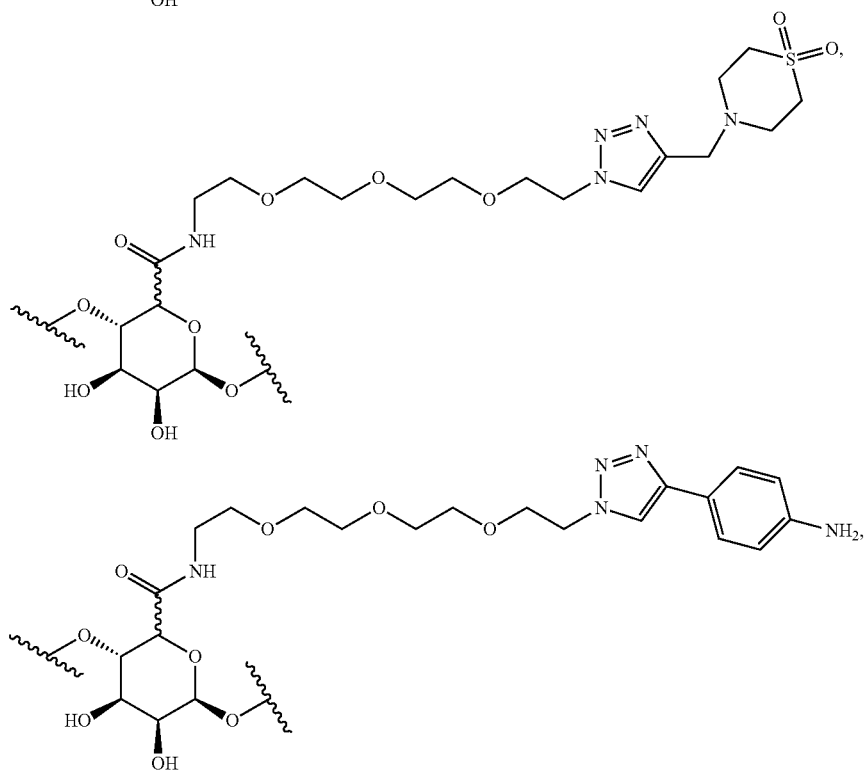

and combinations thereof.

10. The implant of claim 1, wherein the modified alginate polymer has a structure according to Formula III Formula III

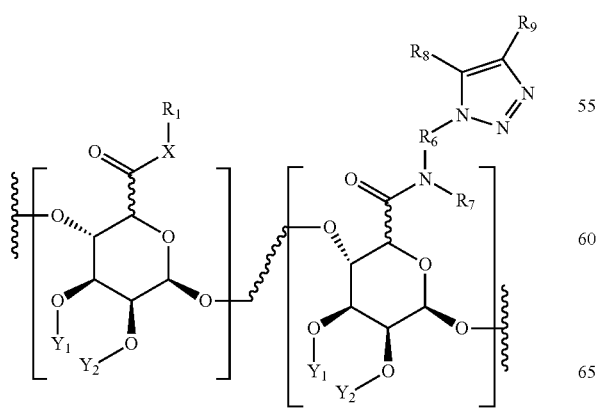

wherein

X is oxygen, sulfur, or $NR_4$, $R_1$, $R_7$, $R_8$, and $R_9$ are, independently, hydrogen, alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(ethylene glycol), peptide, or polypeptide group, $R_6$ is alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(ethylene glycol), peptide, or polypeptide group wherein $Y_1$ and $Y_2$ independently are hydrogen or —PO(OR$_5$)$_2$, or $Y_2$ is absent, and $Y_1$, together with the two oxygen atoms to which $Y_1$ and $Y_2$ are attached form a cyclic structure as shown in Formula IV Formula IV

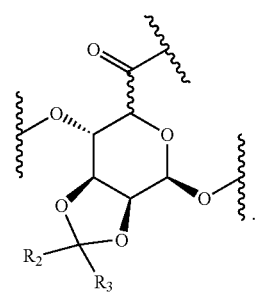

11. The implant of claim 10, wherein $R_1$ is, independently,

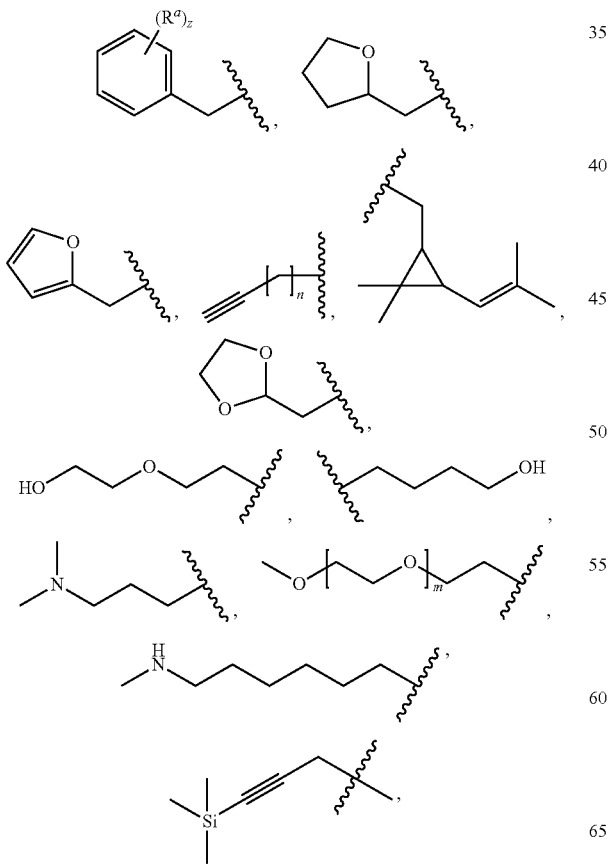

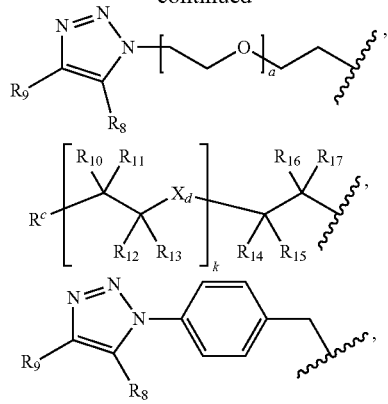

or —$R_6$—$R^b$, wherein a is an integer from 1 to 30, z is an integer from 0 to 5, n is an integer from 1 to 12, m is an integer from 3 to 16, and wherein $R^b$ is Formula XIII

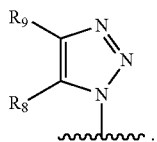

12. The implant of claim 10, wherein $R_6$ is —CH$_2$-aryl- or —CH$_2$—CH$_2$—(O—CH$_2$—CH$_2$)$_3$—, $R_7$ is hydrogen, $R_8$ is hydrogen, methyl, or —CH$_2$—OH, and $R_9$ is methyl, —COCH$_3$, —CH$_2$—N(CH$_2$—CH$_3$)$_2$,

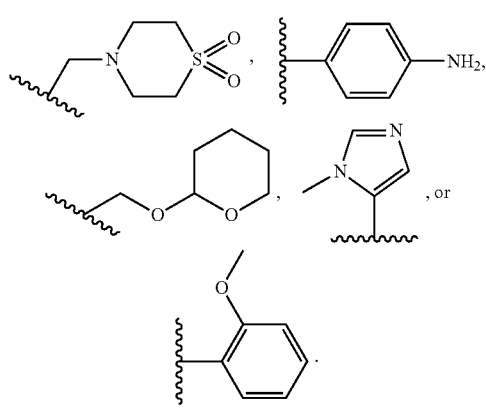

13. The implant of claim 12, wherein $R_8$ is hydrogen, and $R_9$ is

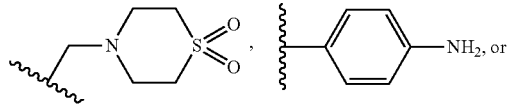

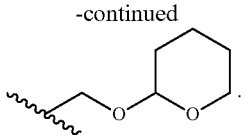

14. The implant of claim 12, wherein
R$_8$ is hydrogen, and
R$_9$ is

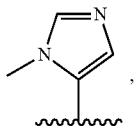 [SMILES: *c1cncn1C], methyl, —COCH$_3$, or —CH$_2$—N(CH$_2$—CH$_3$)$_2$.

15. The implant of claim 10, wherein
X is oxygen or NR$_4$, wherein R$_4$ is hydrogen, methyl, or —CH$_2$—CH$_3$, and
R$_1$ is —CH$_2$—CH$_2$—CH$_2$—CH$_2$—OH, —CH$_2$—CH$_2$—(O—CH$_2$—CH$_2$)$_m$—O—CH$_3$, where m is an integer from 3 to 16, —CH$_2$—CH$_2$—O—CH$_2$—CH$_2$—OH, —(CH$_2$—CH$_2$)$_3$—NH—CH$_3$,

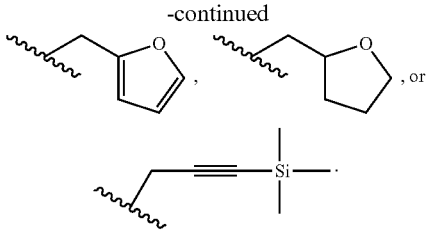

16. The implant of claim 10, wherein Y$_1$ and Y$_2$ are hydrogen.

17. The implant of claim 10, wherein the implant is an implantable device, a cardiac pacemaker, a catheter, a needle injection catheter, a blood clot filter, a balloon, a stent, a coil device, a surgical repair mesh, a transmyocardial revascularization device, a percutaneous myocardial revascularization device, a prosthesis, a heart valve, a tube, a vascular implant, a fiber, a hollow fiber, a membrane, a textile, a blood container, a titer plate, an adsorber media, a dialyzer, a connecting piece, a sensor, a valve, an endoscope, a filter, a pump chamber, or a hemocompatible medical device.

18. The implant of claim 17, wherein the modified alginate polymer is non-covalently associated with the surface of the implant.

19. The implant of claim 17, wherein the modified alginate is covalently associated with the surface of the implant.

* * * * *